United States Patent
Sierks et al.

(10) Patent No.: US 11,175,584 B2
(45) Date of Patent: Nov. 16, 2021

(54) METHODS FOR DETECTING TRAUMATIC BRAIN INJURY

(71) Applicant: ARIZONA BOARD OF REGENTS ON BEHALF OF ARIZONA STATE UNIVERSITY, Scottsdale, AZ (US)

(72) Inventors: Michael Sierks, Ft. McDowell, AZ (US); Stephanie Williams, Phoenix, AZ (US)

(73) Assignee: ARIZONA BOARD OF REGENTS ON BEHALF OF ARIZONA STATE UNIVERSITY, Scottsdale, AZ (US)

( * ) Notice: Subject to any disclaimer, the term of this patent is extended or adjusted under 35 U.S.C. 154(b) by 0 days.

(21) Appl. No.: 16/106,699

(22) Filed: Aug. 21, 2018

(65) Prior Publication Data
US 2018/0364577 A1  Dec. 20, 2018

Related U.S. Application Data

(62) Division of application No. 15/087,682, filed on Mar. 31, 2016, now abandoned.

(60) Provisional application No. 62/141,003, filed on Mar. 31, 2015.

(51) Int. Cl.
| | | |
|---|---|---|
| C12N 15/11 | (2006.01) |
| C12N 15/62 | (2006.01) |
| C07K 14/47 | (2006.01) |
| G03F 7/20 | (2006.01) |

(52) U.S. Cl.
CPC ............ *G03F 7/2004* (2013.01); *C07K 14/47* (2013.01); *C12N 15/11* (2013.01); *C12N 15/62* (2013.01); *G03F 7/201* (2013.01); *G03F 7/2022* (2013.01); *C07K 2318/00* (2013.01); *C07K 2319/70* (2013.01)

(58) Field of Classification Search
CPC ............ C07K 2318/00; C07K 2318/20; C07K 2319/70; C07H 21/00; C12N 15/11; C12N 15/62
See application file for complete search history.

(56) References Cited

U.S. PATENT DOCUMENTS

| | | |
|---|---|---|
| 3,817,837 A | 6/1974 | Rubenstein et al. |
| 3,850,752 A | 11/1974 | Schuurs et al. |
| 3,939,350 A | 2/1976 | Kronick et al. |
| 3,996,345 A | 12/1976 | Ullman et al. |
| 4,275,149 A | 6/1981 | Litman et al. |
| 4,277,437 A | 7/1981 | Maggio |
| 4,366,241 A | 12/1982 | Tom et al. |
| 2010/0239570 A1 | 9/2010 | Nitsch |
| 2016/0291037 A1 | 10/2016 | Sierks et al. |

FOREIGN PATENT DOCUMENTS

| | | |
|---|---|---|
| WO | 2012058308 A2 | 5/2012 |
| WO | 2012058308 A3 | 5/2012 |
| WO | 2012082237 A1 | 6/2012 |
| WO | 2014059442 A2 | 4/2014 |
| WO | 2014059442 A3 | 4/2014 |

OTHER PUBLICATIONS

Binz et al., Designing Repeat Proteins: Well-expressed, Soluble and Stable Proteins from Combinatorial Libraries of Consensus Ankyrin Repeat Proteins, 2003, J. Mol. Biol. 332:489-503 (Year: 2003).*
Kohl et al., Designed to be stable: Crystal structure of a consensus ankyrin repeat protein, Feb. 18, 2003, P.N.A.S. 100(4): 1700-1705 (Year: 2003).*
Forno, "Neuropathology of Parkinson's Disease", Journal of Neuropathology & Experimental Neurology 55(3), 259-272 (1996).
Frost, et al., "Propagation of tau misfolding from the outside to the inside of a cell", J Biol Chem 284(19), 12845-12852 (2009).
Garcia-Sierra, et al., "Conformational changes and truncation of tau protein during tangle evolution in Alzheimer's disease", J Alzheimers Dis 5(2), 65-77 (2003).
Gavett, et al., "Clinical appraisal of chronic traumatic encephalopathy: current perspectives and future directions", Curr Opin Neurol 24(6), 525-531 (2011).
Gavett, et al., "Mild traumatic brain injury: a risk factor for neurodegeneration", Alzheimers Res Ther 2(3), 18 (2010).
Geneservice, "Human Single Fold scFv Libraries I + J (Tomlinson I + J)", Source Bioscience, Reference No. Reln_0017, online: <http://www.lifesciences.sourcebioscience.com/media/143421/tomlinsonij.pdf>.
Georganopoulou, et al., "Nanoparticle-based detection in cerebral spinal fluid of a soluble pathogenic biomarker for Alzheimer's disease", PNAS USA 102(7), 2273-2276 (2005).
Ghosal et al. "Tau conformational changes correspond to impairments of episodic memory in mild cognitive impairment and Alzheimer's disease", Exp Neurol 177(2), 475-493 (2002).
Goedert, et al., "Tau proteins of Alzheimer paired helical filaments: abnormal phosphorylation of all six brain isoforms", Neuron 8(1), 159-168 (1992).
Gomez-Ramos, et al., "Characteristics and consequences of muscarinic receptor activation by tau protein", Eur Neuropsychopharmacol 19(10), 708-717 (2009).
Gong, et al., "Alzheimer's disease-affected brain: presence of oligomeric A beta ligands (ADDLs) suggests a molecular basis for reversible memory loss", PNAS USA 100(18), 10417-10422 (2003).
Grundke-Iqbal, et al., "Abnormal phosphorylation of the microtubule-associated protein tau (tau) in Alzheimer cytoskeletal pathology", Proc Natl Acad Sci U S A 83(13), 4913-4917 (1986).
Guillozet, et al., "Neurofibrillary tangles, amyloid, and memory in aging and mild cognitive impairment", Arch Neurol 60(5), 729-736 (2003).
Halliday, et al., "The progression of pathology in Parkinson's disease", Annals of New York Academy of Sciences 1184, 188-195 (2010).

(Continued)

*Primary Examiner* — Kimberly Ballard
(74) *Attorney, Agent, or Firm* — Duane Morris LLP

(57) ABSTRACT

The present invention provides detection reagents and method for determining risk of traumatic brain injury (TBI), assessment of the amount of neuronal damage, and/or susceptibility to neurodegenerative disease in a subject.

7 Claims, 45 Drawing Sheets

Specification includes a Sequence Listing.

(56) References Cited

OTHER PUBLICATIONS

Harper, et al., "Observation of metastable Abeta amyloid protofibrils by atomic force microscopy", Chem Biol 4(2), 119-125 (1997).
Hellewell, et al., "Post-traumatic hypoxia exacerbates brain tissue damage: Analysis of axonal injury and glial responses", Journal of Neurotrauma 27(11), 1997-2010 (2010).
Henchcliffe, et al., "Biomarkers of Parkinson's disease and Dementia with Lewy bodies", Progress in Neurobiology 95(4), 601-613 (2011).
Herman, et al., "β-amyloid triggers ALS-associated TDP-43 pathology in AD models", Brain Research 1386, 191-199 (2011).
Hipp, et al., "Proteostasis impairment in protein-misfolding and -aggregation diseases", Trends in Cell Biology 24(9), 506-514 (2014).
Hornykiewicz, "Biochemical aspects of Parkinson's disease", Neurology 51(2 Suppl. 2), S2-S9 (1998).
Hortobagyi, et al., "Traumatic axonal damage in the brain can be detected using beta-APP immunohistochemistry within 35 min after head injury to human adults", Neuropathology and Applied Neurobiology 33(2), 226-237 (2007).
Hu, et al., "Biomarkers in frontotemporal lobar degenerations—progress and challenges", Progress in Neurobiology 95 (4), 636-648 (2011).
Iqbal, et al., "Mechanisms of tau-induced neurodegeneration", Acta Neuropathol 118(1, 53-69 (2009).
Iqbal, et al., "Opportunities and challenges in developing Alzheimer disease therapeutics", Acta Neuropathologica 122(5), 543-549 (2011).
Jellinger, et al., "Effects of closed traumatic brain injury and genetic factors on the development of Alzheimer's disease", European Journal of Neurology 8(6), 707-710 (2001).
Jellinger, et al., "Traumatic brain injury as a risk factor for Alzheimer disease. Comparison of two retrospective autopsy cohorts with evaluation of ApoE genotype", BMC Neurology 1(1), 3 (2001).
Johnson, et al., "TDP-43 is intrinsically aggregation-prone, and amyotrophic lateral sclerosis-linked mutations accelerate aggregation and increase toxicity", Journal of Biological Chemistry 284(30), 20329-20339 (2009).
Johnson, et al., "Widespread tau and amyloid-Beta pathology many years after a single traumatic brain injury in humans", Brain Pathol 22(2), 142-149 (2012).
Kasturiranga, et al., "Engineered proteolytic nanobodies reduce Abeta Burden and ameliorate Abeta-induced cytotoxicity", Biochemistry 49(21), 4501-4508 (2010).
Kasturirangan, et al., "Isolation and Characterization of Antibody Fragments Selective for Specific Protein Morphologies from Nanogram Antigen Samples", Biotechnology Progress 29(2), 463-471 (2013).
Kasturirangan, et al., "Nanobody specific for oligomeric β-amyloid stabilizes nontoxic form", Neurobiol Aging 33 (7), 1320-1328 (2012).
Knopman, et al., "Neuropathology of cognitively normal elderly", Journal of Neuropathology & Experimental Neurology 62(11), 1087-1095 (2003).
Koffie, et al., "Oligomeric amyloid beta associates with postsynaptic densities and correlates with excitatory synapse loss near senile plaques", Proc Natl Acad Sci 106 (10), 4012-4017 (2009).
Konzack, et al., "Swimming against the Tide: Mobility of the Microtubile-Associated Protein tau in Neurons", Journal of Neuroscience 27(37), 9916-9927 (2007).
Kotilinek, et al., "Reversible memory loss in a mouse transgenic model of Alzheimer's disease", Journal of Neuroscience 22(15), 6331-6335 (2002).
Kovesdi, et al., "Update on protein biomarkers in traumatic brain injury with emphasis on clinical use in adults and pediatrics", Acta Neurochirurgica 152(1), 1-17 (2010).
Kruger, et al., "Ala30Pro mutation in the gene encoding alpha-synuclein in Parkinson's disease", Nature Genetics 18(2, 106-108 (1998).

Lambert, et al., "Diffusible, nonfibrillar ligands derived from Aβ1-42 are potent central nervous system neurotoxins", Proc. Nat. Acad. Sci. USA 95(11), 6448-6453 (1998).
Lasagna-Reeves, et al., "Alzheimer brain-derived tau oligomers propagate pathology from endogenous tau", Scientific Reports 2, 700 (7 pages) (2012).
Leroy, et al., "Early axonopathy preceding neurofibrillary tangles in mutant tau transgenic mice", Am J Pathol 171(3), 976-992 (2007).
Lesage, et al., "G51D alpha-synuclein mutation causes a novel parkinsonian-pyramidal syndrome", Annals of Neurology 73(4), 459-471 (2013).
Lesne, et al., "A specific amyloid-beta protein assembly in the brain impairs memory", Nature 440(7082), 352-357 (2006).
Li, et al., "Conformational behavior of human alpha-synuclein is modulated by familial Parkinson's disease point mutations A30P and A53T", Neurotoxicology 23(4-5), 553-567 (2002).
Li, et al., "Effect of familial Parkinson's disease point mutations A30P and A53T on the structural properties, aggregation, and fibrillation of human alpha-synuclein", Biochemistry 40(38), 11604-11613 (2001).
Liliang, et al., "Tau proteins in serum predict outcome after severe traumatic brain injury", J Surg Res 160(2, 302-307 (2010).
Liu, et al., "Single chain variable fragments against beta-amyloid (Abeta) can inhibit Abeta aggregation and prevent abeta-induced neurotoxicity", Biochemistry 43(22), 6959-6967 (2004).
Liu, et al., "Tau exon 10 alternative splicing and tauopathies", Molecular Neurodegeneration 3, 8 (10 pages) (2008).
Liu, et al., "Trans-synaptic spread of tau pathology in vivo", PLoS One 7(2),, e31302 (2012).
Lue, et al., "Soluble amyloid beta peptide concentration as a predictior of synaptic change in Alzheimer's disease.", American Journal of Pathology 155(3), 853-862 (1999).
MAEDA, et al., "Increased levels of granular tau oligomers: an early sign of brain aging and Alzheimer's disease", Neurosci Res 54(3), 197-201 (2006).
Mamere, et al., "Evaluation of Delayed Neuronal and Axonal Damage Secondary to Moderate and Severe Traumatic Brain Injury Using Quantitative MR Imaging Techniques", American Journal of Neuroradiology 30(5), 947-952 (2009).
Marcus, et al., "Characterization of an antibody scFv that recognizes fibrillar insulin and beta-amyloid using Atomic Force Microscopy", Nanomedicine 4(1), 1-7 (2008).
Markesbery, et al., "Oxidative alterations in Alzheimer's disease", Brain Pathology 9(1), 133-146 (1999).
Martin, et al., "Post-translational modifications of tau protein: Implications for Alzheimer's disease", Neurochemistry International 58(4):458-471 (2011).
Marx, "Alzheimer's disease. A new take on tau", Science 316(5830), 1416-1417 (2007).
Maxwell, et al., "A mechanistic analysis of nondisruptive axonal injury: a review", Journal of Neurotrauma 14(7), 419-440 (1997).
McKee, et al., "Chronic traumatic encephalopathy in athletes: progressive tauopathy after repetitive head injury", J Neuropathol Exp Neurol 68(7), 709-735 (2009).
McLean, et al., "Soluble Pool of Ab Amyloid as a Determinant of Severity of Neurodegeneration in Alzheimer's Disease", Annals of Neurology 46(6), 860-866 (1999).
McNaught, et al., "Failure of the ubiquitin-proteasome system in Parkinson's disease", Nature Reviews Neuroscience 2(8), 589-594 (2001).
Meraz-Rios, et al., "Tau oligomers and aggregation in Alzheimer's disease", J Neurochem 112(6), 1353-1367 (2010).
Mezey, et al., "Alpha synuclein is present in Lewy bodies in sporadic Parkinson's disease", Molecular Psychiatry 3(6), 493-499 (1998).
Mocanu, et al., "The Potential for beta-Structure in the Repeat Domain of Tau Protein Determines Aggregation, Synaptic Decay, Neuronal Loss, and Coassembly with Endogenous Tau in Inducible Mouse Models of Tauopathy", Journal of Neuroscience 28(3), 737-748 (2008).
Mosharov, et al., "Interplay between cytosolic dopamine, calcium, and alpha-synuclein causes selective death of substantia nigra neurons", Neuron 62(2), 218-229 (2009).

(56) References Cited

OTHER PUBLICATIONS

Mucke, et al. "High-level neuronal expression of abeta 1-42 in wild-type human amyloid protein precursor transgenic mice: synaptotoxicity without plaque formation.", Journal of Neuroscience 20(11), 4050-4058 (2000).
Mukrasch, et al., "The "jaws" of the tau-microtubule interaction", Journal of Biological Chemistry 282(16), 12230-12239 (2007).
Nakamura, et al., "Direct membrane association drives mitochondrial fission by the Parkinson disease-protein alpha-synuclein", Journal of Biological Chemistry 286(23), 20710-20726 (2011).
Narhi, et al. "Both familial Parkinson's disease mutations accelerate alpha-synuclein aggregation", Journal of Biological Chemistry 274(14), 9843-9846 (1999).
Nemetz, et al., "Traumatic brain injury and time to onset of Alzheimer's disease: a population-based study", American Journal of Epidemiology 149(1), 32-40 (1999).
Noto, et al., "Elevated CSF TDP-43 levels in amyotrophic lateral sclerosis: specificity, sensitivity, and a possible prognostic value", Amyotrophic Lateral Sclerosis 12(2), 140-143 (2011).
Oddo, et al., "Reduction of soluble Abeta and tau, but not soluble Abeta alone, ameliorates cognitive decline in transgenic mice with plaques and tangles", J Biol Chem 281(51), 39413-39423 (2006).
Omalu, et al., "Chronic traumatic encephalopathy in an Iraqi war veteran with posttraumatic stress disordelar who commmitted suicide", Neurosurg Focus 31(5), E3, (2011).
Outeiro, et al., "Formation of toxic oligomeric alpha-aynuclein species in living cells", PLoS ONE 3(4), e1867, 10 pages, (2008).
Periquet, et al., "Aggregated alpha-synuclein mediates dopaminergic neurotoxicity in vivo", Journal of Neuroscience 27(12), 3338-3346 (2007).
Polymeropoulos, et al., "Mutation in the alpha-Synuclein Gene Identified in Families with Parkinson's Disease", Science 276(5321), 2045-2047 (1997).
Povlishock, et al., "Update of neuropathology and neurological recovery after traumatic brain injury", Journal of Head Trauma Rehabilitation 20(1), 76-94 (2005).
Rasmusson, et al., "Head injury as a risk factor in Alzheimer's disease", Brain Injury 9(3), 213-219 (1995).
Rath, et al., "Mitochondria at the interface between danger signaling and metabolism: role of unfolded protein responses in chronic inflammation", Inflammatory Bowel Diseases 18(7), 1364-1377 (2012).
Reynolds, et al., "Peroxynitrite-mediated tau modifications stabilize preformed filaments and destabilize microtubules through distinct mechanisms", Biochemistry 45(13), 4314-4326 (2006).
Roberson, et al., "Reducing endogenous tau ameliorates amyloid beta-induced deficits in an Alzheimer's disease mouse model", Science 316(5825), 750-754 (2007).
Rochet, et al., "Inhibition of Fibrillization and Accumulation of Prefibrillar Oligomers in Mixtures of Human and Mouse alpha-Synuclein", Biochemistry 39(35), 10619-10626 (2000).
Roher, et al., "Proteomics-derived cerebrospinal fluid markers of autopsy-confirmed Alzheimer's disease", Biomarkers 14(7), 493-501 (2009).
Sahara, et al., "Tau oligomerization: a role for tau aggregation intermediates linked to neurodegeneration", Curr Alzheimer Res 5(6), 591-598 (2008).
Santacruz, et al., "Tau suppression in a neurodegenerative mouse model improves memory function", Science 309 (5733), 476-481 (2005).
Satake, et al., "Genome-wide association study identifies common variants at four loci as genetic risk factors for Parkinson's disease", Nature Genetics 41(12), 1303-1307 (2009).
Schonheit, et al., "Spatial and temporal relationships between plaques and tangles in Alzheimer-pathology", Neurobiol Aging 25(6), 697-711 (2004).
Schweers, et al., "Structural studies of tau protein and Alzheimer paired helical filaments show no evidence for beta-structure", J Biol Chem 269(39), 24290-24297 (1994).
Selkoe, "Alzheimer disease: mechanistic understanding predicts novel therapies.", Annals of Internal Medicine 140 (8), 627-638 (2004).
Selkoe, "The deposition of amyloid proteins in the aging mammalian brain: Implications for Alzheimer's disease", Annals of Medicine 21(2), 73-76 (1989).
Shaw, et al., "Cerebrospinal fluid biomarker signature in Alzheimer's disease neuroimaging initiative subjects", Annals of Neurology 65(4), 403-413 (2009).
Sierks, et al., "CSF Levels of oligomeric alpha-synuclein and beta-amyloid as biomarkers for neurodegenerative disease", Integrative Biology 3(12), 1188-1196 (2011).
Simon-Sanchez, et al., "Genome-wide association study reveals genetic underlying Parkinson's disease", Nature Genetics 41(12), 1308-1312 (2009).
Singleton, et al., "alpha-Synuclein locus triplication causes Parkinson's disease", Science 302(5646), 841 (2003).
Sivanandam, et al., "Traumatic brain injury: A risk factor for Alzheimer's disease", Neuroscience & Biobehavioral Reviews 36(5), 1376-1381 (2012).
Smith, et al., "Accumulation of amyloid beta and tau and the formation of neurofilament inclusions following diffuse brain injury in the pig", J Neuropathol Exp Neurol 58(9), 982-992 (1999).
Smith, et al., "Diffuse axonal injury in head trauma", Journal of Head Trauma Rehabilitation 18(4), 307-316 (2003).
Smith, et al., "Protein accumulation in traumatic brain injury", NeuroMolecular Medicine 4(1), 59-72 (2003).
Sosin, et al., "Trends in death associated with traumatic brain injury, 1979 through 1992. Success and failure", Jama 273(22), 1778-1780 (1995).
Spillantini, et al., "alpha-Synuclein in filamentous inclusions of Lewy bodies from Parkinson's disease and dementia with lewy bodies", PNAS USA 95(11), 6469-6473 (1998).
Spillantini, et al., "Alpha-synuclein in Lewy bodies", Nature 388, 839-840 (1997).
Spillantini, et al., "Different configurational states of beta-amyloid and their distributions relative to plaques and tangles in Alzheimer disease", PNAS USA 87(10), 3947-3951 (1990).
Spires, et al., "Region-specific dissociation of neuronal loss and neurofibrillary pathology in a mouse model of tauopathy", Am J Pathol 168(5), 1598-1607 (2006).
Terry, et al., "Physical basis of cognitive alterations in Alzheimer's disease: synapse loss is the major correlate of cognitive impairment", Annals of Neurology 30(4), 572-580 (1991).
Tian, et al., "Isolation and characterization of antibody fragments selective for toxic oligomeric tau", Neurobiol Aging 36 (3), 1342-1355 (2015).
Tian, et al., "Trimeric tau is toxic to human neuronal cells at low nanomolar concentrations", Int J Cell Biol vol. 2013, Article ID 260787, 9 pages (2013).
Townsend, et al., "Effects of secreted oligomers of amyloid beta-protein on hippocampal synaptic plasticity: a potent role for trimers", Journal of Physiology 572 (part 2), 477-492 (2006).
Tsai, et al., "Fibrillar amyloid deposition leads to a local synaptic abnormalities and breakage of neuronal branches", Nature Neuroscience 7(11), 1181-1183 (2004).
Tu, et al. "Glial cytoplasmic inclusions in white matter oligodendrocytes of multiple system atrophy brains contain insoluble alpha-synuclein", Annals of Neurology 44(3), 415-422 (1998).
Uryu, et al., "Concomitant TAR-DNA-Binding Protein 43 Pathology Is Present in Alzheimer Disease and Corticobasal Degeneration but Not in Other Tauopathies", Journal of Neuropathology & Experimental Neurology 67(6), 555-564 (2008).
Uryu, et al., "Multiple proteins implicated in neurodegenerative diseases accumulate in axons after brain trauma in humans", Exp Neurol 208(2), 185-192 (2007).
Vandermeeren, et al., "Detection of tau proteins in normal and Alzheimer's disease cerebrospinal fluid with a sensitive sandwich enzyme-linked immunosorbent assay", Journal of Neurochemistry 61(5), 1828-1834 (1993).
Vogiatzi, et al., "Wild type alpha-synuclein is degraded by chaperone-mediated autophagy and macroautophagy in neuronal cells", Journal of Biological Chemistry 283(35), 23542-23556 (2008).

(56) References Cited

OTHER PUBLICATIONS

Von Bergen, et al., "Assembly of tau protein into Alzheimer paired helical filaments depends on a local sequence motif ((306)VQIVYK(311)) forming beta structure", Proc Natl Acad Sci U S A 97(10), 5129-5134 (2000).
Wakabayashi, et al., "Alpha-synuclein immunoreactivity in glial cytoplasmic inclusions in multiple system atrophy", Neuroscience Letters 249(2-3), 180-182 (1998).
Wales, et al., "Limelight on alpha-synuclein: pathological and mechanistic implications in neurodegeneration", Journal of Parkinson's Disease 3(4), 415-459 (2013).
Walker, et al., "Molecular mechanisms of cognitive dysfunction following traumatic brain injury", Frontiers in Aging Neuroscience 5, article 29, 25 pages, (2013).
Walsh, et al., "Amyloid beta-protein fibrillogenesis. Structure and biological activity of protofibrillar intermediates", Journal of Biological Chemistry 274(36), 25945-25952 (1999).
Walsh, et al., "Deciphering the Molecular Basis of Memory Failure in Alzheimer's Disease.", Neuron 44(1), 181-193 (2004).
Walsh, et al., "Naturally secreted oligomers of amyloid beta protein potently inhibit hippocampal long-term potentiation in vivo", Nature 416(6880), 535-539 (2002).
Walsh, et al., "The role of cell-derived oligomers of Abeta in Alzheimer's disease and avenues for therapeutic intervention", Biochemical Society Transactions 33(part 5), 1087-1090 (2005).
Wang, et al., "Microtubule-associated protein tau in development, degeneration and protection of neurons", Progress in Neurobiology 85(2), 148-175 (2008).
Wang, et al., "Soluble oligomers of Beta amyloid (1-42) inhibit long-term potentiation but not long-term depression in rat dentate gyrus.", Brain Research 924(2), 133-140 (2002).
Waxweiler, et al., "Monitoring the impact of traumatic brain injury: a review and update", J Neurotrauma 12(4), 509-516 (1995).
Wilk, et al., "Mild traumatic brain injury (concussion) during combat: lack of association of blast mechanism with persistent postconcussive symptoms", J Head Trauma Rehabil 25(1), 9-14 (2010).
Williams, et al., "A Sensitive phage-based capture ELISA for sub-femtomolar detection of protein variants directly from biological samples", Biotechnology Progress 31(1), 289-298 (2015).
Williams, et al., "Novel Atomic Force Microscopy Based Biopanning for Isolation of Morphology Specific Reagents against TDP-43 Variants in Amyotrophic Lateral Sclerosis", J. Vis Exp 96, e52584, 13 pages (2015).
Wilson, et al., "TDP-43 in aging and Alzheimer's disease—a review", International Journal of Clinical & Experimental Pathology 4(2), 147-155 (2011).
Wolozin, "Physiological Protein Aggregation Run Amuck: Stress Granules and the Genesis of Neurodegenerative Disease", Discovery Medicine 17(91), 47-52 (2014).
Yao, et al., "Detection of protein biomarkers using high-throughput immunoblotting following focal ischemic or penetrating ballistic-like brain injuries in rats", Brain Injury 22(10), 723-732 (2008).
Yoshiyama, et al., "Synapse loss and microglial activation precede tangles in a P301S tauopathy mouse model", Neuron 53(3), 337-351 (2007).
Yuan, et al., "Intracellular targeting and clearance of oligomeric alpha-synuclein alleviates toxicity in mammalian cells", Neuroscience Letters 459(1), 16-18 (2009).
Zameer, et al., "Anti-oligomeric Abeta single-chain variable domain antibody blocks Abeta-induced toxicity against human neuroblastoma cells", J Mol Biol 384 (4), 917-928 (2008).
Zameer, et al., "Single chain Fv antibodies against the 25-35 Abeta fragment inhibit aggregation and toxicity of Abeta42", Biochemistry 45(38), 11532-11539 (2006).
Zarranz, et al., "The new mutation, E46K, of alpha-synuclein causes Parkinson and Lewy body dementia.", Annals of Neurology 55(2), 164-173 (2004).
Zhou, et al., "A human single-chain Fv Intrabody blocks aberrant cellular effects of overexpressed alpha-Synuclein", Molecular Therapy 10 (6), 1023-31 (2004).
Amador-Ortiz, et al., "TDP-43 immunoreactivity in hippocampal sclerosis and Alzheimer's disease", Annals of Neurology 61(5), 435-445 (2007).
Amos, "Microtubule structure and its stabilisation", Org Biomol Chem 2(15), 2153-2160 (2004).
Andorfer, et al., "Hyperphosphorylation and aggregation of tau in mice expressing normal human tau isoforms", J Neurochem 86(3), 582-590 (2003).
Appel-Cresswell, et al., "Alpha-Synuclein p.H50Q, a novel pathogenic mutation for Parkinson's disease", Movement Disorders 28(6), 811-813 (2013).
Arriagada, et al., "Neurofibrillary tangles but not senile plaques parallel duration and severity of Alzheimer's disease", Neurology 42(3), 631-639 (1992).
Asuni, et al., "Immunotherapy targeting pathological tau conformers in a tangle mouse model reduces brain pathology with associated functional improvements", Journal of Neuroscience 27(34), 9115-9129 (2007).
Baba, et al., "Aggregation of alpha-synuclein in Lewy bodies of sporadic Parkinson's disease and dementia with Lewy bodies", American Journal of Pathology 152(4), 879-884 (1998).
Ballatore, et al., "Tau-mediated neurodegeneration in Alzheimer's disease and related disorders", Nat Rev Neurosci 8(9), 663-672 (2007).
Bancher, et al., "Neuropathological staging of Alzheimer lesions and intellectual status in Alzheimer's and Parkinson's disease patients", Neurosci Lett 162(1-2), 179-182 (1993).
Barkhordarian, et al., "Isolating recombinant antibodies against specific protein morphologies using atomic force microscopy and phage display technologies", Protein Eng Des Sel, 19(11), 497-502 (2006).
Bateman, et al., "Clinical and biomarker changes in dominantly inherited Alzheimer's disease", The New England Journal of Medicine 367(9), 795-804 (2012).
Baugh, et al., "Chronic traumatic encephalopathy: neurodegeneration following repetitive concussive and subconcussive brain trauma", Brain Imaging Behav 6(2), 244-2454 (2012).
Beach, et al., "The Sun Health Research Institute Brain Donation Program: description and experience, 1987-2007", Cell Tissue Bank 9(3), 229-245 (2008).
Berger, et al., "Accumulation of pathological tau species and memory loss in a conditional model of tauopathy", J Neurosci 27(14), 3650-3662 (2007).
Blennow, et al., "Cerebrospinal fluid and plasma biomarkers in Alzheimer disease", Nature Reviews Neurology 6(3), 131-144 (2010).
Borza, "A review on the cause-effect relationship between oxidative stress and toxic proteins in the pathogeesis of neurodegenerative diseases", Rev Med Chir Soc Med Nat Iasi 118(1), 19-27 (2014).
Braak, et al., "Evolution of neuronal changes in the course of alzheimer's disease", Journal of Neural Transmission, Supplement 53, 127-140 (1998).
Braak, et al., "Staging of brain pathology related to sporadic Parkinson's disease", Neurobiol Aging 24(2), 197-211 (2003).
Browne, et al., "Mild traumatic brain injury and diffuse axonal injury in swine", Journal of Neurotrauma 28(9), 1747-1755 (2011).
Brunden, "Evidence that non-fibrillar tau causes pathology linked to neurodegeneration and behavioral impairments", J Alzheimers Dis 14(4), 393-399 (2008).
Bucciantini, et al., "Inherent toxicity of aggregates implies a common mechanism for protein misfolding diseases", Nature 416, 507-511 (2002).
Buratti, et al., "Multiple roles of TDP-43 in gene expression, splicing regulation, and human disease", Frontiers in Bioscience 13(3), 867-878 (2008).
Buratti, et al., "Nuclear factor TDP-43 binds to the polymorphic TG repeats in CFTR intron 8 and causes skipping of exon 9: a functional link with disease penetrance", American Journal of Human Genetics 74(6), 1322-1325 (2004).

(56) References Cited

OTHER PUBLICATIONS

Cedazo-Minguez, et al., "Biomarkers for Alzheimer's disease and other forms of dementia: clinical needs, limitations and future aspects", Experimental Gerontology 45(1), 5-14 (2010).
Chang, et al., "Femtomole immunodetection of synthetic and endogenous amyloid-beta oligomers and its application to Alzheimer's disease drug candidate screening", Journal of Molecular Neuroscience 20(3), 305-313 (2003).
Chartier-Harlin, et al., "Alpha-synuclein locus duplication as a cause of familial Parkinson's disease", Lancet 364, 1167-1169 (2004).
Clavaguera, et al., "Transmission and spreading of tauopathy in transgenic mouse brain", Nat Cell Biol 11(7), 909-913 (2009).
Cleary, et al., "Natural oligomers of the amyloid-beta protein specifically disrupt cognitive function", Nature Neuroscience 8(1), 79-84 (2005).
Colla, et al. "Accumulation of Toxic-Synuclein Oligomer within Endoplasmic Reticulum Occurs in a-Synucleinopathy in Vivo", Journal of Neuroscience 32(10), 3301-3305 (2012).
Conrad, et al., "Impact of the hypothalamic-pituitary-adrenal/gonadal axes on trajectory of age-related cognitive decline", Progress in Brain Research (L. Martini, Editor), 31-76 (2010).
Conway, et al., "Accelerated in vitro fibril formation by a mutant alpha-synuclein linked to early-onset Parkinson disease", Nature Medicine 4(11), 1318-1320 (1998).
Cuervo, et al., "Impared degradation of mutant alpha-synuclein by chaperone-mediated autophagy", Science 305 (5688), 1292-1295 (2004).
Danzer, et al., "Different species of alpha-synuclein oligomers induce calcium influx and seeding", Journal of Neuroscience 27(34), 9220-9232 (2007).
Dasuri, et al., "Oxidative stress, neurodegeneration, and the balance of protein degradation and protein synthesis", Free Radical Biology and Medicine 62, 170-185 (2013).
De Calignon, et al., "Propagation of tau pathology in a model of early Alzheimer's disease", Neuron 73(4), 685-697 (2012).
Dias, et al., "The rold of oxidative stress in Parkinson's disease", Journal of Parkinson's Disease 3(4), 461-491 (2013).
Dickson, et al., "Multiple system atrophy: a sporadic synucleinopathy", Brain Pathology 9(4), 721-732 (1999).
Dickson, "TDP-43 Immunoreactivity in Neurodegenerative Disease: Disease versus Mechanism-Specificity", Acta Neuropathologica 115(1), 147-149 (2008).
Diogenes, et al., "Extracellular alpha-synuclein oligomers modulate synaptic transmission and impair LTP via NMDA-receptor activation", Journal of Neurosciences 32(34), 11750-11762 (2012).
Dodart, et al., "Immunization reverses memory deficits without reducing brain Abeta burden in Alzheimer's disease model.", Nature Neuroscience 5(5), 452-457 (2002).
Dubey, et al., "Tau inhibits anterograde axonal transport and pertrubs stability in growing axonal neurites in part by displacing kinesin cargo: neurofilaments attenuate tau-mediated neurite instability", Cell Motility and the Cytoskeleton 65(2), 89-99 (2008).
Duda, et al., "Immunohistochemical and biochemical studies demonstrate a distinct profile of alpha-synuclein permuatations in multiple system atrophy", Journal of Neuropathology & Experimental Neurology 59(9), 830-841 (2000).
Ebrahim-Fakhari, et al., "Alpha-synuclein's degradation in vivo: Opening a new (cranial) window on the roles of degradation pathways in Parkinson disease", Autophagy 8(2), 281-283 (2012).
Edwards, et al., "Genome-wide association study confirms SNPs in SNCA and the MAPT region as common risk factors for Parkinson's disease", Annals of Human Genetics 74(2), 97-109 (2010).
El-Agnaf, et al., "Alpha-synuclein implicated in Parkinson's disease is present in extracellular biological fluids, including human plasma", FASEB 17(11), 1945-1947 (2003).
El-Agnaf, et al., "Detection of oligomeric forms of alpha-synuclein protein in human plasma as a potential biomarker or Parkinson's disease", Faseb J 20, 419-425 (2006).
Emadi, et al., "Detecting morphologically distinct oligomeric forms of alpha-synuclein", J. Biol. Chem. 284 (17), 11048-11058 (2009).
Emadi, et al., "Inhibiting aggregation of alpha-synuclein with human single chain antibody fragments", Biochemistry 43, 2871-8 (2004).
Emadi, et al., "Isolation of a human single chain antibody fragment against oligomeric alpha-synuclein that inhibits aggregation and prevents alpha-synuclein-induced toxicity", J Mol Biol 368, 1132-1144 (2007).
Formichi, et al., "Cerebrospinal fluid tau, A beta, and phosphorylated tau protein for the diagnosis of Alzheimer's disease", Journal of Cellular Physiology 208(1), 39-46 (2006).

\* cited by examiner

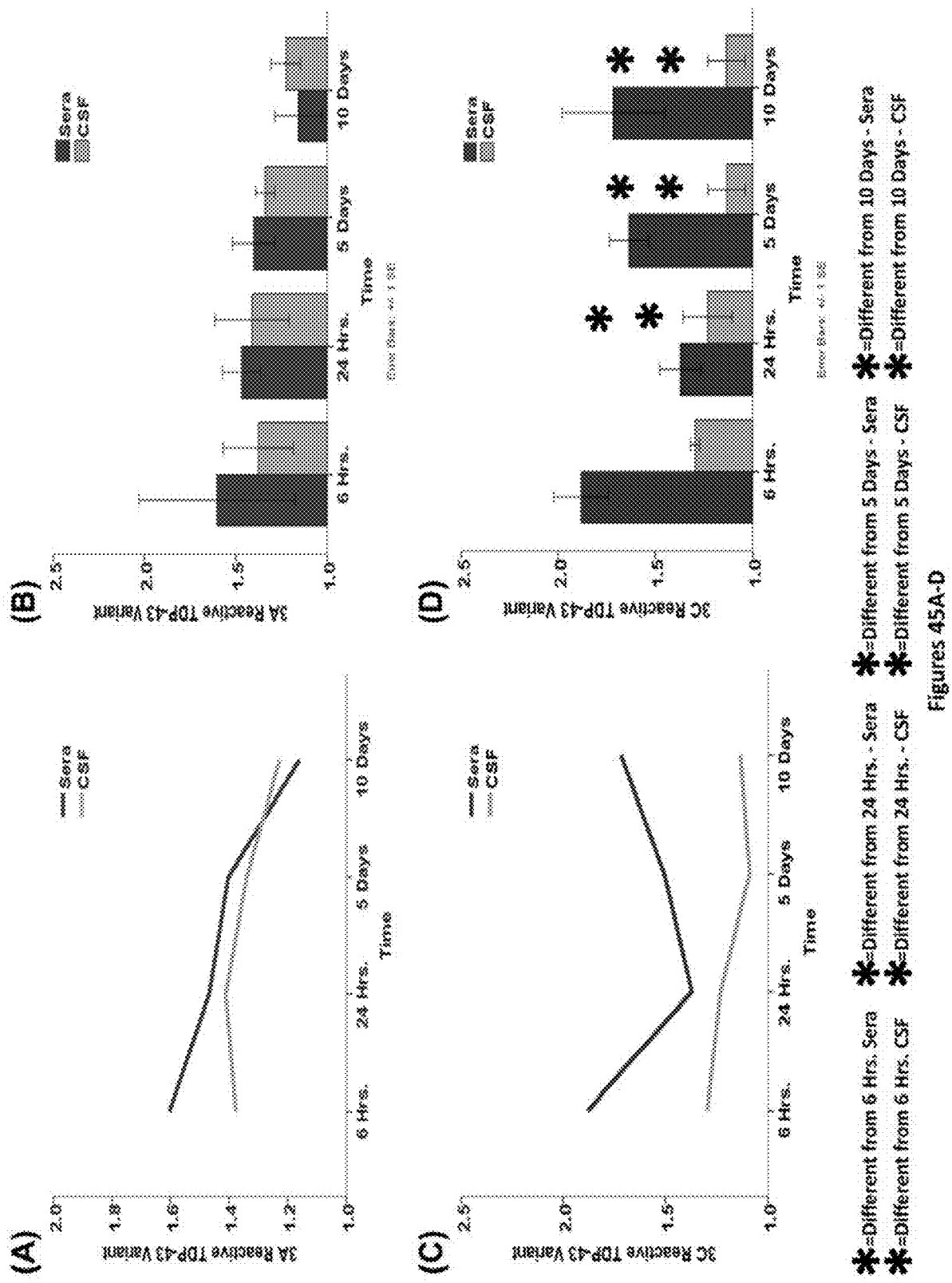
Figures 45A-D

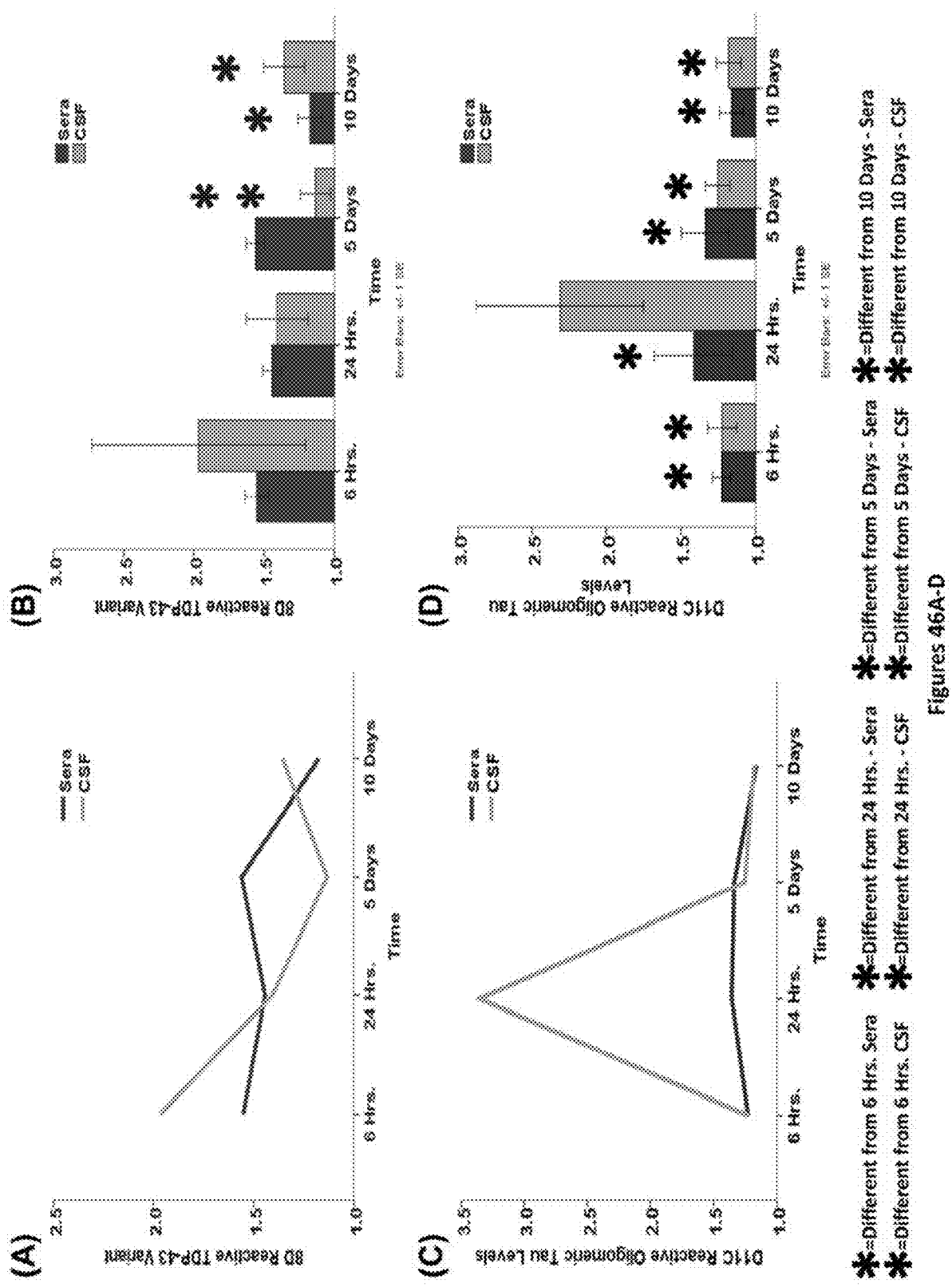
Figures 46A-D

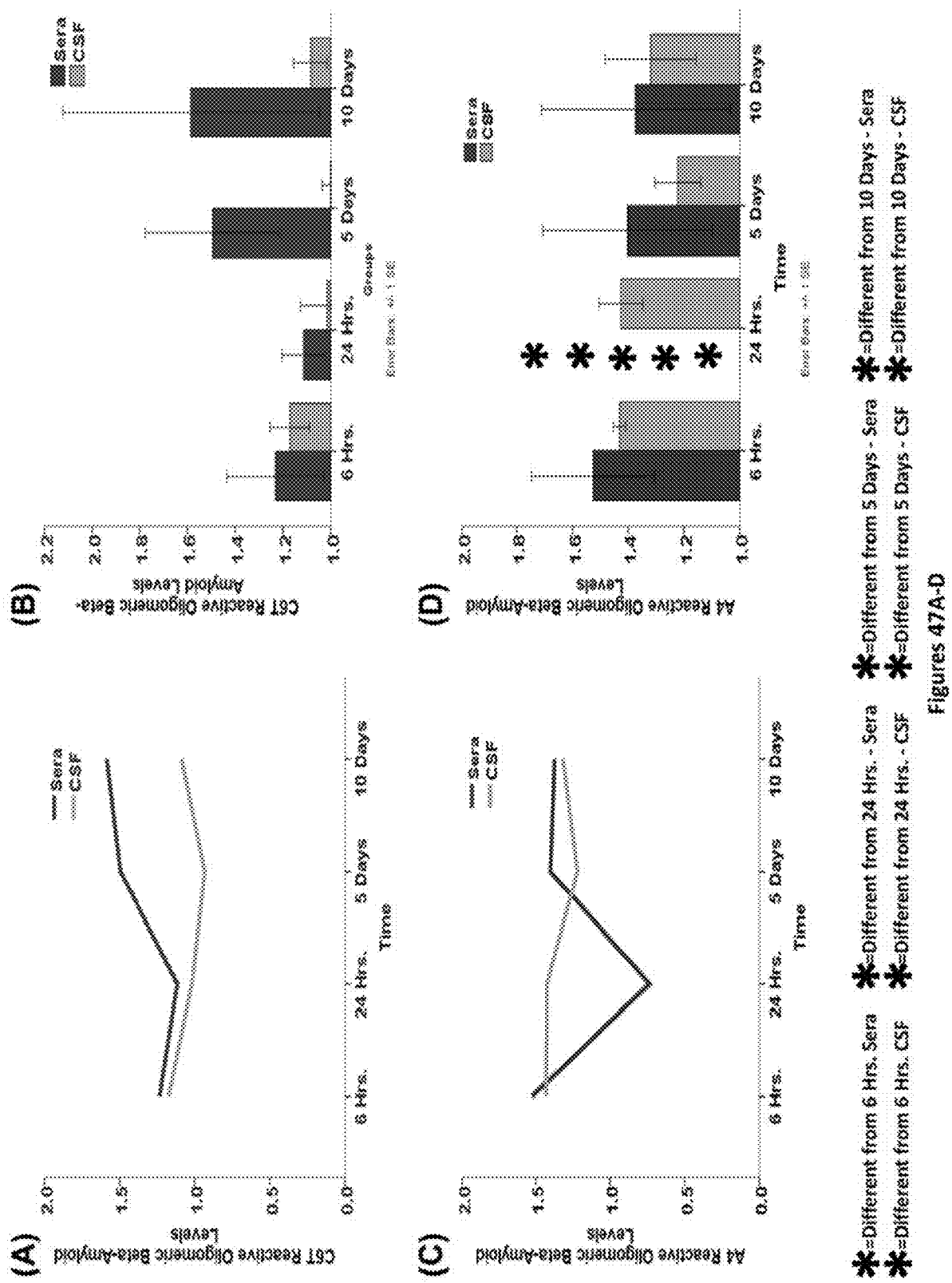
Figures 47A-D

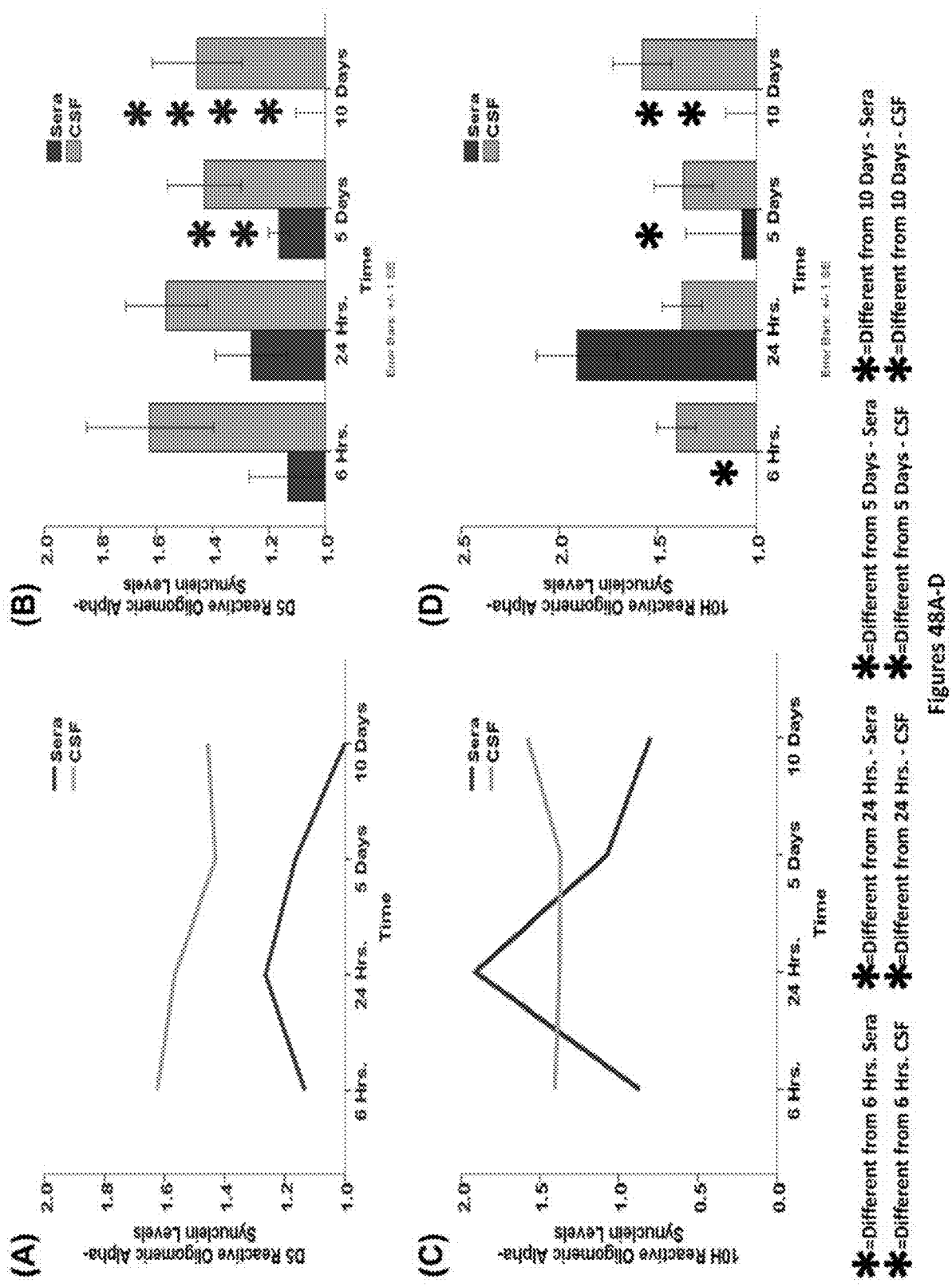
Figures 48A-D

SEQUENCE LISTING

```
<160> NUMBER OF SEQ ID NOS: 45

<210> SEQ ID NO 1
<211> LENGTH: 736
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 1
ccatggccga ggtgcagctg ttggagtctg ggggaggctt ggtacagcct gggggtccc       60 cgagactctc ctgtgcagcc tctggattca cctttagcag ctatgccatg agctgggtcc     120
```

```
gccaggctcc agggaagggg ctggagtggg tctcaactat ttctgcttct ggtacttata    180
caaattacgc agactccgtg aagggccggt tcaccatctc cagagacaat tccaagaaca    240
cgctgtatct gcaaatgaac agcctgagag ccgaggacac ggccgtatat tactgtgcga    300
aaacttcttt ttatttgac tactgggccc agggaaccct ggtcaccgtc tcgagcggtg    360
gaggcggttc aggcggaggt ggcagcggcg gtggcgggtc gacggacatc cagatgaccc    420
agtctccatc ctccctgtct gcatctgtag gagacagagt caccatcact tgccgggcaa    480
gtcagagcat tagcagctat ttaaattggt atcagcagaa accagggaaa gcccctaagc    540
tcctgatcta tgctgcatcc aatttgcaaa gtggggtccc atcaaggttc agtggcagtg    600
gatctgggac agatttcact ctcaccatca gcagtctgca acctgaagat tttgcaactt    660
actactgtca acaggataat tatgctcctt atacgttcgg ccaagggacc aaggtggaaa    720
tcaaacgggc ggccgc                                                    736

<210> SEQ ID NO 2
<211> LENGTH: 514
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 2
ccatggccga ggtgcagctg ttggagtctg ggggaggctt ggtacagcct ggggggtccc     60
tgagactctc ctgtgcagcc tctggattca cctttagcag ctatgccatg agctgggtcc    120
gccaggctcc agggaagggg ctggagtggg tctcaactat tcgccatgct ggtcagtcga    180
cggacatcca gatgacccag tctccatcct ccctgtctgc atctgtagga gacagagtca    240
ccatcacttg ccgggcaagt cagagcatta gcagctattt aaattggtat cagcagaaac    300
cagggaaagc ccctaagctc ctgatctata tggcatcccg tttgcaaagt ggggtcccat    360
caaggttcag tggcagtgga tctgggacag atttcactct caccatcagc agtctgcaac    420
ctgaagattt tgcaacttac tactgtcaac agcagcgtac gaagcctcct acgttcggcc    480
aagggaccaa ggtggaaatc aaacgggcgg ccgc                                514

<210> SEQ ID NO 3
<211> LENGTH: 736
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 3
ccatggccga ggtgcagctg ttggagtctg ggggaggctt ggtacagcct ggggggtccc     60
tgagactctc ctgtgcagcc tctggattca cctttagcag ctatgccatg agctgggtcc    120
gccaggctcc agggaagggg ctggagtggg tctcaactat tgcttctgct ggtactgata    180
cagcttacgc agactccgtg aagggccggt tcaccatctc cagagacaat tccaagaaca    240
cgctgtatct gcaaatgaac agcctgagag ccgaggacac ggccgtatat tactgtgcga    300
aagatactac tgcttttgac tactgggccc agggaaccct ggtcaccgtc tcgagcggtg    360
gaggcggttc aggcggaggt ggcagcggcg gtggcgggtc gacggacatc aagatgaccc    420
agtctccatc ctccctgtct gcatctgtag gagacagagt caccatcact tgccgggcaa    480
```

```
gtcagagcat tagcagctat ttaaattggt atcagcagaa accagggaaa gcccctaagc      540
tcctgatcta tgatgcatcc actttgcaaa gtggggtccc atcaaggttc agtggcagtg      600
gatctgggac agatttcact ctcaccatca gcagtctgca acctgaagat tttgcaactt      660
actactgtca acagtctact tatgctcctg ctacgttcgg ccaagggacc aaggtggaaa      720
tcaaacgggc ggccgc                                                      736
```

<210> SEQ ID NO 4
<211> LENGTH: 436
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 4

```
ccatggccga ggtgtttgac tactggggcc agggaaccct ggtcaccgtc tcgagcggtg       60
gaggcggttc aggcggaggt ggcagcggcg gtggcgggtc gacggacatc cagatgaccc      120
agtctccatc ctccctgtct gcatctgtag gagacagagt caccatcact tgccgggcaa      180
gtcagagcat tagcagctat ttaaattggt atcagcagaa accagggaaa gcccctaagc      240
tcctgatcta ttctgcatcc aatttgcaaa gtggggtccc atcaaggttc agtggcagtg      300
gatctgggac agatttcact ctcaccatca gcagtctgca acctgaagat tttgcaactt      360
actactgtca acagagttat tctagtcctt ctacgttcgg ccaagggacc aaggtggaaa      420
tcaaacgggc ggccgc                                                      436
```

<210> SEQ ID NO 5
<211> LENGTH: 735
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 5

```
ccatggccga ggtgcagctg ttggagtctg ggggaggctt ggtacagcct gggggtccc       60 tgagactctc ctgtgcagcc tctggattca cctttagcag ctatgccatg agctgggtcc      120
gccaggctcc agggaagggg ctggagtggg tctcatctat taataatgct ggtatgatac      180
aaattacgca gactccgtga agggcaggtt caccatctcc agagacaatt ccaagaacac      240
gctgtatctg caaatgaaca gcctgagagc cgaggacacg gccgtatatt actgtgcgaa      300
aaataatgct tattttgact actggggcca gggaaccctg gtcaccgtct cgagcggtgg      360
aggcggttca ggcggaggtg gcagcggcgg tggcgggtcg acggacatcc agatgaccca      420
gtctccatcc tccctgtctg catctgtagg agacagagtc accatcactt gccgggcaag      480
tcagagcatt agcagctatt taaattggta tcagcagaaa ccagggaaag cccctaagct      540
cctgatctat ggtgcatcca gtttgcaaag tgggtccca tcaaggttca gtggcagtgg      600
atctgggaca gatttcactc tcaccatcag cagtctgcaa cctgaagatt ttgcaactta      660
ctactgtcaa cagtatgatt ctgctcctgg tacgttcggc caagggacca aggtggaaat      720
caaacgggcg gccgc                                                      735
```

<210> SEQ ID NO 6
<211> LENGTH: 736
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 6

```
ccatggccga ggtgcagctg ttggagtctg ggggaggctt ggtacagcct gggggtccc      60
tgagactctc ctgtgcagcc tctggattca cctttagcag ctatgccatg agctgggtcc    120
gccaggctcc agggaagggg ctggagtggg tctcaactat taataatagt ggtacttcta    180
caaattacgc agactccgtg aagggccggt tcaccatctc cagagacaat tccaagaaca    240
cgctgtatct gcaaatgaac agcctgagag ccgaggacac ggccgtatat tactgtgcga    300
aaagtactaa ttattttgac tactggggcc agggaaccct ggtcaccgtc tcgagcggtg    360
gaggcggttc aggcggaggt ggcagcggcg gtggcgggtc gacggacatc cagatgaccc    420
agtctccatc ctccctgtct gcatctgtag gagacagagt caccatcact tgccgggcaa    480
gtcagagcat tagcagctat ttaaattggt atcagcagaa accagggaaa gcccctaagc    540
tcctgatcta tgctgcatcc agtttgcaaa gtggggtccc atcaaggttc agtggcagtg    600
gatctgggac agatttcact ctcaccatca gcagtctgca acctgaagat tttgcaactt    660
actactgtca acagaatgct gctgatccta ctacgttcgg ccaagggacc aaggtggaaa    720
tcaaacgggc ggccgc                                                   736
```

<210> SEQ ID NO 7
<211> LENGTH: 977
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (829)..(829)
<223> OTHER INFORMATION: a, c, t, g, unknown or other
<220> FEATURE:
<221> NAME/KEY: modified_base
<222> LOCATION: (843)..(843)
<223> OTHER INFORMATION: a, c, t, g, unknown or other
<220> FEATURE:
<221> NAME/KEY: modified_base
<222> LOCATION: (853)..(853)
<223> OTHER INFORMATION: a, c, t, g, unknown or other
<220> FEATURE:
<221> NAME/KEY: modified_base
<222> LOCATION: (859)..(859)
<223> OTHER INFORMATION: a, c, t, g, unknown or other
<220> FEATURE:
<221> NAME/KEY: modified_base
<222> LOCATION: (885)..(886)
<223> OTHER INFORMATION: a, c, t, g, unknown or other
<220> FEATURE:
<221> NAME/KEY: modified_base
<222> LOCATION: (913)..(913)
<223> OTHER INFORMATION: a, c, t, g, unknown or other
<220> FEATURE:
<221> NAME/KEY: modified_base
<222> LOCATION: (919)..(921)
<223> OTHER INFORMATION: a, c, t, g, unknown or other
<220> FEATURE:
<221> NAME/KEY: modified_base
<222> LOCATION: (939)..(939)
<223> OTHER INFORMATION: a, c, t, g, unknown or other
<220> FEATURE:
<221> NAME/KEY: modified_base
<222> LOCATION: (949)..(949)
<223> OTHER INFORMATION: a, c, t, g, unknown or other
<220> FEATURE:
<221> NAME/KEY: modified_base
<222> LOCATION: (952)..(952)

<223> OTHER INFORMATION: a, c, t, g, unknown or other
<220> FEATURE:
<221> NAME/KEY: modified_base
<222> LOCATION: (954)..(954)
<223> OTHER INFORMATION: a, c, t, g, unknown or other
<220> FEATURE:
<221> NAME/KEY: modified_base
<222> LOCATION: (959)..(960)
<223> OTHER INFORMATION: a, c, t, g, unknown or other
<220> FEATURE:
<221> NAME/KEY: modified_base
<222> LOCATION: (962)..(962)
<223> OTHER INFORMATION: a, c, t, g, unknown or other
<220> FEATURE:
<221> NAME/KEY: modified_base
<222> LOCATION: (964)..(964)
<223> OTHER INFORMATION: a, c, t, g, unknown or other
<220> FEATURE:
<221> NAME/KEY: modified_base
<222> LOCATION: (967)..(967)
<223> OTHER INFORMATION: a, c, t, g, unknown or other
<220> FEATURE:
<221> NAME/KEY: modified_base
<222> LOCATION: (970)..(971)
<223> OTHER INFORMATION: a, c, t, g, unknown or other
<220> FEATURE:
<221> NAME/KEY: modified_base
<222> LOCATION: (973)..(973)
<223> OTHER INFORMATION: a, c, t, g, unknown or other

<400> SEQUENCE: 7

```
gatttggctg gcgctggctg gtttagtttt agcgtttagc gcatcggcgg actacaaaga      60
ggcccagccg gccatggacc tgggtaagaa actgctggaa gctgctcgtg ctggtcagga     120
cgacgaagtt cgtatcctga tggctaacgg tgctgacgtt aacgctgacg actaccgtgg     180
ttctactccg ctgcacctgg ctgctatggc tggtcacctg gaaatcgttg aagttctgct     240
gaagcacggt gctgacgtta acgctcagga caaattcggt aagaccgctt tcgacatctc     300
catcgacaac ggtaacgagg acctggctga atcctgcaa gcggccgcac atcatcatca     360
ccatcacggg gccgcagaac aaaaactcat ctcagaagag gatctgaatg gggccgcata     420
gactgttgaa agttgtttag caaaacctca tacagaaaat tcatttacta acgtctggaa     480
agacgacaaa actttagatc gttacgctaa ctatgagggc tgtctgtgga atgctacagg     540
cgttgtggtt tgtactggtg acgaaactca gtgttacggt acatgggttc ctattgggct     600
tgctatccct gaaaatgagg gtggtggctc tgagggtggc ggttctgagg gtggcggttc     660
tgagggtggc ggtactaaac ctcctgagta cggtgataca cctattccgg gctatactta     720
tatcaacccT ctcgacggca cttatccgcc tggtactgag caaaaccccg ctaatcctaa     780
tccttctctt gaggagtctc agcctcttaa tactttcatg tttcagaana ataggttccg     840
aantaggcag gggngcattna ctgtttatac gggcactgtt actcnnggca ctgaccccgt     900
taaaacttat tancagtann ntcctgtatc atcaaaagnc atgtatgang cntnctggnn     960
cngnaantcn nanactg                                                    977
```

<210> SEQ ID NO 8
<211> LENGTH: 943
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (14)..(14)
<223> OTHER INFORMATION: a, c, t, g, unknown or other
<220> FEATURE:

```
<221> NAME/KEY: modified_base
<222> LOCATION: (28)..(28)
<223> OTHER INFORMATION: a, c, t, g, unknown or other
<220> FEATURE:
<221> NAME/KEY: modified_base
<222> LOCATION: (30)..(36)
<223> OTHER INFORMATION: a, c, t, g, unknown or other
<220> FEATURE:
<221> NAME/KEY: modified_base
<222> LOCATION: (38)..(38)
<223> OTHER INFORMATION: a, c, t, g, unknown or other
<220> FEATURE:
<221> NAME/KEY: modified_base
<222> LOCATION: (864)..(864)
<223> OTHER INFORMATION: a, c, t, g, unknown or other
<220> FEATURE:
<221> NAME/KEY: modified_base
<222> LOCATION: (881)..(882)
<223> OTHER INFORMATION: a, c, t, g, unknown or other
<220> FEATURE:
<221> NAME/KEY: modified_base
<222> LOCATION: (914)..(914)
<223> OTHER INFORMATION: a, c, t, g, unknown or other
<220> FEATURE:
<221> NAME/KEY: modified_base
<222> LOCATION: (921)..(921)
<223> OTHER INFORMATION: a, c, t, g, unknown or other
<220> FEATURE:
<221> NAME/KEY: modified_base
<222> LOCATION: (936)..(936)
<223> OTHER INFORMATION: a, c, t, g, unknown or other

<400> SEQUENCE: 8
ctatttcagg aganagtcat agctagcntn nnnnnnantt ggctggcgct ggctggttta      60
gttttagcgt ttagcgcatc ggcggactac aaagaggccc agccggccat ggacctgggt     120
aagaaactgc tggaagctgc tcgtgctggt caggacgacg aagttcgtat cctgatggct     180
aacggtgctg acgttaacgc tgttgaccgt aaaggtaaca ctccgctgca cctggctgct     240
cagtacggtc acctggaaat cgttgaagtt ctgctgaagc acggtgctga cgttaacgct     300
caggacaaat tcgtaagac cgctttcgac atctccatcg acaacggtaa cgaggacctg     360
gctgaaatcc tgcaagcggc cgcacatcat catcaccatc acggggccgc agaacaaaaa     420
ctcatctcag aagaggatct gaatggggcc gcatagactg ttgaaagttg tttagcaaaa     480
cctcatacag aaaattcatt tactaacgtc tggaaagacg acaaaacttt agatcgttac     540
gctaactatg agggctgtct gtggaatgct acaggcgttg tggtttgtac tggtgacgaa     600
actcagtgtt acggtacatg ggttcctatt gggcttgcta tccctgaaaa tgagggtggt     660
ggctctgagg gtggcggttc tgagggtggc ggttctgagg gtggcggtac taaacctcct     720
gagtacggtg atacacctat tccgggctat acttatatca accctctcga cggcacttat     780
ccgcctggta ctgagcaaaa ccccgctaat cctaatcctt ctcttgagga gtctcagcct     840
cttaatactt tcatgtttca gaanaatagg ttccgaaata nncagggtgc attaactgtt     900
tatacgggca ctgntactca nggcactgac cccgtnaaaa ctt                       943

<210> SEQ ID NO 9
<211> LENGTH: 954
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (175)..(175)
<223> OTHER INFORMATION: a, c, t, g, unknown or other
<220> FEATURE:
```

```
<221> NAME/KEY: modified_base
<222> LOCATION: (178)..(178)
<223> OTHER INFORMATION: a, c, t, g, unknown or other
<220> FEATURE:
<221> NAME/KEY: modified_base
<222> LOCATION: (208)..(212)
<223> OTHER INFORMATION: a, c, t, g, unknown or other
<220> FEATURE:
<221> NAME/KEY: modified_base
<222> LOCATION: (846)..(848)
<223> OTHER INFORMATION: a, c, t, g, unknown or other
<220> FEATURE:
<221> NAME/KEY: modified_base
<222> LOCATION: (854)..(854)
<223> OTHER INFORMATION: a, c, t, g, unknown or other
<220> FEATURE:
<221> NAME/KEY: modified_base
<222> LOCATION: (860)..(860)
<223> OTHER INFORMATION: a, c, t, g, unknown or other
<220> FEATURE:
<221> NAME/KEY: modified_base
<222> LOCATION: (880)..(880)
<223> OTHER INFORMATION: a, c, t, g, unknown or other
<220> FEATURE:
<221> NAME/KEY: modified_base
<222> LOCATION: (886)..(887)
<223> OTHER INFORMATION: a, c, t, g, unknown or other
<220> FEATURE:
<221> NAME/KEY: modified_base
<222> LOCATION: (890)..(891)
<223> OTHER INFORMATION: a, c, t, g, unknown or other
<220> FEATURE:
<221> NAME/KEY: modified_base
<222> LOCATION: (901)..(901)
<223> OTHER INFORMATION: a, c, t, g, unknown or other
<220> FEATURE:
<221> NAME/KEY: modified_base
<222> LOCATION: (914)..(914)
<223> OTHER INFORMATION: a, c, t, g, unknown or other
<220> FEATURE:
<221> NAME/KEY: modified_base
<222> LOCATION: (920)..(921)
<223> OTHER INFORMATION: a, c, t, g, unknown or other

<400> SEQUENCE: 9
gatttggctg gcgctggctg gtttagtttt agcgtttagc gcatcggcgg actacaaaga    60
ggcccagccg gccatggacc tgggtaagaa actgctggaa gctgctcgtg ctggtcagga   120
cgacgaagtt cgtatcctga tggctaacgg tgctgacgtt aacgctgttg acgcncangg   180
tactactccg ctgcacctgg ctgctcgnnn nnggtcacct ggaaatcgtt gaagttctgc   240
tgaagaacgg tgctgacgtt aacgctcagg acaaattcgg taagaccgct ttcgacatct   300
ccatcgacaa cggtaacgag gacctggctg aaatcctgca agcggccgca catcatcatc   360
accatcacgg ggccgcagaa caaaaactca tctcagaaga ggatctgaat ggggccgcat   420
agactgttga agttgttta gcaaaacctc atacagaaaa ttcatttact aacgtctgga   480
aagacgacaa aactttagat cgttacgcta actatgaggg ctgtctgtgg aatgctacag   540
gcgttgtggt ttgtactggt gacgaaactc agtgttacgg tacatgggtt cctattgggc   600
ttgctatccc tgaaaatgag ggtggtggct ctgagggtgg cggttctgag ggtggcggtt   660
ctgagggtgg cggtactaaa cctcctgagt acggtgatac acctattccg ggctatactt   720
atatcaaccc tctcgacggc acttatccgc tggtactga gcaaaacccc gctaatccta   780
atccttctct tgaggagtct cagcctctta atactttcat gtttcagaat aataggttcc   840
gaaatnnnca gggngcattn actgtttata cgggcactgn tactcnnggn nctgaccccg   900
ntaaaactta ttncagtan nctcctgtat catcaaaagc catgtatgac gctt          954
```

<210> SEQ ID NO 10
<211> LENGTH: 801
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (165)..(166)
<223> OTHER INFORMATION: a, c, t, g, unknown or other
<220> FEATURE:
<221> NAME/KEY: modified_base
<222> LOCATION: (172)..(175)
<223> OTHER INFORMATION: a, c, t, g, unknown or other
<220> FEATURE:
<221> NAME/KEY: modified_base
<222> LOCATION: (179)..(180)
<223> OTHER INFORMATION: a, c, t, g, unknown or other
<220> FEATURE:
<221> NAME/KEY: modified_base
<222> LOCATION: (203)..(203)
<223> OTHER INFORMATION: a, c, t, g, unknown or other
<220> FEATURE:
<221> NAME/KEY: modified_base
<222> LOCATION: (206)..(207)
<223> OTHER INFORMATION: a, c, t, g, unknown or other
<220> FEATURE:
<221> NAME/KEY: modified_base
<222> LOCATION: (319)..(319)
<223> OTHER INFORMATION: a, c, t, g, unknown or other
<220> FEATURE:
<221> NAME/KEY: modified_base
<222> LOCATION: (398)..(398)
<223> OTHER INFORMATION: a, c, t, g, unknown or other
<220> FEATURE:
<221> NAME/KEY: modified_base
<222> LOCATION: (516)..(516)
<223> OTHER INFORMATION: a, c, t, g, unknown or other
<220> FEATURE:
<221> NAME/KEY: modified_base
<222> LOCATION: (633)..(633)
<223> OTHER INFORMATION: a, c, t, g, unknown or other
<220> FEATURE:
<221> NAME/KEY: modified_base
<222> LOCATION: (648)..(648)
<223> OTHER INFORMATION: a, c, t, g, unknown or other
<220> FEATURE:
<221> NAME/KEY: modified_base
<222> LOCATION: (663)..(663)
<223> OTHER INFORMATION: a, c, t, g, unknown or other
<220> FEATURE:
<221> NAME/KEY: modified_base
<222> LOCATION: (736)..(736)
<223> OTHER INFORMATION: a, c, t, g, unknown or other
<220> FEATURE:
<221> NAME/KEY: modified_base
<222> LOCATION: (789)..(789)
<223> OTHER INFORMATION: a, c, t, g, unknown or other

<400> SEQUENCE: 10
ttggctggcg ctggctggtt tagttttagc gtttagcgca tcggcggact acaaagaggc    60
ccagccggcc atggacctgg gtaagaaact gctggaagct gctcgtgctg gtcaggacga   120
cgaagttcgt atcctgatgg ctaacggtgc tgacgttaac gctanngacc annnnggtnn   180
tactccgctg cacctggctg ctnggnntgg tcacctggaa atcgttgaag ttctgctgaa   240
gaacggtgct gacgttaacg ctcaggacaa attcggtaag accgctttcg acatctccat   300
cgacaacggt aacgagganc tggctgaaaa tcctgcaagc ggccgcacat catcatcacc   360
atcacggggc cgcagaacaa aaactcatct cagaaganga tctgaatggg ggccgcatag   420
actgttgaaa gttgtttagc aaaacctcat acagaaaatt catttactaa cgtctggaaa   480
gacgacaaaa ctttagatcg ttacgctaac tatganggct gtctgtggaa tgctacaggc   540

```
gttgtggttt gtactggtga cgaaactcag tgttacggta catgggttcc tattgggctt      600
gctatccctg aaaatgaggg tggtggctct ganggtggcg gttctgangg tggcggttct      660
ganggtggcg gtactaaacc tcctgagtac ggtgatacac ctattccggg ctatacttat      720
atcaaccctc tcgacngcac ttatccgcct ggtactgagc aaaacccgc taatcctaat       780 ccttctctng aggagtctca g                                                 801
```

```
<210> SEQ ID NO 11
<211> LENGTH: 939
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (823)..(823)
<223> OTHER INFORMATION: a, c, t, g, unknown or other
<220> FEATURE:
<221> NAME/KEY: modified_base
<222> LOCATION: (826)..(826)
<223> OTHER INFORMATION: a, c, t, g, unknown or other
<220> FEATURE:
<221> NAME/KEY: modified_base
<222> LOCATION: (842)..(842)
<223> OTHER INFORMATION: a, c, t, g, unknown or other
<220> FEATURE:
<221> NAME/KEY: modified_base
<222> LOCATION: (844)..(844)
<223> OTHER INFORMATION: a, c, t, g, unknown or other
<220> FEATURE:
<221> NAME/KEY: modified_base
<222> LOCATION: (856)..(856)
<223> OTHER INFORMATION: a, c, t, g, unknown or other
<220> FEATURE:
<221> NAME/KEY: modified_base
<222> LOCATION: (876)..(876)
<223> OTHER INFORMATION: a, c, t, g, unknown or other
<220> FEATURE:
<221> NAME/KEY: modified_base
<222> LOCATION: (882)..(883)
<223> OTHER INFORMATION: a, c, t, g, unknown or other
<220> FEATURE:
<221> NAME/KEY: modified_base
<222> LOCATION: (895)..(895)
<223> OTHER INFORMATION: a, c, t, g, unknown or other
<220> FEATURE:
<221> NAME/KEY: modified_base
<222> LOCATION: (898)..(898)
<223> OTHER INFORMATION: a, c, t, g, unknown or other
<220> FEATURE:
<221> NAME/KEY: modified_base
<222> LOCATION: (917)..(917)
<223> OTHER INFORMATION: a, c, t, g, unknown or other

<400> SEQUENCE: 11
ttggctggcg ctggctggtt tagttttagc gtttagcgca tcggcggact acaaagaggc      60
ccagccggcc atggacctgg gtaagaaact gctggaagct gctcgtgctg gtcaggacga     120
cgaagttcgt atcctgatgg ctaacggtgc tgacgttaac gctaacgaca tcgaaggtca     180
tactccgctg cacctggctg ctatctacgg tcacctggaa atcgttgaag ttctgctgaa     240
gaacggtgct gacgttaacg ctcaggacaa attcggtaag accgctttcg acatctccat     300
cgacaacggt aacgaggacc tggctgaaat cctgcaagcg gccgcacatc atcatcacca     360
tcacggggcc gcagaacaaa aactcatctc agaagaggat ctgaatgggg ccgcatagac     420
tgttgaaagt tgtttagcaa aacctcatac agaaaattca tttactaacg tctggaagaa     480
cgacaaaact ttagatcgtt acgctaacta tgagggctgt ctgtggaatg ctacaggcgt     540
```

```
tgtggtttgt actggtgacg aaactcagtg ttacggtaca tgggttccta ttgggcttgc      600
tatccctgaa aatgagggtg gtggctctga gggtggcggt tctgagggtg gcggttctga      660
gggtggcggt actaaacctc ctgagtacgg tgatacacct attccgggct atacttatat      720
caaccctctc gacggcactt atccgcctgg tactgagcaa aaccccgcta atcctaatcc      780
ttctcttgag gagtctcagc ctcttaatac tttcatgttt canaanaata ggttccgaaa      840
tngncagggt gcattnactg tttatacggg cactgntact cnnggcactg acccngtnaa      900
aacttattac cagtacnctc ctgtatcatc aaaagccat                             939
```

<210> SEQ ID NO 12
<211> LENGTH: 985
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (16)..(16)
<223> OTHER INFORMATION: a, c, t, g, unknown or other
<220> FEATURE:
<221> NAME/KEY: modified_base
<222> LOCATION: (40)..(40)
<223> OTHER INFORMATION: a, c, t, g, unknown or other
<220> FEATURE:
<221> NAME/KEY: modified_base
<222> LOCATION: (863)..(863)
<223> OTHER INFORMATION: a, c, t, g, unknown or other
<220> FEATURE:
<221> NAME/KEY: modified_base
<222> LOCATION: (866)..(866)
<223> OTHER INFORMATION: a, c, t, g, unknown or other
<220> FEATURE:
<221> NAME/KEY: modified_base
<222> LOCATION: (896)..(896)
<223> OTHER INFORMATION: a, c, t, g, unknown or other
<220> FEATURE:
<221> NAME/KEY: modified_base
<222> LOCATION: (917)..(917)
<223> OTHER INFORMATION: a, c, t, g, unknown or other
<220> FEATURE:
<221> NAME/KEY: modified_base
<222> LOCATION: (923)..(923)
<223> OTHER INFORMATION: a, c, t, g, unknown or other
<220> FEATURE:
<221> NAME/KEY: modified_base
<222> LOCATION: (957)..(957)
<223> OTHER INFORMATION: a, c, t, g, unknown or other
<220> FEATURE:
<221> NAME/KEY: modified_base
<222> LOCATION: (976)..(976)
<223> OTHER INFORMATION: a, c, t, g, unknown or other

<400> SEQUENCE: 12

```
ttctatttca ggaganagtc atagctagca tgaaaaagan ttggctggcg ctggctggtt       60
tagttttagc gtttagcgca tcggcggact acaagagggc ccagccggcc atggacctgg      120
gtaagaaact gctggaagct gctcgtgctg gtcaggacga cgaagttcgt atcctgatgg      180
ctaacggtgc tgacgttaac gctaaagacc atgaaggtca gactccgctg cacctggctg      240
ctcagatcgg tcacctggaa atcgttgaag ttctgctgaa gaacggtgct gacgttaacg      300
ctcaggacaa attcggtaag accgctttcg acatctccat cgacaacggt aacgaggacc      360
tggctgaaat cctgcaagcg gccgcacatc atcatcacca tcacggggcc gcagaacaaa      420
aactcatctc agaagaggat ctgaatgggg ccgcatagac tgttgaaagt tgtttagcaa      480
aacctcatac agaaaattca tttactaacg tctggaaaga cgacaaaact ttagatcgtt      540
```

```
acgctaacta tgagggctgt ctgtggaatg ctacaggcgt tgtggtttgt actggtgacg    600
aaactcagtg ttacggtaca tgggttccta ttgggcttgc tatccctgaa aatgagggtg    660
gtggctctga gggtggcggt tctgagggtg gcggttctga gggtggcggt actaaacctc    720
ctgagtacgg tgatacacct attccgggct atacttatat caaccctctc gacggcactt    780
atccgcctgg tactgagcaa aaccccgcta atcctaatcc ttctcttgag gagtctcagc    840
ctcttaatac tttcatgttt canaanaata ggttccgaaa taggcagggt gcattnactg    900
tttatacggg cactgtnact canggcactg accccgttaa aacttattac cagtacnctc    960
ctgtatcatc aaaagncatg tatga                                          985
```

```
<210> SEQ ID NO 13
<211> LENGTH: 981
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (6)..(6)
<223> OTHER INFORMATION: a, c, t, g, unknown or other
<220> FEATURE:
<221> NAME/KEY: modified_base
<222> LOCATION: (13)..(13)
<223> OTHER INFORMATION: a, c, t, g, unknown or other
<220> FEATURE:
<221> NAME/KEY: modified_base
<222> LOCATION: (30)..(30)
<223> OTHER INFORMATION: a, c, t, g, unknown or other
<220> FEATURE:
<221> NAME/KEY: modified_base
<222> LOCATION: (37)..(37)
<223> OTHER INFORMATION: a, c, t, g, unknown or other
<220> FEATURE:
<221> NAME/KEY: modified_base
<222> LOCATION: (868)..(869)
<223> OTHER INFORMATION: a, c, t, g, unknown or other
<220> FEATURE:
<221> NAME/KEY: modified_base
<222> LOCATION: (902)..(902)
<223> OTHER INFORMATION: a, c, t, g, unknown or other
<220> FEATURE:
<221> NAME/KEY: modified_base
<222> LOCATION: (913)..(914)
<223> OTHER INFORMATION: a, c, t, g, unknown or other
<220> FEATURE:
<221> NAME/KEY: modified_base
<222> LOCATION: (920)..(920)
<223> OTHER INFORMATION: a, c, t, g, unknown or other
<220> FEATURE:
<221> NAME/KEY: modified_base
<222> LOCATION: (923)..(923)
<223> OTHER INFORMATION: a, c, t, g, unknown or other
<220> FEATURE:
<221> NAME/KEY: modified_base
<222> LOCATION: (934)..(935)
<223> OTHER INFORMATION: a, c, t, g, unknown or other
<220> FEATURE:
<221> NAME/KEY: modified_base
<222> LOCATION: (957)..(957)
<223> OTHER INFORMATION: a, c, t, g, unknown or other
<220> FEATURE:
<221> NAME/KEY: modified_base
<222> LOCATION: (971)..(971)
<223> OTHER INFORMATION: a, c, t, g, unknown or other
<220> FEATURE:
<221> NAME/KEY: modified_base
<222> LOCATION: (977)..(977)
<223> OTHER INFORMATION: a, c, t, g, unknown or other

<400> SEQUENCE: 13
```

```
tatttnagga ganagtcata gctagcatgn aaaaganttg gctggcgctg gctggtttag      60
ttttagcgtt tagcgcatcg gcggactaca aagaggccca gccggccatg gacctgggta     120
agaaactgct ggaagctgct cgtgctggtc aggacgacga agttcgtatc ctgatggcta     180
acggtgctga cgttaacgct atggacaacg ctggtactac tccgctgcac ctggctgctc     240
agttcggtca cctggaaatc gttgaagttc tgctgaagaa cggtgctgac gttaacgctc     300
aggacaaatt cggtaagacc gctttcgaca tctccatcga caacggtaac gaggacctgg     360
ctgaaatcct gcaagcggcc gcacatcatc atcaccatca cggggccgca gaacaaaaac     420
tcatctcaga agaggatctg aatggggccg catagactgt tgaaagttgt ttagcaaaac     480
ctcatacaga aaattcattt actaacgtct ggaaagacga caaaacttta gatcgttacg     540
ctaactatga gggctgtctg tggaatgcta caggcgttgt ggtttgtact ggtgacgaaa     600
ctcagtgtta cggtacatgg gttcctattg ggcttgctat ccctgaaaat gagggtggtg     660
gctctgaggg tggcggttct gagggtggcg gttctgaggg tggcggtact aaacctcctg     720
agtacggtga tacacctatt ccgggctata cttatatcaa ccctctcgac ggcacttatc     780
cgcctggtac tgagcaaaac cccgctaatc ctaatccttc tcttgaggag tctcagcctc     840
ttaatacttt catgtttcag aataatannt ccgaaatag gcagggtgca ttaactgttt     900
anacgggcac tgnnactcan ggnactgacc ccgnnaaaac ttattaccag tacactnctg     960
tatcatcaaa nccatgnatg a                                               981
```

<210> SEQ ID NO 14
<211> LENGTH: 944
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (16)..(16)
<223> OTHER INFORMATION: a, c, t, g, unknown or other
<220> FEATURE:
<221> NAME/KEY: modified_base
<222> LOCATION: (40)..(40)
<223> OTHER INFORMATION: a, c, t, g, unknown or other
<220> FEATURE:
<221> NAME/KEY: modified_base
<222> LOCATION: (204)..(204)
<223> OTHER INFORMATION: a, c, t, g, unknown or other
<220> FEATURE:
<221> NAME/KEY: modified_base
<222> LOCATION: (213)..(215)
<223> OTHER INFORMATION: a, c, t, g, unknown or other
<220> FEATURE:
<221> NAME/KEY: modified_base
<222> LOCATION: (221)..(221)
<223> OTHER INFORMATION: a, c, t, g, unknown or other
<220> FEATURE:
<221> NAME/KEY: modified_base
<222> LOCATION: (244)..(245)
<223> OTHER INFORMATION: a, c, t, g, unknown or other
<220> FEATURE:
<221> NAME/KEY: modified_base
<222> LOCATION: (247)..(248)
<223> OTHER INFORMATION: a, c, t, g, unknown or other
<220> FEATURE:
<221> NAME/KEY: modified_base
<222> LOCATION: (863)..(863)
<223> OTHER INFORMATION: a, c, t, g, unknown or other
<220> FEATURE:
<221> NAME/KEY: modified_base
<222> LOCATION: (871)..(872)
<223> OTHER INFORMATION: a, c, t, g, unknown or other
<220> FEATURE:
<221> NAME/KEY: modified_base
<222> LOCATION: (877)..(877)
<223> OTHER INFORMATION: a, c, t, g, unknown or other
<220> FEATURE:
<221> NAME/KEY: modified_base
<222> LOCATION: (882)..(882)
<223> OTHER INFORMATION: a, c, t, g, unknown or other
<220> FEATURE:
<221> NAME/KEY: modified_base
<222> LOCATION: (884)..(884)
<223> OTHER INFORMATION: a, c, t, g, unknown or other
<220> FEATURE:
<221> NAME/KEY: modified_base
<222> LOCATION: (896)..(896)
<223> OTHER INFORMATION: a, c, t, g, unknown or other
<220> FEATURE:
<221> NAME/KEY: modified_base
<222> LOCATION: (908)..(908)
<223> OTHER INFORMATION: a, c, t, g, unknown or other
<220> FEATURE:
<221> NAME/KEY: modified_base
<222> LOCATION: (912)..(912)
<223> OTHER INFORMATION: a, c, t, g, unknown or other
<220> FEATURE:
<221> NAME/KEY: modified_base
<222> LOCATION: (916)..(917)
<223> OTHER INFORMATION: a, c, t, g, unknown or other
<220> FEATURE:
<221> NAME/KEY: modified_base
<222> LOCATION: (922)..(923)
<223> OTHER INFORMATION: a, c, t, g, unknown or other
<220> FEATURE:
<221> NAME/KEY: modified_base
<222> LOCATION: (926)..(926)
<223> OTHER INFORMATION: a, c, t, g, unknown or other

<400> SEQUENCE: 14

```
ttctatttca ggaganagtc atagctagca tgaaaaagan ttggctggcg ctggctggtt      60
tagttttagc gtttagcgca tcggcggact acaaagaggc ccagccggcc atggacctgg     120
gtaagaaact gctggaagct gctcgtgctg gtcaggacga cgaagttcgt atcctgatgg     180
ctaacggtgc tgacgttaac gctngggacc tgnnnggtac nactccgctg cacctggctg     240
ctanngnngg tcacctggaa atcgttgaag ttctgctgaa gaacggtgct gacgttaacg     300
ctcaggacaa attcggtaag accgctttcg acatctccat cgacaacggt aacgaggacc     360
tggctgaaat cctgcaagcg gccgcacatc atcatcacca tcacggggcc gcagaacaaa     420
aactcatctc agaagaggat ctgaatgggg ccgcatagac tgttgaaagt tgtttagcaa     480
aacctcatac agaaaattca tttactaacg tctggaaaga cgacaaaact ttagatcgtt     540
acgctaacta tgagggctgt ctgtggaatg ctacaggcgt tgtggtttgt actggtgacg     600
aaactcagtg ttacggtaca tgggttccta ttgggcttgc tatccctgaa aatgagggtg     660
gtggctctga gggtggcggt tctgaggtg gcggttctga gggtggcggt actaaacctc     720
ctgagtacgg tgatacacct attccgggct atacttatat caaccctctc gacggcactt     780
atccgcctgg tactgagcaa aaccccgcta atcctaatcc ttctcttgag gagtctcagc     840
ctcttaatac tttcatgttt canaataata nnttccnaaa tngncagggt gcattnactg     900
tttatacngg cnctgnnact cnnggnactg accccgttaa aact                     944
```

<210> SEQ ID NO 15
<211> LENGTH: 926
<212> TYPE: DNA
<213> ORGANISM: Artificial Sequence
<220> FEATURE:
<223> OTHER INFORMATION: Description of Artificial Sequence: Synthetic polynucleotide

```
<220> FEATURE:
<221> NAME/KEY: modified_base
<222> LOCATION: (5)..(5)
<223> OTHER INFORMATION: a, c, t, g, unknown or other
<220> FEATURE:
<221> NAME/KEY: modified_base
<222> LOCATION: (690)..(690)
<223> OTHER INFORMATION: a, c, t, g, unknown or other
<220> FEATURE:
<221> NAME/KEY: modified_base
<222> LOCATION: (852)..(852)
<223> OTHER INFORMATION: a, c, t, g, unknown or other
<220> FEATURE:
<221> NAME/KEY: modified_base
<222> LOCATION: (855)..(855)
<223> OTHER INFORMATION: a, c, t, g, unknown or other
<220> FEATURE:
<221> NAME/KEY: modified_base
<222> LOCATION: (859)..(861)
<223> OTHER INFORMATION: a, c, t, g, unknown or other
<220> FEATURE:
<221> NAME/KEY: modified_base
<222> LOCATION: (871)..(873)
<223> OTHER INFORMATION: a, c, t, g, unknown or other
<220> FEATURE:
<221> NAME/KEY: modified_base
<222> LOCATION: (905)..(905)
<223> OTHER INFORMATION: a, c, t, g, unknown or other

<400> SEQUENCE: 15
gaganagtca tagctagcat gaaaaagatt tggctggcgc tggctggttt agttttagcg      60
tttagcgcat cggcggacta caaagaggcc cagccggcca tggacctggg taagaaactg     120
ctggaagctg ctcgtgccgg tcaggacgac gaagttcgta tcctgatggc taacggtgct     180
gacgttaacg ctaacgacct ggaaggtgac actccgctgc acctggctgc ttacatcggt     240
cacctggaaa tcgttgaagt tctgctgaag tacggtgctg acgttaacgc tcaggacaaa     300
ttcggtaaga ccgctttcga catctccatc gacaacggta acgaggacct ggctgaaatc     360
ctgcaagcgg ccgcacatca tcatcaccat cacggggccg cagaacaaaa actcatctca     420
gaagaggatc tgaatggggc cgcatagact gttgaaagtt gtttagcaaa acctcataca     480
gaaaattcat ttactaacgt ctggaaagac gacaaaactt tagatcgtta cgctaactat     540
gagggctgtc tgtggaatgc tacaggcgtt gtggtttgta ctggtgacga aactcagtgt     600
tacggtacat gggttcctat tgggcttgct atccctgaaa atgagggtgg tggctctgag     660
ggtggcggtt ctgagggtgg cggttctgan ggtggcggta ctaaacctcc tgagtacggt     720
gatacaccta ttccgggcta tacttatatc aaccctctcg acggcactta tccgcctggt     780
actgagcaaa accccgctaa tcctaatcct tctcttgagg agtctcagcc tcttaatact     840
ttcatgtttc anaanaatnn nttccgaaat nnncagggtg cattaactgt ttatacgggc     900
actgntactc aaggcactga ccccgt                                          926

<210> SEQ ID NO 16
<211> LENGTH: 965
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (23)..(23)
<223> OTHER INFORMATION: a, c, t, g, unknown or other
<220> FEATURE:
<221> NAME/KEY: modified_base
<222> LOCATION: (898)..(898)
<223> OTHER INFORMATION: a, c, t, g, unknown or other
```

```
<220> FEATURE:
<221> NAME/KEY: modified_base
<222> LOCATION: (900)..(901)
<223> OTHER INFORMATION: a, c, t, g, unknown or other
<220> FEATURE:
<221> NAME/KEY: modified_base
<222> LOCATION: (903)..(903)
<223> OTHER INFORMATION: a, c, t, g, unknown or other
<220> FEATURE:
<221> NAME/KEY: modified_base
<222> LOCATION: (909)..(909)
<223> OTHER INFORMATION: a, c, t, g, unknown or other
<220> FEATURE:
<221> NAME/KEY: modified_base
<222> LOCATION: (913)..(913)
<223> OTHER INFORMATION: a, c, t, g, unknown or other
<220> FEATURE:
<221> NAME/KEY: modified_base
<222> LOCATION: (926)..(926)
<223> OTHER INFORMATION: a, c, t, g, unknown or other
<220> FEATURE:
<221> NAME/KEY: modified_base
<222> LOCATION: (939)..(939)
<223> OTHER INFORMATION: a, c, t, g, unknown or other
<220> FEATURE:
<221> NAME/KEY: modified_base
<222> LOCATION: (944)..(944)
<223> OTHER INFORMATION: a, c, t, g, unknown or other
<220> FEATURE:
<221> NAME/KEY: modified_base
<222> LOCATION: (946)..(946)
<223> OTHER INFORMATION: a, c, t, g, unknown or other
<220> FEATURE:
<221> NAME/KEY: modified_base
<222> LOCATION: (948)..(948)
<223> OTHER INFORMATION: a, c, t, g, unknown or other
<220> FEATURE:
<221> NAME/KEY: modified_base
<222> LOCATION: (954)..(954)
<223> OTHER INFORMATION: a, c, t, g, unknown or other

<400> SEQUENCE: 16
atttggctgg cgctggctgg ttnagtttta gcgtttagcg catcggcgga ctacaaagag      60
gcccagccgg ccatggacct gggtaagaaa ctgctgacgt taacgctatg gacgcttacg     120
gtaacactcc gctgcacctg gctgcttggt ctggtcacct ggaaatcgtt gaagttctgc     180
tgaagtacgg tgctgacgtt aacgctcagg acaaattcgg taagaccgct ttcgacatct     240
ccatcgacaa cggtaacgag gacctggctg aaatcctgca agcggccgca catcatcatc     300
accatcacgg ggccgcagaa caaaaactca tctcagaaga ggatctgaat ggggccgcat     360
agactgttga agttgtttta gcaaaacctc atacagaaaa ttcatttact aacgtctgga     420
aagacgacaa aactttagat cgttacgcta actatgaggg ctgtctgtgg aatgctacag     480
gcgttgtggt ttgtactggt gacgaaactc agtgttacgg tacatgggtt cctattgggc     540
ttgctatccc tgaaaatgag ggtggtggct ctgagggtgg cggttctgag ggtggcggtt     600
ctgagggtgg cggtactaaa cctcctgagt acggtgatac acctattccg ggctatactt     660
atatcaaccc tctcgacggc acttatccgc tggtactga gcaaaacccc gctaatccta     720
atccttctct tgaggagtct cagcctctta atactttcat gtttcagaat aataggttcc     780
gaaataggca gggtgcatta actgtttata cgggcactgt tactcaaggc actgaccccg     840
ttaaaactta ttaccagtac actcctgtat catcaaaagc catgtatgac gcttactngn     900
ncngtaaant canagactgc gctttncatt ctggctttna tgangntnca ttcntttgtg     960
aatat                                                                965

<210> SEQ ID NO 17
```

<211> LENGTH: 894
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (9)..(9)
<223> OTHER INFORMATION: a, c, t, g, unknown or other
<220> FEATURE:
<221> NAME/KEY: modified_base
<222> LOCATION: (11)..(11)
<223> OTHER INFORMATION: a, c, t, g, unknown or other
<220> FEATURE:
<221> NAME/KEY: modified_base
<222> LOCATION: (60)..(62)
<223> OTHER INFORMATION: a, c, t, g, unknown or other
<220> FEATURE:
<221> NAME/KEY: modified_base
<222> LOCATION: (133)..(133)
<223> OTHER INFORMATION: a, c, t, g, unknown or other

<400> SEQUENCE: 17
ttcgccacnt ntgacttgag cgtcgatttt tgtgatgctc gtcaggggg cggagcctan      60 nnaaaaacgc cagcaacgcg gccttttac ggttcctggc cttttgctgg ccttttgctc     120
acatgttctt tcntgcgtta tcccctgatt ctgtggataa ccgtattacc gcctttgagt    180
gagctgatac cgctcgccgc agccgaacga ccgagcgcag cgagtcagtg agcgaggaag    240
cggaagagcg cccaatacgc aaaccgcctc tccccgcgcg ttggccgatt cattaatgca    300
gctggcacga caggtttccc gactggaaag cgggcagtga gcgcaacgca attaatgtga    360
gttagctcac tcattaggca ccccaggctt tacactttat gctcccggct cgtatgttgt    420
gtggaattgt gagcggataa caatttcaca caggaaacag ctatgaccat gattacgcca    480
agcttgcatg caaattctat ttcaaggaga cagtcatagc tagcatgaaa aagatttggc    540
tggcgctggc tggtttagtt ttagcgttta gcgcatcggc ggactacaaa gaggcccagc    600
cggccatgga cctgggtaag aaactgctgg aagctgctcg tgctgacgtt aacgcttacg    660
accgtgttgg tgaaactccg ctgcacctgg ctgctgacaa cggtcacccg gaaatcgttg    720
aagttctgct gaagaacggt gctgacgtta acgctcagga caaattcggt aagaccgctt    780
tcgacatctc catcgacaac ggtaacgagg acctggctga atcctgcaa gcggccgcac    840 atcatcatca ccatcacggg gccgcagaac aaaaactcat ctcagaagag gatc         894

<210> SEQ ID NO 18
<211> LENGTH: 930
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (9)..(10)
<223> OTHER INFORMATION: a, c, t, g, unknown or other
<220> FEATURE:
<221> NAME/KEY: modified_base
<222> LOCATION: (18)..(18)
<223> OTHER INFORMATION: a, c, t, g, unknown or other
<220> FEATURE:
<221> NAME/KEY: modified_base
<222> LOCATION: (26)..(26)
<223> OTHER INFORMATION: a, c, t, g, unknown or other
<220> FEATURE:
<221> NAME/KEY: modified_base
<222> LOCATION: (47)..(47)
<223> OTHER INFORMATION: a, c, t, g, unknown or other
<220> FEATURE:
<221> NAME/KEY: modified_base
<222> LOCATION: (135)..(135)
<223> OTHER INFORMATION: a, c, t, g, unknown or other
<220> FEATURE:
<221> NAME/KEY: modified_base
<222> LOCATION: (915)..(915)
<223> OTHER INFORMATION: a, c, t, g, unknown or other

<400> SEQUENCE: 18

```
ggggaaacnn ctggtatntt tatagncctg tcgggtttcg ccacctntga cttgagcgtc    60
gattttgtg  atgctcgtca gggggcgga  gcctatggaa aaacgccagc aacgcggcct   120
ttttacggtt cctgnccttt tgctggcctt ttgctcacat gttctttcct gcgttatccc   180
ctgattctgt ggataaccgt attaccgcct ttgagtgagc tgataccgct cgccgcagcc   240
gaacgaccga gcgcagcgag tcagtgagcg aggaagcgga agagcgccca atacgcaaac   300
cgcctctccc cgcgcgttgg ccgattcatt aatgcagctg gcacgacagg tttcccgact   360
ggaaagcggg cagtgagcgc aacgcaatta atgtgagtta gctcactcat taggcacccc   420
aggctttaca ctttatgctc ccggctcgta tgttgtgtgg aattgtgagc ggataacaat   480
ttcacacagg aaacagctat gaccatgatt acgccaagct tgcatgcaaa ttctatttca   540
aggagacagt catagctagc atgaaaaaga tttggctggc gctggctggt ttagttttag   600
cgtttagcgc atcggcggac tacaaagagg cccagccggc catggacctg ggtaagaaac   660
tgctggaagc tgctcgtgct gacgttaacg ctcgtgacat gactggttgg actccgctgc   720
acctggctgc tactactggt cacctggaaa tcgttgaagt tctgctgaag aacggtgctg   780
acgttaacgc tcaggacaaa ttcggtaaga ccgctttcga catctccatc gacaacggta   840
acgaggacct ggctgaaatc ctgcaagcgg ccgcacatca tcatcaccat cacggggccg   900
cagaacaaaa actcntctca gaagaggatc                                   930
```

<210> SEQ ID NO 19
<211> LENGTH: 981
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (8)..(8)
<223> OTHER INFORMATION: a, c, t, g, unknown or other
<220> FEATURE:
<221> NAME/KEY: modified_base
<222> LOCATION: (14)..(14)
<223> OTHER INFORMATION: a, c, t, g, unknown or other
<220> FEATURE:
<221> NAME/KEY: modified_base
<222> LOCATION: (31)..(31)
<223> OTHER INFORMATION: a, c, t, g, unknown or other
<220> FEATURE:
<221> NAME/KEY: modified_base
<222> LOCATION: (38)..(38)
<223> OTHER INFORMATION: a, c, t, g, unknown or other
<220> FEATURE:
<221> NAME/KEY: modified_base
<222> LOCATION: (838)..(840)
<223> OTHER INFORMATION: a, c, t, g, unknown or other
<220> FEATURE:
<221> NAME/KEY: modified_base
<222> LOCATION: (916)..(916)
<223> OTHER INFORMATION: a, c, t, g, unknown or other
<220> FEATURE:
<221> NAME/KEY: modified_base
<222> LOCATION: (934)..(934)
<223> OTHER INFORMATION: a, c, t, g, unknown or other
<220> FEATURE:
<221> NAME/KEY: modified_base
<222> LOCATION: (946)..(946)
<223> OTHER INFORMATION: a, c, t, g, unknown or other
<220> FEATURE:
<221> NAME/KEY: modified_base
<222> LOCATION: (952)..(953)
<223> OTHER INFORMATION: a, c, t, g, unknown or other
<220> FEATURE:
<221> NAME/KEY: modified_base
<222> LOCATION: (955)..(955)
<223> OTHER INFORMATION: a, c, t, g, unknown or other
<220> FEATURE:
<221> NAME/KEY: modified_base
<222> LOCATION: (957)..(957)
<223> OTHER INFORMATION: a, c, t, g, unknown or other
<220> FEATURE:
<221> NAME/KEY: modified_base
<222> LOCATION: (961)..(961)
<223> OTHER INFORMATION: a, c, t, g, unknown or other
<220> FEATURE:
<221> NAME/KEY: modified_base
<222> LOCATION: (964)..(965)
<223> OTHER INFORMATION: a, c, t, g, unknown or other
<220> FEATURE:
<221> NAME/KEY: modified_base
<222> LOCATION: (967)..(967)
<223> OTHER INFORMATION: a, c, t, g, unknown or other
<220> FEATURE:
<221> NAME/KEY: modified_base
<222> LOCATION: (973)..(973)
<223> OTHER INFORMATION: a, c, t, g, unknown or other
<220> FEATURE:
<221> NAME/KEY: modified_base
<222> LOCATION: (978)..(978)
<223> OTHER INFORMATION: a, c, t, g, unknown or other

<400> SEQUENCE: 19

```
ctatttcngg aganagtcat agctagcatg naaaagantt ggctggcgct ggctggttta      60
gttttagcgt ttagcgcatc ggcggactac aaagaggccc agccggccat ggacctgggt     120
aagaaactgc tggaagctgc tcgtgctgac gttaacgctt gggacgttca tggtgacact     180
ccgctgcacc tggctgctat ggacggtcac ctggaaatcg ttgaagttct gctgaagtac     240
ggtgctgacg ttaacgctca ggacaaattc ggtaagaccg ctttcgacat ctccatcgac     300
aacggtaacg aggacctggc tgaaatcctg caagcggccg cacatcatca tcaccatcac     360
ggggccgcag aacaaaaact catctcagaa gaggatctga atggggccgc atagactgtt     420
gaaagttgtt tagcaaaacc tcatacagaa aattcattta ctaacgtctg gaaagacgac     480
aaaactttag atcgttacgc taactatgag ggctgtctgt ggaatgctac aggcgttgtg     540
gtttgtactg gtgacgaaac tcagtgttac ggtacatggg ttcctattgg gcttgctatc     600
cctgaaaatg agggtggtgg ctctgagggt ggcggttctg agggtggcgg ttctgagggt     660
ggcggtacta aacctcctga gtacggtgat acacctattc cgggctatac ttatatcaac     720
cctctcgacg gcacttatcc gcctggtact gagcaaaacc ccgctaatcc taatccttct     780
cttgaggagt ctcagcctct taatactttc atgtttcaga ataataggtt ccgaaatnnn     840
cagggtgcat taactgttta tacgggcact gttactcaag gcactgaccc cgttaaaact     900
tattaccagt acactnctgt atcatcaaaa gccntgtatg acgctnactg gnncngnaaa     960
ntcnnanact gcncttttnca t                                              981
```

<210> SEQ ID NO 20
<211> LENGTH: 894
<212> TYPE: DNA
<213> ORGANISM: Artificial Sequence
<220> FEATURE:

```
<223> OTHER INFORMATION: Description of Artificial Sequence: Synthetic
      polynucleotide
<220> FEATURE:
<221> NAME/KEY: modified_base
<222> LOCATION: (10)..(10)
<223> OTHER INFORMATION: a, c, t, g, unknown or other
<220> FEATURE:
<221> NAME/KEY: modified_base
<222> LOCATION: (16)..(17)
<223> OTHER INFORMATION: a, c, t, g, unknown or other
<220> FEATURE:
<221> NAME/KEY: modified_base
<222> LOCATION: (40)..(40)
<223> OTHER INFORMATION: a, c, t, g, unknown or other
<220> FEATURE:
<221> NAME/KEY: modified_base
<222> LOCATION: (876)..(876)
<223> OTHER INFORMATION: a, c, t, g, unknown or other

<400> SEQUENCE: 20
ttctatttcn ggaganngtc atagctagca tgaaaaagan ttggctggcg ctggctggtt      60
tagttttagc gtttagcgca tcggcggact acaaagaggc ccagccggcc atgggcggaa    120
cagcagtttc ttacccaggt ccatggacct gggtaagaaa ctgctggaag ctgctcgtgc    180
tggtcaggac gacgaagttc gtatcctgat ggctaacggt gctgacgtta acgctgaaga    240
ctaccagggt ctgactccgc tgcacctggc tgctgacact ggtcacctgg aaatcgttga    300
agttctgctg aagcacggtg ctgacgttaa cgctcaggac aaattcggta agaccgcttt    360
cgacatctcc atcgacaacg gtaacgagga cctggctgaa atcctgcaag cggccgcaca    420
tcatcatcac catcacgggg ccgcagaaca aaaactcatc tcagaagagg atctgaatgg    480
ggccgcatag actgttgaaa gttgtttagc aaaacctcat acagaaaatt catttactaa    540
cgtctggaaa gacgacaaaa ctttagatcg ttacgctaac tatgagggct gtctgtggaa    600
tgctacaggc gttgtggttt gtactggtga cgaaactcag tgttacggta catgggttcc    660
tattgggctt gctatccctg aaaatgaggg tggtggctct gagggtggcg gttctgaggg    720
tggcggttct gagggtggcg gtactaaacc tcctgagtac ggtgatacac ctattccggg    780
ctatacttat atcaaccctc tcgacggcac ttatccgcct ggtactgagc aaaaccccgc    840
taatcctaat ccttctcttg aggagtctca gcctcntaat actttcatgt ttca          894

<210> SEQ ID NO 21
<211> LENGTH: 826
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (752)..(752)
<223> OTHER INFORMATION: a, c, t, g, unknown or other
<220> FEATURE:
<221> NAME/KEY: modified_base
<222> LOCATION: (807)..(807)
<223> OTHER INFORMATION: a, c, t, g, unknown or other
<220> FEATURE:
<221> NAME/KEY: modified_base
<222> LOCATION: (824)..(824)
<223> OTHER INFORMATION: a, c, t, g, unknown or other

<400> SEQUENCE: 21
tttggctggc gctggctggt ttagttttag cgtttagcgc atcggcggac tacaaagagg     60
cccagccggc catggacctg ggtaagaaac tgctggaagc tgctcgtgct ggtcaggacg    120
acgaagttcg tatcctgatg gctaacggtg ctgacgttaa cgctgttgac atgtacggta    180
```

```
tcactccgct gcacctggct gctgaatacg gtcacctgga atcgttgaa gttctgctga      240 agaacggtgc tgacgttaac gctcaggaca aattcggtaa daccgctttc gacatctcca      300
tcgacaacgg taacgaggac ctggctgaaa tcctgcaagc ggccgcacat catcatcacc      360
atcacggggc cgcagaacaa aaactcatct cagaagagga tctgaatggg gccgcataga      420
ctgttgaaag ttgtttagca aaacctcata cagaaaattc atttactaac gtctggaaag      480
acgacaaaac tttagatcgt tacgctaact atgagggctg tctgtggaat gctacaggcg      540
ttgtggtttg tactggtgac gaaactcagt gttacggtac atgggttcct attgggcttg      600
ctatccctga aaatgagggt ggtggctctg agggtggcgg ttctgagggt ggcggttctg      660
agggtggcgg tactaaacct cctgagtacg gtgatacacc tattccgggc tatacttata      720
tcaaccctct cgacggcact tatccgcctg gnactgagca aaaccccgct aatcctaatc      780
cttctcttga ggagtctcag cctcttnata ctttcatgtt tcanaa                    826
```

<210> SEQ ID NO 22
<211> LENGTH: 907
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<221> NAME/KEY: modified_base
<222> LOCATION: (823)..(823)
<223> OTHER INFORMATION: a, c, t, g, unknown or other
<220> FEATURE:
<221> NAME/KEY: modified_base
<222> LOCATION: (828)..(828)
<223> OTHER INFORMATION: a, c, t, g, unknown or other
<220> FEATURE:
<221> NAME/KEY: modified_base
<222> LOCATION: (855)..(855)
<223> OTHER INFORMATION: a, c, t, g, unknown or other
<220> FEATURE:
<221> NAME/KEY: modified_base
<222> LOCATION: (861)..(863)
<223> OTHER INFORMATION: a, c, t, g, unknown or other
<220> FEATURE:
<221> NAME/KEY: modified_base
<222> LOCATION: (866)..(866)
<223> OTHER INFORMATION: a, c, t, g, unknown or other
<220> FEATURE:
<221> NAME/KEY: modified_base
<222> LOCATION: (870)..(870)
<223> OTHER INFORMATION: a, c, t, g, unknown or other
<220> FEATURE:
<221> NAME/KEY: modified_base
<222> LOCATION: (876)..(877)
<223> OTHER INFORMATION: a, c, t, g, unknown or other
<220> FEATURE:
<221> NAME/KEY: modified_base
<222> LOCATION: (879)..(881)
<223> OTHER INFORMATION: a, c, t, g, unknown or other
<220> FEATURE:
<221> NAME/KEY: modified_base
<222> LOCATION: (887)..(888)
<223> OTHER INFORMATION: a, c, t, g, unknown or other
<220> FEATURE:
<221> NAME/KEY: modified_base
<222> LOCATION: (903)..(903)
<223> OTHER INFORMATION: a, c, t, g, unknown or other
<220> FEATURE:
<221> NAME/KEY: modified_base
<222> LOCATION: (906)..(906)
<223> OTHER INFORMATION: a, c, t, g, unknown or other

<400> SEQUENCE: 22

```
aagatttggc tggcgctggc tggtttagtt ttagcgttta gcgcatcggc ggactacaaa       60
```

```
gaggcccagc cggccatgga cctgggtaag aaactgctgg aagctgctcg tgctggtcag    120
gacgacgaag ttcgtatcct gatggctaac ggtgctgacg ttaacgctgc tgacgttaaa    180
ggtgaaactc cgctgcacct ggctgcttgg gacggtcacc tggaaatcgt tgaagttctg    240
ctgaagaacg gtgctgacgt taacgctcag gacaaattcg gtaagaccgc tttcgacatc    300
tccatcgaca acggtaacga ggacctggct gaaatcctgc aagcggccgc acatcatcat    360
caccatcacg gggccgcaga acaaaaactc atctcagaag aggatctgaa tggggccgca    420
tagactgttg aaagttgttt agcaaaacct catacagaaa attcatttac taacgtctgg    480
aaagacgaca aaactttaga tcgttacgct aactatgagg gctgtctgtg aatgctaca     540 ggcgttgtgg tttgtactgg tgacgaaact cagtgttacg gtacatgggt tcctattggg    600
cttgctatcc ctgaaaatga gggtggtggc tctgagggtg gcggttctga gggtggcggt    660
tctgagggtg gcggtactaa acctcctgag tacggtgata cacctattcc gggctatact    720
tatatcaacc ctctcgacgg cacttatccg cctggtactg agcaaaaccc cgctaatcct    780
aatccttctc ttgaggagtc tcagcctctt aatactttca tgnttcanaa taataggttc    840
cgaaataggc agggngcatt nnntgnttan acgggnncnn ntactcnngg cactgacccc    900 gtnaanc                                                              907
```

<210> SEQ ID NO 23
<211> LENGTH: 953
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (24)..(24)
<223> OTHER INFORMATION: a, c, t, g, unknown or other
<220> FEATURE:
<221> NAME/KEY: modified_base
<222> LOCATION: (827)..(828)
<223> OTHER INFORMATION: a, c, t, g, unknown or other
<220> FEATURE:
<221> NAME/KEY: modified_base
<222> LOCATION: (860)..(861)
<223> OTHER INFORMATION: a, c, t, g, unknown or other
<220> FEATURE:
<221> NAME/KEY: modified_base
<222> LOCATION: (863)..(863)
<223> OTHER INFORMATION: a, c, t, g, unknown or other
<220> FEATURE:
<221> NAME/KEY: modified_base
<222> LOCATION: (870)..(870)
<223> OTHER INFORMATION: a, c, t, g, unknown or other
<220> FEATURE:
<221> NAME/KEY: modified_base
<222> LOCATION: (875)..(875)
<223> OTHER INFORMATION: a, c, t, g, unknown or other
<220> FEATURE:
<221> NAME/KEY: modified_base
<222> LOCATION: (881)..(881)
<223> OTHER INFORMATION: a, c, t, g, unknown or other
<220> FEATURE:
<221> NAME/KEY: modified_base
<222> LOCATION: (887)..(887)
<223> OTHER INFORMATION: a, c, t, g, unknown or other
<220> FEATURE:
<221> NAME/KEY: modified_base
<222> LOCATION: (918)..(918)
<223> OTHER INFORMATION: a, c, t, g, unknown or other
<220> FEATURE:
<221> NAME/KEY: modified_base
<222> LOCATION: (920)..(921)
<223> OTHER INFORMATION: a, c, t, g, unknown or other

<400> SEQUENCE: 23

```
aagatttggc tggcgctggc tggnttagtt ttagcgttta gcgcatcggc ggactacaaa    60
gaggcccagc cggccatgga cctgggtaag aaactgctgg aagctgctcg tgctggtcag   120
gacgacgaag ttcgtatcct gatggctaac ggtgctgacg ttaacgctga cgaccgtaac   180
ggtatgactc cgctgcacct ggctgctcat cagggtcacc tggaaatcgt tgaagttctg   240
ctgaagtacg gtgctgacgt taacgctcag gacaaattcg gtaagaccgc tttcgacatc   300
tccatcgaca acggtaacga ggacctggct gaaatcctgc aagcggccgc acatcatcat   360
caccatcacg gggccgcaga acaaaaactc atctcagaag aggatctgaa tggggccgca   420
tagactgttg aaagttgttt agcaaaacct catacagaaa attcatttac taacgtctgg   480
aaagacgaca aaactttaga tcgttacgct aactatgagg ctgtctgtg gaatgctaca    540
ggcgttgtgg tttgtactgg tgacgaaact cagtgttacg gtacatgggt tcctattggg   600
cttgctatcc ctgaaaatga gggtggtggc tctgagggtg gcggttctga gggtggcggt   660
tctgagggtg gcggtactaa acctcctgag tacggtgata cacctattcc gggctatact   720
tatatcaacc ctctcgacgg cacttatccg cctggtactg agcaaaaccc cgctaatcct   780
aatccttctc ttgaggagtc tcagcctctt aatactttca tgtttcnnaa taataggttc   840
cgaaataggc agggtgcatn nantgtttan acggncactg ntactcnagg cactgaccccc  900
gttaaactta ttaccagnan nctcctgtat catcaaaagc catgtatgac gct          953
```

<210> SEQ ID NO 24
<211> LENGTH: 910
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (459)..(462)
<223> OTHER INFORMATION: a, c, t, g, unknown or other
<220> FEATURE:
<221> NAME/KEY: modified_base
<222> LOCATION: (630)..(630)
<223> OTHER INFORMATION: a, c, t, g, unknown or other
<220> FEATURE:
<221> NAME/KEY: modified_base
<222> LOCATION: (688)..(688)
<223> OTHER INFORMATION: a, c, t, g, unknown or other
<220> FEATURE:
<221> NAME/KEY: modified_base
<222> LOCATION: (788)..(790)
<223> OTHER INFORMATION: a, c, t, g, unknown or other
<220> FEATURE:
<221> NAME/KEY: modified_base
<222> LOCATION: (820)..(820)
<223> OTHER INFORMATION: a, c, t, g, unknown or other
<220> FEATURE:
<221> NAME/KEY: modified_base
<222> LOCATION: (831)..(832)
<223> OTHER INFORMATION: a, c, t, g, unknown or other
<220> FEATURE:
<221> NAME/KEY: modified_base
<222> LOCATION: (838)..(838)
<223> OTHER INFORMATION: a, c, t, g, unknown or other
<220> FEATURE:
<221> NAME/KEY: modified_base
<222> LOCATION: (864)..(865)
<223> OTHER INFORMATION: a, c, t, g, unknown or other
<220> FEATURE:
<221> NAME/KEY: modified_base
<222> LOCATION: (873)..(873)
<223> OTHER INFORMATION: a, c, t, g, unknown or other
<220> FEATURE:
<221> NAME/KEY: modified_base
<222> LOCATION: (876)..(877)
<223> OTHER INFORMATION: a, c, t, g, unknown or other
<220> FEATURE:
<221> NAME/KEY: modified_base
<222> LOCATION: (880)..(880)
<223> OTHER INFORMATION: a, c, t, g, unknown or other
<220> FEATURE:
<221> NAME/KEY: modified_base
<222> LOCATION: (883)..(883)
<223> OTHER INFORMATION: a, c, t, g, unknown or other
<220> FEATURE:
<221> NAME/KEY: modified_base
<222> LOCATION: (893)..(893)
<223> OTHER INFORMATION: a, c, t, g, unknown or other
<220> FEATURE:
<221> NAME/KEY: modified_base
<222> LOCATION: (895)..(895)
<223> OTHER INFORMATION: a, c, t, g, unknown or other

<400> SEQUENCE: 24

```
tggctggcgc tggctggttt agttttagcg tttagcgcat cggcggacta caaagaggcc    60
cagccggcca tggacctggg taagaaactg ctggaagctg ctcgtgctgg tcaggacgac   120
gaagttcgta tcctgatggc taacggtgct gacgttaacg ctaaagactc tgttggtaaa   180
actccgctgc acctggctgc tcattggggt cacctggaaa tcgttgaagt tctgctgaag   240
cacggtgctg acgttaacgc tcaggacaaa ttcggtaaga ccgctttcga catctccatc   300
gacaacggta acgaggacct ggctgaaatc ctgcaagcgg ccgcacatca tcatcaccat   360
cacggggccg cagaacaaaa actcatctca gaagaggatc tgaatggggc cgcatagact   420
gttgaaagtt gtttagcaaa acctcataca gaaaattcnn nnactaacgt ctggaaagac   480
gacaaaactt tagatcgtta cgctaactat gagggctgtc tgtggaatgc tacaggcgtt   540
gtggtttgta ctggtgacga aactcagtgt tacggtacat gggttcctat tgggcttgct   600
atccctgaaa atgagggtgg tggctctgan ggtggcggtt ctgagggtgg cggttctgag   660
ggtggcggta ctaaacctcc tgagtacngt gatacaccta ttccgggcta tacttatatc   720
aaccctctcg acggcactta tccgcctggt actgagcaaa accccgctaa tcctaatcct   780
tctcttgnnn gtctcagcct cttatacttt catgtttcan aataataggt nncgaaanag   840
gcagggtgca ttaactgttt atannggcac tgntanncan ggnactgacc ccntnaaact   900
tattaccagt                                                          910
```

<210> SEQ ID NO 25
<211> LENGTH: 910
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (4)..(4)
<223> OTHER INFORMATION: a, c, t, g, unknown or other
<220> FEATURE:
<221> NAME/KEY: modified_base
<222> LOCATION: (17)..(17)
<223> OTHER INFORMATION: a, c, t, g, unknown or other
<220> FEATURE:
<221> NAME/KEY: modified_base
<222> LOCATION: (459)..(459)
<223> OTHER INFORMATION: a, c, t, g, unknown or other
<220> FEATURE:
<221> NAME/KEY: modified_base
<222> LOCATION: (461)..(462)
<223> OTHER INFORMATION: a, c, t, g, unknown or other
<220> FEATURE:
<221> NAME/KEY: modified_base
<222> LOCATION: (629)..(629)
<223> OTHER INFORMATION: a, c, t, g, unknown or other
<220> FEATURE:
<221> NAME/KEY: modified_base
<222> LOCATION: (821)..(821)
<223> OTHER INFORMATION: a, c, t, g, unknown or other
<220> FEATURE:
<221> NAME/KEY: modified_base
<222> LOCATION: (828)..(830)
<223> OTHER INFORMATION: a, c, t, g, unknown or other
<220> FEATURE:
<221> NAME/KEY: modified_base
<222> LOCATION: (881)..(881)
<223> OTHER INFORMATION: a, c, t, g, unknown or other

<400> SEQUENCE: 25

```
tggntggcgc tggtggntta gttttagcgt ttagcgcatc ggcggactac aaagaggccc      60
agccggccat ggacctgggt aagaaactgc tggaagctgc tcgtgctggt ctggacgacg     120
aagttcgtat cctgatggct aacggtgctg acgttaacgc tactgacact gacggttcta     180
gtccgctgca cctggctgct caggaaggtc acctggaaat cgttgaagtt ctgctgaagt     240
acggtgctga cgttaacgct caggacaaat cggtaagac cgctttcgac atctccatcg     300
acaacggtaa cgaggacctg gctgaaatcc tgcaagcggc cgcacatcat catcaccatc     360
acggggccgc agaacaaaaa ctcatctcag aagaggatct gaatgggggcc gcatagactg     420
ttgaaagttg tttagcaaaa cctcatacag aaaattcant nnctaacgtc tggaaagacg     480
acaaaacttt agatcgttac gctaactatg agggctgtct gtggaatgct acaggcgttg     540
tggtttgtac tggtgacgaa actcagtgtt acggtacatg ggttcctatt gggcttgcta     600
tccctgaaaa tgagggtggt ggctctgang gtggcggttc tgagggtggc ggttctgagg     660
gtggcggtac taaacctcct gagtacggtg atacacctat tccgggctat acttatatca     720
accctctcga cggcacttat ccgcctggta ctgagcaaaa ccccgctaat cctaatcctt     780
ctcttgagga gtctcagcct cttaatactt tcatgtttca naataatnnn ttccgaaata     840
ggcagggtgc attaactgtt tatacgggca ctgttactca nggcactgac cccgttaaac     900
ttattaccag                                                           910
```

<210> SEQ ID NO 26
<211> LENGTH: 842
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<221> NAME/KEY: modified_base
<222> LOCATION: (458)..(461)
<223> OTHER INFORMATION: a, c, t, g, unknown or other
<220> FEATURE:
<221> NAME/KEY: modified_base
<222> LOCATION: (629)..(629)
<223> OTHER INFORMATION: a, c, t, g, unknown or other
<220> FEATURE:
<221> NAME/KEY: modified_base
<222> LOCATION: (797)..(798)
<223> OTHER INFORMATION: a, c, t, g, unknown or other
<220> FEATURE:
<221> NAME/KEY: modified_base
<222> LOCATION: (829)..(831)
<223> OTHER INFORMATION: a, c, t, g, unknown or other

<400> SEQUENCE: 26

```
ggctggcgct ggctggttta gttttagcgt ttagcgcatc ggcggactac aaagaggccc      60
```

```
agccggccat ggacctgggt aagaaactgc tggaagctgc tcgtgctggt caggacgacg    120
aagttcgtat cctgatggct aacggtgctg acgttaacgc tgctgacttc aacggtcaaa    180
ctccgctgca cctggctgct gtttggggtc acctggaaat cgttgaagtt ctgctgaaga    240
acggtgctga cgttaacgct caggacaaat cggtaagac cgctttcgac atctccatcg    300
acaacggtaa cgaggacctg gctgaaatcc tgcaagcggc cgcacatcat catcaccatc    360
acggggccgc agaacaaaaa ctcatctcag aagaggatct gaatgggcc gcatagactg    420 ttgaaagttg tttagcaaaa cctcatacag aaaattcnnn nactaacgtc tggaaagacg    480
acaaaacttt agatcgttac gctaactatg agggctgtct gtggaatgct acaggcgttg    540
tggtttgtac tggtgacgaa actcagtgtt acggtacatg ggttcctatt gggcttgcta    600
tccctgaaaa tgagggtggt ggctctgang gtggcggttc tgagggtggc ggttctgagg    660
gtggcggtac taaacctcct gagtacggtg atacacctat tccgggctat acttatatca    720
accctctcga cggcacttat ccgcctggta ctgagcaaaa ccccgctaat cctaatcctt    780
ctcttgagga gtctcannct cttaatactt tcatgtttca gaataataNN ntccgaaata    840
gg                                                                   842

<210> SEQ ID NO 27
<211> LENGTH: 911
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (14)..(18)
<223> OTHER INFORMATION: a, c, t, g, unknown or other
<220> FEATURE:
<221> NAME/KEY: modified_base
<222> LOCATION: (459)..(459)
<223> OTHER INFORMATION: a, c, t, g, unknown or other
<220> FEATURE:
<221> NAME/KEY: modified_base
<222> LOCATION: (461)..(463)
<223> OTHER INFORMATION: a, c, t, g, unknown or other
<220> FEATURE:
<221> NAME/KEY: modified_base
<222> LOCATION: (815)..(815)
<223> OTHER INFORMATION: a, c, t, g, unknown or other
<220> FEATURE:
<221> NAME/KEY: modified_base
<222> LOCATION: (823)..(823)
<223> OTHER INFORMATION: a, c, t, g, unknown or other
<220> FEATURE:
<221> NAME/KEY: modified_base
<222> LOCATION: (845)..(845)
<223> OTHER INFORMATION: a, c, t, g, unknown or other
<220> FEATURE:
<221> NAME/KEY: modified_base
<222> LOCATION: (875)..(876)
<223> OTHER INFORMATION: a, c, t, g, unknown or other
<220> FEATURE:
<221> NAME/KEY: modified_base
<222> LOCATION: (883)..(883)
<223> OTHER INFORMATION: a, c, t, g, unknown or other
<220> FEATURE:
<221> NAME/KEY: modified_base
<222> LOCATION: (887)..(887)
<223> OTHER INFORMATION: a, c, t, g, unknown or other
<220> FEATURE:
<221> NAME/KEY: modified_base
<222> LOCATION: (890)..(890)
<223> OTHER INFORMATION: a, c, t, g, unknown or other
<220> FEATURE:
<221> NAME/KEY: modified_base
```

```
<222> LOCATION: (897)..(897)
<223> OTHER INFORMATION: a, c, t, g, unknown or other
<220> FEATURE:
<221> NAME/KEY: modified_base
<222> LOCATION: (904)..(904)
<223> OTHER INFORMATION: a, c, t, g, unknown or other

<400> SEQUENCE: 27
ttggctggcg ctgnnnnntt tagttttagc gtttagcgca tcggcggact acaaagaggc      60
ccagccggcc atggacctgg gtaagaaact gctggaagct gctcgtgctg gtcaggacga     120
cgaagttcgt atcctgatgg ctaacggtgc tgacgttaac gctcgtgacg tttctggtgc     180
tactccactg cacctggctg ctacttgggg tcacctggaa atcgttgaag ttctgctgaa     240
gtacggtgct gacgttaacg ctcaggacaa attcggtaag accgctttcg acatctccat     300
cgacaacggt aacgaggacc tggctgaaat cctgcaagcg gccgcacatc atcatcacca     360
tcacggggcc gcagaacaaa aactcatctc agaagaggat ctgaatgggg ccgcatagac     420
tgttgaaagt tgtttagcaa aacctcatac agaaaattna nnnactaacg tctggaaaga     480
cgacaaaact ttagatcgtt acgctaacta tgagggctgt ctgtggaatg ctacaggcgt     540
tgtggtttgt actggtgacg aaactcagtg ttacggtaca tgggttccta ttgggcttgc     600
tatccctgaa aatgagggtg gtggctctga gggtggcggt tctgagggtg gcggttctga     660
gggtggcggt actaaacctc ctgagtacgg tgatacacct attccgggct atacttatat     720
caaccctctc gacggcactt atccgcctgg tactgagcaa aaccccgcta atcctaatcc     780
ttctcttgag gagtctcagc ctcttaatac tttcntgttt canaataata ggttccgaaa     840
taggnagggt gcattaactg tttatacggg cactnntact cangcantgn ccccgtnaaa     900
cttntaccag t                                                         911

<210> SEQ ID NO 28
<211> LENGTH: 869
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (26)..(35)
<223> OTHER INFORMATION: a, c, t, g, unknown or other
<220> FEATURE:
<221> NAME/KEY: modified_base
<222> LOCATION: (38)..(38)
<223> OTHER INFORMATION: a, c, t, g, unknown or other
<220> FEATURE:
<221> NAME/KEY: modified_base
<222> LOCATION: (371)..(371)
<223> OTHER INFORMATION: a, c, t, g, unknown or other
<220> FEATURE:
<221> NAME/KEY: modified_base
<222> LOCATION: (373)..(374)
<223> OTHER INFORMATION: a, c, t, g, unknown or other
<220> FEATURE:
<221> NAME/KEY: modified_base
<222> LOCATION: (429)..(429)
<223> OTHER INFORMATION: a, c, t, g, unknown or other
<220> FEATURE:
<221> NAME/KEY: modified_base
<222> LOCATION: (431)..(432)
<223> OTHER INFORMATION: a, c, t, g, unknown or other
<220> FEATURE:
<221> NAME/KEY: modified_base
<222> LOCATION: (594)..(594)
<223> OTHER INFORMATION: a, c, t, g, unknown or other
<220> FEATURE:
<221> NAME/KEY: modified_base
```

```
<222> LOCATION: (617)..(617)
<223> OTHER INFORMATION: a, c, t, g, unknown or other
<220> FEATURE:
<221> NAME/KEY: modified_base
<222> LOCATION: (624)..(624)
<223> OTHER INFORMATION: a, c, t, g, unknown or other
<220> FEATURE:
<221> NAME/KEY: modified_base
<222> LOCATION: (630)..(630)
<223> OTHER INFORMATION: a, c, t, g, unknown or other
<220> FEATURE:
<221> NAME/KEY: modified_base
<222> LOCATION: (646)..(646)
<223> OTHER INFORMATION: a, c, t, g, unknown or other
<220> FEATURE:
<221> NAME/KEY: modified_base
<222> LOCATION: (702)..(703)
<223> OTHER INFORMATION: a, c, t, g, unknown or other
<220> FEATURE:
<221> NAME/KEY: modified_base
<222> LOCATION: (718)..(720)
<223> OTHER INFORMATION: a, c, t, g, unknown or other
<220> FEATURE:
<221> NAME/KEY: modified_base
<222> LOCATION: (753)..(753)
<223> OTHER INFORMATION: a, c, t, g, unknown or other
<220> FEATURE:
<221> NAME/KEY: modified_base
<222> LOCATION: (763)..(763)
<223> OTHER INFORMATION: a, c, t, g, unknown or other
<220> FEATURE:
<221> NAME/KEY: modified_base
<222> LOCATION: (783)..(784)
<223> OTHER INFORMATION: a, c, t, g, unknown or other
<220> FEATURE:
<221> NAME/KEY: modified_base
<222> LOCATION: (787)..(787)
<223> OTHER INFORMATION: a, c, t, g, unknown or other
<220> FEATURE:
<221> NAME/KEY: modified_base
<222> LOCATION: (789)..(789)
<223> OTHER INFORMATION: a, c, t, g, unknown or other
<220> FEATURE:
<221> NAME/KEY: modified_base
<222> LOCATION: (794)..(795)
<223> OTHER INFORMATION: a, c, t, g, unknown or other
<220> FEATURE:
<221> NAME/KEY: modified_base
<222> LOCATION: (809)..(809)
<223> OTHER INFORMATION: a, c, t, g, unknown or other
<220> FEATURE:
<221> NAME/KEY: modified_base
<222> LOCATION: (811)..(811)
<223> OTHER INFORMATION: a, c, t, g, unknown or other
<220> FEATURE:
<221> NAME/KEY: modified_base
<222> LOCATION: (814)..(814)
<223> OTHER INFORMATION: a, c, t, g, unknown or other
<220> FEATURE:
<221> NAME/KEY: modified_base
<222> LOCATION: (818)..(819)
<223> OTHER INFORMATION: a, c, t, g, unknown or other
<220> FEATURE:
<221> NAME/KEY: modified_base
<222> LOCATION: (833)..(834)
<223> OTHER INFORMATION: a, c, t, g, unknown or other
<220> FEATURE:
<221> NAME/KEY: modified_base
<222> LOCATION: (841)..(841)
<223> OTHER INFORMATION: a, c, t, g, unknown or other
<220> FEATURE:
<221> NAME/KEY: modified_base
<222> LOCATION: (845)..(845)
<223> OTHER INFORMATION: a, c, t, g, unknown or other
<220> FEATURE:
<221> NAME/KEY: modified_base
<222> LOCATION: (847)..(847)
<223> OTHER INFORMATION: a, c, t, g, unknown or other
<220> FEATURE:
```

```
<221> NAME/KEY: modified_base
<222> LOCATION: (862)..(862)
<223> OTHER INFORMATION: a, c, t, g, unknown or other

<400> SEQUENCE: 28
tttagcgcat cggcggacta caaagnnnnn nnnnnggnca tggacctggg taagaaactg      60
ctggaagctg ctcgtgctgg tcaggacgac gaagttcgta tcctgatggc taacggtgct     120
gacgttaacg ctcgtgacgt tactggtgtt actccgttgc acctggctgc taaccgtggt     180
cacctggaaa tcgttgaagt tctgctgaag tacggtgctg acgttaacgc tcaggacaaa     240
ttcggtaaga ccgctttcga catctccatc gacaacggta acgaggacct ggctgaaatc     300
ctgcaagcgg ccgcacatca tcatcaccat cacggggccg cagaacaaaa actcatctca     360
gaagaggatc ngnntggggc cgcatagact gttgaaagtt gtttagcaaa acctcataca     420
gaaaattcna nnactaacgt ctggaaagac gacaaaactt tagatcgtta cgctaactat     480
gagggctgtc tgtggaatgc tacaggcgtt gtggtttgta ctggtgacga aactcagtgt     540
tacggtacat gggttcctat tgggcttgct atccctgaaa atgagggtgg tggntctgag     600
ggtggcggtt ctgaggntgg cggntctgan ggtggcggta ctaaanctcc tgagtacggt     660
gatacaccta ttccgggcta tacttatatc aaccctctcg anngcactta tccgcctnnn     720
actgagcaaa accccgctaa tcctaatcct tcncttgagg agnctcagcc tcttaatact     780
ttnntgntnc agannatagg ttccgaaant nggnaggnng cattaactgt ttnnacgggc     840
nctgntnctt caaggcactg ancccgtta                                       869

<210> SEQ ID NO 29
<211> LENGTH: 634
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (181)..(183)
<223> OTHER INFORMATION: a, c, t, g, unknown or other
<220> FEATURE:
<221> NAME/KEY: modified_base
<222> LOCATION: (187)..(192)
<223> OTHER INFORMATION: a, c, t, g, unknown or other
<220> FEATURE:
<221> NAME/KEY: modified_base
<222> LOCATION: (196)..(198)
<223> OTHER INFORMATION: a, c, t, g, unknown or other
<220> FEATURE:
<221> NAME/KEY: modified_base
<222> LOCATION: (220)..(225)
<223> OTHER INFORMATION: a, c, t, g, unknown or other

<400> SEQUENCE: 29
gctagcatga aaaagatttg gctggcgctg gctggtttag ttttagcgtt tagcgcatcg      60
gcggactaca agaggcccca gccggccatg gacctggta agaaactgct ggaagctgct     120
cgtgctggtc aggacgacga agttcgtatc ctgatggcta acggtgctga cgttaacgct     180
nnngacnnnn nnggtnnnac tccgctgcac ctggctgctn nnnnggtca cctggaaatc     240
gttgaagttc tgctgaagha cggtgctgac gttaacgctc aggacaaatt cggtaagacc     300
gctttcgaca tctccatcga caacggtaac gaggacctgg ctgaaatcct gcaagcggcc     360
gcacatcatc atcaccatca cggggccgca gaacaaaaac tcatctcaga agaggatctg     420
aatggggccg catagactgt tgaaagttgt ttagcaaaac tcatacagaa aattcatttt     480
```

```
actaacgtct ggaaagacga caaaacttta gatcgttacg ctaactatga gggctgtctg    540
tggaatgcta caggcgttgt ggtttgtact ggtgacgaaa ctcagtgtta cggtacatgg    600
gttcctattg ggcttgctat ccctgaaaat gagg                                634
```

<210> SEQ ID NO 30
<211> LENGTH: 118
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 30

```
ttccgcccat ggacctgggt aagaaactgc tggaagctgc tcgtgctggt caggacgacg     60
aagttcgtat cctgatggct aacggtgctg acgttgtctt ctaggcggcc gccccaaa     118
```

<210> SEQ ID NO 31
<211> LENGTH: 124
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 31

```
ttccgcccat ggtaggaaga cctgacgtta acgctcagga caaattcggt aagaccgctt     60
tcgacatctc catcgacaac ggtaacgagg acctggctga atcctgcaa gcggccgccc    120 caaa                                                                124
```

<210> SEQ ID NO 32
<211> LENGTH: 736
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 32

```
ccatggccga ggtgcagctg ttggagtctg ggggaggctt ggtacagcct ggggggtccc     60
tgagactctc ctgtgcagcc tctggattca ccttttagcag ctatgccatg agctgggtcc   120
gccaggctcc agggaagggg ctagagtggg tctcaactat taatactgct ggtaatggta   180
caaattacgc agactccgtg aagggccggt tcaccatctc cagagacaat tccaagaaca   240
cgctgtatct gcaaatgaac agcctgagag ccgaggacac ggccgtatat tactgtgcga   300
aaggtactgc tgcttttgac tactggggcc agggaaccct ggtcaccgtc tcgagcggtg   360
gaggcggttc aggcggaggt ggcagcggcg gtggcgggtc gacggacatc cagatgaccc   420
agtctccatc ctccctgtct gcatctgtag gagacagagt caccatcact tgccgggcaa   480
gtcagagcat tagcagctat ttaaattggt atcagcagaa accagggaaa gcccctaagc   540
tcctggtcta ttctgcatcc gctttgcaaa gtggggtccc atcaaggttc agtggcagtg   600
gatctgggac agatttcact ctcaccatca gcagtctgca acctgaagat tttgcaactt   660
actactgtca acaggctggt gatagtcctg ctacgttcgg ccaagggacc aaggtggaaa   720
tcaaacgggc ggccgc                                                   736
```

<210> SEQ ID NO 33
<211> LENGTH: 436
<212> TYPE: DNA

<213> ORGANISM: Artificial Sequence
<220> FEATURE:
<223> OTHER INFORMATION: Description of Artificial Sequence: Synthetic
      polynucleotide

<400> SEQUENCE: 33

```
ccatggccga ggtgtttgac tactggggcc agggaaccct ggtcaccgtc tcgagcggtg      60
gaggcggttc aggcggaggt ggcagcggcg gtggcgggtc gacggacatc cagatgaccc     120
agtctccatc ctccctgtct gcatctgtag gagacagagt caccatcact tgccgggcaa     180
gtcagagcat tagcagctat ttaaattggt atcagcagaa accagggaaa gcccctaagc     240
tcctgatcta ttatgcatcc actttgcaaa gtggggtccc atcaaggttc agtggcagtg     300
gatctgggac agatttcact ctcaccatca gcagtctgca acctgaagat tttgcaactt     360
actactgtca acagaattat aattctcctt atacgttcgg ccaagggacc aaggtggaaa     420
tcaaacgggc ggccgc                                                     436
```

<210> SEQ ID NO 34
<211> LENGTH: 736
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 34

```
ccatggccga ggtgcagctg ttggagtctg ggggaggctt ggtacagcct ggggggtccc      60
tgagactctc ctgtgcagcc tctggattca cctttagcag ctatgccatg agctgggtcc     120
gccaggctcc agggaagggg ctggagtggg tctcaactat taataatagt ggtacttcta     180
caaattacgc agactccgtg aagggccggt tcaccatctc cagagacaat tccaagaaca     240
cgctgtatct gcaaatgaac agcctgagag ccgaggacac ggccgtatat tactgtgcga     300
aaagtactaa ttatttttgac tactggggcc agggaaccct ggtcaccgtc tcgagcggtg     360
gaggcggttc aggcggaggt ggcagcggcg gtggcgggtc gacggacatc cagatgaccc     420
agtctccatc ctccctgtct gcatctgtag gagacagagt caccatcact tgccgggcaa     480
gtcagagcat tagcagctat ttaaattggt atcagcagaa accagggaaa gcccctaagc     540
tcctgatcta tgctgcatcc agtttgcaaa gtggggtccc atcaaggttc agtggcagtg     600
gatctgggac agatttcact ctcaccatca gcagtctgca acctgaagat tttgcaactt     660
actactgtca acagaatgct gctgatccta ctacgttcgg ccaagggacc aaggtggaaa     720
tcaaacgggc ggccgc                                                     736
```

<210> SEQ ID NO 35
<211> LENGTH: 877
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (715)..(718)
<223> OTHER INFORMATION: a, c, t, g, unknown or other
<220> FEATURE:
<221> NAME/KEY: modified_base
<222> LOCATION: (725)..(725)
<223> OTHER INFORMATION: a, c, t, g, unknown or other
<220> FEATURE:
<221> NAME/KEY: modified_base
<222> LOCATION: (729)..(729)

```
<223> OTHER INFORMATION: a, c, t, g, unknown or other
<220> FEATURE:
<221> NAME/KEY: modified_base
<222> LOCATION: (733)..(733)
<223> OTHER INFORMATION: a, c, t, g, unknown or other
<220> FEATURE:
<221> NAME/KEY: modified_base
<222> LOCATION: (737)..(737)
<223> OTHER INFORMATION: a, c, t, g, unknown or other
<220> FEATURE:
<221> NAME/KEY: modified_base
<222> LOCATION: (789)..(789)
<223> OTHER INFORMATION: a, c, t, g, unknown or other
<220> FEATURE:
<221> NAME/KEY: modified_base
<222> LOCATION: (807)..(807)
<223> OTHER INFORMATION: a, c, t, g, unknown or other
<220> FEATURE:
<221> NAME/KEY: modified_base
<222> LOCATION: (810)..(810)
<223> OTHER INFORMATION: a, c, t, g, unknown or other
<220> FEATURE:
<221> NAME/KEY: modified_base
<222> LOCATION: (833)..(833)
<223> OTHER INFORMATION: a, c, t, g, unknown or other
<220> FEATURE:
<221> NAME/KEY: modified_base
<222> LOCATION: (844)..(844)
<223> OTHER INFORMATION: a, c, t, g, unknown or other
<220> FEATURE:
<221> NAME/KEY: modified_base
<222> LOCATION: (852)..(852)
<223> OTHER INFORMATION: a, c, t, g, unknown or other
<220> FEATURE:
<221> NAME/KEY: modified_base
<222> LOCATION: (858)..(859)
<223> OTHER INFORMATION: a, c, t, g, unknown or other
<220> FEATURE:
<221> NAME/KEY: modified_base
<222> LOCATION: (865)..(867)
<223> OTHER INFORMATION: a, c, t, g, unknown or other

<400> SEQUENCE: 35
ttgttattac tcgcggccca gccggccatg gccgaggtgc agctgttgga gtctggggga      60
ggcttggtac agcctggggg gtccctgaga ctctcctgtg cagcctctgg attcaccttt     120
agcagctatc ccatgagctg gtccgccag gctccaggga aggggctgga gtgggtctca     180
gcgattcagc atactggtgc gccgacaact tacgcagact ccgtgaaggg ccggttcacc     240
atctccagag acaattccaa gaacacgctg tatctgcaaa tgaacagcct gagagccgag     300
gacacggccg tatattactg tgcgaaagcg tttccgccgt ttgactactg gggccaggga     360
accctggtca ccgtctcgag cggtggaggc ggttcaggcg gaggtggcag cggcggtggc     420
gggtcgacgg acatccagat gacccagtct ccatcctccc tgtctgcatc tgtaggagac     480
agagtcacca tcacttgccg ggcaagtcag agcattagca gctatttaaa ttggtatcag     540
cagaaaccag ggaaagcccc taagctcctg atctattctg catcctcttt gcaaagtggg     600
gtcccatcaa ggttcagtgg cagtggatct gggacagatt tcactctcac catcagcagt     660
ctgcaacctg aagattttgc aacttactac tgtcaacagc gggagactgg gcctnnnngt     720
tcggncaang gancaangtg gaaatcaaac gggcggccgc acatcatcat caccatcacg     780
gggccgcana acaaaaactc atctcanaan aggatctgaa tggggccgca tanactgttg     840
aaanttgttt ancaaacnnc atacnnnaaa ttcattt                              877

<210> SEQ ID NO 36
<211> LENGTH: 268
<212> TYPE: PRT
<213> ORGANISM: Artificial Sequence
```

<220> FEATURE:
<223> OTHER INFORMATION: Description of Artificial Sequence: Synthetic
      polypeptide

<400> SEQUENCE: 36

```
Met Ala Glu Val Gln Leu Leu Glu Ser Gly Gly Gly Leu Val Gln Pro
1               5                   10                  15

Gly Gly Ser Leu Arg Leu Ser Cys Ala Ala Ser Gly Phe Thr Phe Ser
            20                  25                  30

Ser Tyr Pro Met Ser Trp Val Arg Gln Ala Pro Gly Lys Gly Leu Glu
        35                  40                  45

Trp Val Ser Ala Ile Gln His Thr Gly Ala Pro Thr Thr Tyr Ala Asp
    50                  55                  60

Ser Val Lys Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Lys Ala Phe Pro Pro Phe Asp Tyr Trp Gly Gln Gly Thr
            100                 105                 110

Leu Val Thr Val Ser Ser Gly Gly Gly Gly Ser Gly Gly Gly Gly Ser
        115                 120                 125

Gly Gly Gly Gly Ser Thr Asp Ile Gln Met Thr Gln Ser Pro Ser Ser
    130                 135                 140

Leu Ser Ala Ser Val Gly Asp Arg Val Thr Ile Thr Cys Arg Ala Ser
145                 150                 155                 160

Gln Ser Ile Ser Ser Tyr Leu Asn Trp Tyr Gln Gln Lys Pro Gly Lys
                165                 170                 175

Ala Pro Lys Leu Leu Ile Tyr Ser Ala Ser Ser Leu Gln Ser Gly Val
            180                 185                 190

Pro Ser Arg Phe Ser Gly Ser Gly Ser Gly Thr Asp Phe Thr Leu Thr
        195                 200                 205

Ile Ser Ser Leu Gln Pro Glu Asp Phe Ala Thr Tyr Tyr Cys Gln Gln
    210                 215                 220

Arg Glu Thr Gly Pro Lys Ala Phe Gly Gln Gly Thr Lys Val Glu Ile
225                 230                 235                 240

Lys Arg Ala Ala Ala His His His His His His Gly Ala Ala Glu Gln
                245                 250                 255

Lys Leu Ile Ser Glu Glu Asp Leu Asn Gly Ala Ala
            260                 265
```

<210> SEQ ID NO 37
<211> LENGTH: 821
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 37

```
ccatggccca ggtacagctg caggagtcgg gggaggcttg gtacagcctg gggggtccct      60
gagactctcc tgtgcagcct ctggattcac ctttagcagc tatgccatga gctgggtccg     120
ccaggctcca gggaaggggc tggagtgggt ctcagctatt agtggtagtg gtggtagcac     180
atactacgca gactccgtga agggccgatt caccatctcc agagacaatt ccaagaacac     240
gctgtatctg caaatgaaca gcctgagagc tgaggacacg gctgtgtatt actgtgcgaa     300
gagctatggt tcagttaaaa taagctgctt tgactactgg ggccagagca ccctggtcac     360
```

```
cgtctcctca ggtggaggcg gttcaggcgg aggtggctct ggcggtggcg gatcggaaat    420
tgtgctgacg cagtctccag actccctggc tgtgtctctg ggcgagaggg ccaccatcaa    480
ctgcaagtcc agccagagtg ttctttacaa ctccaacaat aagaactact tagcttggta    540
ccagcagaaa ccaggacagt ctcctgagtt gctcatttac tgggcatcaa cccgggaatc    600
cggggtccct gaccgattca gtggcagcgg gtctgggaca gaattcactc ttaccatcag    660
cagcctgcag gctgaggatg tggcagttta ttactgtcag caattttata gtactcctcc    720 gactttggc cagggaccaa gctggagat caaacgtgcg gccgcacatc atcatcacca    780
tcacggggcc gcagaacaaa aactcatctc agaagaggat c                         821
```

<210> SEQ ID NO 38
<211> LENGTH: 278
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 38

```
Met Ala Gln Val Gln Leu Gln Glu Ser Gly Gly Gly Leu Val Gln Pro
1               5                   10                  15

Gly Gly Ser Leu Arg Leu Ser Cys Ala Ala Ser Gly Phe Thr Phe Ser
            20                  25                  30

Ser Tyr Ala Met Ser Trp Val Arg Gln Ala Pro Gly Lys Gly Leu Glu
        35                  40                  45

Trp Val Ser Ala Ile Ser Gly Ser Gly Gly Ser Thr Tyr Tyr Ala Asp
    50                  55                  60

Ser Val Lys Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Lys Ser Tyr Gly Ser Val Lys Ile Ser Cys Phe Asp Tyr
            100                 105                 110

Trp Gly Gln Ser Thr Leu Val Thr Val Ser Ser Gly Gly Gly Gly Ser
        115                 120                 125

Gly Gly Gly Gly Ser Gly Gly Gly Ser Glu Ile Val Leu Thr Gln
    130                 135                 140

Ser Pro Asp Ser Leu Ala Val Ser Leu Gly Glu Arg Ala Thr Ile Asn
145                 150                 155                 160

Cys Lys Ser Ser Gln Ser Val Leu Tyr Asn Ser Asn Asn Lys Asn Tyr
                165                 170                 175

Leu Ala Trp Tyr Gln Gln Lys Pro Gly Gln Ser Pro Glu Leu Leu Ile
            180                 185                 190

Tyr Trp Ala Ser Thr Arg Glu Ser Gly Val Pro Asp Arg Phe Ser Gly
        195                 200                 205

Ser Gly Ser Gly Thr Glu Phe Thr Leu Thr Ile Ser Ser Leu Gln Ala
    210                 215                 220

Glu Asp Val Ala Val Tyr Tyr Cys Gln Gln Phe Tyr Ser Thr Pro Pro
225                 230                 235                 240

Thr Phe Gly Gln Gly Thr Lys Leu Glu Ile Lys Arg Ala Ala His
                245                 250                 255

His His His His His Gly Ala Ala Glu Gln Lys Leu Ile Ser Glu Glu
            260                 265                 270
```

Asp Leu Asn Gly Ala Ala
              275

<210> SEQ ID NO 39
<211> LENGTH: 843
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (816)..(816)
<223> OTHER INFORMATION: a, c, t, g, unknown or other
<220> FEATURE:
<221> NAME/KEY: modified_base
<222> LOCATION: (826)..(826)
<223> OTHER INFORMATION: a, c, t, g, unknown or other
<220> FEATURE:
<221> NAME/KEY: modified_base
<222> LOCATION: (832)..(833)
<223> OTHER INFORMATION: a, c, t, g, unknown or other
<220> FEATURE:
<221> NAME/KEY: modified_base
<222> LOCATION: (836)..(836)
<223> OTHER INFORMATION: a, c, t, g, unknown or other
<220> FEATURE:
<221> NAME/KEY: modified_base
<222> LOCATION: (840)..(840)
<223> OTHER INFORMATION: a, c, t, g, unknown or other

<400> SEQUENCE: 39
ccatggccga ggtgcagctg ttggagtctg ggggaggctt ggtacagcct ggggggtccc     60
tgagactctc ctgtgcagcc tctggattca cctttagcag ctatgccatg agctgggtcc    120
gccaggctcc agggaagggg ctggagtggg tctcaaatat tagtagtgca gggaaggggc    180
tggagtgggt ctcaagtatt gatgattctg gtgcttctac atattacgca gactccgtga    240
agggccggtt caccatctcc agagacaatt ccaagaacac gctgtatctg caaatgaaca    300
gcctgagagc cgaggacacg gccgtatatt actgtgcgaa agattctgct tcttttgact    360
actggggcca gggaaccctg gtcaccgtct cgagcggtgg aggcggttca ggcggaggtg    420
gcagcggcgg tggcgggtcg acggacatcc agatgaccca gtctccatcc tcccgtctg    480 catctgtagg agacagagtc accatcactt gccgggcaag tcagagcatt agcagctatt    540
taaattggta tcagcagaaa ccagggaaag cccctaagct cctgatctat actgcatcca    600
gtttgcaaag tggggtccca tcaaggttca gtggcagtgg atctgggaca gatttcactc    660
tcaccatcag cagtctgcaa cctgaagatt ttgcaactta ctactgtcaa cagtctgctg    720
ctagtccttc tacgttcggc caagggacca aggtggaaat caaacgggcg gccgcacatc    780
accatcacca tcacggggcc gcagaacaaa aactcntctc agaagnggat cnnaangggn    840
ccg                                                                  843

<210> SEQ ID NO 40
<211> LENGTH: 281
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 40

Met Ala Glu Val Gln Leu Leu Glu Ser Gly Gly Gly Leu Val Gln Pro
1               5                   10                  15

Gly Gly Ser Leu Arg Leu Ser Cys Ala Ala Ser Gly Phe Thr Phe Ser

```
            20                  25                  30
Ser Tyr Ala Met Ser Trp Val Arg Gln Ala Pro Gly Lys Gly Leu Glu
        35                  40                  45

Trp Val Ser Asn Ile Ser Ser Ala Gly Lys Gly Leu Glu Trp Val Ser
    50                  55                  60

Ser Ile Asp Asp Ser Gly Ala Ser Thr Tyr Tyr Ala Asp Ser Val Lys
65                  70                  75                  80

Gly Arg Phe Thr Ile Ser Arg Asp Asn Ser Lys Asn Thr Leu Tyr Leu
                85                  90                  95

Gln Met Asn Ser Leu Arg Ala Glu Asp Thr Ala Val Tyr Tyr Cys Ala
            100                 105                 110

Lys Asp Ser Ala Ser Phe Asp Tyr Trp Gly Gln Gly Thr Leu Val Thr
        115                 120                 125

Val Ser Ser Gly Gly Gly Gly Ser Gly Gly Gly Gly Ser Gly Gly Gly
    130                 135                 140

Gly Ser Thr Asp Ile Gln Met Thr Gln Ser Pro Ser Ser Leu Ser Ala
145                 150                 155                 160

Ser Val Gly Asp Arg Val Thr Ile Thr Cys Arg Ala Ser Gln Ser Ile
                165                 170                 175

Ser Ser Tyr Leu Asn Trp Tyr Gln Gln Lys Pro Gly Lys Ala Pro Lys
            180                 185                 190

Leu Leu Ile Tyr Thr Ala Ser Ser Leu Gln Ser Gly Val Pro Ser Arg
        195                 200                 205

Phe Ser Gly Ser Gly Ser Gly Thr Asp Phe Thr Leu Thr Ile Ser Ser
    210                 215                 220

Leu Gln Pro Glu Asp Phe Ala Thr Tyr Tyr Cys Gln Gln Ser Ala Ala
225                 230                 235                 240

Ser Pro Ser Thr Phe Gly Gln Gly Thr Lys Val Glu Ile Lys Arg Ala
                245                 250                 255

Ala Ala His His His His His His Gly Ala Ala Glu Gln Lys Leu Ile
            260                 265                 270

Ser Glu Glu Asp Leu Asn Gly Ala Ala
        275                 280

<210> SEQ ID NO 41
<211> LENGTH: 822
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 41
ccatggccga ggtgcagctg ttggagtctg ggggaggctt ggtacagcct ggggggtccc      60
tgagactctc ctgtgcagcc tctggattca cctttagcag ctatgccatg agctgggtcc     120
gccaggctcc agggaagggg ctggagtggg tctcatcgat tgatagcgga ggtggtggta     180
cacagtacgc agactccgtg aagggccggt tcaccatctc cagagacaat tccaagaaca     240
cgctgtatct gcaaatgaac agcctgagag ccgaggacac ggccgtatat tactgtgcga     300
aacattttga atttttgac tactggggcc agggaaccct ggtcaccgtc tcgagcggtg     360
gaggcggttc aggcggaggt ggcagcggcg gtggcgggtc gacggacatc cagatgaccc     420
agtctccatc ctccctgtct gcatctgtag gagacagagt caccatcact tgccgggcaa     480
gtcagagcat tagcagctat ttaaattggt atcagcagaa accagggaaa gcccctaagc     540
```

```
tcctgatcta tgctgcatcc catttgcaaa gtggggtccc atcaaggttc agtggcagtg    600
gatctgggac agatttcact ctcaccatca gcagtctgca acctgaagat tttgcaactt    660
actactgtca acagacgcgt aggccgcctt ctacgttcgg ccaagggacc aaggtggaaa    720
tcaaacgggc ggccgcacat catcatcacc atcacggggc cgcagaacaa aaactcatct    780
cagaagagaa tcactagtgc ggccgcctgc aggtcgacca ta                      822
```

<210> SEQ ID NO 42  
<211> LENGTH: 268  
<212> TYPE: PRT  
<213> ORGANISM: Artificial Sequence  
<220> FEATURE:  
<223> OTHER INFORMATION: Description of Artificial Sequence: Synthetic polypeptide

<400> SEQUENCE: 42

```
Met Ala Glu Val Gln Leu Leu Glu Ser Gly Gly Gly Leu Val Gln Pro
1               5                   10                  15

Gly Gly Ser Leu Arg Leu Ser Cys Ala Ala Ser Gly Phe Thr Phe Ser
            20                  25                  30

Ser Tyr Ala Met Ser Trp Val Arg Gln Ala Pro Gly Lys Gly Leu Glu
        35                  40                  45

Trp Val Ser Ser Ile Gly Gln Lys Gly Gly Thr Gln Tyr Ala Asp
    50                  55                  60

Ser Val Lys Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Lys His Phe Glu Asn Phe Asp Tyr Trp Gly Gln Gly Thr
            100                 105                 110

Leu Val Thr Val Ser Ser Gly Gly Gly Gly Ser Gly Gly Gly Gly Ser
        115                 120                 125

Gly Gly Gly Gly Ser Thr Asp Ile Gln Met Thr Gln Ser Pro Ser Ser
    130                 135                 140

Leu Ser Ala Ser Val Gly Asp Arg Val Thr Ile Thr Cys Arg Ala Ser
145                 150                 155                 160

Gln Ser Ile Ser Ser Tyr Leu Asn Trp Tyr Gln Gln Lys Pro Gly Lys
                165                 170                 175

Ala Pro Lys Leu Leu Ile Tyr Ala Ala Ser His Leu Gln Ser Gly Val
            180                 185                 190

Pro Ser Arg Phe Ser Gly Ser Gly Ser Gly Thr Asp Phe Thr Leu Thr
        195                 200                 205

Ile Ser Ser Leu Gln Pro Glu Asp Phe Ala Thr Tyr Tyr Cys Gln Gln
    210                 215                 220

Thr Arg Arg Pro Pro Ser Thr Phe Gly Gln Gly Thr Lys Val Glu Ile
225                 230                 235                 240

Lys Arg Ala Ala Ala His His His His His Gly Ala Ala Glu Gln
                245                 250                 255

Lys Leu Ile Ser Glu Glu Asp Leu Asn Gly Ala Ala
            260                 265
```

<210> SEQ ID NO 43  
<211> LENGTH: 1033  
<212> TYPE: DNA  
<213> ORGANISM: Artificial Sequence  
<220> FEATURE:  
<223> OTHER INFORMATION: Description of Artificial Sequence: Synthetic

```
          polynucleotide
<220> FEATURE:
<221> NAME/KEY: modified_base
<222> LOCATION: (4)..(4)
<223> OTHER INFORMATION: a, c, t, g, unknown or other
<220> FEATURE:
<221> NAME/KEY: modified_base
<222> LOCATION: (8)..(8)
<223> OTHER INFORMATION: a, c, t, g, unknown or other
<220> FEATURE:
<221> NAME/KEY: modified_base
<222> LOCATION: (13)..(15)
<223> OTHER INFORMATION: a, c, t, g, unknown or other
<220> FEATURE:
<221> NAME/KEY: modified_base
<222> LOCATION: (876)..(876)
<223> OTHER INFORMATION: a, c, t, g, unknown or other
<220> FEATURE:
<221> NAME/KEY: modified_base
<222> LOCATION: (895)..(895)
<223> OTHER INFORMATION: a, c, t, g, unknown or other
<220> FEATURE:
<221> NAME/KEY: modified_base
<222> LOCATION: (900)..(901)
<223> OTHER INFORMATION: a, c, t, g, unknown or other
<220> FEATURE:
<221> NAME/KEY: modified_base
<222> LOCATION: (914)..(914)
<223> OTHER INFORMATION: a, c, t, g, unknown or other
<220> FEATURE:
<221> NAME/KEY: modified_base
<222> LOCATION: (917)..(917)
<223> OTHER INFORMATION: a, c, t, g, unknown or other
<220> FEATURE:
<221> NAME/KEY: modified_base
<222> LOCATION: (921)..(922)
<223> OTHER INFORMATION: a, c, t, g, unknown or other
<220> FEATURE:
<221> NAME/KEY: modified_base
<222> LOCATION: (926)..(928)
<223> OTHER INFORMATION: a, c, t, g, unknown or other
<220> FEATURE:
<221> NAME/KEY: modified_base
<222> LOCATION: (934)..(934)
<223> OTHER INFORMATION: a, c, t, g, unknown or other
<220> FEATURE:
<221> NAME/KEY: modified_base
<222> LOCATION: (939)..(939)
<223> OTHER INFORMATION: a, c, t, g, unknown or other
<220> FEATURE:
<221> NAME/KEY: modified_base
<222> LOCATION: (951)..(953)
<223> OTHER INFORMATION: a, c, t, g, unknown or other
<220> FEATURE:
<221> NAME/KEY: modified_base
<222> LOCATION: (958)..(958)
<223> OTHER INFORMATION: a, c, t, g, unknown or other
<220> FEATURE:
<221> NAME/KEY: modified_base
<222> LOCATION: (965)..(968)
<223> OTHER INFORMATION: a, c, t, g, unknown or other
<220> FEATURE:
<221> NAME/KEY: modified_base
<222> LOCATION: (970)..(975)
<223> OTHER INFORMATION: a, c, t, g, unknown or other
<220> FEATURE:
<221> NAME/KEY: modified_base
<222> LOCATION: (985)..(986)
<223> OTHER INFORMATION: a, c, t, g, unknown or other
<220> FEATURE:
<221> NAME/KEY: modified_base
<222> LOCATION: (989)..(990)
<223> OTHER INFORMATION: a, c, t, g, unknown or other
<220> FEATURE:
<221> NAME/KEY: modified_base
<222> LOCATION: (992)..(992)
<223> OTHER INFORMATION: a, c, t, g, unknown or other
<220> FEATURE:
<221> NAME/KEY: modified_base
```

<222> LOCATION: (996)..(997)
<223> OTHER INFORMATION: a, c, t, g, unknown or other
<220> FEATURE:
<221> NAME/KEY: modified_base
<222> LOCATION: (1002)..(1002)
<223> OTHER INFORMATION: a, c, t, g, unknown or other
<220> FEATURE:
<221> NAME/KEY: modified_base
<222> LOCATION: (1004)..(1007)
<223> OTHER INFORMATION: a, c, t, g, unknown or other
<220> FEATURE:
<221> NAME/KEY: modified_base
<222> LOCATION: (1012)..(1017)
<223> OTHER INFORMATION: a, c, t, g, unknown or other
<220> FEATURE:
<221> NAME/KEY: modified_base
<222> LOCATION: (1021)..(1021)
<223> OTHER INFORMATION: a, c, t, g, unknown or other
<220> FEATURE:
<221> NAME/KEY: modified_base
<222> LOCATION: (1023)..(1025)
<223> OTHER INFORMATION: a, c, t, g, unknown or other
<220> FEATURE:
<221> NAME/KEY: modified_base
<222> LOCATION: (1027)..(1027)
<223> OTHER INFORMATION: a, c, t, g, unknown or other
<220> FEATURE:
<221> NAME/KEY: modified_base
<222> LOCATION: (1029)..(1032)
<223> OTHER INFORMATION: a, c, t, g, unknown or other

<400> SEQUENCE: 43

| | | | | | |
|---|---|---|---|---|---|
| gcanttcnat | ttnnngagac | agtcataatg | aaatacctat | tgcctacggc | agccgctgga | 60 |
| ttgttattac | tcgcggccca | gccggccatg | gcccaggtgc | agctggtgga | gtctggggga | 120 |
| ggcttggtac | agcctggggg | gtccctgaga | ctctcctgtg | cagcctctgg | attcaccttt | 180 |
| agcagctatg | ccatgagctg | gtccgccag | gctccaggga | aggggctgga | gtgggtctca | 240 |
| gctattagtg | gtagtggtgg | tagcacatac | tacgcagact | ccgtgaaggg | ccggttcacc | 300 |
| atctccagag | acaattccaa | gaacacgctg | tatctgcaaa | tgaacagcct | gagagccgag | 360 |
| gacacggctg | tatattactg | tgcaagaggt | ggcgattatg | gctcagggga | ctactggggc | 420 |
| cagggaaccc | tggtcaccgt | ctcctcaggt | ggaggcggtt | caggcggagg | tggctctggc | 480 |
| ggtggcggat | cgaattttat | gctgactcag | accctgctgt | tgtctgtggc | cttgggacag | 540 |
| acagtcagaa | tcacatgcca | aggagacagc | ctcagaagct | attatgcaag | ttggtaccag | 600 |
| cagaagccag | gacaggcccc | tctccttgtc | atctatggta | aaaacatccg | gccctcaggg | 660 |
| atcccagacc | gattctctgg | ctccagctca | ggaaactcag | cttccttgac | catcactggg | 720 |
| gctcaggcgg | aagatgaggc | tgactattac | tgtcactccc | gggacagcag | tggtacccat | 780 |
| ctaagggtat | tcggcggagg | gaccaaggtc | accgtcctag | gtgcggccgc | agaacaaaaa | 840 |
| ctcatctcag | aagaggatct | gaatgggccg | gcatanactg | ttgaaagttg | tttancaaan | 900 |
| nctcatacag | aaanttnatt | nnctannntc | tggnaagang | acaaaacttt | nnntcgtnac | 960 |
| gctannnntn | nnnntgtct | gtganngcnn | cnggcnntgt | gntnnnnact | gnnnnnnaaa | 1020 |
| ntnnngntnn | nng | | | | | 1033 |

<210> SEQ ID NO 44
<211> LENGTH: 327
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES

```
<222> LOCATION: (2)..(3)
<223> OTHER INFORMATION: Any amino acid
<220> FEATURE:
<221> NAME/KEY: MOD_RES
<222> LOCATION: (5)..(5)
<223> OTHER INFORMATION: Any amino acid
<220> FEATURE:
<221> NAME/KEY: MOD_RES
<222> LOCATION: (292)..(292)
<223> OTHER INFORMATION: Any amino acid
<220> FEATURE:
<221> NAME/KEY: MOD_RES
<222> LOCATION: (299)..(301)
<223> OTHER INFORMATION: Any amino acid
<220> FEATURE:
<221> NAME/KEY: MOD_RES
<222> LOCATION: (305)..(310)
<223> OTHER INFORMATION: Any amino acid
<220> FEATURE:
<221> NAME/KEY: MOD_RES
<222> LOCATION: (312)..(313)
<223> OTHER INFORMATION: Any amino acid
<220> FEATURE:
<221> NAME/KEY: MOD_RES
<222> LOCATION: (317)..(318)
<223> OTHER INFORMATION: Any amino acid
<220> FEATURE:
<221> NAME/KEY: MOD_RES
<222> LOCATION: (320)..(320)
<223> OTHER INFORMATION: Any amino acid
<220> FEATURE:
<221> NAME/KEY: MOD_RES
<222> LOCATION: (322)..(325)
<223> OTHER INFORMATION: Any amino acid

<400> SEQUENCE: 44

Ala Xaa Xaa Phe Xaa Glu Thr Val Ile Met Lys Tyr Leu Leu Pro Thr
1               5                   10                  15

Ala Ala Ala Gly Leu Leu Leu Ala Ala Gln Pro Ala Met Ala Gln
            20                  25                  30

Val Gln Leu Val Glu Ser Gly Gly Leu Val Gln Pro Gly Gly Ser
        35                  40                  45

Leu Arg Leu Ser Cys Ala Ala Ser Gly Phe Thr Phe Ser Ser Tyr Ala
    50                  55                  60

Met Ser Trp Val Arg Gln Ala Pro Gly Lys Gly Leu Glu Trp Val Ser
65                  70                  75                  80

Ala Ile Ser Gly Ser Gly Gly Ser Thr Tyr Tyr Ala Asp Ser Val Lys
                85                  90                  95

Gly Arg Phe Thr Ile Ser Arg Asp Asn Ser Lys Asn Thr Leu Tyr Leu
            100                 105                 110

Gln Met Asn Ser Leu Arg Ala Glu Asp Thr Ala Val Tyr Tyr Cys Ala
        115                 120                 125

Arg Gly Gly Asp Tyr Gly Ser Gly Asp Tyr Trp Gly Gln Gly Thr Leu
    130                 135                 140

Val Thr Val Ser Ser Gly Gly Gly Gly Ser Gly Gly Gly Gly Ser Gly
145                 150                 155                 160

Gly Gly Gly Ser Asn Phe Met Leu Thr Gln Asp Pro Ala Val Ser Val
                165                 170                 175

Ala Leu Gly Gln Thr Val Arg Ile Thr Cys Gln Gly Asp Ser Leu Arg
            180                 185                 190

Ser Tyr Tyr Ala Ser Trp Tyr Gln Gln Lys Pro Gly Gln Ala Pro Leu
        195                 200                 205

Leu Val Ile Tyr Gly Lys Asn Ile Arg Pro Ser Gly Ile Pro Asp Arg
    210                 215                 220
```

```
Phe Ser Gly Ser Ser Ser Gly Asn Ser Ala Ser Leu Thr Ile Thr Gly
225                 230                 235                 240

Ala Gln Ala Glu Asp Glu Ala Asp Tyr Tyr Cys His Ser Arg Asp Ser
                245                 250                 255

Ser Gly Thr His Leu Arg Val Phe Gly Gly Gly Thr Lys Val Thr Val
            260                 265                 270

Leu Gly Ala Ala Ala Glu Gln Lys Leu Ile Ser Glu Glu Asp Leu Asn
        275                 280                 285

Gly Ala Ala Xaa Thr Val Glu Ser Cys Leu Xaa Xaa Xaa His Thr Glu
        290                 295                 300

Xaa Xaa Xaa Xaa Xaa Xaa Trp Xaa Xaa Asp Lys Thr Xaa Xaa Arg Xaa
305                 310                 315                 320

Ala Xaa Xaa Xaa Xaa Cys Leu
                325

<210> SEQ ID NO 45
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(8)
<223> OTHER INFORMATION: Any amino acid
<220> FEATURE:
<221> NAME/KEY: MOD_RES
<222> LOCATION: (10)..(11)
<223> OTHER INFORMATION: Any amino acid
<220> FEATURE:
<221> NAME/KEY: MOD_RES
<222> LOCATION: (13)..(16)
<223> OTHER INFORMATION: Any amino acid

<400> SEQUENCE: 45

Xaa Xaa Xaa Xaa Xaa Xaa Xaa Xaa Leu Xaa Xaa Lys Xaa Xaa Xaa Xaa
1               5                   10                  15
```

METHODS FOR DETECTING TRAUMATIC BRAIN INJURY

PRIORITY OF INVENTION

This application is a division of U.S. application Ser. No. 15/087,682, filed Mar. 31, 2016, which claims the benefit of U.S. Provisional Application Ser. No. 62/141,003 that was filed on Mar. 31, 2015. The entire content of the applications referenced above are hereby incorporated by reference herein.

STATEMENT REGARDING FEDERALLY SPONSORED RESEARCH

This invention was made with government support under W81XWH-12-1-0583 and W81XWH-14-1-0467 awarded by the ARMY/MRMC. The government has certain rights in the invention.

SEQUENCE LISTING

The instant application contains a Sequence Listing which has been submitted electronically in ASCII format and is hereby incorporated by reference in its entirety. Said ASCII copy, created on Apr. 11, 2016, is named 17555.027US1_SL.txt and is 87,626 bytes in size.

BACKGROUND

Traumatic Brain Injury (TBI) affects around 2 million people each year. This is likely an underestimate as many people with mild TBI may not seek medical care. Chronic stress and especially traumatic brain injury (TBI) disrupt cognitive function. Even mild traumatic brain injury (mTBI) frequently leads to chronic traumatic encephalopathy (CTE) and an increased frequency and earlier onset of other brain disorders including Alzheimer's disease (AD), Parkinson's disease (PD), frontotemporal dementia (FTD) and amyotrophic lateral sclerosis (ALS), so potential long term consequences of TBI can be quite devastating. There currently are no reliable methods to determine which TBI cases will develop neurodegenerative disorders, and mechanisms by which TBI leads to neurodegeneration are poorly understood. Biomarkers of chronic TBI have not been systematically studied and identification of biomarkers that can help identify which patients incurring TBI are most susceptible to neurodegenerative diseases such as AD would be extremely valuable clinical tools to help determine the appropriate course of care for veterans and others that have suffered brain injuries. There are currently no reliable physical diagnostic tests to determine traumatic brain injury (TBI). Thus, methods and reagents are still needed to aid in the diagnosis of TBI.

SUMMARY

Methods have been developed that enable generation of reagents that selectively bind disease related protein variants. The inventors have developed methods and reagents to assess neuronal damage following TBI. Phage display antibody libraries are used as a source to isolate the protein variant specific reagents. Also, a DARPin (Designed ankyrin repeat protein) phage display library is used to generate and isolate additional reagents selective for TBI. These libraries are used to identify biomarkers that are indicative of different stages and severity of TBI.

In certain embodiments, the present invention provides a designed ankyrin repeat protein (DARPin) comprising
(a) an N-Terminal Capping ankyrin repeat (AR) (SEQ ID NO:30),
(b) a C-Terminal Capping AR (SEQ ID NO:31), and
(c) three to six AR modules of about 30 to 35 amino acids, wherein each AR module binds with a target.

In certain embodiments, the present invention provides a method for determining risk of traumatic brain injury (TBI), assessment of the amount of neuronal damage, and/or susceptibility to neurodegenerative disease in a subject, comprising the steps of:
(A) providing samples obtained from a subject at two or more times post-injury;
(B) assessing protein levels of toxic variants of TDP-43, tau, abeta and/or alpha-synuclein in the sample by detecting protein levels of toxic variants of TDP-43, tau, abeta and/or alpha-synuclein in the samples;
(C) comparing the protein levels of toxic variants of TDP-43, tau, abeta and/or alpha-synuclein in the sample at each time point with protein levels of toxic variants of TDP-43, tau, abeta and/or alpha-synuclein in a normal control; and
(D) determining whether the subject has a risk of TBI in accordance with the result of step (C);
wherein a subject having elevated protein levels of toxic variants of TDP-43 tau, abeta and/or alpha-synuclein has a high risk of TBI.

As used herein, the term "toxic variant of TDP-43" is defined as variants of TDP-43 that are preferentially present in diseased human tissue samples but not healthy control samples. Diseased tissue samples include Alzheimer's disease, Parkinson's disease, Frontotemporal Dementia, Lewy Body Dementia, Amyotrophic Lateral Sclerosis and other neurodegenerative diseases.

As used herein, the term "toxic variant of tau" is defined as oligomeric tau. In certain embodiments the oligomeric tau is dimeric tau, trimeric tau, tetrameric tau, pentameric tau, hexameric tau, heptameric tau, octameric tau, nonameric tau, decameric tau, undecameric tau or dodecameric tau. In certain embodiments, the oligomeric tau is dimeric tau or trimeric tau. In certain embodiments, the oligomeric tau is trimeric tau. (See, e.g., WO 2014/059442, which is incorporated by reference herein.)

As used herein, the term "toxic variant of abeta" is defined a small oligomeric variant including trimeric and/or tetrameric forms of abeta. (See, e.g., WO 2012/058308, which is incorporated by reference herein.) As used herein, the term "toxic variant of alpha-synuclein" is defined as oligomeric form of alpha-synuclein including dimeric, trimeric, tetrameric and higher order assemblies. (See, e.g., WO 2014/059442, which is incorporated by reference herein.)

In certain embodiments, a sample is obtained from the subject within 6 hours post-injury.

In certain embodiments, a sample is obtained from the subject about 12 to 36 hours post-injury.

In certain embodiments, a sample is obtained from the subject about 5 to 10 days post injury.

In certain embodiments, a sample is obtained from the subject about 2 to 4 weeks days post injury.

In certain embodiments, the sample and the normal control are blood product samples or cerebrospinal fluid (CSF) samples. In certain embodiments, the blood product is serum.

In certain embodiments, the detecting in step (B) is by means of a ligand specific for the protein.

In certain embodiments, the ligand is an antibody.

In certain embodiments, the ligand is a designed ankyrin repeat protein (DARPin).

In certain embodiments, the protein levels are detected by means of ELISA.

In certain embodiments, the present invention provides a method for determining risk of traumatic brain injury (TBI), assessment of the amount of neuronal damage, and/or susceptibility to neurodegenerative disease in a subject, comprising the steps of:

(A) providing samples obtained from a subject at about 6-hours, about 24-hours, about 5-days and about 10-days post-injury;

(B) assessing levels of a toxic variant of TDP-43 in the sample by detecting protein levels of a toxic variant of TDP-43 in the samples;

(C) comparing the protein levels of the toxic variant of TDP-43 in the sample at each time point with protein levels of the toxic variant of TDP-43 in a normal control; and (D) determining whether the subject has a risk of TBI in accordance with the result of step (C);

wherein a subject having increased protein levels of the toxic variant of TDP-43 in the samples at all four time points than those of the normal control, and having a decreased level of the toxic variant of TDP-43 at the 24-hour time point as compared to the 6-hour time point, having a decreased level of TDP-43 at the 5-day time point as compared to the 24-hour time point, and having an increased level of TDP-43 at the 10-day time point as compared to either the 24-hour or 5-day time point has a high risk of TBI.

In certain embodiments, the present invention provides a method for determining risk of traumatic brain injury (TBI), assessment of the amount of neuronal damage, and/or susceptibility to neurodegenerative disease in a subject, comprising the steps of:

(A) providing samples obtained from a subject at about 6-hours, about 24-hours, about 5-days and about 10-days post-injury;

(B) assessing levels of a toxic variant of tau in the sample by detecting the protein levels of the toxic variant of tau in the samples;

(C) comparing the protein levels of the toxic variant of tau in the sample at each time point with protein levels of the toxic variant of tau in a normal control; and (D) determining whether the subject has a risk of TBI in accordance with the result of step (C);

wherein a subject having an increased protein levels of the toxic variant of tau in the sample at the 24-hour time point and at the 5-day time point as compared to that of the normal control, having comparable protein levels of the toxic variant of tau at the 6-hour and 10-day time points as compared to that of the normal control, and having an increased protein level of the toxic variant of tau at the 5-day time point as compared to the 24-hour time point has a high risk of TBI.

In certain embodiments, the present invention provides a method for determining risk of traumatic brain injury (TBI), assessment of the amount of neuronal damage, and/or susceptibility to neurodegenerative disease in a subject, comprising the steps of:

(A) providing samples obtained from a subject at about 6-hours, about 24-hours, about 5-days and about 10-days post-injury;

(B) assessing protein levels of a toxic variant of abeta in the sample by detecting protein levels of the toxic variant of abeta in the samples;

(C) comparing protein levels of the toxic variant of abeta in the sample at each time point with protein levels of the toxic variant of abeta in a normal control; and (D) determining whether the subject has a risk of TBI in accordance with the result of step (C);

wherein a subject having an increased protein levels of the toxic variant of abeta in the sample at the 24-hour time point, the 5-day time point and the 10-day time point as compared to that of the normal control, having comparable protein level of the toxic variant of abeta at the 6-hour as compared to that of the normal control, and having an increased protein level of the toxic variant of abeta at the 5-day time point as compared to the 24-hour time point and 10-day time point has a high risk of TBI.

In certain embodiments, the present invention provides a method for determining risk of traumatic brain injury (TBI), assessment of the amount of neuronal damage, and/or susceptibility to neurodegenerative disease in a subject, comprising the steps of:

(A) providing samples obtained from a subject at about 6-hours, about 24-hours, about 5-days and about 10-days post-injury;

(B) assessing protein levels of a toxic variant of alpha-synuclein in the sample by detecting protein levels of the toxic variant of alpha-synuclein in the samples;

(C) comparing the protein levels of the toxic variant of alpha-synuclein in the sample at each time point with protein levels of the toxic variant of alpha-synuclein in a normal control; and (D) determining whether the subject has a risk of TBI in accordance with the result of step (C);

wherein a subject having an increased protein levels of the toxic variant of alpha-synuclein in the sample at the 5 day time point, the 10-day time point as compared to that of the normal control, having comparable protein level of the toxic variant of alpha-synuclein at the 6-hour time point and 24-hour time point as compared to that of the normal control, and having an increased protein level of the toxic variant of alpha-synuclein at the 5-day time point as compared to the 10-day time point has a high risk of TBI.

The present invention provides in certain embodiments a method for measuring the presence of a biomarker in a human sample from a patient having traumatic brain injury (TBI), the improvement comprising measuring the levels of toxic variants of TDP-43, tau, abeta and/or alpha-synuclein in the sample for use in predicting the amount of neuronal damage, and/or susceptibility to neurodegenerative disease in a subject.

BRIEF DESCRIPTION OF THE FIGURES

FIG. 45A. Line Graph Comparison of 3A Reactive TDP-43 Variant in Human TBI Sera and CSF. FIG. 45B. Bar Graph Comparison of 3A Reactive TDP-43 Variant in Human TBI Sera and CSF. FIG. 45C. Line Graph Comparison of 3C Reactive TDP-43 Variant in Human TBI Sera and CSF. FIG. 45D. Bar Graph Comparison of 3C Reactive TDP-43 Variant in Human TBI Sera and CSF.

FIG. 46A. Line Graph Comparison of 8D Reactive TDP-43 Variant in Human TBI Sera and CSF. FIG. 46B. Bar Graph Comparison of 8D Reactive TDP-43 Variant in Human TBI Sera and CSF. FIG. 46C. Line Graph Comparison of D11C Reactive Oligomeric Tau in Human TBI Sera and CSF. FIG. 46D. Bar Graph Comparison of D11C Reactive Oligomeric Tau in Human TBI Sera and CSF.

FIG. 47A. Line Graph Comparison of C6T Reactive Oligomeric Beta-Amyloid in Human TBI Sera and CSF. FIG. 47B. Bar Graph Comparison of C6T Reactive Oligomeric Beta-Amyloid in Human TBI Sera and CSF. FIG. 47C. Line Graph Comparison of A4 Reactive Oligomeric Beta-Amyloid in Human TBI Sera and CSF. FIG. 47D. Bar Graph Comparison of A4 Reactive Oligomeric Beta-Amyloid in Human TBI Sera and CSF.

FIG. 48A. Line Graph Comparison of D5 Reactive Oligomeric Alpha-Synuclein in Human TBI Sera and CSF. FIG. 48B. Bar Graph Comparison of D5 Reactive Oligomeric Alpha-Synuclein in Human TBI Sera and CSF. FIG. 48C. Line Graph Comparison of 10H Reactive Oligomeric Alpha-Synuclein in Human TBI Sera and CSF. FIG. 48D. Bar Graph Comparison of 10H Reactive Oligomeric Alpha-Synuclein in Human TBI Sera and CSF.

DETAILED DESCRIPTION

Figure 1:
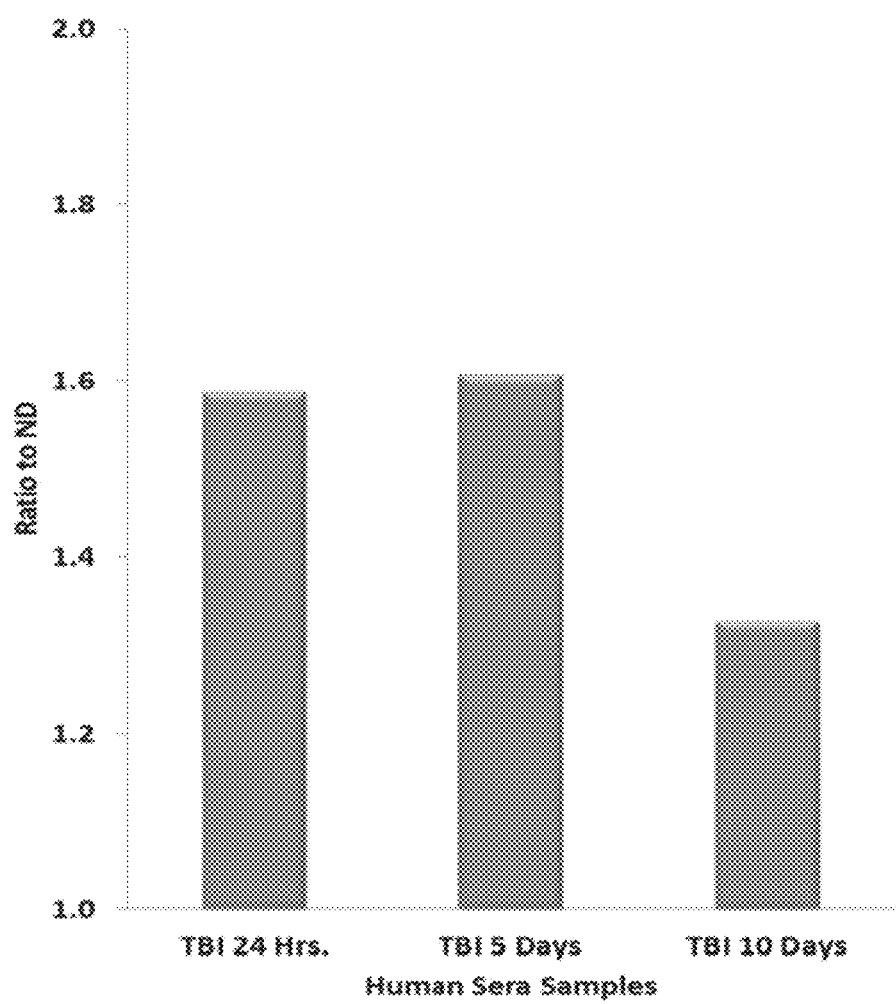
FIG. 1. provides ELISA analysis of a DARPin clone with the TBI cases, which revealed reactivity at 24 hours, 5 days and 10 days, with reactivity decreasing after 5 days.

In order to determine which patients suffering TBI are at high risk of incurring AD, it is necessary to understand the pathology and risk factors of AD. The primary constituents of the two major pathological features of AD, neurofibrillary tangles and amyloid plaques, are respectively, the tau and Aβ proteins. The two most promising biomarkers for AD to date are variants of tau and Aβ, in particular phosphorylated variants of tau and the 42 amino acid variant of Aβ (Aβ42). While tau and Aβ biomarkers suffer from a relatively low sensitivity and specificity for diagnosing AD, they still hold great promise for early detection of AD as changes in CSF levels of tau and Aβ42 have been shown to occur well before symptoms develop, up to 25 years earlier for Aβ42. While CSF tau and Aβ levels correlate with AD, the vast majority of studies have focused on detection of non-toxic monomeric forms of Aβ42 and phosphorylated tau rather than on detection of the actual toxic protein species responsible for neurodegeneration. Both tau and Aβ can exist in a variety of different forms and aggregate morphologies and numerous studies indicate that specific oligomeric forms of both tau and Aβ are involved in neuron degeneration and spread of toxicity, and can interfere with important functions such as long term potentiation. Therefore a potential route for pre-symptomatic diagnosis of AD which can also help to identify those at high-risk of incurring AD is to specifically detect the individual protein species that are involved in very early stages of disease onset and progression. Because misfolded and aggregated variants of tau and Aβ are intimately involved in the progression of AD, detection of specific variants of these proteins in CSF and especially serum has great promise for an early definitive diagnosis of AD. In a parallel manner, misfolded toxic oligomeric variants of the protein a-syn have been correlated with the onset and progression of PD and related synucleinopathies and aggregated toxic variants of Tar DNA binding protein 43 (TDP-43) have been correlated with ALS, FTD and AD. Therefore the presence of selected toxic variants of tau, Aβ, TDP-43 and a-syn all have potential value as early and sensitive diagnostic biomarkers for different neurodegenerative diseases and also to identify individuals at high risk of incurring these diseases.

The brain is very sensitive to stress and injury and responds by expressing a variety of neuromorphological and neurochemical changes. Injury to the brain can alter neuronal protein function through a variety of different ways. Cellular stress can affect processing of proteins by altering genetic splicing, protein production and post-translational modification, it can alter how RNA binding proteins interact with mRNA affecting protein translation, and it can also alter protein folding and aggregation states. All of these changes can result in formation of toxic protein variants that result in a loss of neuronal function and potentially cell death. Some of the key biochemical changes observed in the brain following TBI are similar to changes seen in patients suffering from neurodegenerative diseases including AD, PD, ALS and FTD. As one example, stress induces increased neuronal expression of two proteins implicated in AD, the Amyloid Precursor Protein (APP) and BACE-1 a protease which cleaves APP to generate the amyloid-beta (Aβ) protein. Increase in expression levels of APP and BACE-1 can lead to an increase in Aβ deposition, similar to what is seen in AD patients, an important feature since patients suffering brain trauma are at greater risk of developing AD and at an earlier age. A second example of biochemical changes observed following TBI mirroring those that occur in neurodegenerative diseases are the morphological changes induced in the protein tau. Neuronal axons are particularly vulnerable to the high sheer forces and mechanical deformation induced by TBI. Resulting damage to the neuronal axons can impair protein transport leading to accumulation of proteins including tau and subsequent swelling causing the typical axon pathology observed with TBI. Tau plays a critical role in neuronal damage following TBI and increased levels of tau in brain fluid, CSF and serum samples are all predictive of adverse long-term clinical outcomes after TBI. Neurofibrillary tau aggregates have been identified in soldiers suffering from TBI and in athletes such as football players who suffer repeated head trauma. Aggregates of tau are also the major component of the hallmark neurofibrillary tangles in AD brain, and TBI is a risk factor for AD. Therefore TBI can directly lead to formation of Aβ and tau variants that are also associated with AD.

Injury and cellular stress can contribute to an increase in production of other misfolded and aggregated proteins in addition to Aβ and tau, all of which can overwhelm cell clearance mechanisms affecting proteostasis eventually leading to neuronal degeneration. Similar to the roles of Aβ and tau in AD and other tauopathies, the protein alpha-synuclein (a-syn) plays an important role in the onset and progression of PD and other related neurodegenerative disorders as it is a major component of the hallmark Lewy body aggregates associated with PD. Specific variants of a-syn including aggregated and phosphorylated variants have been correlated with PD, so formation of toxic a-syn variants following TBI may also play a role in the increased incidence of PD associated with brain trauma. Similarly cytoplasmic misfolding and aggregation of TDP-43 have been associated with ALS. TDP-43 binds to a variety of RNA and DNA sequences, particularly to poly-UG RNA sequences accounting for its location in the nucleus, but it can shuttle back and forth from the cytoplasm. In affected neurons and glial cells of ALS cases a variety of different TDP-43 forms accumulate in inclusion bodies in the cytoplasm and/or nucleus rather than in their normal diffuse distribution pattern in the nucleus. Following brain injury or stress, TDP-43 co-localizes with stress granules in the cytoplasm promoting formation of inclusion bodies containing aggregated TDP-43 variants. TDP-43 aggregates have also been correlated with FTD and AD pathology. Therefore brain injury and the neuronal stress and cellular changes resulting from the injury can lead to generation of a variety of different protein variants in particular toxic variants of tau, Aβ, a-syn and TDP-43 all of which have also been implicated in the onset and progression of neurodegenerative diseases including AD, PD, FTD and ALS.

While misfolding of certain proteins has been associated with neuronal damage and disease, more than one protein is likely to misfold and aggregate in brain tissue complicating diagnosis and treatment strategies. Since cellular stress induced by misfolding and aggregation of one protein may well lead to misfolding and aggregation of other proteins, the presence of multiple misfolded proteins in different diseases should be expected. For example injury induced aggregation of tau can lead to misfolding, aggregation or altered processing of Aβ and a-syn, complicating diagnosis of a specific neurodegenerative disease. Increased levels of Aβ variants are known to increase both tau and TDP-43 pathology indicating a link between key aggregation prone neuronal proteins including Aβ, tau, a-syn, and TDP-43. Therefore, there is likely a spectrum of diseases that can be caused by brain injury involving various different toxic protein variants targeting different cells and regions. Since this spectrum of neurodegenerative diseases share overlapping features, carefully characterizing the different protein variants that are present in patient serum samples and comparing these to the protein variant profiles that are characteristic of different neurodegenerative disease would greatly facilitate early diagnosis of the appropriate neurodegenerative disease and also help to identify and monitor the most appropriate treatment strategies. The presence of select key disease related variants of tau, Aβ, a-syn, and TDP-43 in serum following TBI therefore represents a very powerful diagnostic tool to assess the type and extent of neuronal damage induced by the injury and can be useful to predict which patients are most susceptible to particular neurodegenerative diseases. While a number of CSF based biomarkers including different monomeric forms of Aβ, tau and a-syn have shown promise for diagnosing some neurodegenerative diseases, early and accurate diagnosis of different neurodegenerative diseases is still not feasible. Detection and quantification of selected toxic protein variants that are associated with the onset and progression of AD and other neurodegenerative diseases have great promise as tools to facilitate early diagnosis and to identify patients who are at high risk of neurodegenerative disease. Current biomarker studies of TBI patients have not been particularly successful as S100B, a calcium binding protein has been the only marker to consistently predict TBI and outcome. Since S100B has also been implicated in various other diseases including diabetes, melanoma and epilepsy, its use in predicting TBI is limited, and supplemental information regarding toxic protein variants would be very beneficial. This proposal seeks to develop appropriate biomarkers to identify which patients are at risk of AD and other neurodegenerative diseases and to determine the extent of neuronal damage following TBI.

In order to determine the most promising biomarkers to identify individuals at high risk of developing specific neurodegenerative diseases such as AD, it was first necessary need to identify the most relevant protein variants associated with each neurodegenerative disease. While the fibrillar forms of both tau and Aβ are respectively found in the neurofibrillary tangles and amyloid plaques characteristic of AD, these aggregates are not particularly neurotoxic and do not correlate well with disease onset and severity. Small soluble oligomeric forms of both proteins however do correlate much better with disease outcomes and different oligomeric forms are thought to be responsible for spread of pathology in the brain. Oligomeric forms of both Aβ and tau are acutely neurotoxic and are key features in the neurodegenerative phenotype. Oligomeric Aβ and tau species have been shown to contribute to neurotoxicity through an "infectious" model of disease progression. Extracellular tau aggregates can initiate tau misfolding intracellularly, tau pathology spreads contiguously throughout the brain from early to late stage disease, and brain extract from a transgenic mouse with aggregated mutant human tau transmits tau pathology when introduced into the brains of mice expressing normal human tau. Therefore oligomeric forms of both Aβ and tau are promising early biomarkers to track neuronal damage following TBI.

In a parallel manner to the roles of oligomeric Aβ and tau in AD, numerous studies also indicate that oligomeric aggregates of a-syn cause neuronal toxicity and induce spread of pathology in PD. Different oligomeric variants of a-syn were shown to be toxic to dopaminergic neurons in vivo and in cell models. We have shown that oligomeric but not fibrillar forms of a-syn are toxic to neuronal cells. Toxic oligomeric a-syn forms were identified in living cells and in human plasma from PD patients. Therefore oligomeric a-syn variants are also promising early biomarkers for neuronal damage following TBI that may be indicative of PD and other synucleinopathies. Detection of specific toxic protein variants of Aβ, a-syn or tau has shown promise for diagnosis of AD and PD providing strong precedent that identifying the toxic protein variant fingerprint associated with different neurodegenerative diseases has excellent potential to be a powerful tool to facilitate early diagnosis of specific neurodegenerative diseases and to identify patients at risk of incurring these diseases. While protein variants of Aβ, a-syn and tau have demonstrated value in diagnosing different neurodegenerative diseases, the presence of different variants of a fourth protein, TDP-43, also has promise to sharpen the diagnostic capabilities of the protein variants because of its important role in ALS, FTD and AD. TDP-43 accumulation occurs in different brain regions in ALS and in different types of FTD, suggesting that TDP-43 aggregation can be a useful diagnostic biomarker for these diseases. Presence of TDP-43 inclusions is also evident in a subset of AD cases, primarily in limbic regions where it can overlap with tau pathology. FTD-43 pathology can be induced by increased expression of Aβ providing additional evidence of the link between key aggregation prone proteins in the brain including Aβ, tau, a-syn, and TDP-43. Since tau, Aβ, a-syn, and TDP-43 all play key roles in brain function and neurodegeneration, following is a brief discussion of how each protein contributes to neuronal function and the different protein variants that lead to neurodegeneration.

Tau.

The microtubule associating protein tau is a major component of the neurofibrillary tangles associated with AD and tauopathies that are characterized by hyperphosphorylation and aggregation of tau. Tau plays an important role in assembly and stabilization of microtubules. Tau is a natively unfolded protein, and similar to a number of other natively unfolded proteins, it can aberrantly fold into various aggregate morphologies including β-sheet rich fibrillar forms. The different types of post-translational modifications of tau in AD include phosphorylation, glycosylation, glycation, prolyl-isomerization, cleavage or truncation, nitration, polyamination, ubiquitination, sumoylation, oxidation and aggregation. Tau has 85 putative phosphorylation sites, and excess phosphorylation can interfere with microtubule assembly. Tau can be modified by phosphorylation or by reactive nitrogen and oxygen species among others. Tau is an intrinsically unstructured protein due to its very low hydrophobic content containing a projection domain, a basic proline-rich region, and an assembly domain. Hexapeptide motifs in repeat regions of tau give the protein a propensity to form β-sheet structures which facilitate interaction with tubulin to form microtubules as well as self-interaction to form pathological aggregates such as paired helical filaments (PHF). Hyperphosphorylation of tau, particularly in the assembly domain, decreases the affinity of tau to the microtubules and impairs its ability to regulate microtubule dynamics and axonal transport. In addition, parts of the basic proline-rich domain and the pseudo-repeat also stabilize microtubules by interacting with its negatively charged surface. Alternative splicing of the second, third and tenth exons of tau result in formation of six tau isoforms. The assembly domain in the carboxyl-terminal portion of the protein contains either three or four repeats (3R or 4R) of a conserved tubulin-binding motif depending on alternative splicing of exon 10. Tau 4R isoforms have greater microtubule binding and stabilizing ability than the 3R isoforms. Human adult brains have similar levels of 3R and 4R isoforms, while only 3R tau is expressed at the fetal stage. Mutations altering splicing of tau transcript and the ratio of 3R to 4R tau isoforms are sufficient to cause neurodegenerative disease. Therefore tau in human brain tissue can exist in a variety of different lengths and morphologies and with multiple post-translational modifications.

Tau plays a critical role in the pathogenesis of AD and studies show that reduction of tau levels in AD animal models reverses disease phenotypes and that tau is necessary for the development of cognitive deficits in AD models caused by over-expression of Aβ. While neurofibrillary tangles (NFTs) have been implicated in mediating neurodegeneration in AD and tauopathies, animal models of tauopathy have shown that memory impairment and neuron loss do not associate well with accumulation of NFT. Animal studies showed improvement in memory and reduction in neuron loss despite the accumulation of NFTs, a regional dissociation of neuron loss and NFT pathology, and hippocampal synapse loss and dysfunction and microglial activation months before the accumulation of filamentous tau inclusions. The pathological structures of tau most closely associated with AD progression are tau oligomers. All these studies suggest that tau tangles are not acutely neurotoxic, but rather that pretangle oligomeric tau species are responsible for the neurodegenerative phenotype, similar to toxic role of oligomeric Aβ species.

Numerous studies suggest that extracellular tau species contribute to neurotoxicity through an "infectious" model of disease progression. For example, tau pathology spreads contiguously throughout the brain from early to late stage disease, extracellular tau aggregates can propagate tau misfolding from the outside to the inside of a cell, brain extract from a transgenic mouse with aggregated mutant human tau transmits tau pathology throughout the brain in mice expressing normal human tau, induction of pro-aggregation human tau induces formation of tau aggregates and tangles composed of both human and normal murine tau (coaggregation), and levels of tau rise in CSF in AD, whereas Aβ levels decrease. A receptor-mediated mechanism for the spread of tau pathology by extracellular tau has been identified.

Elevated total tau concentration in CSF has been correlated with AD, as has the presence of various phosphorylated tau forms, and the ratio of tau to Aβ42. Reactive nitrogen and oxygen can modify tau facilitating formation of aggregate forms including oligomeric species. Levels of oligomeric tau have also been implicated as a potential early diagnostic for AD. Therefore, while determination of total tau and phosphorylated tau levels has demonstrated value for diagnosis of AD and other tauopathies, reagents that can selectively recognize the tau species that are most selectively involved in AD and TBI, especially those present in sera samples, would have particular value in early diagnostics of neurodegenerative diseases including tauopathies and AD and assessing neuronal damage and risk of AD in TBI patients.

Aβ.

The principle component of the extracellular neuritic plaques implicated in AD is the β-amyloid protein (Aβ), an approximately 4 kDa fragment proteolytically derived from the larger amyloid precursor protein (APP). A vast amount of literature has implicated Aβ accumulation as being central to the progression of AD, leading to formation of the Aβ hypothesis postulating a central role for Aβ in AD. Mutations or polymorphisms in four genes, APP, Presenilins 1 and 2, and Apolipoprotein E4 were correlated with AD and each of these genes was connected with an increased production or decreased clearance of Aβ, particularly Aβ42. An increased gene dosage of APP resulting from trisomy 21 of Down Syndrome also leads to increased presence of neuritic plaques and AD. Numerous in vitro studies demonstrated the cytotoxicity of aggregated Aβ samples, and defined various conditions that favor aggregation. Despite all the evidence suggesting a strong role of Aβ in the progression of AD, the major weakness of the Aβ hypothesis is that the presence of amyloid plaques does not correlate well with the progression of AD, and considerable controversy exists over the role and mechanism of Aβ in AD. Deterioration of synapse integrity, particularly dendritic arbors, correlates well with dementia, however in animal models of AD fibrillar amyloid deposits were not necessary for synapse loss, and in immunized mice memory loss could be reversed without the removal of amyloid plaques. Small soluble oligomeric Aβ aggregates were shown to be potent neurotoxins suggesting that other non-amyloid aggregate forms of Aβ may be the relevant toxic species in AD, leading to a revised "oligomer Aβ hypothesis".

Many studies have confirmed the role of oligomeric Aβ in AD pathology, although not without considerable confusion. Cortical levels of soluble Aβ correlate well with cognitive impairment and loss of synaptic function. Small, soluble aggregates of Aβ termed Aβ-derived diffusible ligands (ADDLs) and spherical or annular aggregates termed protofibrils were shown to be neurotoxic. Oligomeric forms of Aβ, created in vitro or derived from cell cultures, were shown to inhibit long term potentiation (LTP). Early stage memory loss associated with inhibition of LTP could be reversed by administering anti-Aβ antibodies to transgenic mouse models of AD. The concentration of oligomeric forms of Aβ are also elevated in transgenic mouse models of AD and in AD brain. Disruption of neural connections was shown to occur near Aβ plaques and fibrils, suggesting a toxic role for the fibrillar form, although the disruption also occurred in regions without fibrillar Aβ deposition suggesting that the toxicity may be due to small amounts of oligomeric Aβ, some in equilibrium with the fibrillar form, some existing on their own. A halo of oligomeric Aβ was shown to surround Aβ plaques and correlate with synapse loss. Oligomeric Aβ was also shown to disrupt cognitive function in transgenic animal models of AD. These selected studies, along with many others as a whole, suggest that oligomeric Aβ is involved in synapse failure and early memory loss in AD. In addition, levels of small soluble Aβ aggregates in CSF were shown to correlate with advanced AD cases. Therefore there are numerous studies indicating that various soluble aggregated Aβ species are intimately involved in the neurological decline associated with AD.

A-Syn.

PD is the second most prevalent neurodegenerative disease following AD, affecting around 2% of the people over the age of 65, although the disease progresses over many years. PD results in disturbances in motor function characterized by tremor, rigidity and bradykinesia. A 50 to 70% loss of dopaminergic neurons in the substantia nigra and loss in other regions of the nervous system and the presence of Lewy bodies and Lewy neurites are all indicative of PD. Lewy bodies are intracellular protein inclusions composed of a dense core of filamentous and granular material coated with radially oriented filaments. Lewy neurites contain filaments that are structurally and immunologically similar to those found in Lewy bodies. Lewy body and neurites are present in both peripheral and central neurons in PD and seem to progress in a caudal to rostral fashion; they are likely associated either with neuronal dysfunction or with neuronal death depending on the brain region and the stage of the disease. While most cases of PD are sporadic, or non-familial linked, there are a small percentage of cases that are genetically inherited. From these early onset familial PD cases, several mutations in the a-syn gene have been correlated with PD. The a-syn protein is expressed rather abundantly in brain cells, localizing in the presynaptic terminal and is a major component of Lewy bodies and neurites. Expression levels of a-syn contribute to PD as increased gene expression of wild type a-syn was correlated with early onset cases of PD. Genome Wide Association studies have also confirmed the association of a-syn with sporadic PD. Two other genetic factors that correlate with PD, Parkin, and ubiquitin C-terminal hydrolase L1, are involved in the ubiquitin-proteasome pathway, a clearance system that fails in PD, resulting in the accumulation of heavily ubiquitinated a-syn aggregates. There is considerable controversy over the role that clearance of a-syn plays in PD. Studies indicate that a-syn can be cleared from cells by either the ubiquitin-proteosome system or by the autophagy-lysosomal pathway. The two clearance systems may work in concert with each other as inhibiting clearance of a-syn by one system increases clearance through the other system. A-syn contains a chaperone mediated autophagy sequence that may facilitate translocation across the lysosomal membrane through interaction with the heat shock cognate protein 70 facilitating its degradation. Blocking this clearance mechanism leads to accumulation of insoluble oligomeric a-syn. Mutant forms of a-syn including A30P and A53T that are more prone to aggregation bind more readily to the lysosomal membrane, but are less efficiently internalized providing further evidence that the aggregation state of a-syn is a critical factor in its function and toxicity. The aggregation state of a-syn has been strongly correlated with synucleinopathies including PD and LBD. Aggregated forms of a-syn induce toxicity in dopaminergic neurons in vivo, several different oligomeric morphologies were shown to have different toxic mechanisms and we have shown among others that oligomeric but not fibrillar forms of the protein are neurotoxic. Toxic oligomeric a-syn forms were identified in living cells and in human plasma and CSF from human PD patients. We showed that intracellular targeting and clearance of oligomeric a-syn completely protected mammalian cells against toxicity induced by a-syn overexpression. Oligomeric but not monomeric forms of a-syn induce fragmentation of mitochondria. Monomeric and oligomeric a-syn can also interfere with mitochondrial function by interacting with the endoplasmic reticulum (ER) and inducing stress. Increased levels of a-syn and in particular oligomeric a-syn species can increase Ca+2 influx into cells, which can then promote further aggregation of a-syn. Oligomeric species of a-syn also have been shown to affect neurotransmitters, disrupting the glutamatergic system. Clearly different protein variants of a-syn play key roles in the onset and progression of PD and therefore have great promise as early biomarkers for PD and other synucleinopathies.

TDP-43.

Increasing evidence indicates that aggregates of TDP-43 play a role in FTD, ALS and other neurodegenerative diseases including traumatic brain injury. Similar to other neuronal proteins including Aβ, a-syn and tau, TDP-43 is prone to form aggregate species, where TDP-43 mutations linked to increased risk of sporadic ALS aggregate more readily. Initial studies implicated superoxide dismutase (SOD-1) in ALS, however only a small percentage of ALS cases are linked to mutations in SOD-1 whereas cytoplasmic aggregates of TDP-43, a protein normally primarily located in the nucleus, are found in a vast majority of sporadic ALS cases. TDP-43 is a DNA binding protein which has a number of different alternatively spliced forms. TDP-43 binds to a variety of RNA and DNA sequences, particularly to poly-UG RNA sequences accounting for its location in the nucleus, but it can shuttle back and forth from the cytoplasm. In FTD and ALS cases, affected neurons and glial cells show similar pathology where a variety of different TDP-43 forms accumulate in inclusion bodies in the cytoplasm and/or nucleus with loss of the normal diffuse nuclear distribution. TDP-43 accumulation occurs in different regions with different types of FTD, suggesting that TDP-43 aggregation can be a useful diagnostic biomarker for these diseases. Presence of TDP-43 inclusions is also evident in a subset of AD cases, primarily in limbic regions where it can overlap with tau pathology. TDP-43 co-localizes with stress granules in the cytoplasm following stress and it contains a prion like domain which may account for the ability of TDP-43 pathology to spread from diseased to healthy cells. Increased CSF levels of TDP-43 have been observed in ALS patients providing evidence that toxic TDP variants can spread from cell to cell. TDP-43 aggregates have also been correlated with FTD and AD pathology. Aggregation of TDP-43 in cell cytoplasm is considered to induce toxicity by both a toxic gain of function of the TDP-43 aggregates and a loss of beneficial function of soluble TDP-43 in the nucleus. Stress and aging are both factors that contribute to an increase in production of misfolded and aggregated proteins, which in turn can overwhelm cell clearance mechanisms affecting proteostasis eventually leading to neuronal degeneration. FTD-43 pathology can be induced by increased expression of Aβ providing additional evidence of the link between key aggregation prone proteins in the brain including Aβ, tau, a-syn, and TDP-43. There is therefore substantial evidence that aggregation of TDP-43 is an important factor in FTD, ALS and other neurodegenerative diseases, and detection of specific disease related TDP-43 variants also has great promise as early biomarkers for neurodegenerative diseases including AD, ALS and FTD.

Protein misfolding and aggregation is clearly a critically important feature in neurodegenerative diseases, so determining how concentration profiles of selected key forms and morphologies of tau, Aβ, TDP-43 and a-syn vary in AD, TBI and cognitively normal patients facilitates development of an effective diagnostic assay for these disorders. Different toxic oligomeric aggregates are generated in the brain following TBI increasing the subsequent risk for a spectrum of neurodegenerative disorders including AD, PD, FTD and other dementias. Accurate characterization of which specific protein variants or aggregates are present in tissue and serum samples at different timepoints following TBI provide very powerful biomarkers to both produce a more precise picture of the molecular processes that occur in the brain as a function of time after brain injury and also to facilitate diagnosis and direct appropriate therapeutic strategies for each individual injury case.

Quantification of serum levels of the actual toxic protein variants involved in onset and progression of key neurodegenerative diseases provide a much more sensitive and powerful set of biomarkers to assess neuronal damage following TBI and for early detection and staging of resulting neurodegenerative diseases such as AD that result from TBI. While detection of these specific protein variants has great promise, such studies have not been feasible due to the low concentrations of the target protein variants in CSF and particularly serum samples and the poor specificity of reagents for the different protein species. To overcome this problem, novel technology was developed that combines the imaging capabilities of AFM with the binding diversity of phage display antibody technology which enables allow us to identify the presence of specific protein variants and then isolate reagents that bind the target variant (Barkhordarian, H., et al., Protein Eng Des Sel, 2006. 19(11): p. 497-502). Utilizing this technology antibody based (nanobody) reagents were generated that very selectively recognize different toxic variants of tau, Aβ, TDP-43 and a-syn (Emadi, S., et al., J Mol Biol, 2007. 368(4): p. 1132-44; Barkhordarian, H., et al., Protein Eng Des Sel, 2006; Emadi, S., et al., J Biol Chem, 2009. 284(17): p. 11048-58; Emadi, S., et al., Biochemistry, 2004. 43(10): p. 2871-2878; Zhou, C., et al., Mol Ther, 2004. 10(6): p. 1023-31; Liu, R., et al., Biochemistry, 2004. 43(22): p. 6959-67; Zameer, A., et al., J Mol Biol, 2008. 384(4): p. 917-28; Zameer, A., et al., Biochemistry, 2006. 45(38): p. 11532-9; Kasturirangan, S., et al., Neurobiol Aging, 2012. 33(7): p. 1320-8) Also, a simple novel sandwich ELISA was developed that enables femtomolar or better detection of specific target antigens directly from biological samples including CSF and serum samples. Here a panel of nanobody reagents against variants of tau, Aβ, TDP-43 and a-syn are utilized to demonstrate that different specific protein variant species are generated following TBI depending on the extent and type of injury, and that detection and quantification of these different protein variants may identify patients at high risk of specific neurodegenerative diseases including AD.

There is an urgent need for biomarkers for TBI as S100B he only marker to consistently predict TBI and outcome to date, however S100B has also been implicated in other diseases including AD, diabetes, melanoma and epilepsy. The nanobodies we generated for use here selectively recognize toxic protein variant biomarkers that are associated with specific neurodegenerative diseases, therefore these nanobodies are recognizing biomarkers that are selectively associated with the onset and progression of different types of neuronal damage rather than recognizing a more generic secondary effect such as inflammatory signals, microglial activation or apoptotic markers. Three different nanobodies against different oligomeric Aβ species have been shown to selectively distinguish between AD and PD or healthy samples in post-mortem human tissue (Zameer, A., et al., J Mol Biol, 2008. 384(4): p. 917-28) and CSF samples (Sierks, M. R., et al., Integrative Biology, 2011. 3(12): p. 1188-96). It has similarly been shown that two different nanobodies against different toxic oligomeric a-syn species both selectively distinguish between PD and AD or healthy post-mortem human tissue (Emadi, S., et al., J Mol Biol, 2007. 368(4): p. 1132-44; Emadi, S., et al., J Biol Chem, 2009. 284(17): p. 11048-58) and CSF samples (Sierks, M. R., et al., Integrative Biology, 2011. 3(12): p. 1188-96). It has also been shown that nanobodies against a toxic trimeric tau species distinguish AD from healthy post-mortem human tissue, and that we can generate nanobodies against TDP-43 variants that distinguish ALS and FTD post-mortem human tissue samples from healthy samples.

As described below a bank of well characterized serum samples from taken from patients show incurred different severities of TBI taken at various acute (up to 24 hours after injury) and chronic (12-36 months) time points following injury was established. The results show that it was possible to readily distinguish and stage progression of neurodegenerative diseases when using particular nanobodies to assay post-mortem tissue, CSF and serum samples. The results also show the ability to readily distinguish longitudinal serum samples from patients subsequently diagnosed with AD from aged matched cognitively normal patients. The results readily detect oligomeric Aβ in sera samples of patients that converted to AD at least seven years prior to initial diagnosis of mild-cognitive impairment (MCI) providing strong precedent for a blood based presymptomatic diagnosis of AD. The results also show that nanobodies against an AD variant of TDP-43 can also readily distinguish AD serum samples from controls. Finally, the results show the ability to detect the presence of neurodegenerative disease related variants of tau, Aβ, a-syn and TDP-43 in serum samples from patients that have suffered severe acute TBI, and that different patients show distinctly different protein variant fingerprints, some indicative of AD, others indicative of PD or FTD. These results indicate that distinctly different cellular processes occur in individual patients after suffering TBI, the different cellular process leave distinct protein variant fingerprints and that these fingerprints may indicate increased risk for specific neurodegenerative diseases. Since all the nanobodies used here recognize protein variants that are found in different diseased but not healthy samples, these nanobodies have great utility as presymptomatic biomarkers for different neurodegenerative diseases, and to identify individuals who are susceptible to AD following TBI.

Designed Ankyrin Repeat Proteins

DARPins (designed ankyrin repeat proteins) are genetically engineered non-immunoglobulin antibody-mimetic proteins that offer advantages over antibodies for target binding in drug discovery and drug development. DARPins have been successfully used, for example, for the inhibition of kinases, proteases and drug-exporting membrane proteins. DARPins typically exhibiting highly specific and high-affinity target protein binding. They are derived from natural ankyrin proteins and consist of at least three, usually four or five repeat motifs of these proteins. Their molecular mass is about 14 or 18 kDa (kilodaltons) for four- or five-repeat DARPins, respectively.

Naturally occurring ankyrin proteins form a class of proteins that mediate high-affinity protein-protein interactions in nature. Several thousand natural ankyrin repeat motifs (of about 33 amino acids each) are known, and can be combined with structure based design and recombinant DNA methods for generation of novel proteins. These repetitive structural units form a stable DARPin protein domain with a large potential target interaction surface. Typically, DARPins are composed of four or five repeats, corresponding to the average size of natural ankyrin repeat protein domains. Proteins with less than three repeats do not form a tertiary structure. Libraries of DARPins with randomized potential target interaction residues with diversities of over $10^{12}$ variants have been generated at the DNA level. From these libraries, DARPins binding the target of choice with picomolar affinity and specificity can be selected using ribosome display or signal recognition particle (SRP) phage display.

DARPins can be designed to act as receptor agonists, antagonists, inverse agonists, enzyme inhibitors, or simple target protein binders. The DARPins exhibit high thermal and thermodynamic stability (denaturation midpoint: Tm>66° C., equilibrium unfolding: ΔG>9.5 kcal/mol), which increases with increasing repeat number. DARPins are stable in human blood serum and do not contain T-cell epitopes. The high specificity and affinity of binding DARPins has been attributed rigid body binding mode. Multi-specific or multi-valent constructs made by genetic fusion show similar properties as single domain DARPins. The absence of cysteines in the scaffold enables engineering of site-specific cysteines, allowing site-directed coupling of chemicals to the molecule.

In certain embodiments, the present invention provides a designed ankyrin repeat protein (DARPin) comprising
(a) an N-Terminal Capping ankyrin repeat (AR),
(b) a C-Terminal Capping AR, and
(c) three to six AR modules of about 30 to 35 amino acids, wherein each AR module binds with a target.

N-Terminal Capping AR
(SEQ ID NO: 30)
5'-tTCCGCccatggACCTGGGTAAGAAACTGCTGGAAGCTGCTCGTGC

TGGTCAGGACGACGAAGTTCGTATCCTGATGGCTAACGGTGCTGACGTT

GTCTTCTAGgcggccgcCCCAAA-3'

C-Terminal Capping AR
(SEQ ID NO: 31)
5'-TTCCGCccatggTAGGAAGACCTGACGTTAACGCTCAGGACAAATTC

GGTAAGACCGCTTTCGACATCTCCATCGACAACGGTAACGAGGACCTGG

CTGAAATCCTGCAAgcggccgcCCCAAA-3'

In certain embodiments, all of the AR modules are the same. In certain embodiments, one or more of the AR modules differ. In certain embodiments, an AR modules bind with TDP-43, tau, abeta or alpha-synuclein.

In certain embodiments, the DARPin is encoded by a sequence having at least 90% sequence identity of any one of SEQ ID NO:7-28. In certain embodiments, the DARPin is encoded by a sequence having at least 91%, 92%, 93%, 94%, 95%, 96%, 97%, 98%, 99%, or even 100% sequence identity of any one of SEQ ID NO:7-28.

A "variant" of an amino acid sequence of a ligand or ligand fragment described herein, or a nucleic acid sequence encoding such an amino acid sequence, is a sequence that is substantially similar to SEQ ID NO:1-28. Variant amino acid and nucleic acid sequences include synthetically derived amino acid and nucleic acid sequences, or recombinantly derived amino acid or nucleic acid sequences. Generally, amino acid or nucleic acid sequence variants of the invention will have at least 40, 50, 60, to 70%, e.g., 71%, 72%, 73%, 74%, 75%, 76%, 77%, 78%, to 79%, generally at least 80%, e.g., 81%-84%, at least 85%, e.g., 86%, 87%, 88%, 89%, 90%, 91%, 92%, 93%, 94%, 95%, 96%, 97%, to 98%, sequence identity to SEQ ID NO: 1-28. The present invention includes variants of the amino acid sequences of the antibodies and antibody fragments described herein, as well as variants of the nucleic acid sequences encoding such amino acid sequences (i.e., SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, or SEQ ID NO:28).

"Variants" are intended to include sequences derived by deletion (so-called truncation) or addition of one or more amino acids to the N-terminal and/or C-terminal end, and/or addition of one or more bases to the 5' or 3' end of the nucleic acid sequence; deletion or addition of one or more amino acids/nucleic acids at one or more sites in the sequence; or substitution of one or more amino acids/nucleic acids at one or more sites in the sequence. The DARPins described herein may be altered in various ways including amino acid substitutions, deletions, truncations, and insertions. Methods for such manipulations are generally known in the art. For example, amino acid sequence variants can be prepared by mutations in the DNA. Methods for mutagenesis and nucleotide sequence alterations are well known in the art. The substitution may be a conserved substitution. A "conserved substitution" is a substitution of an amino acid with another amino acid having a similar side chain. A conserved substitution would be a substitution with an amino acid that makes the smallest change possible in the charge of the amino acid or size of the side chain of the amino acid (alternatively, in the size, charge or kind of chemical group within the side chain) such that the overall protein retains its spatial conformation but does not alter its biological activity. For example, common conserved changes might be Asp to Glu, Asn or Gln; His to Lys, Arg or Phe; Asn to Gln, Asp or Glu and Ser to Cys, Thr or Gly. Alanine is commonly used to substitute for other amino acids. The 20 essential amino acids can be grouped as follows: alanine, valine, leucine, isoleucine, proline, phenylalanine, tryptophan and methionine having nonpolar side chains; glycine, serine, threonine, cystine, tyrosine, asparagine and glutamine having uncharged polar side chains; aspartate and glutamate having acidic side chains; and lysine, arginine, and histidine having basic side chains.

As used herein, "sequence identity" or "identity" in the context of two nucleic acid or polypeptide sequences makes reference to a specified percentage of residues in the two sequences that are the same when aligned for maximum correspondence over a specified comparison window, as measured by sequence comparison algorithms or by visual inspection. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity." Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif.).

Nucleic Acids and Vectors

In certain embodiments, the present invention provides a nucleic acid encoding the DARPin described herein.

In certain embodiments, the present invention provides a vector comprising the nucleic acid described herein.

In certain embodiments, the vector is a pIT2 vector. In certain embodiments, the pIT2 vector lacks a BsaI restriction site. In certain embodiments, the vector lacks a PelB signal and comprises a DsbA signal.

In certain embodiments, the present invention provides a phage comprising the vector described herein.

As used herein, the term "nucleic acid" and "polynucleotide" refers to deoxyribonucleotides or ribonucleotides and polymers thereof in either single- or double-stranded form, composed of monomers (nucleotides) containing a sugar, phosphate and a base that is either a purine or pyrimidine. Unless specifically limited, the term encompasses nucleic acids containing known analogs of natural nucleotides which have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions) and complementary sequences as well as the sequence explicitly indicated. Specifically, degenerate codon substitutions may be achieved by generating sequences in which the third position of one or more selected (or all) codons is substituted with mixed-base and/or deoxyinosine residues.

A "nucleic acid fragment" is a portion of a given nucleic acid molecule. Deoxyribonucleic acid (DNA) in the majority of organisms is the genetic material while ribonucleic acid (RNA) is involved in the transfer of information contained within DNA into proteins. The term "nucleotide sequence" refers to a polymer of DNA or RNA which can be single- or double-stranded, optionally containing synthetic, non-natural or altered nucleotide bases capable of incorporation into DNA or RNA polymers.

The terms "nucleic acid," "nucleic acid molecule," "nucleic acid fragment," "nucleic acid sequence or segment," or "polynucleotide" may also be used interchangeably with gene, cDNA, DNA and RNA encoded by a gene, e.g., genomic DNA, and even synthetic DNA sequences. The term also includes sequences that include any of the known base analogs of DNA and RNA.

By "fragment" or "portion" is meant a full length or less than full length of the nucleotide sequence.

A "variant" of a molecule is a sequence that is substantially similar to the sequence of the native molecule. For nucleotide sequences, variants include those sequences that, because of the degeneracy of the genetic code, encode the identical amino acid sequence of the native protein. Naturally occurring allelic variants such as these can be identified with the use of well-known molecular biology techniques, as, for example, with polymerase chain reaction (PCR) and hybridization techniques. Variant nucleotide sequences also include synthetically derived nucleotide sequences, such as those generated, for example, by using site-directed mutagenesis that encode the native protein, as well as those that encode a polypeptide having amino acid substitutions. Generally, nucleotide sequence variants of the invention will have in at least one embodiment 40%, 50%, 60%, to 70%, e.g., 71%, 72%, 73%, 74%, 75%, 76%, 77%, 78%, to 79%, generally at least 80%, e.g., 81%-84%, at least 85%, e.g., 86%, 87%, 88%, 89%, 90%, 91%, 92%, 93%, 94%, 95%, 96%, 97%, to 98%, sequence identity to the native (endogenous) nucleotide sequence.

As used herein, "sequence identity" or "identity" in the context of two nucleic acid sequences makes reference to a specified percentage of residues in the two sequences that are the same when aligned by sequence comparison algorithms or by visual inspection.

As used herein, "percentage of sequence identity" means the value determined by comparing two optimally aligned sequences, wherein the portion of the polynucleotide sequence may comprise additions or deletions (i.e., gaps) as compared to the reference sequence (which does not comprise additions or deletions) for optimal alignment of the two sequences. The percentage is calculated by determining the number of positions at which the identical nucleic acid base occurs in both sequences to yield the number of matched positions, dividing the number of matched positions by the total number of positions in the window of comparison, and multiplying the result by 100 to yield the percentage of sequence identity.

The term "substantial identity" of polynucleotide sequences means that a polynucleotide comprises a sequence that has at least 70%, 71%, 72%, 73%, 74%, 75%, 76%, 77%, 78%, or 79%; at least 80%, 81%, 82%, 83%, 84%, 85%, 86%, 87%, 88%, or 89%; at least 90%, 91%, 92%, 93%, or 94%; or even at least 95%, 96%, 97%, 98%, or 99% sequence identity, compared to a reference sequence using one of the alignment programs described using standard parameters.

Another indication that nucleotide sequences are substantially identical is if two molecules hybridize to each other under stringent conditions (see below). Generally, stringent conditions are selected to be about 5° C. lower than the thermal melting point ($T_m$) for the specific sequence at a defined ionic strength and pH. However, stringent conditions encompass temperatures in the range of about 1° C. to about 20° C., depending upon the desired degree of stringency as otherwise qualified herein. Nucleic acids that do not hybridize to each other under stringent conditions are still substantially identical if the polypeptides they encode are substantially identical. This may occur, e.g., when a copy of a nucleic acid is created using the maximum codon degeneracy permitted by the genetic code.

As noted above, another indication that two nucleic acid sequences are substantially identical is that the two molecules hybridize to each other under stringent conditions. The phrase "hybridizing specifically to" refers to the binding, duplexing, or hybridizing of a molecule only to a particular nucleotide sequence under stringent conditions when that sequence is present in a complex mixture (e.g., total cellular) DNA or RNA. "Bind(s) substantially" refers to complementary hybridization between a probe nucleic acid and a target nucleic acid and embraces minor mismatches that can be accommodated by reducing the stringency of the hybridization media to achieve the desired detection of the target nucleic acid sequence.

"Stringent hybridization conditions" and "stringent hybridization wash conditions" in the context of nucleic acid hybridization experiments such as Southern and Northern hybridizations are sequence dependent, and are different under different environmental parameters. Longer sequences hybridize specifically at higher temperatures. The $T_m$ is the temperature (under defined ionic strength and pH) at which 50% of the target sequence hybridizes to a perfectly matched nucleic acid. Specificity is typically the function of post-hybridization washes, the critical factors being the ionic strength and temperature of the final wash solution. For DNA-DNA hybrids, the $T_m$ can be approximated from the equation of Meinkoth and Wahl: $T_m$ 81.5° C.+16.6 (log M)+0.41 (% GC)−0.61 (% form)−500/L. M is the molarity of monovalent cations, % GC is the percentage of guanosine and cytosine nucleotides in the DNA, % form is the percentage of formamide in the hybridization solution, and L is the length of the hybrid in base pairs. $T_m$ is reduced by about 1° C. for each 1% of mismatching; thus, $T_m$, hybridization, and/or wash conditions can be adjusted to hybridize to sequences of the desired identity. For example, if sequences with >90% identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3, or 4° C. lower than the thermal melting point ($T_m$); moderately stringent conditions can utilize a hybridization and/or wash at 6, 7, 8, 9, or 10° C. lower than the thermal melting point ($T_m$); low stringency conditions can utilize a hybridization and/or wash at 11, 12, 13, 14, 15, or 20° C. lower than the thermal melting point ($T_m$). Using the equation, hybridization and wash compositions, and desired T, those of ordinary skill will understand that variations in the stringency of hybridization and/or wash solutions are inherently described. If the desired degree of mismatching results in a T of less than 45° C. (aqueous solution) or 32° C. (formamide solution), it is preferred to increase the SSC concentration so that a higher temperature can be used. Generally, highly stringent hybridization and wash conditions are selected to be about 5° C. lower than the thermal melting point ($T_m$) for the specific sequence at a defined ionic strength and pH.

An example of highly stringent wash conditions is 0.15 M NaCl at 72° C. for about 15 minutes. An example of stringent wash conditions is a 0.2×SSC wash at 65° C. for 15 minutes. Often, a high stringency wash is preceded by a low stringency wash to remove background probe signal. An example medium stringency wash for a duplex of, e.g., more than 100 nucleotides, is 1×SSC at 45° C. for 15 minutes. An example low stringency wash for a duplex of, e.g., more than 100 nucleotides, is 4-6×SSC at 40° C. for 15 minutes. For short probes (e.g., about 10 to 50 nucleotides), stringent conditions typically involve salt concentrations of less than about 1.5 M, more preferably about 0.01 to 1.0 M, Na ion concentration (or other salts) at pH 7.0 to 8.3, and the temperature is typically at least about 30° C. and at least about 60° C. for long probes (e.g., >50 nucleotides). Stringent conditions may also be achieved with the addition of destabilizing agents such as formamide. In general, a signal to noise ratio of 2× (or higher) than that observed for an unrelated probe in the particular hybridization assay indicates detection of a specific hybridization.

Very stringent conditions are selected to be equal to the $T_m$ for a particular probe. An example of stringent conditions for hybridization of complementary nucleic acids which have more than 100 complementary residues on a filter in a Southern or Northern blot is 50% formamide, e.g., hybridization in 50% formamide, 1 M NaCl, 1% SDS at 37° C., and a wash in 0.1×SSC at 60 to 65° C. Exemplary low stringency conditions include hybridization with a buffer solution of 30 to 35% formamide, 1M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1.0 M NaCl, 1% SDS at 37° C., and a wash in 0.5× to 1×SSC at 55 to 60° C.

"Operably-linked" nucleic acids refers to the association of nucleic acid sequences on single nucleic acid fragment so that the function of one is affected by the other, e.g., an arrangement of elements wherein the components so described are configured so as to perform their usual function. For example, a regulatory DNA sequence is said to be "operably linked to" or "associated with" a DNA sequence that codes for an RNA or a polypeptide if the two sequences are situated such that the regulatory DNA sequence affects expression of the coding DNA sequence (i.e., that the coding sequence or functional RNA is under the transcriptional control of the promoter). Coding sequences can be operably-linked to regulatory sequences in sense or anti sense orientation. Control elements operably linked to a coding sequence are capable of effecting the expression of the coding sequence. The control elements need not be contiguous with the coding sequence, so long as they function to direct the expression thereof. Thus, for example, intervening untranslated yet transcribed sequences can be present between a promoter and the coding sequence and the promoter can still be considered "operably linked" to the coding sequence.

The terms "isolated and/or purified" refer to in vitro isolation of a nucleic acid, e.g., a DNA or RNA molecule from its natural cellular environment, and from association with other components of the cell or test solution (e.g. RNA pool), such as nucleic acid or polypeptide, so that it can be sequenced, replicated, and/or expressed. For example, "isolated nucleic acid" may be a DNA molecule containing less than 31 sequential nucleotides that is transcribed into an RNAi molecule. Such an isolated RNAi molecule may, for example, form a hairpin structure with a duplex 21 base pairs in length that is complementary or hybridizes to a sequence in a gene of interest, and remains stably bound under stringent conditions (as defined by methods well known in the art, e.g., in Sambrook and Russell, 2001). Thus, the RNA or DNA is "isolated" in that it is free from at least one contaminating nucleic acid with which it is normally associated in the natural source of the RNA or DNA and is preferably substantially free of any other mammalian RNA or DNA. The phrase "free from at least one contaminating source nucleic acid with which it is normally associated" includes the case where the nucleic acid is reintroduced into the source or natural cell but is in a different chromosomal location or is otherwise flanked by nucleic acid sequences not normally found in the source cell, e.g., in a vector or plasmid.

Nucleic acid molecules having base substitutions (i.e., variants) are prepared by a variety of methods known in the art. These methods include, but are not limited to, isolation from a natural source (in the case of naturally occurring sequence variants) or preparation by oligonucleotide-mediated (or site-directed) mutagenesis, PCR mutagenesis, and cassette mutagenesis of an earlier prepared variant or a non-variant version of the nucleic acid molecule.

"Operably-linked" refers to the association of nucleic acid sequences on single nucleic acid fragment so that the function of one of the sequences is affected by another. For example, a regulatory DNA sequence is said to be "operably linked to" or "associated with" a DNA sequence that codes for an RNA or a polypeptide if the two sequences are situated such that the regulatory DNA sequence affects expression of the coding DNA sequence (i.e., that the coding sequence or functional RNA is under the transcriptional control of the promoter). Coding sequences can be operably-linked to regulatory sequences in sense or antisense orientation.

As used herein, the term "derived" or "directed to" with respect to a nucleotide molecule means that the molecule has complementary sequence identity to a particular molecule of interest.

In certain embodiments, the expression cassette further contains a promoter. In certain embodiments, the promoter is a regulatable promoter. In certain embodiments, the promoter is a constitutive promoter. In certain embodiments, the promoter is a PGK, CMV or RSV promoter.

The present invention provides a vector containing the expression cassette described above. Expression vectors include, but are not limited to, viruses, plasmids, and other vehicles for delivering heterologous genetic material to cells. Accordingly, the term "expression vector" as used herein refers to a vehicle for delivering heterologous genetic material to a cell. In particular, the expression vector is a recombinant adenoviral, adeno-associated virus, or lentivirus or retrovirus vector. In certain embodiments, the viral vector is an adenoviral, lentiviral, adeno-associated viral (AAV), poliovirus, HSV, or murine Maloney-based viral vector.

"Expression cassette" as used herein means a nucleic acid sequence capable of directing expression of a particular nucleotide sequence in an appropriate host cell, which may include a promoter operably linked to the nucleotide sequence of interest that may be operably linked to termination signals. It also may include sequences required for proper translation of the nucleotide sequence. The coding region usually codes for a protein of interest. The expression cassette including the nucleotide sequence of interest may be chimeric. The expression cassette may also be one that is naturally occurring but has been obtained in a recombinant form useful for heterologous expression. The expression of the nucleotide sequence in the expression cassette may be under the control of a constitutive promoter or of a regulatable promoter that initiates transcription only when the host cell is exposed to some particular stimulus. In the case of a multicellular organism, the promoter can also be specific to a particular tissue or organ or stage of development.

Binding Molecules

As used herein, the term "binding molecule" includes antibodies, which includes scFvs (also called a "nanobodies"), humanized, fully human or chimeric antibodies, single-chain antibodies, diabodies, and antigen-binding fragments of antibodies (e.g., Fab fragments), and DARPins.

In certain embodiments, the binding molecule does not contain the constant domain region of an antibody.

In certain embodiments, the binding molecule is less than 500 amino acids in length, such as between 200-450 amino acids in length, or less than 400 amino acids in length.

In certain embodiments, the antibodies that are used in the present invention are those described in WO 2012/058308 (amyloid β-protein (Aβ or beta amyloid)); WO 2012/082237 (amyloid β-protein (Aβ or beta amyloid)); WO 2014/059442 (tau).

In certain embodiments, the binding molecule specifically recognizes TDP-43 associated with frontotemporal dementia (FTD), but not TDP-43 associated with amyotrophic lateral sclerosis (ALS) or TDP-43 associated with healthy human brain tissue.

In certain embodiments, the binding molecule that specifically recognizes TDP-43 associated with amyotrophic lateral sclerosis (ALS), but not TDP-43 associated with frontotemporal dementia (FTD) or TDP-43 associated with healthy human brain tissue.

In certain embodiments, the binding molecule binds to TDP-43 associated with ALS and does not bind TDP-43 from healthy human brain tissue or TDP-43 associated with FTD. In certain embodiments, the binding molecule comprises an amino acid sequence encoded by a nucleic acid, wherein the nucleic acid has at least 80% identity to SEQ ID NO:1, SEQ ID NO:2, SEQ ID NO:3, SEQ ID NO:4, SEQ ID NO:5, or SEQ ID NO:6.

SEQ ID NO: 1

```
5'-CCATGGCCGAGGTGCAGCTGTTGGAGTCTGGGGGAGGCTTGGTACA
GCCTGGGGGGTCCCCGAGACTCTCCTGTGCAGCCTCTGGATTCACCTTT
AGCAGCTATGCCATGAGCTGGGTCCGCCAGGCTCCAGGGAAGGGGCTGG
AGTGGGTCTCAACTATTTCTGCTTCTGGTACTTATACAAATTACGCAGA
CTCCGTGAAGGGCCGGTTCACCATCTCCAGAGACAATTCCAAGAACACG
CTGTATCTGCAAATGAACAGCCTGAGAGCCGAGGACACGGCCGTATATT
ACTGTGCGAAAACTTCTTCTTATTTTGACTACTGGGGCCAGGGAACCCT
GGTCACCGTCTCGAGCGGTGGAGGCGGTTCAGGCGGAGGTGGCAGCGGC
GGTGGCGGGTCGACGGACATCCAGATGACCCAGTCTCCATCCTCCCTGT
CTGCATCTGTAGGAGACAGAGTCACCATCACTTGCCGGGCAAGTCAGAG
CATTAGCAGCTATTTAAATTGGTATCAGCAGAAACCAGGGAAAGCCCCT
AAGCTCCTGATCTATGCTGCATCCAATTTGCAAAGTGGGGTCCCATCAA
GGTTCAGTGGCAGTGGATCTGGGACAGATTTCACTCTCACCATCAGCAG
TCTGCAACCTGAAGATTTTGCAACTTACTACTGTCAACAGGATAATTAT
```

GCTCCTTATACGTTCGGCCAAGGGACCAAGGTGGAAATCAAACGGGCGG

CCGC-3'

SEQ ID NO: 2
5'-CCATGGCCGAGGTGCAGCTGTTGGAGTCTGGGGGAGGCTTGGTACA

GCCTGGGGGTCCCTGAGACTCTCCTGTGCAGCCTCTGGATTCACCTTT

AGCAGCTATGCCATGAGCTGGGTCCGCCAGGCTCCAGGGAAGGGGCTGG

AGTGGGTCTCAACTATTCGCCATGCTGGTCAGTCGACGGACATCCAGAT

GACCCAGTCTCCATCCTCCCTGTCTGCATCTGTAGGAGACAGAGTCACC

ATCACTTGCCGGGCAAGTCAGAGCATTAGCAGCTATTTAAATTGGTATC

AGCAGAAACCAGGGAAAGCCCCTAAGCTCCTGATCTATATGGCATCCCG

TTTGCAAAGTGGGGTCCCATCAAGGTTCAGTGGCAGTGGATCTGGGACA

GATTTCACTCTCACCATCAGCAGTCTGCAACCTGAAGATTTTGCAACTT

ACTACTGTCAACAGCAGCGTACGAAGCCTCCTACGTTCGGCCAAGGGAC

CAAGGTGGAAATCAAACGGGCGGCCGC-3'

SEQ ID NO: 3
5'-CCATGGCCGAGGTGCAGCTGTTGGAGTCTGGGGGAGGCTTGGTACA

GCCTGGGGGTCCCTGAGACTCTCCTGTGCAGCCTCTGGATTCACCTTT

AGCAGCTATGCCATGAGCTGGGTCCGCCAGGCTCCAGGGAAGGGGCTGG

AGTGGGTCTCAACTATTGCTTCTGCTGGTACTGATACAGCTTACGCAGA

CTCCGTGAAGGGCCGGTTCACCATCTCCAGAGACAATTCCAAGAACACG

CTGTATCTGCAAATGAACAGCCTGAGAGCCGAGGACACGGCCGTATATT

ACTGTGCGAAAGATACTACTGCTTTTGACTACTGGGGCCAGGGAACCCT

GGTCACCGTCTCGAGCGGTGGAGGCGGTTCAGGCGGAGGTGGCAGCGGC

GGTGGCGGGTCGACGGACATCAAGATGACCCAGTCTCCATCCTCCCTGT

CTGCATCTGTAGGAGACAGAGTCACCATCACTTGCCGGGCAAGTCAGAG

CATTAGCAGCTATTTAAATTGGTATCAGCAGAAACCAGGGAAAGCCCCT

AAGCTCCTGATCTATGATGCATCCACTTTGCAAAGTGGGGTCCCATCAA

GGTTCAGTGGCAGTGGATCTGGGACAGATTTCACTCTCACCATCAGCAG

TCTGCAACCTGAAGATTTTGCAACTTACTACTGTCAACAGTCTACTTAT

GCTCCTGCTACGTTCGGCCAAGGGACCAAGGTGGAAATCAAACGGGCGG

CCGC-3'

SEQ ID NO: 4
5'-CCATGGCCGAGGTGTTTGACTACTGGGGCCAGGGAACCCTGGTCAC

CGTCTCGAGCGGTGGAGGCGGTTCAGGCGGAGGTGGCAGCGGCGGTGGC

GGGTCGACGGACATCCAGATGACCCAGTCTCCATCCTCCCTGTCTGCAT

CTGTAGGAGACAGAGTCACCATCACTTGCCGGGCAAGTCAGAGCATTAG

CAGCTATTTAAATTGGTATCAGCAGAAACCAGGGAAAGCCCCTAAGCTC

CTGATCTATTCTGCATCCAATTTGCAAAGTGGGGTCCCATCAAGGTTCA

GTGGCAGTGGATCTGGGACAGATTTCACTCTCACCATCAGCAGTCTGCA

ACCTGAAGATTTTGCAACTTACTACTGTCAACAGAGTTATTCTAGTCCT

TCTACGTTCGGCCAAGGGACCAAGGTGGAAATCAAACGGGCGGCCG

C-3'

SEQ ID NO: 5
5'-CCATGGCCGAGGTGCAGCTGTTGGAGTCTGGGGGAGGCTTGGTACA

GCCTGGGGGTCCCTGAGACTCTCCTGTGCAGCCTCTGGATTCACCTTT

AGCAGCTATGCCATGAGCTGGGTCCGCCAGGCTCCAGGGAAGGGGCTGG

AGTGGGTCTCATCTATTAATAATGCTGGTATGATACAAATTACGCAGAC

TCCGTGAAGGGCAGGTTCACCATCTCCAGAGACAATTCCAAGAACACGC

TGTATCTGCAAATGAACAGCCTGAGAGCCGAGGACACGGCCGTATATTA

CTGTGCGAAAAATAATGCTTATTTTGACTACTGGGGCCAGGGAACCCTG

GTCACCGTCTCGAGCGGTGGAGGCGGTTCAGGCGGAGGTGGCAGCGGCG

GTGGCGGGTCGACGGACATCCAGATGACCCAGTCTCCATCCTCCCTGTC

TGCATCTGTAGGAGACAGAGTCACCATCACTTGCCGGGCAAGTCAGAGC

ATTAGCAGCTATTTAAATTGGTATCAGCAGAAACCAGGGAAAGCCCCTA

AGCTCCTGATCTATGGTGCATCCAGTTTGCAAAGTGGGGTCCCATCAAG

GTTCAGTGGCAGTGGATCTGGGACAGATTTCACTCTCACCATCAGCAGT

CTGCAACCTGAAGATTTTGCAACTTACTACTGTCAACAGTATGATTCTG

CTCCTGGTACGTTCGGCCAAGGGACCAAGGTGGAAATCAAACGGGCGGC

CGC-3'

SEQ ID NO: 6
5'-CCATGGCCGAGGTGCAGCTGTTGGAGTCTGGGGGAGGCTTGGTACA

GCCTGGGGGTCCCTGAGACTCTCCTGTGCAGCCTCTGGATTCACCTTT

AGCAGCTATGCCATGAGCTGGGTCCGCCAGGCTCCAGGGAAGGGGCTGG

AGTGGGTCTCAACTATTAATAATAGTGGTACTTCTACAAATTACGCAGA

CTCCGTGAAGGGCCGGTTCACCATCTCCAGAGACAATTCCAAGAACACG

CTGTATCTGCAAATGAACAGCCTGAGAGCCGAGGACACGGCCGTATATT

ACTGTGCGAAAAGTACTAATTATTTTGACTACTGGGGCCAGGGAACCCT

GGTCACCGTCTCGAGCGGTGGAGGCGGTTCAGGCGGAGGTGGCAGCGGC

GGTGGCGGGTCGACGGACATCCAGATGACCCAGTCTCCATCCTCCCTGT

CTGCATCTGTAGGAGACAGAGTCACCATCACTTGCCGGGCAAGTCAGAG

CATTAGCAGCTATTTAAATTGGTATCAGCAGAAACCAGGGAAAGCCCCT

AAGCTCCTGATCTATGCTGCATCCAGTTTGCAAAGTGGGGTCCCATCAA

GGTTCAGTGGCAGTGGATCTGGGACAGATTTCACTCTCACCATCAGCAG

TCTGCAACCTGAAGATTTTGCAACTTACTACTGTCAACAGAATGCTGCT

GATCCTACTACGTTCGGCCAAGGGACCAAGGTGGAAATCAAACGGGCGG

CCGC-3'

Detection Reagents and Assays

For purposes of the diagnostic methods of the invention, the compositions or ligand of the invention (e.g., binding molecule such as an antibody or DARPin) may be conjugated to a detecting reagent that facilitates detection of the ligand. For example, example, the detecting reagent may be a direct label or an indirect label. The labels can be directly attached to or incorporated into the detection reagent by chemical or recombinant methods.

In one embodiment, a label is coupled to the ligand through a chemical linker. Linker domains are typically polypeptide sequences, such as poly gly sequences of between about 5 and 200 amino acids. In some embodiments, proline residues are incorporated into the linker to prevent the formation of significant secondary structural elements by the linker. In certain embodiments, linkers are flexible amino acid subsequences that are synthesized as part of a recombinant fusion protein comprising the RNA recognition domain. In one embodiment, the flexible linker is an amino acid subsequence that includes a proline, such as Gly(x)-Pro-Gly(x) where x is a number between about 3 and about 100. In other embodiments, a chemical linker is used to connect synthetically or recombinantly produced recognition and labeling domain subsequences. Such flexible linkers are known to persons of skill in the art. For example, poly(ethylene glycol) linkers are available from Shearwater Polymers, Inc. Huntsville, Ala. These linkers optionally have amide linkages, sulfhydryl linkages, or heterofunctional linkages.

The detectable labels can be used in the assays of the present invention to diagnose TBI, these labels are attached to the ligand of the invention, can be primary labels (where the label comprises an element that is detected directly or that produces a directly detectable element) or secondary labels (where the detected label binds to a primary label, e.g., as is common in immunological labeling). An introduction to labels, labeling procedures and detection of labels is found in Polak and Van Noorden (1997) Introduction to Immunocytochemistry, 2nd ed., Springer Verlag, N.Y. and in Haugland (1996) Handbook of Fluorescent Probes and Research Chemicals, a combined handbook and catalogue Published by Molecular Probes, Inc., Eugene, Oreg. Patents that described the use of such labels include U.S. Pat. Nos. 3,817,837; 3,850,752; 3,939,350; 3,996,345; 4,277,437; 4,275,149; and 4,366,241.

Primary and secondary labels can include undetected elements as well as detected elements. Useful primary and secondary labels in the present invention can include spectral labels such as green fluorescent protein, fluorescent dyes (e.g., fluorescein and derivatives such as fluorescein isothiocyanate (FITC) and Oregon Green™, rhodamine and derivatives (e.g., Texas red, tetrarhodimine isothiocynate (TRITC), etc.), digoxigenin, biotin, phycoerythrin, AMCA, CyDyes™, and the like), radiolabels (e.g., $^3H$, $^{125}I$, $^{35}S$, $^{14}C$, $^{32}P$, $^{33}P$, etc.), enzymes (e.g., horse radish peroxidase, alkaline phosphatase etc.), spectral calorimetric labels such as colloidal gold or colored glass or plastic (e.g. polystyrene, polypropylene, latex, etc.) beads. The label can be coupled directly or indirectly to a component of the detection assay (e.g., the detection reagent) according to methods well known in the art. As indicated above, a wide variety of labels may be used, with the choice of label depending on sensitivity required, ease of conjugation with the compound, stability requirements, available instrumentation, and disposal provisions.

Exemplary labels that can be used include those that use: 1) chemiluminescence (using horseradish peroxidase and/or alkaline phosphatase with substrates that produce photons as breakdown products as described above) with kits being available, e.g., from Molecular Probes, Amersham, Boehringer-Mannheim, and Life Technologies/Gibco BRL; 2) color production (using both horseradish peroxidase and/or alkaline phosphatase with substrates that produce a colored precipitate (kits available from Life Technologies/Gibco BRL, and Boehringer-Mannheim)); 3) fluorescence using, e.g., an enzyme such as alkaline phosphatase, together with the substrate AttoPhos (Amersham) or other substrates that produce fluorescent products, 4) fluorescence (e.g., using Cy-5 (Amersham), fluorescein, and other fluorescent tags); 5) radioactivity. Other methods for labeling and detection will be readily apparent to one skilled in the art.

Where the ligand-based compositions of the invention are contemplated to be used in a clinical setting, the labels are preferably non-radioactive and readily detected without the necessity of sophisticated instrumentation. In certain embodiments, detection of the labels will yield a visible signal that is immediately discernable upon visual inspection. One example of detectable secondary labeling strategies uses an antibody or DARPin that recognizes oligomers in which the antibody or DARPin is linked to an enzyme (typically by recombinant or covalent chemical bonding). The antibody or DARPin is detected when the enzyme reacts with its substrate, producing a detectable product. In certain embodiments, enzymes that can be conjugated to detection reagents of the invention include, e.g., β-galactosidase, luciferase, horse radish peroxidase, and alkaline phosphatase. The chemiluminescent substrate for luciferase is luciferin. One embodiment of a fluorescent substrate for β-galactosidase is 4-methylumbelliferyl-β-D-galactoside. Embodiments of alkaline phosphatase substrates include p-nitrophenyl phosphate (pNPP), which is detected with a spectrophotometer; 5-bromo-4-chloro-3-indolyl phosphate/nitro blue tetrazolium (BCIP/NBT) and fast red/napthol AS-TR phosphate, which are detected visually; and 4-methoxy-4-β-phosphonophenyl) spiro[1,2-dioxetane-3,2'-adamantane], which is detected with a luminometer. Embodiments of horse radish peroxidase substrates include 2,2'azino-bis(3-ethylbenzthiazoline-6 sulfonic acid) (ABTS), 5-aminosalicylic acid (5AS), o-dianisidine, and o-phenylenediamine (OPD), which are detected with a spectrophotometer, and 3,3,5,5'-tetramethylbenzidine (TMB), 3,3' diaminobenzidine (DAB), 3-amino-9-ethylcarbazole (AEC), and 4-chloro-1-naphthol (4C1N), which are detected visually. Other suitable substrates are known to those skilled in the art. The enzyme-substrate reaction and product detection are performed according to standard procedures known to those skilled in the art and kits for performing enzyme immunoassays are available as described above.

The presence of a label can be detected by inspection, or a detector which monitors a particular probe or probe combination is used to detect the detection reagent label. Typical detectors include spectrophotometers, phototubes and photodiodes, microscopes, scintillation counters, cameras, film and the like, as well as combinations thereof. Examples of suitable detectors are widely available from a variety of commercial sources known to persons of skill. Commonly, an optical image of a substrate comprising bound labeling moieties is digitized for subsequent computer analysis.

The ligand compositions of the invention can be used in any diagnostic assay format to determine the presence of tau oligomers. A variety of immunodetection methods are contemplated for this embodiment. Such immunodetection methods include enzyme linked immunosorbent assay (ELISA), radioimmunoassay (RIA), immunoradiometric assay, fluoroimmunoassay, chemiluminescent assay, bioluminescent assay, and Western blot, though several others are well known to those of ordinary skill. The steps of various useful immunodetection methods have been described in the scientific literature.

In general, the binding methods include obtaining a sample suspected of containing a protein, polypeptide and/or peptide (e.g., TDP-43), and contacting the sample with a first antibody, monoclonal or polyclonal, or DARPin, in accordance with the present invention, as the case may be, under conditions effective to allow the formation of complexes.

The binding methods include methods for detecting and quantifying the amount of the target oligomer component in a sample and the detection and quantification of any complexes formed during the binding process. Here, one would obtain a sample suspected of containing target oligomers, and contact the sample with an antibody fragment or DARPin of the invention, and then detect and quantify the amount of complexes formed under the specific conditions.

Contacting the chosen biological sample with the antibody or DARPin under effective conditions and for a period of time sufficient to allow the formation of complexes (primary complexes) is generally a matter of simply adding the antibody composition to the sample and incubating the mixture for a period of time long enough for the antibodies or DARPin to form complexes with, i.e., to bind to, any antigens present. After this time, the sample-antibody composition, such as a tissue section, ELISA plate, dot blot or western blot, will generally be washed to remove any non-specifically bound antibody species, allowing only those scFv molecules specifically bound within the primary complexes to be detected.

In general, the detection of immunocomplex formation is well known in the art and may be achieved through the application of numerous approaches. These methods are generally based upon the detection of a label or marker, such as any of those radioactive, fluorescent, biological and enzymatic tags. U.S. patents concerning the use of such labels include U.S. Pat. Nos. 3,817,837; 3,850,752; 3,939,350; 3,996,345; 4,277,437; 4,275,149 and 4,366,241, each incorporated herein by reference. Of course, one may find additional advantages through the use of a secondary binding ligand such as a second antibody and/or a biotin/avidin ligand binding arrangement, as is known in the art.

As noted above, a ligand of the invention may itself be linked to a detectable label, wherein one would then simply detect this label, thereby allowing the amount of the primary complexes in the composition to be determined. Alternatively, a first antibody that becomes bound within the primary complexes may be detected by means of a second binding ligand that has binding affinity for the complex. In these cases, the second binding ligand may be linked to a detectable label. The second binding ligand is itself often an antibody, which may thus be termed a "secondary" ligand. The primary complexes are contacted with the labeled, secondary binding ligand or antibody under effective conditions and for a period of time sufficient to allow the formation of secondary complexes. The secondary complexes are then generally washed to remove any non-specifically bound labeled secondary antibodies or ligands, and the remaining label in the secondary complexes is then detected.

Further methods include the detection of primary complexes by a two-step approach. A second binding ligand, such as an antibody, that has binding affinity for the scFV (e.g., F9T or D11C) is used to form secondary complexes, as described above. After washing, the secondary complexes are contacted with a third binding ligand or antibody that has binding affinity for the second antibody, again under effective conditions and for a period of time sufficient to allow the formation of complexes (tertiary complexes). The third ligand or antibody is linked to a detectable label, allowing detection of the tertiary complexes thus formed. This system may provide for signal amplification if this is desired.

One method of immunodetection designed by Charles Cantor uses two different antibodies. A first step biotinylated, monoclonal or polyclonal antibody (in the present example a scFv or DARPin) is used to detect the target antigen(s), and a second step antibody is then used to detect the biotin attached to the complex. In this method the sample to be tested is first incubated in a solution containing the first step ligand. If the target antigen is present, some of the ligand binds to the antigen to form a biotinylated ligand/antigen complex. The ligand/antigen complex is then amplified by incubation in successive solutions of streptavidin (or avidin), biotinylated DNA, and/or complementary biotinylated DNA, with each step adding additional biotin sites to the ligand/antigen complex. The amplification steps are repeated until a suitable level of amplification is achieved, at which point the sample is incubated in a solution containing the second step antibody against biotin. This second step antibody is labeled, as for example with an enzyme that can be used to detect the presence of the antibody/antigen complex by histoenzymology using a chromogen substrate. With suitable amplification, a conjugate can be produced which is macroscopically visible.

Another known method of detection takes advantage of the immuno-PCR (Polymerase Chain Reaction) methodology. The PCR method is similar to the Cantor method up to the incubation with biotinylated DNA, however, instead of using multiple rounds of streptavidin and biotinylated DNA incubation, the DNA/biotin/streptavidin/antibody complex is washed out with a low pH or high salt buffer that releases the antibody. The resulting wash solution is then used to carry out a PCR reaction with suitable primers with appropriate controls. At least in theory, the enormous amplification capability and specificity of PCR can be utilized to detect a single antigen molecule.

As detailed above, the assays in their most simple and/or direct sense are binding assays. Certain preferred assays are the various types of enzyme linked immunosorbent assays (ELISAs) and/or radioimmunoassays (RIA) known in the art. Immunohistochemical detection using tissue sections is also particularly useful. However, it will be readily appreciated that detection is not limited to such techniques, and/or western blotting, dot blotting, FACS analyses, and/or the like may also be used.

The diagnostic assay format that may be used in the present invention could take any conventional format such as ELISA or other platforms such as luminex or biosensors. The present invention provides various ligands (e.g., DARPins). These ligands can readily be modified to facilitate diagnostic assays, for example a tag (such as GFP) can be added to these ligands to increase sensitivity. In one exemplary ELISA, ligand (e.g., antibodies or DARPins) are immobilized onto a selected surface exhibiting protein affinity, such as a well in a polystyrene microtiter plate. Then, a test composition suspected of containing a target oligomer, such as a clinical sample (e.g., a biological sample obtained from the subject), is added to the wells. After binding and/or washing to remove non-specifically bound complexes, the bound antigen may be detected. Detection is generally achieved by the addition of an antibody that is linked to a detectable label. This type of ELISA is a simple "sandwich ELISA." Detection may also be achieved by the addition of a second antibody, followed by the addition of a third antibody that has binding affinity for the second antibody, with the third antibody being linked to a detectable label.

In another exemplary ELISA, the samples suspected of containing the antigen are immobilized onto the well surface and/or then contacted with binding agents. After binding and/or washing to remove non-specifically bound complexes, the bound anti-binding agents are detected. Where the initial binding agents are linked to a detectable label, the complexes may be detected directly. Again, the complexes may be detected using a second antibody that has binding affinity for the first binding agents, with the second antibody being linked to a detectable label.

Another ELISA in which the antigens are immobilized, involves the use of antibody competition in the detection. In this ELISA, labeled antibodies (or nanobodies or DARPins) against an antigen are added to the wells, allowed to bind, and/or detected by means of their label. The amount of an antigen in an unknown sample is then determined by mixing the sample with the labeled antibodies against the antigen during incubation with coated wells. The presence of an antigen in the sample acts to reduce the amount of antibody against the antigen available for binding to the well and thus reduces the ultimate signal. This is also appropriate for detecting antibodies against an antigen in an unknown sample, where the unlabeled antibodies bind to the antigen-coated wells and also reduces the amount of antigen available to bind the labeled antibodies.

Irrespective of the format employed, ELISAs have certain features in common, such as coating, incubating and binding, washing to remove non-specifically bound species, and detecting the bound immune complexes.

In coating a plate with either target oligomers or a ligand (e.g., antibody or DARPin) of the invention, one will generally incubate the wells of the plate with a solution of the antigen or ligand, either overnight or for a specified period of hours. The wells of the plate will then be washed to remove incompletely adsorbed material. Any remaining available surfaces of the wells are then "coated" with a nonspecific protein that is antigenically neutral with regard to the test antisera. These include bovine serum albumin (BSA), casein or solutions of milk powder. The coating allows for blocking of nonspecific adsorption sites on the immobilizing surface and thus reduces the background caused by nonspecific binding of antisera onto the surface.

In ELISAs, it is probably more customary to use a secondary or tertiary detection means rather than a direct procedure. Thus, after binding of a protein or antibody to the well, coating with a non-reactive material to reduce background, and washing to remove unbound material, the immobilizing surface is contacted with the biological sample to be tested under conditions effective to allow immune complex (antigen/antibody) formation. Detection of the immune complex then requires a labeled secondary binding ligand or antibody, and a secondary binding ligand or antibody in conjunction with a labeled tertiary antibody or a third binding ligand.

"Under conditions effective to allow immune complex (antigen/antibody) formation" means that the conditions preferably include diluting the tau oligomers and/or scFv composition with solutions such as BSA, bovine gamma globulin (BGG) or phosphate buffered saline (PBS)/Tween. These added agents also tend to assist in the reduction of nonspecific background.

The "suitable" conditions also mean that the incubation is at a temperature or for a period of time sufficient to allow effective binding. Incubation steps are typically from about 1 to 2 to 4 hours or so, at temperatures preferably on the order of 25° C. to 27° C., or may be overnight at about 4° C. or so.

Following all incubation steps in an ELISA, the contacted surface is washed so as to remove non-complexed material. An example of a washing procedure includes washing with a solution such as PBS/Tween, or borate buffer. Following the formation of specific immune complexes between the test sample and the originally bound material, and subsequent washing, the occurrence of even minute amounts of immune complexes may be determined.

To provide a detecting means, the second or third antibody will have an associated label to allow detection. This may be an enzyme that will generate color development upon incubating with an appropriate chromogenic substrate. Thus, for example, one will desire to contact or incubate the first and second immune complex with a urease, glucose oxidase, alkaline phosphatase or hydrogen peroxidase-conjugated antibody for a period of time and under conditions that favor the development of further immune complex formation (e.g., incubation for 2 hours at room temperature in a PBS-containing solution such as PBS-Tween).

After incubation with the labeled antibody, and subsequent to washing to remove unbound material, the amount of label is quantified, e.g., by incubation with a chromogenic substrate such as urea, or bromocresol purple, or 2,2'-azino-di-(3-ethyl-benzthiazoline-6-sulfonic acid (ABTS), or $H_2O_2$, in the case of peroxidase as the enzyme label. Quantification is then achieved by measuring the degree of color generated, e.g., using a visible spectra spectrophotometer.

Diagnostic Methods

In certain embodiments, the present invention provides a method for determining risk of traumatic brain injury (TBI), assessment of the amount of neuronal damage, and/or susceptibility to neurodegenerative disease in a subject by measuring levels of TDP-43, tau, abeta and/or alpha-synuclein at two or more time points. In certain embodiments, one, two, three or all four proteins will be measured to determine different types of damage that has occurred. It would be expected that increased damage and increased risk of further neurodegenerative disorders are indicated by higher concentrations of the different toxic protein variants for longer periods of time after injury. Different protein variants will indicate different types of damage and likely indicate increased risk for different neurodegenerative disorders. Some patients may have only one protein, others multiple or all four. Certain combinations are likely to lead to certain disorders (for example, abeta and tau would indicate Alzheimer's, and a-syn and tau would indicate Parkinson's), but they all indicate brain injury. Protein concentration trajectories are key, as higher concentrations of the proteins for longer times is detrimental; levels that go down quickly are good; and levels that increase would be very bad. It can be beneficial, therefore to measure levels over a period of time for further predictive accuracy.

In certain embodiments, the present invention provides a method for determining risk of traumatic brain injury (TBI), assessment of the amount of neuronal damage, and/or susceptibility to neurodegenerative disease in a subject, comprising the steps of:

(A) providing samples obtained from a subject at two or more times post-injury;

(B) assessing protein levels of toxic variants of TDP-43, tau, abeta and/or alpha-synuclein in the sample by detecting protein levels of toxic variants of TDP-43, tau, abeta and/or alpha-synuclein in the samples;

(C) comparing the protein levels of toxic variants of TDP-43, tau, abeta and/or alpha-synuclein protein levels in the sample at each time point with protein levels of toxic variants of TDP-43, tau, abeta and/or alpha-synuclein in a normal control; and (D) determining whether the subject has a risk of TBI in accordance with the result of step (C);

wherein a subject having elevated protein levels of toxic variants of TDP-43 tau, abeta and/or alpha-synuclein has a high risk of TBI.

In certain embodiments, a sample is obtained from the subject within 6 hours post-injury.

In certain embodiments, a sample is obtained from the subject about 12 to 36 hours post-injury.

In certain embodiments, a sample is obtained from the subject about 5 to 10 days post injury.

In certain embodiments, a sample is obtained from the subject about 2 to 4 weeks days post injury.

In certain embodiments, the sample and the normal control are blood product samples or cerebrospinal fluid (CSF) samples. In certain embodiments, the blood product is serum.

In certain embodiments, the detecting in step (B) is by means of a ligand specific for the protein.

In certain embodiments, the ligand is an antibody.

In certain embodiments, the ligand is a designed ankyrin repeat protein (DARPin).

In certain embodiments, the protein levels are detected by means of ELISA.

In certain embodiments, the present invention provides a method for determining risk of traumatic brain injury (TBI), assessment of the amount of neuronal damage, and/or susceptibility to neurodegenerative disease in a subject, comprising the steps of:

(A) providing samples obtained from a subject at about 6-hours, about 24-hours, about 5-days and about 10-days post-injury;

(B) assessing protein levels of a toxic variant of TDP-43 in the sample by detecting protein levels of toxic variants of TDP-43 in the samples;

(C) comparing the protein levels of toxic variants of TDP-43 in the sample at each time point with protein levels of toxic variants of TDP-43 in a normal control; and (D) determining whether the subject has a risk of TBI in accordance with the result of step (C);

wherein a subject having increased protein levels of toxic variants of TDP-43 in the samples at all four time points than those of the normal control, and having a decreased level of the toxic variants of TDP-43 at the 24-hour time point as compared to the 6-hour time point, having a decreased level of TDP-43 at the 5-day time point as compared to the 24-hour time point, and having an increased level of TDP-43 at the 10-day time point as compared to either the 24-hour or 5-day time point has a high risk of TBI.

In certain embodiments, the present invention provides a method for determining risk of traumatic brain injury (TBI), assessment of the amount of neuronal damage, and/or susceptibility to neurodegenerative disease in a subject, comprising the steps of:

(A) providing samples obtained from a subject at about 6-hours, about 24-hours, about 5-days and about 10-days post-injury;

(B) assessing protein levels of a toxic variant of tau in the sample by detecting the protein levels of the toxic variant of tau protein levels in the samples;

(C) comparing the protein level of the toxic variant of tau in the sample at each time point with the protein level the toxic variant of tau in a normal control; and (D) determining whether the subject has a risk of TBI in accordance with the result of step (C);

wherein a subject having an increased protein level of the toxic variant of tau in the sample at the 24-hour time point and at the 5-day time point as compared to that of the normal control, having comparable protein levels of the toxic variant of tau at the 6-hour and 10-day time points as compared to that of the normal control, and having an increased protein level of the toxic variant of tau at the 5-day time point as compared to the 24-hour time point has a high risk of TBI.

In certain embodiments, the present invention provides a method for determining risk of traumatic brain injury (TBI), assessment of the amount of neuronal damage, and/or susceptibility to neurodegenerative disease in a subject, comprising the steps of:

(A) providing samples obtained from a subject at about 6-hours, about 24-hours, about 5-days and about 10-days post-injury;

(B) assessing protein levels of a toxic variant of abeta in the sample by detecting protein levels of the toxic variant of abeta in the samples;

(C) comparing protein levels of the toxic variant of the abeta in the sample at each time point with abeta protein levels in a normal control; and (D) determining whether the subject has a risk of TBI in accordance with the result of step (C);

wherein a subject having an increased protein levels of the toxic variant of abeta in the sample at the 24-hour time point, the 5-day time point and the 10-day time point as compared to that of the normal control, having comparable protein level of the toxic variant of abeta at the 6-hour as compared to that of the normal control, and having an increased protein level of the toxic variant of abeta at the 5-day time point as compared to the 24-hour time point and 10-day time point has a high risk of TBI.

In certain embodiments, the present invention provides a method for determining risk of traumatic brain injury (TBI), assessment of the amount of neuronal damage, and/or susceptibility to neurodegenerative disease in a subject, comprising the steps of:

(A) providing samples obtained from a subject at about 6-hours, about 24-hours, about 5-days and about 10-days post-injury;

(B) assessing protein levels of a toxic variant of alpha-synuclein in the sample by detecting protein levels of the toxic variant of alpha-synuclein in the samples;

(C) comparing the protein levels of the toxic variant of alpha-synuclein in the sample at each time point with protein levels of the toxic variant of alpha-synuclein in a normal control; and (D) determining whether the subject has a risk of TBI in accordance with the result of step (C);

wherein a subject having an increased protein levels of the toxic variant of alpha-synuclein in the sample at the 5 day time point, the 10-day time point as compared to that of the normal control, having comparable protein level of the toxic variant of alpha-synuclein at the 6-hour time point and 24-hour time point as compared to that of the normal control, and having an increased protein level of the toxic variant of alpha-synuclein at the 5-day time point as compared to the 10-day time point has a high risk of TBI.

In certain embodiments, the sample and the normal control are blood product samples or cerebrospinal fluid (CSF) samples. In certain embodiments, the blood product is serum.

In certain embodiments, the detecting in step (B) is by means of a ligand specific for the protein. In certain embodiments, the ligand is an antibody. In certain embodiments, the ligand is a designed ankyrin repeat protein (DARPin).

In certain embodiments, the protein levels are detected by means of ELISA.

Example 1

DARPins and Traumatic Brain Injury

The morphology specific reagents described above were selected from antibody fragment (scFv) libraries. ScFvs are susceptible to misfolding and aggregation which makes them difficult to produce in large scale. Designed ankyrin repeat proteins (DARPins) have been suggested as more stable alternative to scFvs. To isolate DARPins against several protein variants, a new DARPin library as generated. In the present library, the proteins contained an N-Terminal capping AR, one AR module and the C-Terminal capping AR. In the AR module, there were seven locations where the amino acids were varied.

This DARPin library was utilized in various AFM based biopannings to isolate antibodies against several protein variants. One set of biopanning was conducted against any protein variant present in both brain tissue and sera from individuals with Alzheimer's disease (AD). ELISA analysis of one of these clones with the TBI cases revealed reactivity at 24 hours, 5 days and 10 days, with reactivity decreasing after 5 days (FIG. 1). We are in the initial stages of characterizing the clones from this and the other DARPin biopannings, but results thus far indicate a preference for disease tissue over healthy controls. Since these panning were not against a specific known target, we still need to identify the protein target by mass spectrometry. However, clearly the DARPin library is a valuable resource to isolate DARPins that selectively bind protein variants associated with TBI. The DARPin shown here has a different reactivity profile than the protein variants discussed above as the DARPin shows high reactivity at the early time points and then decreases.

Example 2

Generation of a DARPin Library of $10^{10}$ Diversity Consisting of a Core of 3-4 Repeat Ankyrin Units with a Randomized 7 Amino Acid Binding Loop A designed ankyrin repeat protein (DARPin) N1C library was generated by ligating the N1 product with a SRP modified pIT2 vector containing the C-Terminal capping AR. After the ligation procedure, through electroporation the N1C library was produced. Titration of the library indicated that there were $10^{10}$ cells/ml. DNA sequencing of 20 clones revealed 45% of the clones were correct and each had a different AR module (SEQ ID NOs: 7-15), 25% had errors in the N-Cap or pre-N-Cap, 20% had errors in the N-Cap, and AR module (SEQ ID NOs: 16-20), and 10% were empty. A library consisting of 3-4 AR module repeats was the desired size. After multiple ligation attempts and some difficulty in ligating these AR repeats together, phage were produced from the N1C library and these phage particles were used in the panning procedures. Phage particles were produced in a manner similar to the steps outlined in the Tomlinson I and J protocols.

```
N1C Library Generic Sequence
                                      (SEQ ID NO: 29)
5'-gctagcATGAAAAAGATTTggctggcgctggctggTTTAGTTTTAG CGTTTAGCGCATCGGCGGACTACAAAGAggcccagccggccATGGACCT

GGGTAAGAAACTGCTGGAAGCTGCTCGTGCTGGTCAGGACGACGAAGTT

CGTATCCTGATGGCTAACGGTGCTGACGTTAACGCTNNNGACNNNNNNG

GTNNNACTCCGCTGCACCTGGCTGCTNNNNNNGGTCACCTGGAAATCGT

TGAAGTTCTGCTGAAGHACGGTGCTGACGTTAACGCTCAGGACAAATTC

GGTAAGACCGCTTTCGACATCTCCATCGACAACGGTAACGAGGACCTGG

CTGAAATCCTGCAAgcggccgcACATCATCATCACCATCACGGGGCCGC

AGAACAAAAACTCATCTCAGAAGAGGATCTGAATGGGGCCGCATAGACT

GTTGAAAGTTGTTTAGCAAAACCTCATACAGAAAATTCATTTACTAACG

TCTGGAAAGACGACAAAACTTTAGATCGTTACGCTAACTATGAGGGCTG

TCTGTGGAATGCTACAGGCGTTGTGGTTTGTACTGGTGACGAAACTCAG

TGTTACGGTACATGGGTTCCTATTGGGCTTGCTATCCCTGAAAATGAG

G-3'

The 9 of 20 DARPins that were correct when
sequenced are below (45%).
DARPin 1
                                       (SEQ ID NO: 7)
5'-GATTTGGCTGGCGCTGGCTGGTTTAGTTTTAGCGTTTAGCGCATCG

GCGGACTACAAAGAGGCCCAGCCGGCCATGGACCTGGGTAAGAAACTGC

TGGAAGCTGCTCGTGCTGGTCAGGACGACGAAGTTCGTATCCTGATGGC

TAACGGTGCTGACGTTAACGCTGACGACTACCGTGGTTCTACTCCGCTG

CACCTGGCTGCTATGGCTGGTCACCTGGAAATCGTTGAAGTTCTGCTGA

AGCACGGTGCTGACGTTAACGCTCAGGACAAATTCGGTAAGACCGCTTT

CGACATCTCCATCGACAACGGTAACGAGGACCTGGCTGAAATCCTGCAA

GCGGCCGCACATCATCATCACCATCACGGGCCGCAGAACAAAAACTCA

TCTCAGAAGAGGATCTGAATGGGCCGCATAGACTGTTGAAAGTTGTTT

AGCAAAACCTCATACAGAAAATTCATTTACTAACGTCTGGAAAGACGAC

AAAACTTTAGATCGTTACGCTAACTATGAGGGCTGTCTGTGGAATGCTA

CAGGCGTTGTGGTTTGTACTGGTGACGAAACTCAGTGTTACGGTACATG

GGTTCCTATTGGGCTTGCTATCCCTGAAAATGAGGGTGGTGGCTCTGAG

GGTGGCGGTTCTGAGGGTGGCGGTTCTGAGGGTGGCGGTACTAAACCTC

CTGAGTACGGTGATACACCTATTCCGGGCTATACTTATATCAACCCTCT

CGACGGCACTTATCCGCCTGGTACTGAGCAAAACCCCGCTAATCCTAAT

CCTTCTCTTGAGGAGTCTCAGCCTCTTAATACTTTCATGTTTCAGAANA

ATAGGTTCCGAANTAGGCAGGGNGCATTNACTGTTTATACGGGCACTGT

TACTCNNGGCACTGACCCCGTTAAAACTTATTANCAGTANNNTCCTGTA

TCATCAAAAGNCATGTATGANGCNTNCTGGNNCNGNAANTCNNANACT

G-3'

DARPin 2
                                      (SEQ ID NO: 8)
5'-CTATTTCAGGAGANAGTCATAGCTAGCNTNNNNNNNANTTGGCTGG

CGCTGGCTGGTTTAGTTTTAGCGTTTAGCGCATCGGCGGACTACAAAGA

GGCCCAGCCGGCCATGGACCTGGGTAAGAAACTGCTGGAAGCTGCTCGT

GCTGGTCAGGACGACGAAGTTCGTATCCTGATGGCTAACGGTGCTGACG

TTAACGCTGTTGACCGTAAAGGTAACACTCCGCTGCACCTGGCTGCTCA
```

-continued

```
GTACGGTCACCTGGAAATCGTTGAAGTTCTGCTGAAGCACGGTGCTGAC
GTTAACGCTCAGGACAAATTCGGTAAGACCGCTTTCGACATCTCCATCG
ACAACGGTAACGAGGACCTGGCTGAAATCCTGCAAGCGGCCGCACATCA
TCATCACCATCACGGGGCCGCAGAACAAAAACTCATCTCAGAAGAGGAT
CTGAATGGGGCCGCATAGACTGTTGAAAGTTGTTTAGCAAAACCTCATA
CAGAAAATTCATTTACTAACGTCTGGAAAGACGACAAAACTTTAGATCG
TTACGCTAACTATGAGGGCTGTCTGTGGAATGCTACAGGCGTTGTGGTT
TGTACTGGTGACGAAACTCAGTGTTACGGTACATGGGTTCCTATTGGGC
TTGCTATCCCTGAAAATGAGGGTGGTGGCTCTGAGGGTGGCGGTTCTGA
GGGTGGCGGTTCTGAGGGTGGCGGTACTAAACCTCCTGAGTACGGTGAT
ACACCTATTCCGGGCTATACTTATATCAACCCTCTCGACGGCACTTATC
CGCCTGGTACTGAGCAAAACCCCGCTAATCCTAATCCTTCTCTTGAGGA
GTCTCAGCCTCTTAATACTTTCATGTTTCAGAANAATAGGTTCCGAAAT
ANNCAGGGTGCATTAACTGTTTATACGGGCACTGNTACTCANGGCACTG
ACCCCGTNAAAACTT-3'
```

DARPin 3 (SEQ ID NO: 9)
```
5'-GATTTGGCTGGCGCTGGCTGGTTTAGTTTTAGCGTTTAGCGCATCG
GCGGACTACAAAGAGGCCCAGCCGGCCATGGACCTGGGTAAGAAACTGC
TGGAAGCTGCTCGTGCTGGTCAGGACGACGAAGTTCGTATCCTGATGGC
TAACGGTGCTGACGTTAACGCTGTTGACGCNCANGGTACTACTCCGCTG
CACCTGGCTGCTCGNNNNNGGTCACCTGGAAATCGTTGAAGTTCTGCTG
AAGAACGGTGCTGACGTTAACGCTCAGGACAAATTCGGTAAGACCGCTT
TCGACATCTCCATCGACAACGGTAACGAGGACCTGGCTGAAATCCTGCA
AGCGGCCGCACATCATCATCACCATCACGGGGCCGCAGAACAAAAACTC
ATCTCAGAAGAGGATCTGAATGGGGCCGCATAGACTGTTGAAAGTTGTT
TAGCAAAACCTCATACAGAAAATTCATTTACTAACGTCTGGAAAGACGA
CAAAACTTTAGATCGTTACGCTAACTATGAGGGCTGTCTGTGGAATGCT
ACAGGCGTTGTGGTTTGTACTGGTGACGAAACTCAGTGTTACGGTACAT
GGGTTCCTATTGGGCTTGCTATCCCTGAAAATGAGGGTGGTGGCTCTGA
GGGTGGCGGTTCTGAGGGTGGCGGTTCTGAGGGTGGCGGTACTAAACCT
CCTGAGTACGGTGATACACCTATTCCGGGCTATACTTATATCAACCCTC
TCGACGGCACTTATCCGCCTGGTACTGAGCAAAACCCCGCTAATCCTAA
TCCTTCTCTTGAGGAGTCTCAGCCTCTTAATACTTTCATGTTTCAGAAT
AATAGGTTCCGAAATNNNCAGGGNGCATTNACTGTTTATACGGGCACTG
NTACTCNNGGNNCTGACCCCGNTAAAACTTATTANCAGTANNCTCCTGT
ATCATCAAAAGCCATGTATGACGCTT-3'
```

DARPin 4 (SEQ ID NO 10)
```
5'-TTGGCTGGCGCTGGCTGGTTTAGTTTTAGCGTTTAGCGCATCGGCG
GACTACAAAGAGGCCCAGCCGGCCATGGACCTGGGTAAGAAACTGCTGG
AAGCTGCTCGTGCTGGTCAGGACGACGAAGTTCGTATCCTGATGGCTAA
CGGTGCTGACGTTAACGCTANNGACCANNNNGGTNNTACTCCGCTGCAC
CTGGCTGCTNGGNNTGGTCACCTGGAAATCGTTGAAGTTCTGCTGAAGA
ACGGTGCTGACGTTAACGCTCAGGACAAATTCGGTAAGACCGCTTTCGA
CATCTCCATCGACAACGGTAACGAGGANCTGGCTGAAATCCTGCAAGC
GGCCGCACATCATCATCACCATCACGGGGCCGCAGAACAAAAACTCATC
TCAGAAGANGATCTGAATGGGGCCGCATAGACTGTTGAAAGTTGTTTA
GCAAAACCTCATACAGAAAATTCATTTACTAACGTCTGGAAAGACGACA
AAACTTTAGATCGTTACGCTAACTATGANGGCTGTCTGTGGAATGCTAC
AGGCGTTGTGGTTTGTACTGGTGACGAAACTCAGTGTTACGGTACATGG
GTTCCTATTGGGCTTGCTATCCCTGAAAATGAGGGTGGTGGCTCTGANG
GTGGCGGTTCTGANGGTGGCGGTTCTGANGGTGGCGGTACTAAACCTCC
TGAGTACGGTGATACACCTATTCCGGGCTATACTTATATCAACCCTCTC
GACNGCACTTATCCGCCTGGTACTGAGCAAAACCCCGCTAATCCTAATC
CTTCTCTNGAGGAGTCTCAG-3'
```

DARPin 5 (SEQ ID NO: 11)
```
5'-TTGGCTGGCGCTGGCTGGTTTAGTTTTAGCGTTTAGCGCATCGGCG
GACTACAAAGAGGCCCAGCCGGCCATGGACCTGGGTAAGAAACTGCTGG
AAGCTGCTCGTGCTGGTCAGGACGACGAAGTTCGTATCCTGATGGCTAA
CGGTGCTGACGTTAACGCTAACGACATCGAAGGTCATACTCCGCTGCAC
CTGGCTGCTATCTACGGTCACCTGGAAATCGTTGAAGTTCTGCTGAAGA
ACGGTGCTGACGTTAACGCTCAGGACAAATTCGGTAAGACCGCTTTCGA
CATCTCCATCGACAACGGTAACGAGGACCTGGCTGAAATCCTGCAAGCG
GCCGCACATCATCATCACCATCACGGGGCCGCAGAACAAAAACTCATCT
CAGAAGAGGATCTGAATGGGGCCGCATAGACTGTTGAAAGTTGTTTAGC
AAAACCTCATACAGAAAATTCATTTACTAACGTCTGGAAAGACGACAAA
ACTTTAGATCGTTACGCTAACTATGAGGGCTGTCTGTGGAATGCTACAG
GCGTTGTGGTTTGTACTGGTGACGAAACTCAGTGTTACGGTACATGGGT
TCCTATTGGGCTTGCTATCCCTGAAAATGAGGGTGGTGGCTCTGAGGGT
GGCGGTTCTGAGGGTGGCGGTTCTGAGGGTGGCGGTACTAAACCTCCTG
AGTACGGTGATACACCTATTCCGGGCTATACTTATATCAACCCTCTCGA
CGGCACTTATCCGCCTGGTACTGAGCAAAACCCCGCTAATCCTAATCCT
TCTCTTGAGGAGTCTCAGCCTCTTAATACTTTCATGTTTCANAANAATA
GGTTCCGAAATNGNCAGGGTGCATTNACTGTTTATACGGGCACTGNTAC
TCNNGGCACTGACCCCGNTNAAAACTTATTACCAGTACNCTCCTGTATCA
TCAAAAGCCAT-3'
```

DARPin 6 (SEQ ID NO: 12)
```
5'-TTCTATTTCAGGAGANAGTCATAGCTAGCATGAAAAAGANTTGGCT
GGCGCTGGCTGGTTTAGTTTTAGCGTTTAGCGCATCGGCGGACTACAAA
GAGGCCCAGCCGGCCATGGACCTGGGTAAGAAACTGCTGGAAGCTGCTC
GTGCTGGTCAGGACGACGAAGTTCGTATCCTGATGGCTAACGGTGCTGA
CGTTAACGCTAAAGACCATGAAGGTCAGACTCCGCTGCACCTGGCTGCT
```

-continued

CAGATCGGTCACCTGGAAATCGTTGAAGTTCTGCTGAAGAACGGTGCTG

ACGTTAACGCTCAGGACAAATTCGGTAAGACCGCTTTCGACATCTCCAT

CGACAACGGTAACGAGGACCTGGCTGAAATCCTGCAAGCGGCCGCACAT

CATCATCACCATCACGGGGCCGCAGAACAAAAACTCATCTCAGAAGAGG

ATCTGAATGGGGCCGCATAGACTGTTGAAAGTTGTTTAGCAAAACCTCA

TACAGAAAATTCATTTACTAACGTCTGGAAAGACGACAAAACTTTAGAT

CGTTACGCTAACTATGAGGGCTGTCTGTGGAATGCTACAGGCGTTGTGG

TTTGTACTGGTGACGAAACTCAGTGTTACGGTACATGGGTTCCTATTGG

GCTTGCTATCCCTGAAAATGAGGGTGGTGGCTCTGAGGGTGGCGGTTCT

GAGGGTGGCGGTTCTGAGGGTGGCGGTACTAAACCTCCTGAGTACGGTG

ATACACCTATTCCGGGCTATACTTATATCAACCCTCTCGACGGCACTTA

TCCGCCTGGTACTGAGCAAAACCCCGCTAATCCTAATCCTTCTCTTGAG

GAGTCTCAGCCTCTTAATACTTTCATGTTTCANAANAATAGGTTCCGAA

ATAGGCAGGGTGCATTNACTGTTTATACGGGCACTGTNACTCANGGCAC

TGACCCCGTTAAAACTTATTACCAGTACNCTCCTGTATCATCAAAAGNC

ATGTATGA-3'

DARPin 7

(SEQ ID NO: 13)
5'-TATTTNAGGAGANAGTCATAGCTAGCATGNAAAAGANTTGGCTGGC

GCTGGCTGGTTTAGTTTTAGCGTTTAGCGCATCGGCGGACTACAAAGAG

GCCCAGCCGGCCATGGACCTGGGTAAGAAACTGCTGGAAGCTGCTCGTG

CTGGTCAGGACGACGAAGTTCGTATCCTGATGGCTAACGGTGCTGACGT

TAACGCTATGGACAACGCTGGTACTACTCCGCTGCACCTGGCTGCTCAG

TTCGGTCACCTGGAAATCGTTGAAGTTCTGCTGAAGAACGGTGCTGACG

TTAACGCTCAGGACAAATTCGGTAAGACCGCTTTCGACATCTCCATCGA

CAACGGTAACGAGGACCTGGCTGAAATCCTGCAAGCGGCCGCACATCAT

CATCACCATCACGGGGCCGCAGAACAAAAACTCATCTCAGAAGAGGATC

TGAATGGGGCCGCATAGACTGTTGAAAGTTGTTTAGCAAAACCTCATAC

AGAAAATTCATTTACTAACGTCTGGAAAGACGACAAAACTTTAGATCGT

TACGCTAACTATGAGGGCTGTCTGTGGAATGCTACAGGCGTTGTGGTTT

GTACTGGTGACGAAACTCAGTGTTACGGTACATGGGTTCCTATTGGGCT

TGCTATCCCTGAAAATGAGGGTGGTGGCTCTGAGGGTGGCGGTTCTGAG

GGTGGCGGTTCTGAGGGTGGCGGTACTAAACCTCCTGAGTACGGTGATA

CACCTATTCCGGGCTATACTTATATCAACCCTCTCGACGGCACTTATCC

GCCTGGTACTGAGCAAAACCCCGCTAATCCTAATCCTTCTCTTGAGGAG

TCTCAGCCTCTTAATACTTTCATGTTTCAGAATAATANNTTCCGAAATA

GGCAGGGTGCATTAACTGTTTANACGGGCACTGNNACTCANGGNACTGA

CCCCGNNAAAACTTATTACCAGTACACTNCTGTATCATCAAANCCATGN

ATGA-3'

DARPin 8

(SEQ ID NO: 14)
5'-TTCTATTTCAGGAGANAGTCATAGCTAGCATGAAAAAGANTTGGCT

GGCGCTGGCTGGTTTAGTTTTAGCGTTTAGCGCATCGGCGGACTACAAA

GAGGCCCAGCCGGCCATGGACCTGGGTAAGAAACTGCTGGAAGCTGCTC

GTGCTGGTCAGGACGACGAAGTTCGTATCCTGATGGCTAACGGTGCTGA

CGTTAACGCTNGGGACCTGNNNGGTACNACTCCGCTGCACCTGGCTGCT

ANNGNNGGTCACCTGGAAATCGTTGAAGTTCTGCTGAAGAACGGTGCTG

ACGTTAACGCTCAGGACAAATTCGGTAAGACCGCTTTCGACATCTCCAT

CGACAACGGTAACGAGGACCTGGCTGAAATCCTGCAAGCGGCCGCACAT

CATCATCACCATCACGGGGCCGCAGAACAAAAACTCATCTCAGAAGAGG

ATCTGAATGGGGCCGCATAGACTGTTGAAAGTTGTTTAGCAAAACCTCA

TACAGAAAATTCATTTACTAACGTCTGGAAAGACGACAAAACTTTAGAT

CGTTACGCTAACTATGAGGGCTGTCTGTGGAATGCTACAGGCGTTGTGG

TTTGTACTGGTGACGAAACTCAGTGTTACGGTACATGGGTTCCTATTGG

GCTTGCTATCCCTGAAAATGAGGGTGGTGGCTCTGAGGGTGGCGGTTCT

GAGGGTGGCGGTTCTGAGGGTGGCGGTACTAAACCTCCTGAGTACGGTG

ATACACCTATTCCGGGCTATACTTATATCAACCCTCTCGACGGCACTTA

TCCGCCTGGTACTGAGCAAAACCCCGCTAATCCTAATCCTTCTCTTGAG

GAGTCTCAGCCTCTTAATACTTTCATGTTTCANAATAATANNTTCCNAA

ATNGNCAGGGTGCATTNACTGTTTATACNGGCNCTGNNACTCNNGGNAC

TGACCCCGTTAAAACT-3'

DARPin 9

(SEQ ID NO: 15)
5'-GAGANAGTCATAGCTAGCATGAAAAAGATTTGGCTGGCGCTGGCTG

GTTTAGTTTTAGCGTTTAGCGCATCGGCGGACTACAAAGAGGCCCAGCC

GGCCATGGACCTGGGTAAGAAACTGCTGGAAGCTGCTCGTGCCGGTCAG

GACGACGAAGTTCGTATCCTGATGGCTAACGGTGCTGACGTTAACGCTA

ACGACCTGGAAGGTGACACTCCGCTGCACCTGGCTGCTTACATCGGTCA

CCTGGAAATCGTTGAAGTTCTGCTGAAGTACGGTGCTGACGTTAACGCT

CAGGACAAATTCGGTAAGACCGCTTTCGACATCTCCATCGACAACGGTA

ACGAGGACCTGGCTGAAATCCTGCAAGCGGCCGCACATCATCATCACCA

TCACGGGGCCGCAGAACAAAAACTCATCTCAGAAGAGGATCTGAATGGG

GCCGCATAGACTGTTGAAAGTTGTTTAGCAAAACCTCATACAGAAAATT

CATTTACTAACGTCTGGAAAGACGACAAAACTTTAGATCGTTACGCTAA

CTATGAGGGCTGTCTGTGGAATGCTACAGGCGTTGTGGTTTGTACTGGT

GACGAAACTCAGTGTTACGGTACATGGGTTCCTATTGGGCTTGCTATCC

CTGAAAATGAGGGTGGTGGCTCTGAGGGTGGCGGTTCTGAGGGTGGCGG

TTCTGANGGTGGCGGTACTAAACCTCCTGAGTACGGTGATACACCTATT

CCGGGCTATACTTATATCAACCCTCTCGACGGCACTTATCCGCCTGGTA

CTGAGCAAAACCCCGCTAATCCTAATCCTTCTCTTGAGGAGTCTCAGCC

TCTTAATACTTTCATGTTTCANAANAATNNNTTCCGAAATNNNCAGGGT

GCATTAACTGTTTATACGGGCACTGNTACTCAAGGCACTGACCCCG

T-3'

The 5 of 20 DARPins that had errors in the N-Cap or pre-N-Cap are below (25%).

DARPin 10

(SEQ ID NO: 16)
```
5'-ATTTGGCTGGCGCTGGCTGGTTNAGTTTTAGCGTTTAGCGCATCGG
CGGACTACAAAGAGGCCCAGCCGGCCATGGACCTGGGTAAGAAACTGCT
GACGTTAACGCTATGGACGCTTACGGTAACACTCCGCTGCACCTGGCTG
CTTGGTCTGGTCACCTGGAAATCGTTGAAGTTCTGCTGAAGTACGGTGC
TGACGTTAACGCTCAGGACAAATTCGGTAAGACCGCTTTCGACATCTCC
ATCGACAACGGTAACGAGGACCTGGCTGAAATCCTGCAAGCGGCCGCAC
ATCATCATCACCATCACGGGGCCGCAGAACAAAAACTCATCTCAGAAGA
GGATCTGAATGGGGCCGCATAGACTGTTGAAAGTTGTTTAGCAAAACCT
CATACAGAAAATTCATTTACTAACGTCTGGAAAGACGACAAAACTTTAG
ATCGTTACGCTAACTATGAGGGCTGTCTGTGGAATGCTACAGGCGTTGT
GGTTTGTACTGGTGACGAAACTCAGTGTTACGGTACATGGGTTCCTATT
GGGCTTGCTATCCCTGAAAATGAGGGTGGTGGCTCTGAGGGTGGCGGTT
CTGAGGGTGGCGGTTCTGAGGGTGGCGGTACTAAACCTCCTGAGTACGG
TGATACACCTATTCCGGGCTATACTTATATCAACCCTCTCGACGGCACT
TATCCGCCTGGTACTGAGCAAAACCCCGCTAATCCTAATCCTTCTCTTG
AGGAGTCTCAGCCTCTTAATACTTTCATGTTTCAGAATAATAGGTTCCG
AAATAGGCAGGGTGCATTAACTGTTTATACGGGCACTGTTACTCAAGGC
ACTGACCCCGTTAAAACTTATTACCAGTACACTCCTGTATCATCAAAAG
CCATGTATGACGCTTACTNGNNCNGTAAANTCANAGACTGCGCTTTNCA
TTCTGGCTTTNATGANGNTNCATTCNTTTGTGAATAT-3'
```

DARPin 11

(SEQ ID NO: 17)
```
5'-TTCGCCACNTNTGACTTGAGCGTCGATTTTTGTGATGCTCGTCAGG
GGGGCGGAGCCTANNNAAAAACGCCAGCAACGCGGCCTTTTTACGGTTC
CTGGCCTTTTGCTGGCCTTTTGCTCACATGTTCTTTCNTGCGTTATCCC
CTGATTCTGTGGATAACCGTATTACCGCCTTTGAGTGAGCTGATACCGC
TCGCCGCAGCCGAACGACCGAGCGCAGCGAGTCAGTGAGCGAGGAAGCG
GAAGAGCGCCCAATACGCAAACCGCCTCTCCCCGCGCGTTGGCCGATTC
ATTAATGCAGCTGGCACGACAGGTTTCCCGACTGGAAAGCGGGCAGTGA
GCGCAACGCAATTAATGTGAGTTAGCTCACTCATTAGGCACCCCAGGCT
TTACACTTTATGCTCCCGGCTCGTATGTTGTGTGGAATTGTGAGCGGAT
AACAATTTCACACAGGAAACAGCTATGACCATGATTACGCCAAGCTTGC
ATGCAAATTCTATTTCAAGGAGACAGTCATAGCTAGCATGAAAAGATT
TGGCTGGCGCTGGCTGGTTTAGTTTTAGCGTTTAGCGCATCGGCGGACT
ACAAAGAGGCCCAGCCGGCCATGGACCTGGGTAAGAAACTGCTGGAAGC
TGCTCGTGCTGACGTTAACGCTTACGACCGTGTTGGTGAAACTCCGCTG
CACCTGGCTGCTGACAACGGTCACCCGGAAATCGTTGAAGTTCTGCTGA
AGAACGGTGCTGACGTTAACGCTCAGGACAAATTCGGTAAGACCGCTTT
CGACATCTCCATCGACAACGGTAACGAGGACCTGGCTGAAATCCTGCAA
GCGGCCGCACATCATCATCACCATCACGGGGCCGCAGAACAAAAACTCA
TCTCAGAAGAGGATC-3'
```

DARPin 12

(SEQ ID NO: 18)
```
5'-GGGGAAACNNCTGGTATNTTTATAGNCCTGTCGGGTTTCGCCACCT
NTGACTTGAGCGTCGATTTTTGTGATGCTCGTCAGGGGGGCGGAGCCTA
TGGAAAAACGCCAGCAACGCGGCCTTTTTACGGTTCCTGNCCTTTTGCT
GGCCTTTTGCTCACATGTTCTTTCCTGCGTTATCCCCTGATTCTGTGGA
TAACCGTATTACCGCCTTTGAGTGAGCTGATACCGCTCGCCGCAGCCGA
ACGACCGAGCGCAGCGAGTCAGTGAGCGAGGAAGCGGAAGAGCGCCCAA
TACGCAAACCGCCTCTCCCCGCGCGTTGGCCGATTCATTAATGCAGCTG
GCACGACAGGTTTCCCGACTGGAAAGCGGGCAGTGAGCGCAACGCAATT
AATGTGAGTTAGCTCACTCATTAGGCACCCCAGGCTTTACACTTTATGC
TCCCGGCTCGTATGTTGTGTGGAATTGTGAGCGGATAACAATTTCACAC
AGGAAACAGCTATGACCATGATTACGCCAAGCTTGCATGCAAATTCTAT
TTCAAGGAGACAGTCATAGCTAGCATGAAAAGATTTGGCTGGCGCTGG
CTGGTTTAGTTTTAGCGTTTAGCGCATCGGCGGACTACAAAGAGGCCCA
GCCGGCCATGGACCTGGGTAAGAAACTGCTGGAAGCTGCTCGTGCTGAC
GTTAACGCTCGTGACATGACTGGTTGGACTCCGCTGCACCTGGCTGCTA
CTACTGGTCACCTGGAAATCGTTGAAGTTCTGCTGAAGAACGGTGCTGA
CGTTAACGCTCAGGACAAATTCGGTAAGACCGCTTTCGACATCTCCATC
GACAACGGTAACGAGGACCTGGCTGAAATCCTGCAAGCGGCCGCACATC
ATCATCACCATCACGGGGCCGCAGAACAAAAACTCNTCTCAGAAGAGGA
TC-3'
```

DARPin 13

(SEQ ID NO: 19)
```
5'-CTATTTCNGGAGANAGTCATAGCTAGCATGNAAAAGANTTGGCTGG
CGCTGGCTGGTTTAGTTTTAGCGTTTAGCGCATCGGCGGACTACAAAGA
GGCCCAGCCGGCCATGGACCTGGGTAAGAAACTGCTGGAAGCTGCTCGT
GCTGACGTTAACGCTTGGGACGTTCATGGTGACACTCCGCTGCACCTGG
CTGCTATGGACGGTCACCTGGAAATCGTTGAAGTTCTGCTGAAGTACGG
TGCTGACGTTAACGCTCAGGACAAATTCGGTAAGACCGCTTTCGACATC
TCCATCGACAACGGTAACGAGGACCTGGCTGAAATCCTGCAAGCGGCCG
CACATCATCATCACCATCACGGGGCCGCAGAACAAAAACTCATCTCAGA
AGAGGATCTGAATGGGGCCGCATAGACTGTTGAAAGTTGTTTAGCAAAA
CCTCATACAGAAAATTCATTTACTAACGTCTGGAAAGACGACAAAACTT
TAGATCGTTACGCTAACTATGAGGGCTGTCTGTGGAATGCTACAGGCGT
TGTGGTTTGTACTGGTGACGAAACTCAGTGTTACGGTACATGGGTTCCT
ATTGGGCTTGCTATCCCTGAAAATGAGGGTGGTGGCTCTGAGGGTGGCG
GTTCTGAGGGTGGCGGTTCTGAGGGTGGCGGTACTAAACCTCCTGAGTA
CGGTGATACACCTATTCCGGGCTATACTTATATCAACCCTCTCGACGGC
ACTTATCCGCCTGGTACTGAGCAAAACCCCGCTAATCCTAATCCTTCTC
TTGAGGAGTCTCAGCCTCTTAATACTTTCATGTTTCAGAATAATAGGTT
```

-continued

CCGAAATNNNCAGGGTGCATTAACTGTTTATACGGGCACTGTTACTCAA
GGCACTGACCCCGTTAAAACTTATTACCAGTACACTNCTGTATCATCAA
AAGCCNTGTATGACGCTNACTGGNNCNGNAAAANTCNNANACTGCNCTTT
NCAT-3'

DARPin 14

(SEQ ID NO: 20)
5'-TTCTATTTCNGGAGANNGTCATAGCTAGCATGAAAAAGANTTGGCT
GGCGCTGGCTGGTTTAGTTTTAGCGTTTAGCGCATCGGCGGACTACAAA
GAGGCCCAGCCGGCCATGGGCGGAACAGCAGTTTCTTACCCAGGTCCAT
GGACCTGGGTAAGAAACTGCTGGAAGCTGCTCGTGCTGGTCAGGACGAC
GAAGTTCGTATCCTGATGGCTAACGGTGCTGACGTTAACGCTGAAGACT
ACCAGGGTCTGACTCCGCTGCACCTGGCTGCTGACACTGGTCACCTGGA
AATCGTTGAAGTTCTGCTGAAGCACGGTGCTGACGTTAACGCTCAGGAC
AAATTCGGTAAGACCGCTTTCGACATCTCCATCGACAACGGTAACGAGG
ACCTGGCTGAAATCCTGCAAGCGGCCGCACATCATCATCACCATCACGG
GGCCGCAGAACAAAAACTCATCTCAGAAGAGGATCTGAATGGGGCCGCA
TAGACTGTTGAAAGTTGTTTAGCAAAACCTCATACAGAAAATTCATTTA
CTAACGTCTGGAAAGACGACAAAACTTTAGATCGTTACGCTAACTATGA
GGGCTGTCTGTGGAATGCTACAGGCGTTGTGGTTTGTACTGGTGACGAA
ACTCAGTGTTACGGTACATGGGTTCCTATTGGGCTTGCTATCCCTGAAA
ATGAGGGTGGTGGCTCTGAGGGTGGCGGTTCTGAGGGTGGCGGTTCTGA
GGGTGGCGGTACTAAACCTCCTGAGTACGGTGATACACCTATTCCGGGC
TATACTTATATCAACCCTCTCGACGGCACTTATCCGCCTGGTACTGAGC
AAAACCCCGCTAATCCTAATCCTTCTCTTGAGGAGTCTCAGCCTCNTAA
TACTTTCATGTTTCA-3'

ALS DARPin Clone (SEQ ID NO: 21)
5'-TTTGGCTGGCGCTGGCTGGTTTAGTTTTAGCGTTTAGCGCATCGGC
GGACTACAAAGAGGCCCAGCCGGCCATGGACCTGGGTAAGAAACTGCTG
GAAGCTGCTCGTGCTGGTCAGGACGACGAAGTTCGTATCCTGATGGCTA
ACGGTGCTGACGTTAACGCTGTTGACATGTACGGTATCACTCCGCTGCA
CCTGGCTGCTGAATACGGTCACCTGGAAATCGTTGAAGTTCTGCTGAAG
AACGGTGCTGACGTTAACGCTCAGGACAAATTCGGTAAGACCGCTTTCG
ACATCTCCATCGACAACGGTAACGAGGACCTGGCTGAAATCCTGCAAGC
GGCCGCACATCATCATCACCATCACGGGGCCGCAGAACAAAAACTCATC
TCAGAAGAGGATCTGAATGGGGCCGCATAGACTGTTGAAAGTTGTTTAG
CAAAACCTCATACAGAAAATTCATTTACTAACGTCTGGAAAGACGACAA
AACTTTAGATCGTTACGCTAACTATGAGGGCTGTCTGTGGAATGCTACA
GGCGTTGTGGTTTGTACTGGTGACGAAACTCAGTGTTACGGTACATGGG
TTCCTATTGGGCTTGCTATCCCTGAAAATGAGGGTGGTGGCTCTGAGGG
TGGCGGTTCTGAGGGTGGCGGTTCTGAGGGTGGCGGTACTAAACCTCCT
GAGTACGGTGATACACCTATTCCGGGCTATACTTATATCAACCCTCTCG
ACGGCACTTATCCGCCTGGNACTGAGCAAAACCCCGCTAATCCTAATCC
TTCTCTTGAGGAGTCTCAGCCTCTTNATACTTTCATGTTTCANAA-3'

PD DARPin Clone (SEQ ID NO: 22)
5'-AAGATTTGGCTGGCGCTGGCTGGTTTAGTTTTAGCGTTTAGCGCAT
CGGCGGACTACAAAGAGGCCCAGCCGGCCATGGACCTGGGTAAGAAACT
GCTGGAAGCTGCTCGTGCTGGTCAGGACGACGAAGTTCGTATCCTGATG
GCTAACGGTGCTGACGTTAACGCTGCTGACGTTAAAGGTGAAACTCCGC
TGCACCTGGCTGCTTGGGACGGTCACCTGGAAATCGTTGAAGTTCTGCT
GAAGAACGGTGCTGACGTTAACGCTCAGGACAAATTCGGTAAGACCGCT
TTCGACATCTCCATCGACAACGGTAACGAGGACCTGGCTGAAATCCTGC
AAGCGGCCGCACATCATCATCACCATCACGGGGCCGCAGAACAAAAACT
CATCTCAGAAGAGGATCTGAATGGGGCCGCATAGACTGTTGAAAGTTGT
TTAGCAAAACCTCATACAGAAAATTCATTTACTAACGTCTGGAAAGACG
ACAAAACTTTAGATCGTTACGCTAACTATGAGGGCTGTCTGTGGAATGC
TACAGGCGTTGTGGTTTGTACTGGTGACGAAACTCAGTGTTACGGTACA
TGGGTTCCTATTGGGCTTGCTATCCCTGAAAATGAGGGTGGTGGCTCTG
AGGGTGGCGGTTCTGAGGGTGGCGGTTCTGAGGGTGGCGGTACTAAACC
TCCTGAGTACGGTGATACACCTATTCCGGGCTATACTTATATCAACCCT
CTCGACGGCACTTATCCGCCTGGTACTGAGCAAAACCCCGCTAATCCTA
ATCCTTCTCTTGAGGAGTCTCAGCCTCTTAATACTTTCATGNTTCANAA
TAATAGGTTCCGAAATAGGCAGGGNGCATTNNNTGNTTANACGGGNNCN
NNTACTCNNGGCACTGACCCCGTNAANC-3'

AD DARPin Clone 1

(SEQ ID NO: 23)
5'-AAGATTTGGCTGGCGCTGgctggNTTAGTTTTAGCGTTTAGCGCAT
CGGCGGACTACAAAGAGGCCCAGCCGGCCATGGACCTGGGTAAGAAACT
GCTGGAAGCTGCTCGTGCTGGTCAGGACGACGAAGTTCGTATCCTGATG
GCTAACGGTGCTGACGTTAACGCTGACGACCGTAACGGTATGACTCCGC
TGCACCTGGCTGCTCATCAGGGTCACCTGGAAATCGTTGAAGTTCTGCT
GAAGTACGGTGCTGACGTTAACGCTCAGGACAAATTCGGTAAGACCGCT
TTCGACATCTCCATCGACAACGGTAACGAGGACCTGGCTGAAATCCTGC
AAGCGGCCGCACATCATCATCACCATCACGGGGCCGCAGAACAAAAACT
CATCTCAGAAGAGGATCTGAATGGGGCCGCATAGACTGTTGAAAGTTGT
TTAGCAAAACCTCATACAGAAAATTCATTTACTAACGTCTGGAAAGACG
ACAAAACTTTAGATCGTTACGCTAACTATGAGGGCTGTCTGTGGAATGC
TACAGGCGTTGTGGTTTGTACTGGTGACGAAACTCAGTGTTACGGTACA
TGGGTTCCTATTGGGCTTGCTATCCCTGAAAATGAGGGTGGTGGCTCTG
AGGGTGGCGGTTCTGAGGGTGGCGGTTCTGAGGGTGGCGGTACTAAACC
TCCTGAGTACGGTGATACACCTATTCCGGGCTATACTTATATCAACCCT
CTCGACGGCACTTATCCGCCTGGTACTGAGCAAAACCCCGCTAATCCTA
ATCCTTCTCTTGAGGAGTCTCAGCCTCTTAATACTTTCATGTTTCNNAA
TAATAGGTTCCGAAATAGGCAGGGTGCATNNANTGTTTANACGGNCACT -continued

GNTACTCNAGGCACTGACCCCGTTAAACTTATTACCAGNANNCTCCTGT
ATCATCAAAAGCCATGTATGACGCT-3'

AD DARPin Clone 2

(SEQ ID NO: 24)
5'-TGGCTGGCGCTGgctggTTTAGTTTTAGCGTTTAGCGCATCGGCGG
ACTACAAAGAGGCCCAGCCGGCCATGGACCTGGGTAAGAAACTGCTGGAA
AGCTGCTCGTGCTGGTCAGGACGACGAAGTTCGTATCCTGATGGCTAAC
GGTGCTGACGTTAACGCTAAAGACTCTGTTGGTAAAACTCCGCTGCACC
TGGCTGCTCATTGGGGTCACCTGGAAATCGTTGAAGTTCTGCTGAAGCA
CGGTGCTGACGTTAACGCTCAGGACAAATTCGGTAAGACCGCTTTCGAC
ATCTCCATCGACAACGGTAACGAGGACCTGGCTGAAATCCTGCAAGCGG
CCGCACATCATCATCACCATCACGGGGCCGCAGAACAAAAACTCATCTC
AGAAGAGGATCTGAATGGGGCCGCATAGACTGTTGAAAGTTGTTTAGCA
AAAACCTCATACAGAAAATTCNNNNACTAACGTCTGGAAAGACGACAAAA
CTTTAGATCGTTACGCTAACTATGAGGGCTGTCTGTGGAATGCTACAGG
CGTTGTGGTTTGTACTGGTGACGAAACTCAGTGTTACGGTACATGGGTT
CCTATTGGGCTTGCTATCCCTGAAAATGAGGGTGGTGGCTCTGANGGTG
GCGGTTCTGAGGGTGGCGGTTCTGAGGGTGGCGGTACTAAACCTCCTGA
GTACNGTGATACACCTATTCCGGGCTATACTTATATCAACCCTCTCGAC
GGCACTTATCCGCCTGGTACTGAGCAAAACCCCGCTAATCCTAATCCTT
CTCTTGNNNGTCTCAGCCTCTTATACTTTCATGTTTCANAATAATAGGT
NNCGAAANAGGCAGGGTGCATTAACTGTTTATANNGGCACTGNTANNCA
NGGNACTGACCCCNTNAAACTTATTACCAGT-3'

AD DARPin Clone 3

(SEQ ID NO: 25)
5'-TGGNTGGCGCTGgtggNTTAgTTTTAGCGTTTAGCGCATCGGCGGA
CTACAAAGAGGCCCAGCCGGCCATGGACCTGGGTAAGAAACTGCTGGAA
GCTGCTCGTGCTGGTCTGGACGACGAAGTTCGTATCCTGATGGCTAACG
GTGCTGACGTTAACGCTACTGACACTGACGGTTCTAGTCCGCTGCACCT
GGCTGCTCAGGAAGGTCACCTGGAAATCGTTGAAGTTCTGCTGAAGTAC
GGTGCTGACGTTAACGCTCAGGACAAATTCGGTAAGACCGCTTTCGACA
TCTCCATCGACAACGGTAACGAGGACCTGGCTGAAATCCTGCAAGCGGC
CGCACATCATCATCACCATCACGGGGCCGCAGAACAAAAACTCATCTCA
GAAGAGGATCTGAATGGGGCCGCATAGACTGTTGAAAGTTGTTTAGCAA
AACCTCATACAGAAAATTCANTNNCTAACGTCTGGAAAGACGACAAAAC
TTTAGATCGTTACGCTAACTATGAGGGCTGTCTGTGGAATGCTACAGGC
GTTGTGGTTTGTACTGGTGACGAAACTCAGTGTTACGGTACATGGGTTC
CTATTGGGCTTGCTATCCCTGAAAATGAGGGTGGTGGCTCTGANGGTGG
CGGTTCTGAGGGTGGCGGTTCTGAGGGTGGCGGTACTAAACCTCCTGAG
TACGGTGATACACCTATTCCGGGCTATACTTATATCAACCCTCTCGACG
GCACTTATCCGCCTGGTACTGAGCAAAACCCCGCTAATCCTAATCCTTC
TCTTGAGGAGTCTCAGCCTCTTAATACTTTCATGTTTCANAATAATNNN
TTCCGAAATAGGCAGGGTGCATTAACTGTTTATACGGGCACTGTTACTC
ANGGCACTGACCCCGTTAAACTTATTACCAG-3'

AD DARPin Clone 4

(SEQ ID NO: 26)
5'-GGCTGGCGCTGgctggttTAGTTTTAGCGTTTAGCGCATCGGCGGA
CTACAAAGAGGCCCAGCCGGCCATGGACCTGGGTAAGAAACTGCTGGAA
GCTGCTCGTGCTGGTCAGGACGACGAAGTTCGTATCCTGATGGCTAACG
GTGCTGACGTTAACGCTGCTGACTTCAACGGTCAAACTCCGCTGCACCT
GGCTGCTGTTTGGGGTCACCTGGAAATCGTTGAAGTTCTGCTGAAGAAC
GGTGCTGACGTTAACGCTCAGGACAAATTCGGTAAGACCGCTTTCGACA
TCTCCATCGACAACGGTAACGAGGACCTGGCTGAAATCCTGCAAGCGGC
CGCACATCATCATCACCATCACGGGGCCGCAGAACAAAAACTCATCTCA
GAAGAGGATCTGAATGGGGCCGCATAGACTGTTGAAAGTTGTTTAGCAA
AACCTCATACAGAAAATTCNNNNACTAACGTCTGGAAAGACGACAAAAC
TTTAGATCGTTACGCTAACTATGAGGGCTGTCTGTGGAATGCTACAGGC
GTTGTGGTTTGTACTGGTGACGAAACTCAGTGTTACGGTACATGGGTTC
CTATTGGGCTTGCTATCCCTGAAAATGAGGGTGGTGGCTCTGANGGTGG
CGGTTCTGAGGGTGGCGGTTCTGAGGGTGGCGGTACTAAACCTCCTGAG
TACGGTGATACACCTATTCCGGGCTATACTTATATCAACCCTCTCGACG
GCACTTATCCGCCTGGTACTGAGCAAAACCCCGCTAATCCTAATCCTTC
TCTTGAGGAGTCTCANNCTCTTAATACTTTCATGTTTCAGAATAATANN
NTCCGAAATAGG-3'

AD DARPin Clone 5

(SEQ ID NO: 27)
5'-TTGGCTGGCGCTGNNNNNTTTAGTTTTAGCGTTTAGCGCATCGGCG
GACTACAAAGAGGCCCAGCCGGCCATGGACCTGGGTAAGAAACTGCTGG
AAGCTGCTCGTGCTGGTCAGGACGACGAAGTTCGTATCCTGATGGCTAA
CGGTGCTGACGTTAACGCTCGTGACGTTTCTGGTGCTACTCCACTGCAC
CTGGCTGCTACTTGGGGTCACCTGGAAATCGTTGAAGTTCTGCTGAAGT
ACGGTGCTGACGTTAACGCTCAGGACAAATTCGGTAAGACCGCTTTCGA
CATCTCCATCGACAACGGTAACGAGGACCTGGCTGAAATCCTGCAAGCG
GCCGCACATCATCATCACCATCACGGGGCCGCAGAACAAAAACTCATCT
CAGAAGAGGATCTGAATGGGGCCGCATAGACTGTTGAAAGTTGTTTAGC
AAAAACCTCATACAGAAAATTNANNNACTAACGTCTGGAAAGACGACAAA
ACTTTAGATCGTTACGCTAACTATGAGGGCTGTCTGTGGAATGCTACAG
GCGTTGTGGTTTGTACTGGTGACGAAACTCAGTGTTACGGTACATGGGT
TCCTATTGGGCTTGCTATCCCTGAAAATGAGGGTGGTGGCTCTGAGGGT
GGCGGTTCTGAGGGTGGCGGTTCTGAGGGTGGCGGTACTAAACCTCCTG
AGTACGGTGATACACCTATTCCGGGCTATACTTATATCAACCCTCTCGA
CGGCACTTATCCGCCTGGTACTGAGCAAAACCCCGCTAATCCTAATCCT
TCTCTTGAGGAGTCTCAGCCTCTTAATACTTTCNTGTTTCANAATAATA
GGTTCCGAAATAGGNAGGGTGCATTAACTGTTTATACGGGCACTNNTAC
TCANGCANTGNCCCCGTNAAACTTNTACCAGT-3'

-continued

AD DARPin Clone 6

(SEQ ID NO: 28)
```
5'-TTTAGCGCATCGGCGGACTACAAAGNNNNNNNGGNCATGGACCTGG

GTAAGAAACTGCTGGAAGCTGCTCGTGCTGGTCAGGACGACGAAGTTCG

TATCCTGATGGCTAACGGTGCTGACGTTAACGCTCGTGACGTTACTGGT

GTTACTCCGTTGCACCTGGCTGCTAACCGTGGTCACCTGGAAATCGTTG

AAGTTCTGCTGAAGTACGGTGCTGACGTTAACGCTCAGGACAAATTCGG

TAAGACCGCTTTCGACATCTCCATCGACAACGGTAACGAGGACCTGGCT

GAAATCCTGCAAGCGGCCGCACATCATCATCACCATCACGGGCCGCAG

AACAAAAACTCATCTCAGAAGAGGATCNGNNTGGGGCCGCATAGACTGT

TGAAAGTTGTTTAGCAAAACCTCATACAGAAAATTCNANNACTAACGTC

TGGAAAGACGACAAAACTTTAGATCGTTACGCTAACTATGAGGGCTGTC

TGTGGAATGCTACAGGCGTTGTGGTTTGTACTGGTGACGAAACTCAGTG

TTACGGTACATGGGTTCCTATTGGGCTTGCTATCCCTGAAAATGAGGGT

GGTGGNTCTGAGGGTGGCGGTTCTGAGGNTGGCGGNTCTGANGGTGGCG

GTACTAAANCTCCTGAGTACGGTGATACACCTATTCCGGGCTATACTTA

TATCAACCCTCTCGANNGCACTTATCCGCCTNNNACTGAGCAAAACCCC

GCTAATCCTAATCCTTCNCTTGAGGAGNCTCAGCCTCTTAATACTTTNN

TGNTNCAGANNATAGGTTCCGAAANTNGGNAGGNNGCATTAACTGTTTN

NACGGGCNCTGNTNCTTCAAGGCACTGANCCCGTTA-3'
```

The following is a description of the plasmid and library construction. When generating the DARPin library the pIT2 phagemid is used. BsaI is one of the restriction enzymes used to assemble the DARPin library and it was discovered that the restriction site for this enzyme was also present on the pIT2 vector. To remedy this problem, a PCR product was first produced using primers that mutated one of the bases in the BsaI restriction site. This PCR product was then used in a second reaction along with another primer to generate the new pIT2 vector lacking the BsaI restriction site.

It was observed that the expression of the DARPin library improved when using the signal recognition particle (SRP) translocation pathway. The pIT2 vector has the PelB signal sequence and so the PelB was changed to the DsbA signal sequence. The DsbA signal was generated using assembly PCR with four oligonucleotides. To facilitate the replacement of PelB signal with the DsbA signal, an additional restriction site was also added to the pIT2 vector lacking the BsaI site. After transformation of this SRP modified BsaI lacking pIT2 vector into TG1 competent cells, some of the clones were sequenced and the results indicated that PelB was replaced by the DsbA signal.

To ensure that the DsbA signal allows for correct expression of proteins, this modified pIT2 vector was digested with NcoI and NotI restriction enzymes and inserted two different scFvs that were previously isolated. The c-myc tag on the scFv was used in the Western blotting process to determine if the scFv of interest was produced. The results indicated that the SRP modified pIT2 vector was able to produce both scFvs. One of the scFvs was purified using Nickel bead purification to ensure the scFv could be purified. Western blotting showed bands at the correct location for the scFvs. The two scFvs were inserted into the vector in order to have better protein production results with one of the scFvs as compared to the other. The production of both scFvs was satisfactory. Since the SRP modified vector was able to produce proteins, protein expression is attainable in the DARPin library.

Next, it was verified that the SRP modified pIT2 vector displayed the proteins on the phages, since the DARPin library is used in the biopanning process. So again, using the NcoI and NotI restriction sites, another scFv was inserted into the vector. Using the Tomlinson I and J library protocol, phage displaying this scFv was produced. The titer of the phage produced was good. These phages were then used in an ELISA to determine binding to it corresponding targets. Based on the binding results of the ELISA, the scFv was being displayed properly. Therefore, the new SRP modified pIT2 vector was also able to display proteins correctly in the phage display process.

To produce the AR proteins, the N-Terminal capping AR, the AR modules and the C-Terminal capping AR were need. The N-Terminal capping AR and C-Terminal capping AR were generated using assembly PCR. The C-Terminal capping AR was then cloned into the SRP modified pIT2 vector since once the N-Terminal capping AR and the AR modules are ligated together, they are cloned into this vector containing the C-Terminal capping AR. The N-Terminal capping AR was also cloned into the SRP modified pIT2 vector to verify the correct sequence was assembled in the PCR. This vector was then used with the N-Terminal capping AR and two primers to produce large number of copies of this sequence rather than using the products generated from assembly PCR to ligate the N-Terminal capping AR to the AR modules, so as to reduce any errors in the N-Terminal capping AR region that may occur during assembly PCR.

Using six oligonucleotides the AR module was assembled, and based on DNA gel electrophoresis, the product produced was the correct size. The band was then gel extracted. The AR module and the N-Terminal capping AR were digested and ligated together and the product (labeled as the N1) was run on a DNA gel. The band produced was present at the correct location on the gel. Large quantities of the SRP modified pIT2 vector containing the C-Terminal capping AR were produced. This vector and the N1 product were digested with the appropriate restriction enzymes and these two products are ligated together.

These vectors are transformed into TG1 cells to produce the complete N1C library. Once the N1C library is generated, the sequences are checked to ensure correct assembly of the N-Terminal capping AR, the AR module, and the C-Terminal capping AR. The N1 product is amplified and more AR modules are added to N1 to generate the N2, N3 and N4 products, which are ligated into the vector containing the C-Terminal capping AR to produce the N2C, N3C and N4C libraries, respectively. These libraries are then used in the biopanning process to isolate DARPin proteins that specifically recognize different morphologies of a-synuclein using the novel AFM/phage display-based biopanning techniques.

Example 3

Figure 2:
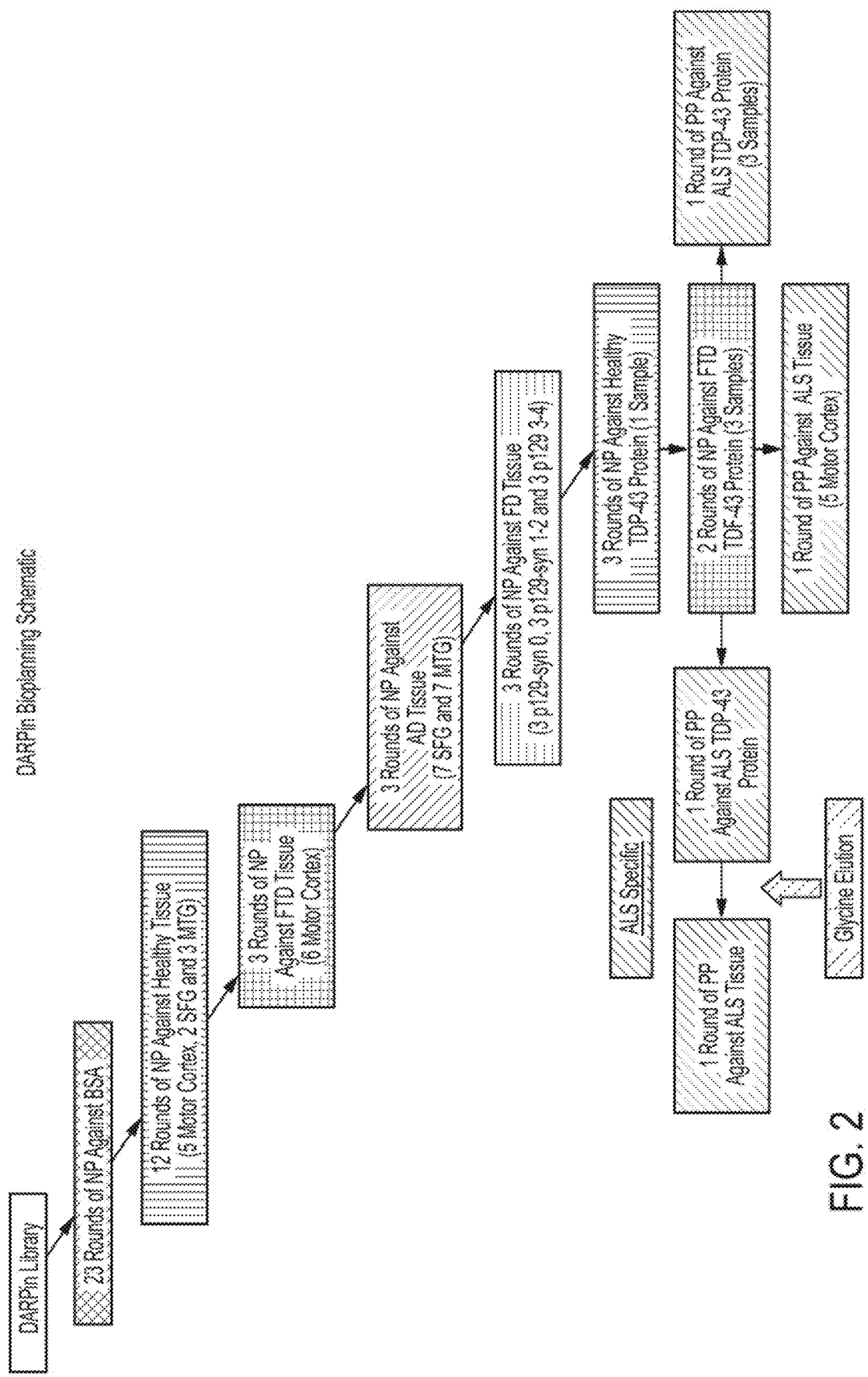
FIG. 2. provides details of the DARPin ALS biopanning procedures.

Isolation of DARPin Proteins that Specifically Recognize Different Morphologies of a-Synuclein Using Novel AFM/Phage Display Based Biopanning Techniques The role of TDP-43 in Amyotrophic Lateral Sclerosis (ALS) has been of interest. Reagents are developed that are reactive with the various forms of TDP-43 present in the brain of individuals with ALS, as well as the detection of such targets in cerebrospinal fluid (CSF) and sera samples. A N1C phage library was used to isolate such reagents against TDP-43, and the library was compared with a commercially available scFv library. A schematic summarizing the details of the DARPin ALS biopanning procedures is illustrated in FIG. 2.

Atomic force microscopy (AFM) was used in the biopanning protocol to provide two main advantages, including the verification of successful removal of off-targets and secondly to reduce the required quantity of the target antigen (whether purified or in a crude mixture). Briefly, 23 immunotubes were coated with 1 mg/ml of bovine serum albumin (BSA). The BSA solution from tube #1 was removed, the tube washed and the DARPin library added. The tube was allowed to rotate for 30 minutes. The BSA was removed from the second tube and the phage transferred to the second tube from the first. This was repeated for all 23 tubes. In the past 12 immunotubes were sufficient to removed negative binders to BSA. However, using AFM visualization showed that phages binding to BSA were still visible after 12 rounds. Only after 23 rounds of negative panning (NP) were the reagents reactive to BSA removed. Utilizing the phage after the 23 rounds of NP against BSA, reactivity to healthy human tissue (HT) was visible. The healthy human tissue is a mixture of five samples from the motor cortex, two samples from the superior frontal gyms (SFG) and three from the middle temporal gyms (MTG). After 12 rounds of NP against HT using immunotubes, the phages that were reactive to HT were removed. TDP-43 also plays a role in some cases of Frontotemporal Dementia (FTD) and any potential ALS clones that are cross-reactive to FTD are less beneficial as an ALS diagnostic or therapeutic reagent. Thus using a combination of six FTD human tissue samples from the motor cortex, reactivity of the phages after the NP against HT to FTD tissue were examined. Phage binding was visible, but not after eight rounds of NP against FTD tissue using immunotubes. TDP-43 may also play a role in other neurodegenerative diseases such as Alzheimer's (AD) and Parkinson's (PD).

Using seven AD human brain tissue samples from the MTG and seven from the SFG and the phage after the NP against FTD tissue, reactivity was visible. After eight rounds of NP against the AD tissue using immunotubes no reactivity was visible. For the NP against PD human brain tissue nine samples from the MTG were utilized with varying p129-syn levels. After eight rounds of NP against AD tissue the phage displayed reactivity to PD tissue. After eight rounds of NP against PD tissue using immunotubes reactivity was not detected.

Since the protein TDP-43 is of particular interest, phages were removed that would bind healthy TDP-43 variants as well. TDP-43 was immunoprecipitated from the brain of a healthy individual and employed in three rounds of negative panning using mica (instead of immunotubes due to limited sample quantity). Mica was utilized for the remaining panning steps. TDP-43 was also immunoprecipitated from the brains of three individuals with ALS and three with FTD. After the NP against healthy TDP-43, two rounds of NP against FTD TDP-43 were carried out. Some of the phages were then used in one round of positive panning (PP) against ALS TDP-43 and for comparison one round of PP against ALS human brain tissue (a combination of 5 samples from the motor cortex) was also performed. Numerous clones were eluted from both positive Panning steps. To reduce the quantity of clones needed for assessments in the further characterization studies, some of the remaining phage was used after the two rounds of NP against the FTE TEP-43 and one more round of PP against ALS TDP-43 was completed. The phages that bound were eluted with glycine allowing the antibody to remain attached to the phage (normally, trypsin elution is employed but was not here in order to avoid cleavage of the phage article). The eluted phages were then added to mica with the ALS tissue mixture and the bound phages eluted. From this procedure two clones were eluted. The intent in performing this 2-step PP procedure was that the clones obtained are reactive with both the TDP-43 protein and the ALS tissue. Tissue reactivity was ensured in the event that some forms to the immunoprecipitated TDP-43 proteins were altered during the imunoprecipitation process. DNA sequencing of the two clones revealed one clone with no errors (complete protein sequence). This clone is characterized in future studies for ALS specificity. Clones were also obtained that bound only to the ALS TDP-43 or ALS Tissue. (FIG. 2)

Reviewing the schematic in FIG. 2, it is noted that extensive negative biopanning procedures were carried out to obtain the potential ALS TDP-43 DARPin clones. After each set of NP against a particular target a small quantity of phage was saved in case of contamination. Some of these phages were used in other PP procedures to isolate potential DARPin clones against other targets of interest. First, potential DARPins against protein variants present in both PD human brain tissue and sera samples were examined.

Figure 3:
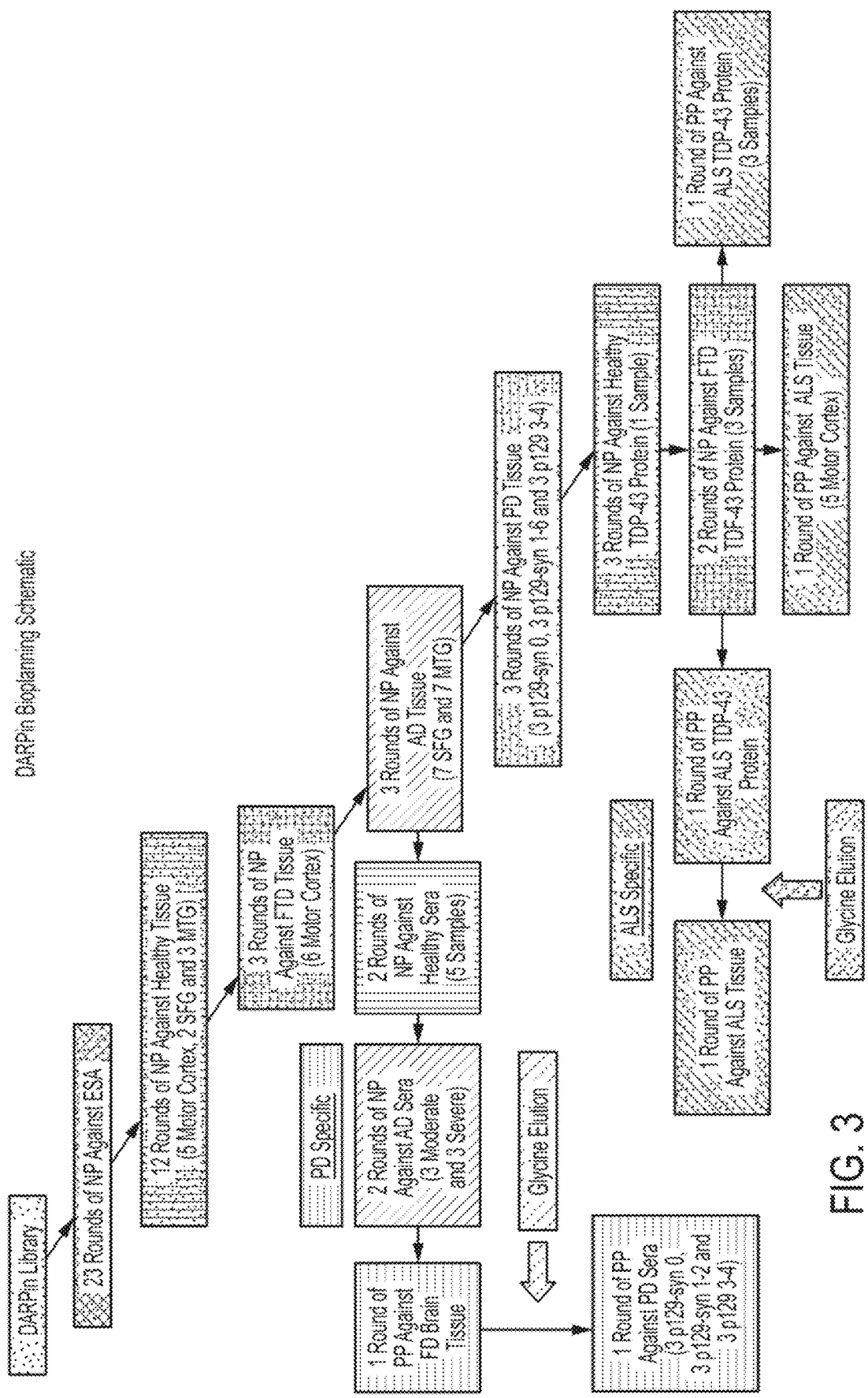
FIG. 3. provides highlights the procedures completed to obtain the potential PD specific DARPins.

FIG. 3 highlights the procedures completed to obtain the potential PD specific DARPins. The phages were selected that remained after eight rounds of NP against AD human brain tissue (since this is before phages were removed with PD tissue). All these panning steps were achieved using mica. First, two rounds of NP were carried out against health sera (mixture of five samples) and two rounds of NP against AD sera (mixture of three samples with moderate AD plaques and three samples with severe AD plaques). These steps eliminate DARPins reactive to antigens present in normal or AD sera samples. Next, one round of PP was performed against PD brain tissue (same mixture as above) and carried out the glycine elution procedures. These phages were then added to mica containing PD sera (from the same nine individuals that were obtained the brain samples). After elution one clone was acquired. DNA sequencing revealed that this clone had a complete protein sequence with no errors. The sequence of this clone was different from the one ALS clone reactive with both the ALS TDP-43 protein and tissue. The phages were collected that bound only to the PD tissue as backup.

Figure 4:
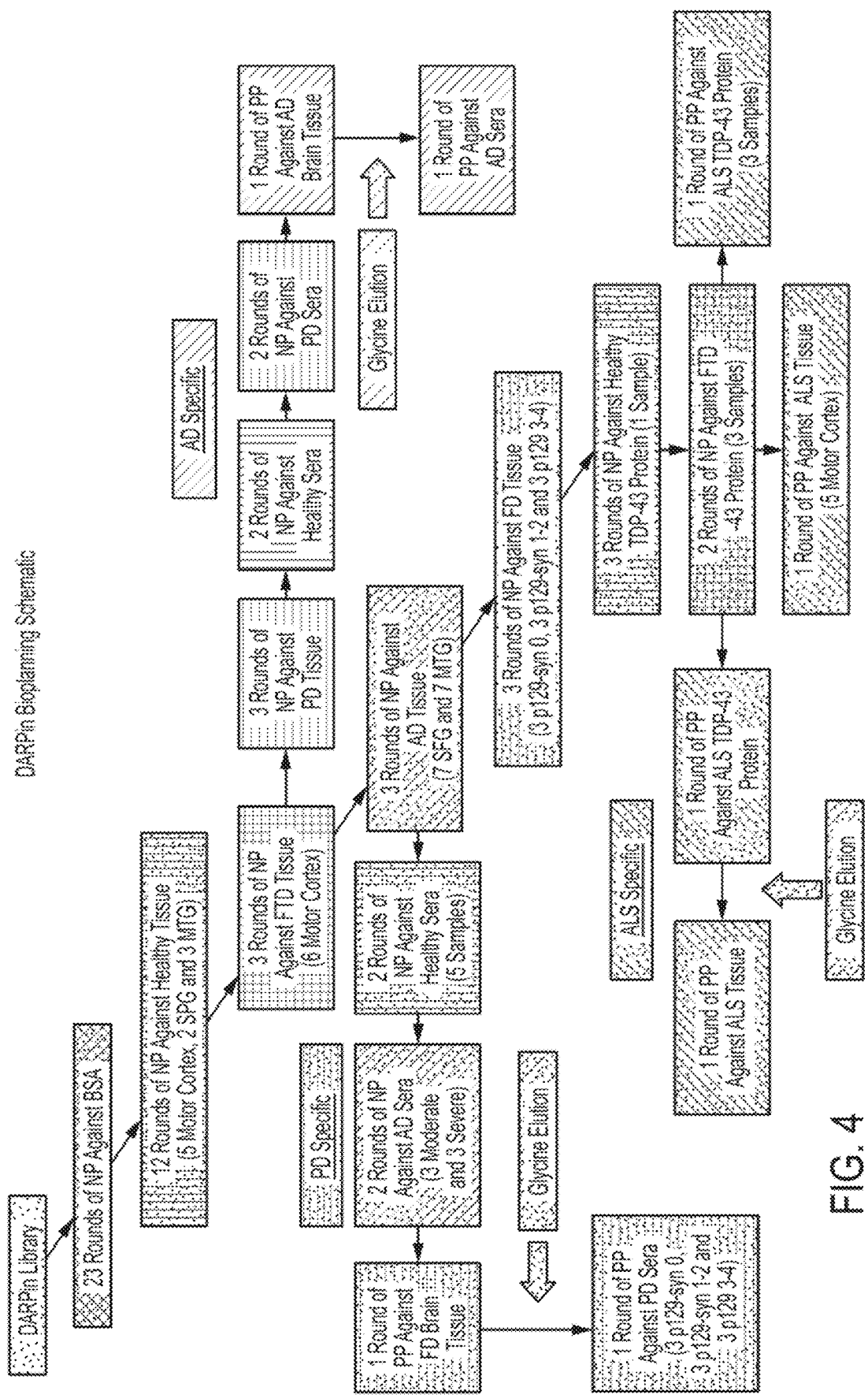
FIG. 4. provides highlights the portion of the schematic that summarizes the AD biopanning procedures.

Potential DARPins that are reactive to both AD brain tissue and sera samples are also of interest. To isolate such clones the starting material was the phages that remained after the NP against FTD tissue (since the DARPins that would bind AD tissue were still present). FIG. 4 highlights the portion of the schematic that summarizes the AD biopanning procedures. It is important to note that the DARPins reactive with PD tissue were still present since these binders were not removed until future NP steps. Therefore, eight rounds of NP against PD tissue were completed using immunotubes. Next, two rounds of NP against healthy human sera and two rounds of NP against PD sera (using mica) were carried out. These phages were then used in one round of PP against AD human brain tissue followed by glycine elution. The eluted phages were added to AD human sea samples. After the incubation step the bound phages were eluted. Several DARPin clones were eluted from this 2-step PP procedure. DNA sequencing results of some of the clones revealed six clones with complete sequences (no errors). These six clones were different from the one ALS and one PD clones above. The DARPins that were reactive only to AD tissue were also kept.

Example 4

Use of Serum Protein Variant Biomarkers to Assess Risk of AD Following TBI

Generation of Nanobodies with Specificity for Disease Specific Protein Variants.

Selected protein variants including various soluble oligomeric protein species are key factors in the onset and progression of many human diseases. Variants of four key neuronal proteins, tau, Aβ, TDP-43 and a-syn, have been implicated in the most prevalent neurodegenerative diseases including AD, PD, FTD, ALS and other tauopathies and synucleinopathies. The protein variants are generated by stressed cells in diseased brains, they occur early during disease progression, different variants have different toxic effects on neuronal cells, and different protein variant species preferentially occur in patients with different neurodegenerative diseases. Therefore the ability to detect the presence of specific protein variants in CSF and especially blood samples is a very powerful tool to help early and definitive diagnosis of different types of brain damage. Toward this end, novel biopanning technologies were developed that combine the imaging capabilities of Atomic Force Microscopy (AFM) with the diversity of antibody libraries. This unique biopanning combination of antibody diversity and imaging capability has enabled the isolation of single chain antibody variable domain fragment (scFv or nanobody) reagents to an array of morphologies of key proteins involved in neurodegenerative diseases including tau, Aβ, TDP-43 and a-syn. Nanobodies were isolated that specifically recognize monomeric (Emadi, S., et al., Biochemistry, 2004. 43(10): p. 2871-2878), fibrillar (Barkhordarian, H., et al., Protein Eng Des Sel, 2006. 19(11): p. 497-502), and two different oligomeric a-syn morphologies (Emadi, S., et al., J Mol Biol, 2007. 368(4): p. 1132-44; Emadi, S., et al., J Biol Chem, 2009. 284(17): p. 11048-58). In addition, nanobodies were isolated to different regions of monomeric (Liu, R., et al., Biochemistry, 2004. 43(22): p. 6959-67; Zameer, A., et al., Biochemistry, 2006. 45(38): p. 11532-9) and fibrillar Aβ (Marcus, W. D., et al., Nanomedicine, 2008. 4(1): p. 1-7) and to three distinct naturally occurring oligomeric Aβ morphologies (Zameer, A., et al., J Mol Biol, 2008. 384(4): p. 917-28). Nanoscale methods were developed to characterize nanobody binding specificities again using AFM to image whether the nanobodies bind different target antigens (Kasturirangan, S., et al., Biotechnol Prog, 2013. 29(2): p. 463-71). Also, nanobodies were isolated to key forms of tau. Nanobodies were generated that selectively bind the toxic trimeric tau species, but not monomeric or fibrillar tau. Biopanning protocols were improved in order to readily isolate nanobodies that selectively bind disease related protein variants directly from minimal amounts of human samples including tissue, CSF or sera samples. Using these biopanning protocols, nanobodies were generated that selectively bind TDP-43 variants that are present in both human ALS and FTD brain samples but not healthy samples, and ones that are present in ALS but not FTD or healthy and FTD but not ALS or healthy brain tissue. The diversity of protein variant specific nanobodies that we are able to generate indicates the powerful and unique capabilities of our panning technology.

Detection of Disease Related Protein Variants in Human Samples. A) Sandwich ELISA with Sub-Femtomolar Sensitivity.

Figure 5:
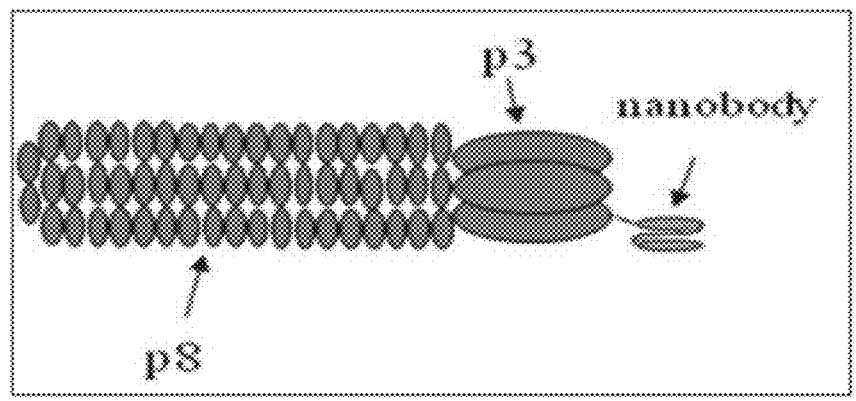
FIG. 5. Schematic of nanobody displayed on surface of phage particle. Multiple copies of pVIII coat protein enable over 1000-fold enhancement of nanobody signal.

An electronic impedance biosensor was initially utilized to detect oligomeric protein variants in post-mortem human CSF samples using nanobodies showing that it was possible to distinguish between cognitively normal (ND), PD and AD samples (Sierks, M. R., et al., Integrative Biology, 2011. 3(12): p. 1188-96). To facilitate quantitative analysis of multiple samples in a format that can be utilized in most labs, a simple yet sensitive sandwich ELISA was developed to detect low concentrations of target antigens in human samples (Williams, S., P. Schulz, and M. R. Sierks, Biotechnol Prog, 2014). In a typical sandwich ELISA, one antibody is used to capture the target antigen and a second detection antibody, often conjugated with a fluorescent marker or enzyme such as horseradish peroxidase (HRP) is used to quantify the amount of bound target. For oligomeric protein variants, either the same nanobody can be used to both capture and detect the target species since the oligomeric aggregates have multiple binding sites on each target molecule, or an oligomeric specific nanobody can be used to capture the target and a non-morphology selective nanobody to detect the bound target. As an example, for the capture antibody a nanobody is used that selectively binds oligomeric tau, and for the detection antibody a nanobody is used that binds all forms of tau. To amplify the detection signal for increased sensitivity a phage displayed version of the detection antibody similar to what was use in the biopanning studies is used. A single detection antibody is thus connected to a phage particle which contains over 2000 copies of the gp8 coat protein (FIG. 5). Biotinylation of the coat proteins enables several thousand-fold amplification of the detection signal compared to using the nanobody alone. A streptavidin/HRP complex is used to bind the biotinylated phage and a colorimetric or chemiluminescence substrate to quantify the bound target. It was possible to detect antigen over a large linear concentration range with detection limits well below femtomolar concentrations using a chemiluminescence substrate (Williams, S., P. Schulz, and M. R. Sierks, Biotechnol Prog, 2014). Using this sandwich ELISA, it was possible to readily detect the presence of oligomeric protein aggregates not only in human brain tissue homogenates, but also in human CSF and serum samples as well, as shown in the following section.

B) Morphology Specific Nanobodies to Distinguish and Stage AD Using Human Tissue, CSF and Serum Samples. i) Human Tissue.

It has been shown that morphology specific nanobodies distinguish human post-mortem ND, AD and PD brain tissue samples. The oligomeric a-syn specific nanobodies selectively label PD tissue (Emadi, S., et al., J Mol Biol, 2007. 368(4): p. 1132-44; Emadi, S., et al., J Biol Chem, 2009. 284(17): p. 11048-58) and the oligomeric Aβ specific nanobodies (Zameer, A., et al., J Mol Biol, 2008. 384(4): p. 917-28; Kasturirangan, S., et al., Neurobiol Aging, 2012. 33(7): p. 1320-8) and oligomeric tau specific nanobodies selectively label AD tissue. To further demonstrate the potential value of protein variant specific nanobodies in diagnosing neurodegenerative diseases, well characterized brain samples from the middle temporal gyms of six non-demented (ND), six AD and nine Parkinson's (PD) patients were analyzed using the sandwich ELISA protocol described above. Post-mortem human brain tissue Wwase analyzed using two anti-oligomeric Aβ nanobodies, A4 and C6T (Zameer, A., et al., J Mol Biol, 2008. 384(4): p. 917-28; Kasturirangan, S., et al., Biotechnol Prog, 2013. 29(2): p.

Figure 6:
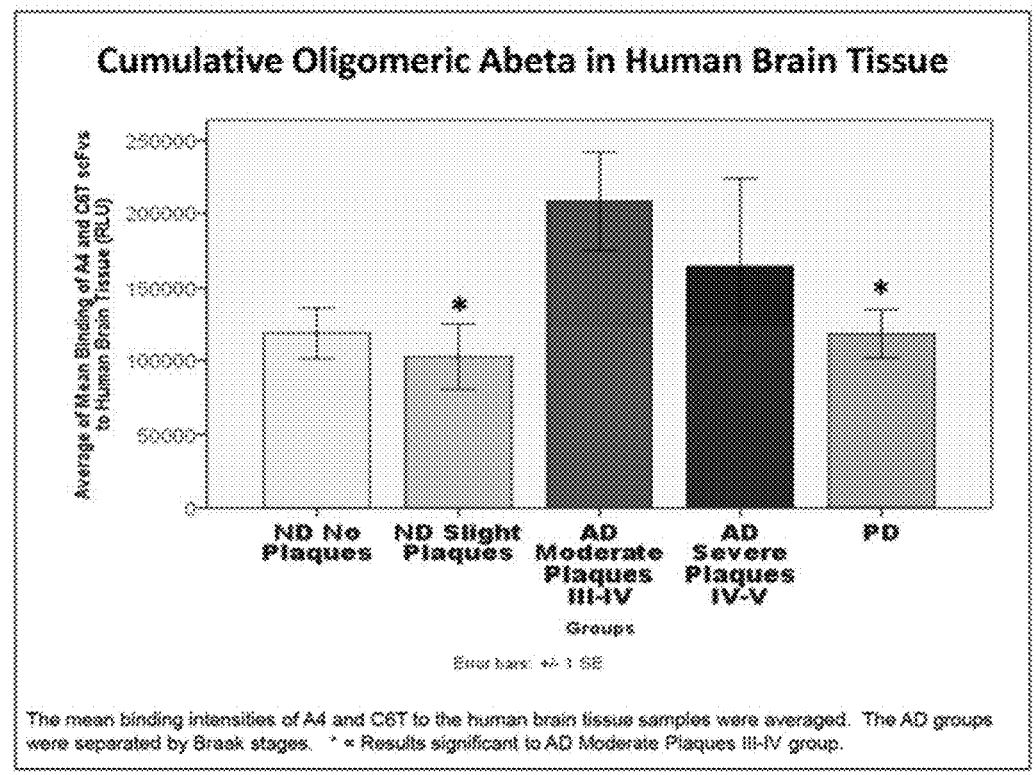
FIG. 6. Oligomeric Aβ levels in human brain tissue from cognitively normal (ND), AD and PD samples. Combined oligomeric Aβ levels obtained with both A4 and C6T nanobodies are shown. The highest oligomeric Aβ levels are observed in AD samples with moderate plaques, then in AD samples with severe plaques.
Figure 7:
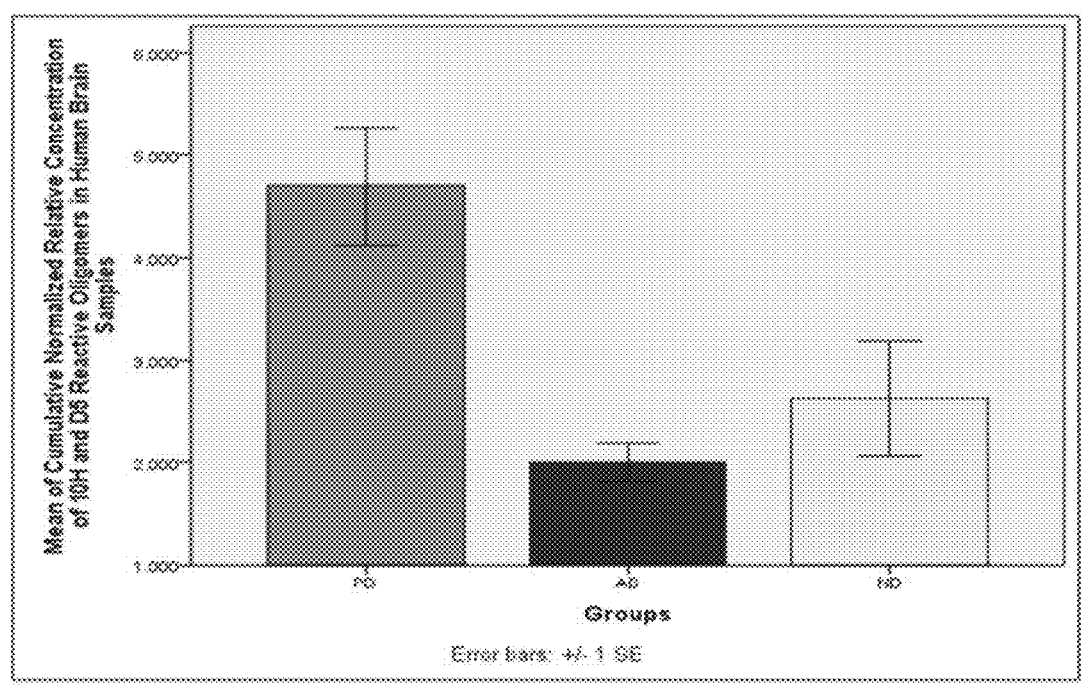
FIG. 7. Oligomeric a-syn levels in human brain tissue from cognitively normal (ND), AD and PD samples. Combined oligomeric a-syn levels obtained with both D5 and 10H nanobodies are shown. High oligomeric a-syn levels were present in PD samples but not AD or ND samples.
Figure 8:
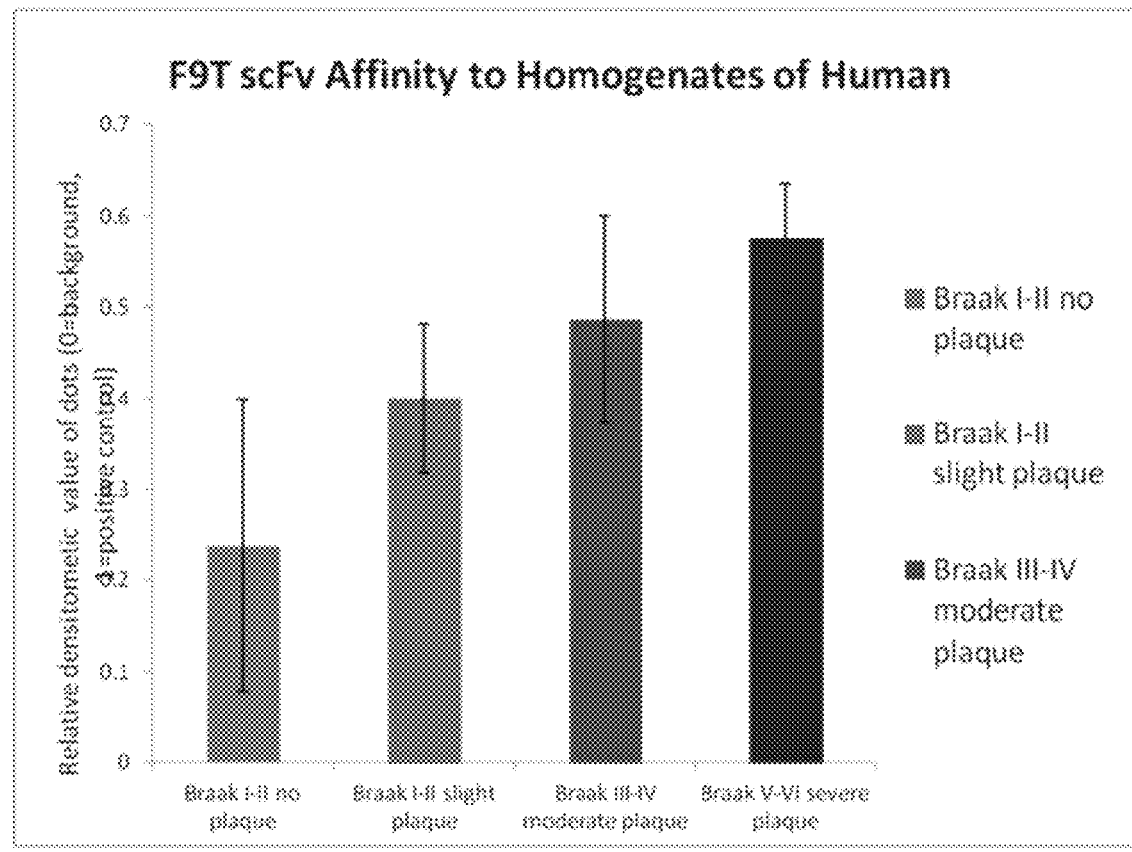
FIG. 8. Oligomeric tau levels in human brain tissue correlate with Braak stage. Oligomeric tau levels of brain homogenates were probed with the anti-oligomeric tau nanobody F9T. First bar: ND Braak stage I-II, no amyloid plaques. Second bar: ND Braak stage I-II slight plaques. Third bar: AD Braak stage III-IV moderate plaques. Fourth bar: AD Braak stage V-VI severe plaques. Oligomeric tau levels increase with Braak stage and the presence of amyloid plaques.

463-71), two anti-oligomeric a-syn nanobody 10H and D5 (Emadi, S., et al., J Mol Biol, 2007. 368(4): p. 1132-44; Emadi, S., et al., J Biol Chem, 2009. 284(17): p. 11048-58), and an anti-oligomeric tau nanobody F9T. Samples were prepared as described (Emadi, S., et al., J Mol Biol, 2007. 368(4): p. 1132-44; Emadi, S., et al., J Biol Chem, 2009. 284(17): p. 11048-58). Protein concentrations of each sample were normalized and equal volumes used where the samples were diluted on average around 1/70 for analysis. When assaying oligomeric Aβ levels, both the A4 and C6T nanobodies could readily distinguish between AD and PD and ND samples and could stage AD as higher levels of oligomeric Aβ were observed in AD samples with moderate plaques compared to AD samples with severe plaques (FIG. 6). What is particularly exciting about the data is that the anti-oligomeric Aβ nanobodies readily distinguish between ND and AD cases even in samples that have similar amyloid plaque loads. Therefore while amyloid plaque deposition, a commonly used diagnostic test for AD, does not correlate very well with AD disease progression, presence of specific oligomeric Aβ species correlates very well. As expected, the oligomeric Aβ levels decrease as the disease progresses from moderate to severe plaque loads. When the same samples were analyzed for presence of oligomeric a-syn using the 10H and D5 anti-oligomeric a-syn nanobodies, all the PD samples reacted strongly, whereas the AD and ND samples showed only background levels (FIG. 7) indicating that oligomeric a-syn levels can be used to distinguish between PD and AD and ND samples. Finally, when the same samples were analyzed for the presence of oligomer tau using the F9T nanobody again we could readily distinguish between AD and ND samples with oligomeric tau levels increasing with Braak stage (FIG. 8). Of particular interest, the anti-oligomeric tau antibody can distinguish between Braak stage I and II samples with and without the presence of plaques, showing higher oligomeric tau levels in brain samples that also contain the presence of slight amount of amyloid plaques. These results suggest that the presence of oligomeric tau may be a valuable early diagnostic for AD and other tauopathies and further validate that morphology specific reagents can be a powerful tool to detect different neurodegenerative diseases. When the results of the post-mortem human brain tissue sample analysis with all the nanobodies are combined, we have a very powerful set of reagents that can not only readily distinguish between different neurodegenerative diseases, but potentially can stage these diseases as well. While the analysis of post-mortem brain tissue with our nanobodies is a very powerful tool, for diagnostic applications we need to be able to make similar distinctions in CSF and ideally serum samples as well for practical applications. Results using post-mortem AD, PD and control CSF and serum samples are presented in the following sections.

ii) Human Post-Mortem CSF and Serum.

Figure 9:
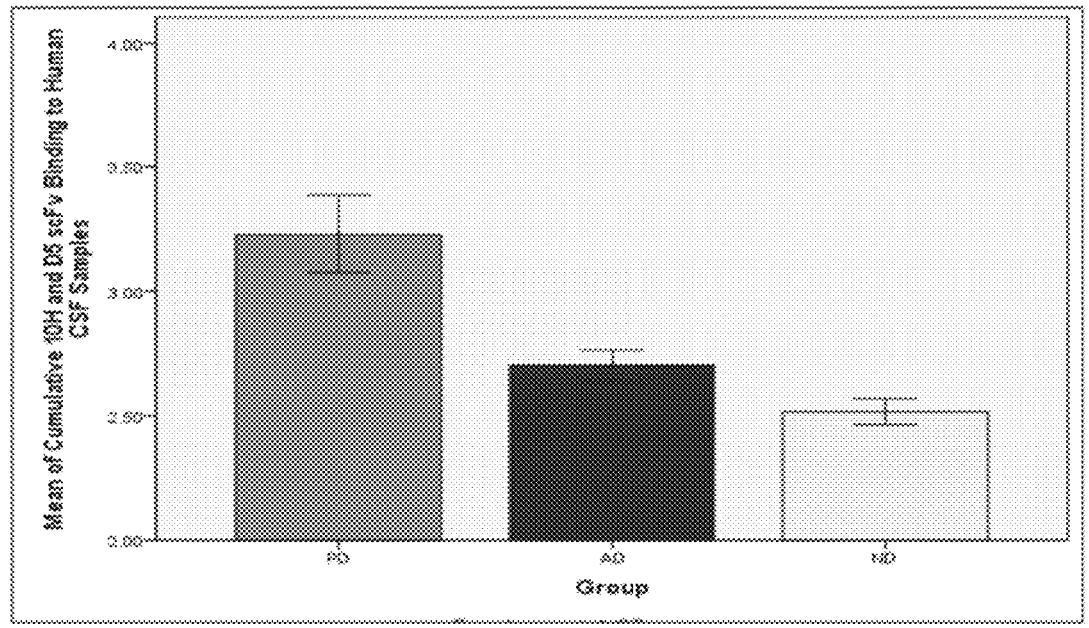
FIG. 9. Oligomeric a-syn levels in post-mortem human CSF samples readily distinguish PD from AD and ND cases. Combined oligomeric a-syn levels obtained with both D5 and 10H nanobodies are shown. First bar: PD samples, Second bar: AD samples, Third bar: ND samples High oligomeric a-syn levels were present in PD samples but not AD or ND samples.

Morphology specific nanobodies can recognize disease related protein variants in postmortem human CSF and serum samples and can distinguish between diseased and cognitively normal samples. The nanobodies in conjunction with an electronic biosensor could detect the presence of oligomeric Aβ and a-syn in these CSF samples and could readily distinguish between CSF samples from age matched cognitively normal (ND), AD and PD patients (Sierks, M. R., et al., Integrative Biology, 2011. 3(12): p. 1188-96). Here, the sandwich ELISA described above was used to analyze additional post-mortem CSF samples for presence of different oligomeric protein variants using the anti-oligomeric a-syn nanobodies D5 and 10H. CSF samples were diluted 1/100 for analysis. PD was readily distinguished from AD and ND samples (FIG. 9).

Figure 10:
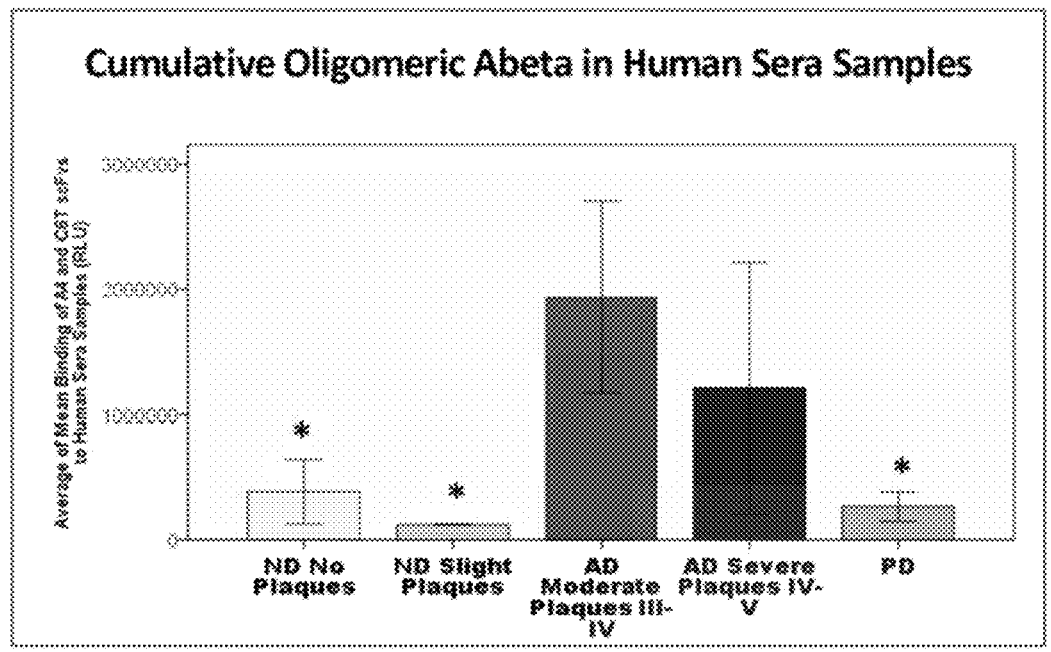
FIG. 10. Oligomeric Aβ levels in human sera from cognitively normal (ND), AD and PD samples. Combined reactivity with A4 and C6T anti-oligomeric nanobodies are shown. First bar: ND samples with no plaques, Second bar: ND with moderate plaques. Third bar: AD with moderate plaques. Fourth bar: AD with severe plaques. Fifth bar: PD samples. Highest oligomeric AP levels are observed in AD samples with moderate plaques, then in AD samples with severe plaques.
Figure 11:
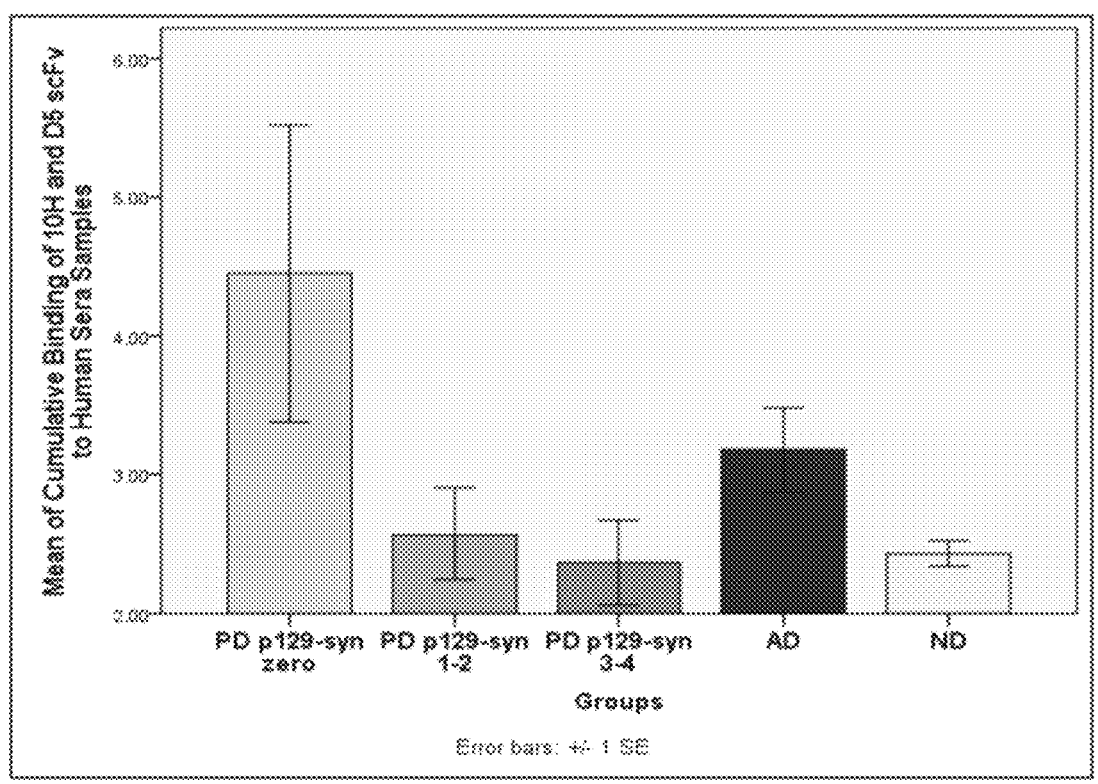
FIG. 11. Oligomeric a-syn levels in human sera from cognitively normal (ND), AD and PD samples. Combined oligomeric a-syn levels obtained with both D5 and 10H nanobodies are shown. First bar: PD samples with low p129 a-syn reactivity. Second bar: PD with moderate p129 a-syn reactivity; Third bar: PD with high p129 a-syn reactivity. Fourth bar: AD samples. Fifth bar: ND. Highest oligomeric a-syn levels are observed in early stage PD samples with low levels in late stage PD, AD and ND samples.

A set of post-mortem serum samples were also analyzed. The serum samples were from the same patients used for the brain tissue studies described above (FIGS. 6-8). The sandwich ELISA described above was used to determine the concentrations of oligomeric variants of Aβ and a-syn in the serum samples. Serum samples were diluted 1/100 in PBS for analysis. When testing for oligomeric Aβ species using the C6T and A4 nanobodies, the results essentially mirrored what was obtained with the brain tissue homogenates as it was possible to readily distinguish between AD and PD and ND samples (FIG. 10). Again very impressively, it was possible to very readily distinguish between the AD and ND serum samples even when similar amyloid plaque loads were present and again higher levels of oligomeric Aβ were observed in samples with moderate plaques and lower levels in samples with severe plaques. Similarly, when testing serum samples for oligomeric a-syn species using the D5 and 10H nanobodies, it was possible to readily distinguish between PD and AD and ND samples (FIG. 11) where higher signals were obtained with samples from early disease stages and lower signals with later stages.

Figure 12:
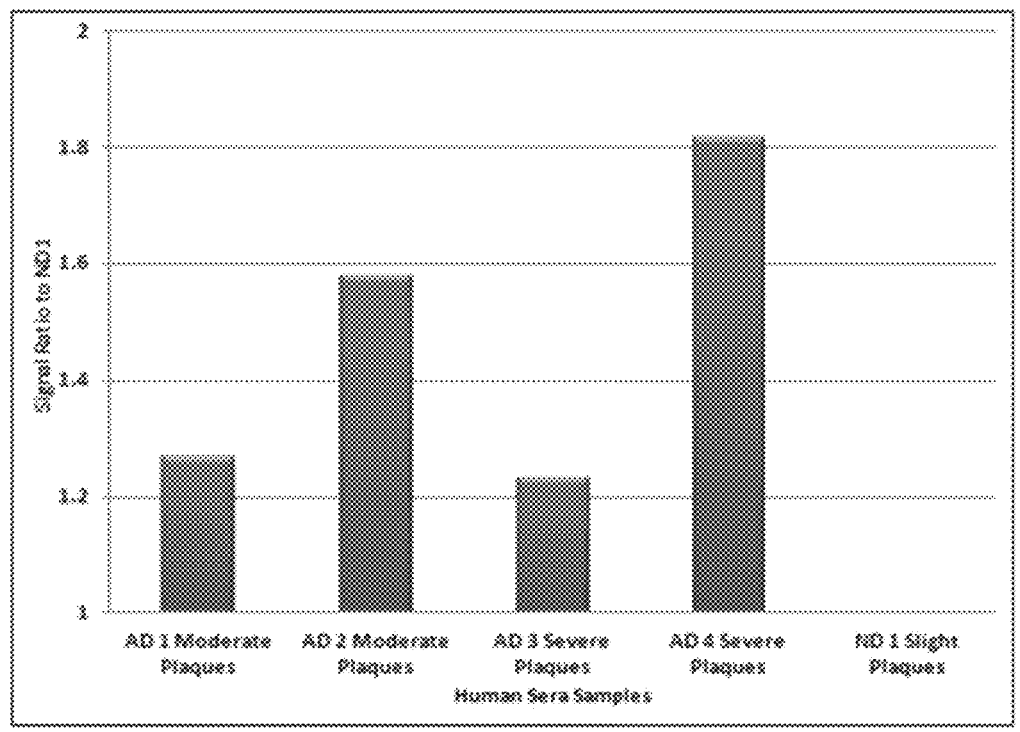
FIG. 12. An AD related TDP-43 variant is present in post-mortem human sera samples of AD but not cognitively normal (ND) samples. Samples were analyzed with a nanobody that selectively recognizes a TDP-43 variant present in AD and ALS but not ND brain tissue.

Studies were also performed to analyze serum samples for the presence of TDP-43 variants using a nanobody we isolated that recognizes a TDP-43 variant that is present in both AD and ALS brain tissue but not healthy or FTD brain tissue. The TDP-43 protein variant was present at significant levels in all four AD sera samples studied, but not in the healthy serum sample (FIG. 12). Taken together, these very exciting results indicate the possibility of detecting the presence of specific disease related protein variants in both CSF and serum samples and that the levels of the different protein variants correlate very well with specific neurodegenerative diseases and with different stages of disease.

Figure 13:
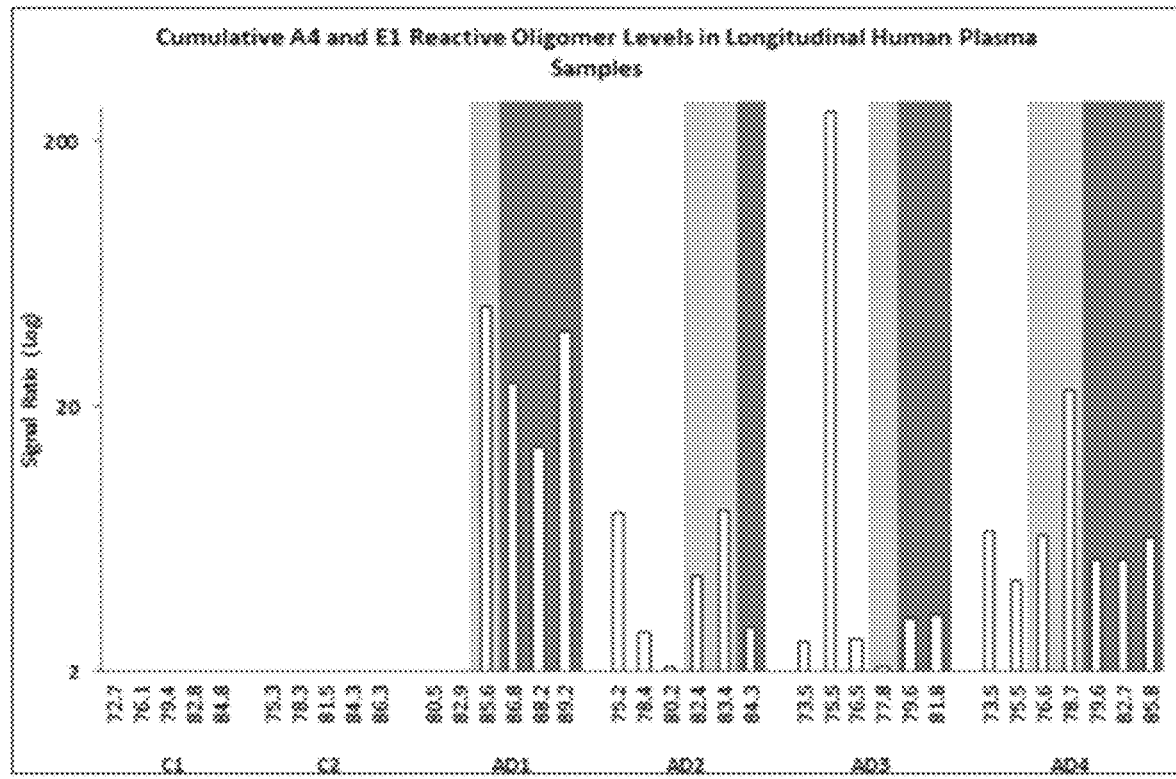
FIG. 13. Longitudinal plasma samples of AD (AD1-4) and control patients (C1-2) show presence of oligomeric AP in samples from all four patients that eventually converted to AD but not in control patients. Cumulative levels of A4 and E1 reactive oligomeric Aβ variants are shown. Patient ages are shown on x-axis. Samples taken after initial diagnosis of MCI are indicated by light shading and after diagnosis of AD by dark shading. Levels of oligomeric are detectable in all four patients that converted to AD but not in control patients. Significant oligomeric Aβ levels are present in AD samples well before conversion to AD, even up to 7 years before initial diagnosis of MCI.

The nanobodies generated against disease related protein variants can very effectively detect the presence of the target biomarkers in post-mortem human tissue, CSF and sera samples and readily distinguish AD, PD and ND samples. The nanobodies can also be used to distinguish ante-mortem sera or plasma samples. Longitudinal plasma samples were obtained, and plasma samples were analyzed from six different patients including two controls and four cases that converted first to MCI and then to AD during the time period of the study. The samples were analyzed for the presence of different oligomeric Aβ variants using the A4 (Zameer, A., et al., J Mol Biol, 2008. 384(4): p. 917-28) and E1 (Kasturirangan, S., et al., Neurobiol Aging, 2012. 33(7): p. 1320-8) nanobodies. The plasma samples obtained from the two control cases did not show any reactivity at any of the time points with either nanobody, however the samples from the four cases that converted to AD show significant reactivity with the nanobodies at almost every time point, even in samples taken seven years prior to an initial diagnosis of MCI (FIG. 13). These results indicate the possibility for presymptomatic diagnosis of neurodegenerative disease using blood based protein variant biomarkers.

Figure 14:
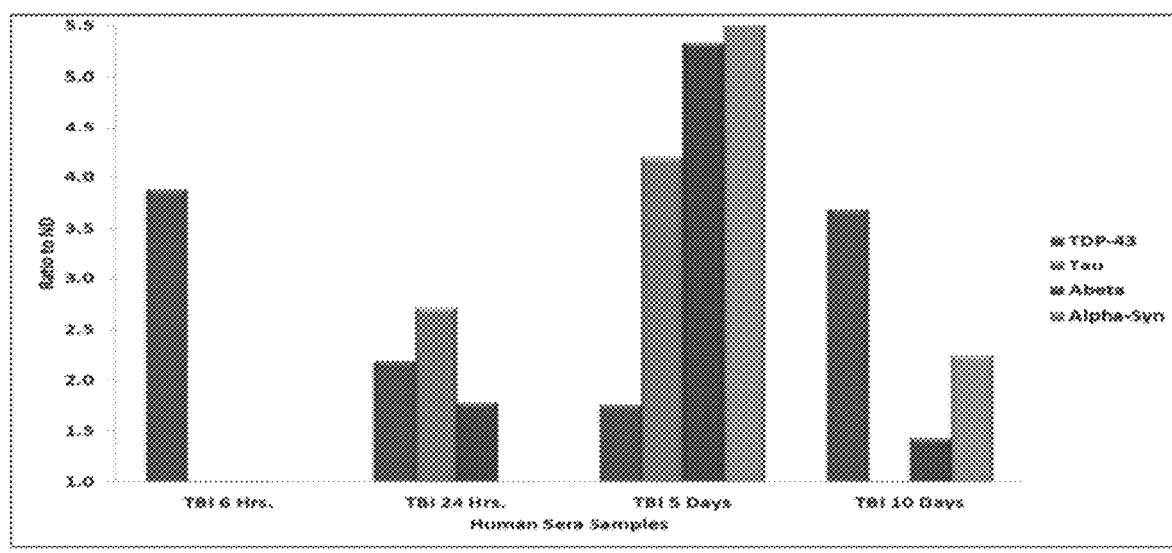
FIG. 14. Time course analysis of neurodegenerative disease related variants of tau, Aβ, a-syn and TDP-43 in composite sera sample of patients after suffering acute severe traumatic brain injury. The signal obtained with each different protein variant is expressed relative to the signal obtained with the control sera samples. Samples of 2 aged control and 5 TBI cases were combined for analysis. TBI samples were taken 6 hrs, 24 hrs, 5 days and 10 days after injury. Protein variant levels are shown in different color bars: Tau (teal), Aβ (purple), a-syn, (orange) and TDP-43 (red). The tau, Aβ, a-syn and TDP-43 variants are all present in the TBI composite sample, and all show different time dependencies following severe acute brain injury.

Detection of specific protein variants in human tissue, CSF and serum samples both from pathologically confirmed post-mortem samples and from longitudinal ante-mortem samples has great promise for presymptomatic and early diagnosis of specific neurodegenerative diseases has been shown. Also, data was obtained that demonstrates that detection of disease related protein variants can be a very powerful tool to help assess neuronal damage following TBI and to determine which patients are at risk of incurring specific neurodegenerative diseases. Sera samples were obtained at different time points from patients incurring severe acute TBI. To get a preliminary assessment of what the protein variant fingerprints might look like following TBI, a composite TBI sample was generated by combining sera samples from five different severe TBI patients and compared the different protein variant signals obtained with the composite TBI sample to a composite control sample comprised of two aged control samples obtained from post-mortem cognitively normal patients (ages 83 and 89). Pooled sera samples taken 6 hours, 24 hours, 5 days and 10 days following injury was analyzed for the presence of target protein variants of tau, Aβ, a-syn and TDP-43. The samples were tested for oligomeric tau using the F9T nanobody, for oligomeric Aβ using the A4 nanobody, for oligomeric a-syn using the 10H nanobody, and for an AD related TDP-43 variant using a nanobody that recognized TDP-43 in AD and ALS brain tissue and compared the signals obtained with the TBI samples to those obtained with the post-mortem aged control ND samples (FIG. 14). All four protein variants were present in the various different TBI time point samples, showing different time course dependencies. Levels of oligomeric tau and Aβ were present early following injury and peak around 5 days after injury, levels of oligomeric a-syn also peak around 5 days, whereas TDP-43 levels were high immediately after injury, decrease at 24 hours and 5 days after injury and increase again 10 days after injury. These studies with the composite sample show that different toxic protein variants are generated in brain tissue following severe TBI and that they can be detected in sera samples as a potential tool to assess neuronal damage.

Figure 15:
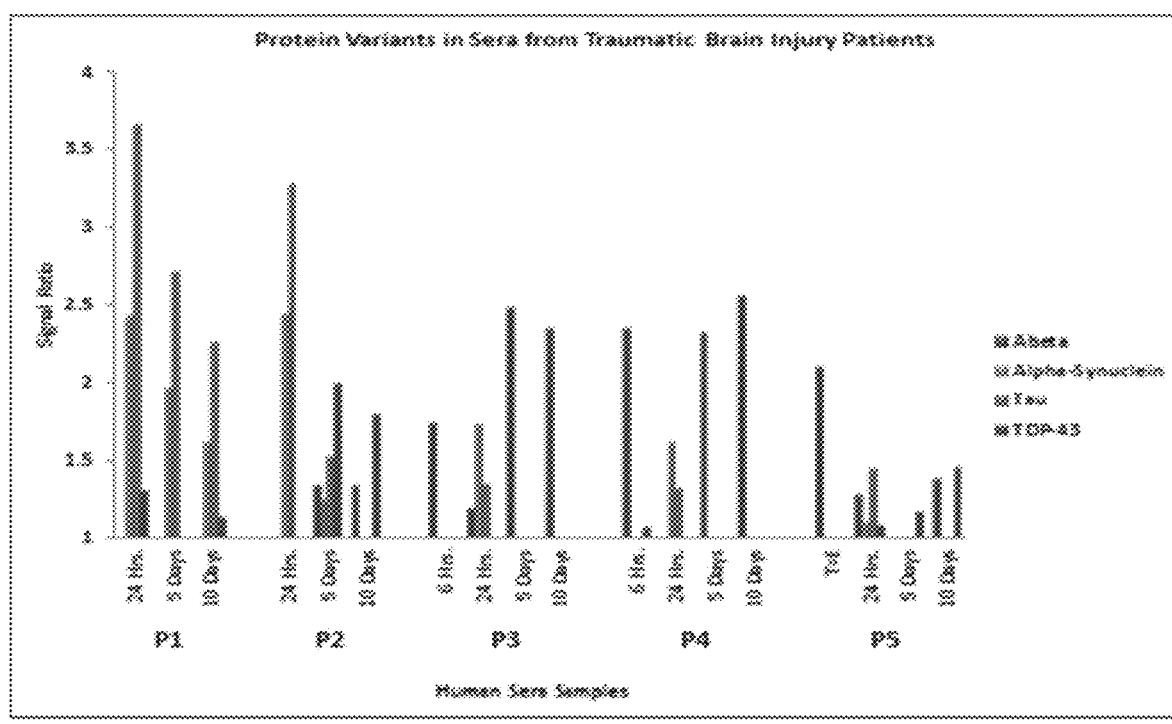
FIG. 15. Time course analysis of neurodegenerative disease related variants of tau, Aβ, a-syn and TDP-43 in sera samples of five different patients after suffering acute severe traumatic brain injury. The signal obtained with each different protein variant is expressed relative to the signal obtained with two aged control sera samples. TBI samples were taken 6 hrs, 24 hrs, 5 days and 10 days after injury. Protein variant levels are shown in different color bars: Tau (teal), Aβ (purple), a-syn, (orange) and TDP-43 (red). Patients P1 and P2 have primarily tau and a-syn toxic variants, P3 and P4 primarily toxic Aβ variants, and P5 does not display significant levels of any toxic protein variants. These results indicate that patients P1 and P2 have neuronal pathology mediated by tau and a-syn consistent with a risk of tauopathies and synucleinopathies such as FTD and PD while patients P3 and P4 have neuronal pathology mediated by Aβ consistent with a risk of AD.

Each of the five severe TBI cases were analyzed separately to determine if different patients had different protein variant fingerprints indicating potential susceptibility to different neurodegenerative diseases. Analysis of the individual cases suggests three distinctly different injury patterns (FIG. 15). Patients P1 and P2 have high persistent levels of both tau and a-syn variants following injury, but very little or no oligomeric Aβ, while patients P3 and P4 show high persistent levels of Aβ variants, but low levels of a-syn and tau, and patient P5 has relatively low levels of all the protein variants tested (FIG. 15).

These biomarker results from the TBI sera samples indicate that there are distinctly different biochemical changes occurring in brain tissue of the different patients following their respective injuries, and that these differences may account for increased susceptibilities for various neurodegenerative diseases following TBI. For example, patients P1 and P2 show biochemical changes that produce toxic variants of tau and a-syn and these patients are likely more susceptible to neurodegenerative disease associated with tauopathies and synucleinopathies such as PD and FTD. Patients P3 and P4 on the other hand show biochemical changes that produce toxic variants of Aβ and are likely more susceptible to amyloid-based diseases such as AD or cerebral amyloid angiopathy. Further analysis indicates that patient P1 still has high levels of toxic oligomeric tau and a-syn 10 days after injury, indicating that significant neuronal damage is still occurring and likely making this case at greater risk of subsequent PD or FTD than patient P2. Similarly, patients P3 and P4 still have high levels of toxic oligomeric Aβ 10 days after injury, again indicating ongoing neuronal damage and likely making these patients at greater risk for AD.

Thus, it has been shown that it is possible to readily distinguish different neurodegenerative diseases using sera samples from post-mortem AD and PD patients, that it is possible to readily distinguish AD from healthy ante-mortem sera samples even many years prior to initial diagnosis of MCI, and that we can readily distinguish not only severe acute TBI sera samples from control samples, and also to distinguish individual TBI cases for the presence of biomarkers indicative of specific neurodegenerative diseases.

Example 5

Protein Variants Profile in Traumatic Brain Injury

Following head injury, detection of any resulting damage to the brain and the magnitude of the trauma would be advantageous for proposed treatment strategies. The degree of damage in traumatic brain injury (TBI) can range from mild to severe and the resulting ramifications can be immediate or gradual. Exposure of such damage via blood or cerebrospinal fluid (CSF) based biomarker detection would provide a simplified diagnostic approach and more importantly, allude to potential impending neurological dysfunctions including neurodegenerative disorders like Alzheimer's, Parkinson's or Amyotrophic Lateral Sclerosis (ALS). Conformations of oligomeric beta-amyloid and tau have been implicated in Alzheimer's, oligomeric alpha-synuclein in Parkinson's and protein variants of TDP-43 in ALS. The potential association between TBI and neurological deficits suggests the emergence of these protein variants post injury and their plausible role as indicators of trauma to the brain. We previously isolated the single-chain variable fragments (scFvs) 3A, 3C and 8D for reactivity with variants of TDP-43, A4 and C6T for specificity with different conformations of oligomeric beta-amyloid, 10H and D5 for recognition of certain oligomeric alpha-synuclein variants and D11C for selection of oligomeric tau. Studies examining the binding specificity of all eight scFvs have been published. Of late we assessed the reactivity of these scFvs with longitudinal sera and CSF samples acquired from severe TBI patients and the details of our findings are presented below.

3A (SEQ ID NO: 32)

5'-CCATGGCCGAGGTGCAGCTGTTGGAGTCTGGGGGAGGCTTGGTACA

GCCTGGGGGGTCCCTGAGACTCTCCTGTGCAGCCTCTGGATTCACCTTT

AGCAGCTATGCCATGAGCTGGGTCCGCCAGGCTCCAGGGAAGGGGCTAG

AGTGGGTCTCAACTATTAATACTGCTGGTAATGGTACAAATTACGCAGA

CTCCGTGAAGGGCCGGTTCACCATCTCCAGAGACAATTCCAAGAACACG

CTGTATCTGCAAATGAACAGCCTGAGAGCCGAGGACACGGCCGTATATT

ACTGTGCGAAAGGTACTGCTGCTTTTGACTACTGGGGCCAGGGAACCCT

GGTCACCGTCTCGAGCGGTGGAGGCGGTTCAGGCGGAGGTGGCAGCGGC

GGTGGCGGGTCGACGGACATCCAGATGACCCAGTCTCCATCCTCCCTGT

CTGCATCTGTAGGAGACAGAGTCACCATCACTTGCCGGGCAAGTCAGAG

CATTAGCAGCTATTTAAATTGGTATCAGCAGAAACCAGGGAAAGCCCCT

AAGCTCCTGGTCTATTCTGCATCCGCTTTGCAAAGTGGGGTCCCATCAA

GGTTCAGTGGCAGTGGATCTGGGACAGATTTCACTCTCACCATCAGCAG

TCTGCAACCTGAAGATTTTGCAACTTACTACTGTCAACAGGCTGGTGAT

-continued

AGTCCTGCTACGTTCGGCCAAGGGACCAAGGTGGAAATCAAACGGGCGG
CCGC-3'

3C (SEQ ID NO: 33)
5'-CCATGGCCGAGGTGTTTGACTACTGGGGCCAGGGAACCCTGGTCAC
CGTCTCGAGCGGTGGAGGCGGTTCAGGCGGAGGTGGCAGCGGCGGTGGC
GGGTCGACGGACATCCAGATGACCCAGTCTCCATCCTCCCTGTCTGCAT
CTGTAGGAGACAGAGTCACCATCACTTGCCGGGCAAGTCAGAGCATTAG
CAGCTATTTAAATTGGTATCAGCAGAAACCAGGGAAAGCCCCTAAGCTC
CTGATCTATTATGCATCCACTTTGCAAAGTGGGGTCCCATCAAGGTTCA
GTGGCAGTGGATCTGGGACAGATTTCACTCTCACCATCAGCAGTCTGCA
ACCTGAAGATTTTGCAACTTACTACTGTCAACAGAATTATAATTCTCCT
TATACGTTCGGCCAAGGGACCAAGGTGGAAATCAAACGGGCGGCCG
C-3'

8D (SEQ ID NO: 34)
5'-CCATGGCCGAGGTGCAGCTGTTGGAGTCTGGGGGAGGCTTGGTACA
GCCTGGGGGGTCCCTGAGACTCTCCTGTGCAGCCTCTGGATTCACCTTT
AGCAGCTATGCCATGAGCTGGGTCCGCCAGGCTCCAGGGAAGGGGCTGG
AGTGGGTCTCAACTATTAATAATAGTGGTACTTCTACAAATTACGCAGA
CTCCGTGAAGGGCCGGTTCACCATCTCCAGAGACAATTCCAAGAACACG
CTGTATCTGCAAATGAACAGCCTGAGAGCCGAGGACACGGCCGTATATT
ACTGTGCGAAAAGTACTAATTATTTTGACTACTGGGGCCAGGGAACCCT
GGTCACCGTCTCGAGCGGTGGAGGCGGTTCAGGCGGAGGTGGCAGCGGC
GGTGGCGGGTCGACGGACATCCAGATGACCCAGTCTCCATCCTCCCTGT
CTGCATCTGTAGGAGACAGAGTCACCATCACTTGCCGGGCAAGTCAGAG
CATTAGCAGCTATTTAAATTGGTATCAGCAGAAACCAGGGAAAGCCCCT
AAGCTCCTGATCTATGCTGCATCCAGTTTGCAAAGTGGGGTCCCATCAA
GGTTCAGTGGCAGTGGATCTGGGACAGATTTCACTCTCACCATCAGCAG
TCTGCAACCTGAAGATTTTGCAACTTACTACTGTCAACAGAATGCTGCT
GATCCTACTACGTTCGGCCAAGGGACCAAGGTGGAAATCAAACGGGCGG
CCGC-3'

A4

(SEQ ID NO: 35)
Ttgttattactcgcggcccagccggccatggccgaggtgcagctgttgg
agtctgggggaggcttggtacagcctgggggggtccctgagactctcctg
tgcagcctctggattcacctttagcagctatccatgagctgggtccgc
caggctccagggaaggggctggagtgggtctcagcgattcagcatactg
gtgcgccgacaacttacgcagactccgtgaagggccggttcaccatctc
cagagacaattccaagaacacgctgtatctgcaaatgaacagcctgaga
gccgaggacacggccgtatattactgtgcgaaagcgtttccgccgtttg
actactggggccagggaaccctggtcaccgtctcgagcggtggaggcgg
ttcaggcggaggtggcagcggcggtggcgggtcgacggacatccagatg acccagtctccatcctccctgtctgcatctgtaggagacagagtcacca
tcacttgccgggcaagtcagagcattagcagctatttaaattggtatca
gcagaaaccagggaaagcccctaagctcctgatctattctgcatcctct
ttgcaaagtggggtcccatcaaggttcagtggcagtggatctgggacag
atttcactctcaccatcagcagtctgcaacctgaagattttgcaactta
ctactgtcaacagcgggagactgggcctnnnngttcggncaaggganca
angtggaaatcaaacgggcggccgcacatcatcatcaccatcacggggc
cgcanaacaaaaactcatctcanaanaggatctgaatgggccgcatan
actgttgaaanttgtttancaaacnncatacnnnaaaattcattt

A4

(SEQ ID NO: 36)
MAEVQLLESGGGLVQPGGSLRLSCAASGFTFSSYPMSWVRQAPGKGLEW
VSAIQHTGAPTTYADSVKGRFTISRDNSKNTLYLQMNSLRAEDTAVYYC
AKAFPPFDYWGQGTLVTVSSGGGGSGGGGSGGGGSTDIQMTQSPSSLSA
SVGDRVTITCRASQSISSYLNWYQQKPGKAPKLLIYSASSLQSGVPSRF
SGSGSGTDFTLTISSLQPEDFATYYCQQRETGPKAFGQGTKVEIKRAAA
HHHHHHGAAEQKLISEEDLNGAA*

C6T (SEQ ID NO: 37)
ccatggcccaggtacagctgcaggagtcgggggaggcttggtacagcct
ggggggtccctgagactctcctgtgcagcctctggattcacctttagca
gctatgccatgagctgggtccgccaggctccagggaaggggctggagtg
ggtctcagctattagtggtagtggtggtagcacatactacgcagactcc
gtgaagggccgattcaccatctccagagacaattccaagaacacgctgt
atctgcaaatgaacagcctgagagctgaggacacggctgtgtattactg
tgcgaagagctatggttcagttaaaataagctgctttgactactggggc
cagagcaccctggtcaccgtctcctcaggtggaggcggttcaggcggag
gtggctctggcggtggcggatcggaaattgtgctgacgcagtctccaga
ctccctggctgtgtctctgggcgagagggccaccatcaactgcaagtcc
agccagagtgttctttacaactccaacaataagaactacttagcttggt
accagcagaaaccaggacagtctcctgagttgctcatttactgggcatc
aacccgggaatccggggtccctgaccgattcagtggcagcgggtctggg
acagaattcactcttaccatcagcagcctgcaggctgaggatgtggcag
tttattactgtcagcaatttatagtactcctccgacttttggccaggg
gaccaagctggagatcaaacgtgcggccgcacatcatcatcaccatcac
ggggccgcagaacaaaaactcatctcagaagaggatc

C6T (SEQ ID NO: 38)
MAQVQLQESGGGLVQPGGSLRLSCAASGFTFSSYAMSWVRQAPGKGLEW
VSAISGSGGSTYYADSVKGRFTISRDNSKNTLYLQMNSLRAEDTAVYYC
AKSYGSVKISCFDYWGQSTLVTVSSGGGGSGGGGSGGGGSEIVLTQSPD
SLAVSLGERATINCKSSQSVLYNSNNKNYLAWYQQKPGQSPELLIYWAS
TRESGVPDRFSGSGSGTEFTLTISSLQAEDVAVYYCQQFYSTPPTFGQG
TKLEIKRAAAHHHHHHGAAEQKLISEEDLNGAA*

-continued

10H (SEQ ID NO: 39)
Ccatggccgaggtgcagctgttggagtctgggggaggcttggtacagcc tggggggtccctgagactctcctgtgcagcctctggattcacctttagc <u>agctatgccatgagc</u>tgggtccgccaggctccagggaaggggctggagt gggtctca<u>aatattagtagtgcagggaaggggctggagtgggtctcaag</u>

<u>tattgatgattctggtgcttctacatattacgcagactccgtgaaggc</u> cggttcaccatctccagagacaattccaagaacacgctgtatctgcaaa tgaacagcctgagagccgaggacacggccgtatattactgtgcgaaa<u>ga</u>

<u>ttctgcttcttttgactac</u>tggggccagggaaccctggtcaccgtctcg agcggtggaggcggttcaggcggaggtggcagcggcggtggcgggtcga cggacatccagatgacccagtctccatcctccctgtctgcatctgtagg agacagagtcaccatcacttgc<u>cgggcaagtcagagcattagcagctat</u>

<u>ttaaat</u>tggtatcagcagaaaccagggaaagcccctaagctcctgatct at<u>actgcatccagtttgcaaagt</u>ggggtcccatcaaggttcagtggcag tggatctgggacagatttcactctcaccatcagcagtctgcaacctgaa gattttgcaacttactactgt<u>caacagtctgctgctagtccttctacgt</u> tcggccaagggaccaaggtggaaatcaaacgggcggccgcacatcacca tcaccatcacggggccgcagaacaaaaactcntctcagaagnggatcnn aangggnccg

10H (SEQ ID NO: 40)
MAEVQLLESGGGLVQPGGSLRLSCAASGFTFS<u>SYAMS</u>WVRQAPGKGLEW

VS<u>NISSAGKGLEWVSSIDDSGASTYYADSVKGRFTISRDNSKNTLYLQM</u>

NSLRAEDTAVYYCAK<u>DSASFDY</u>WGQGTLVTVSSGGGGSGGGGSGGGGST

DIQMTQSPSSLSASVGDRVTITC<u>RASQSISSYLN</u>WYQQKPGKAPKLLIY

<u>TASSLQS</u>GVPSRFSGSGSGTDFTLTISSLQPEDFATYYC<u>QQSAASPSTF</u>

GQGTKVEIKRAAAHHHHHHGAAEQKLISEEDLNGAA*

D5

(SEQ ID NO: 41)
ccatggccgaggtgcagctgttggagtctgggggaggcttggtacagcc tggggggtccctgagactctcctgtgcagcctctggattcacctttagc <u>agctatgccatgagc</u>tgggtccgccaggctccagggaaggggctggagt gggtctc<u>atcgattggtcagaaggggtggtggtacacagtacgcagactc</u>

<u>cgtgaagggc</u>cggttcaccatctccagagacaattccaagaacacgctg tatctgcaaatgaacagcctgagagccgaggacacggccgtatattact gtgcgaaa<u>cattttgagaattttgactac</u>tggggccagggaaccctggt caccgtctcgagcggtggaggcggttcaggcggaggtggcagcggcggt ggcgggtcgacggacatccagatgacccagtctccatcctccctgtctg catctgtaggagacagagtcaccatcacttgc<u>cgggcaagtcagagcat</u>

<u>tagcagctatttaaat</u>tggtatcagcagaaaccagggaaagcccctaag ctcctgatct<u>atgctgcatccatttgcaaagt</u>ggggtcccatcaaggt tcagtggcagtggatctgggacagatttcactctcaccatcagcagtct gcaacctgaagattttgcaacttactactgt<u>caacagacgcgtaggccg</u>

<u>ccttctacg</u>ttcggccaagggaccaaggtggaaatcaaacgggcggccg cacatcatcatcaccatcacggggccgcagaacaaaaactcatctcaga agagaatcactagtgcggccgcctgcaggtcgaccata

D5

(SEQ ID NO: 42)
MAEVQLLESGGGLVQPGGSLRLSCAASGFTFS<u>SYAMS</u>WVRQAPGKGLEW

VS<u>SIGQKGGGTQYADSVKGRFTISRDNSKNTLYLQMNSLRAEDTAVYYC

AK<u>HFENFDY</u>WGQGTLVTVSSGGGGSGGGGSGGGGSTDIQMTQSPSSLSA

SVGDRVTITC<u>RASQSISSYLN</u>WYQQKPGKAPKLLIY<u>AASHLQS</u>GVPSRF

SGSGSGTDFTLTISSLQPEDFATYYC<u>QQTRRPPST</u>FGQGTKVEIKRAAA

HHHHHHGAAEQKLISEEDLNGAA*

D11C (SEQ ID NO: 43)
GCANTTCNATTTNNNGAGACAGTCATAATGAAATACCTATTGCCTACGG

CAGCCGCTGGATTGTTATTACTCGCGGCCCAGCCGGCCATGGCCCAGGT

GCAGCTGGTGGAGTCTGGGGGAGGCTTGGTACAGCCTGGGGGGTCCCTG

AGACTCTCCTGTGCAGCCTCTGGATTCACCTTTAGCAGCTATGCCATGA

GCTGGGTCCGCCAGGCTCCAGGGAAGGGGCTGGAGTGGGTCTCAGCTAT

TAGTGGTAGTGGTGGTAGCACATACTACGCAGACTCCGTGAAGGGCCGG

TTCACCATCTCCAGAGACAATTCCAAGAACACGCTGTATCTGCAAATGA

ACAGCCTGAGAGCCGAGGACACGGCTGTATATTACTGTGCAAGAGGTGG

CGATTATGGCTCAGGGGACTACTGGGGCCAGGGAACCCTGGTCACCGTC

TCCTCAGGTGGAGGCGGTTCAGGCGGAGGTGGCTCTGGCGGTGGCGGAT

CGAATTTTATGCTGACTCAGGACCCTGCTGTGTCTGTGGCCTTGGGACA

GACAGTCAGAATCACATGCCAAGGAGACAGCCTCAGAAGCTATTATGCA

AGTTGGTACCAGCAGAAGCCAGGACAGGCCCCTCTCCTTGTCATCTATG

GTAAAAACATCCGGCCCTCAGGGATCCCAGACCGATTCTCTGGCTCCAG

CTCAGGAAACTCAGCTTCCTTGACCATCACTGGGGCTCAGGCGGAAGAT

GAGGCTGACTATTACTGTCACTCCCGGGACAGCAGTGGTACCCATCTAA

GGGTATTCGGCGGA<u>GG</u>GACCAAGGTCACCGTCCTAGGTGCGGCCGCAGA

ACAAAAACTCATCTCAGAAGAGGATCTGAATGGGGCCGCATANACTGTT

GAAAGTTGTTTANCAAANNCTCATACAGAAANTTNATTNNCTANNNTCT

GGNAAGANGACAAAACTTTNNNTCGTNACGCTANNNNNTNNNNNNTGTCT

GTGANNGCNNCNGGCNNTGTGNTNNNNACTGNNNNNNAAANTNNNGNTN

NNNG

D11C (SEQ ID NOS 44 and 45, respectively)
A X X F X E T V I Met K Y L L P T A A A G L L L L A A Q P A Met A Q V Q L V E S G G G L V Q P G G S L R L S C A A S G F T F S S Y A Met S W V R Q A P

G K G L E W V S A I S G S G G S T Y Y A D S V K G

R F T I S R D N S K N T L Y L Q Met N S L R A E D

T A V Y Y C A R G G D Y G S G D Y W G Q G T L V T

-continued

```
V S S G G G G S G G G G S G G G G S N F Met L T Q
D P A V S V A L G Q T V R I T C Q G D S L R S Y Y
A S W Y Q Q K P G Q A P L L V I Y G K N I R P S G
I P D R F S G S S S G N S A S L T I T G A Q A E D
E A D Y Y C H S R D S S G T H L R V F G G G T K V
T V L G A A A E Q K L I S E E D L N G A A X T V E
S C L X X X H T E X X X X X X W X X D K T X X R X
A X X X X C L Stop X X X X X X X X L X X K X X X X
```

Figure 16:
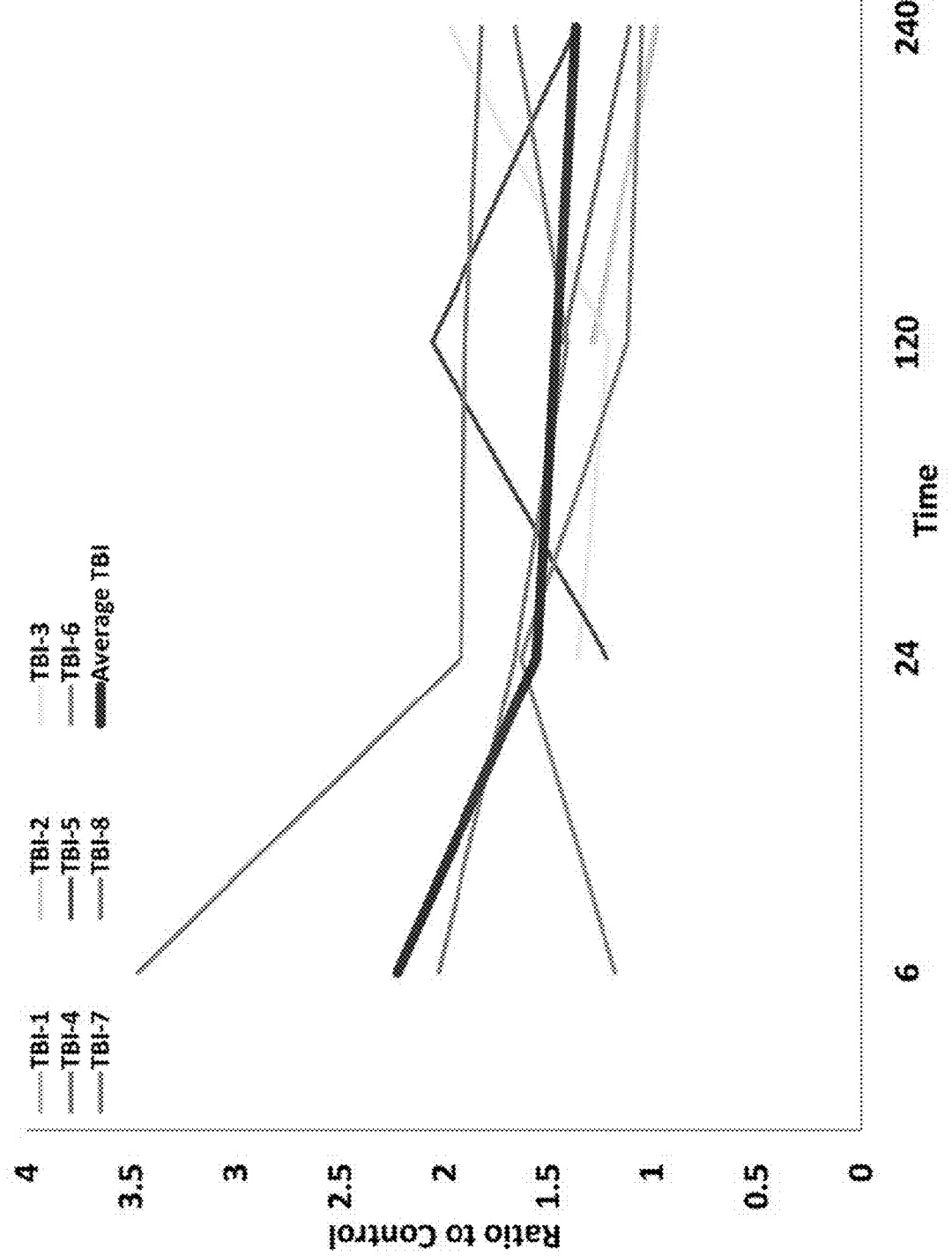
FIG. 16. 3A Reactive TDP-43 Variant in Human TBI Sera.
Figure 17:
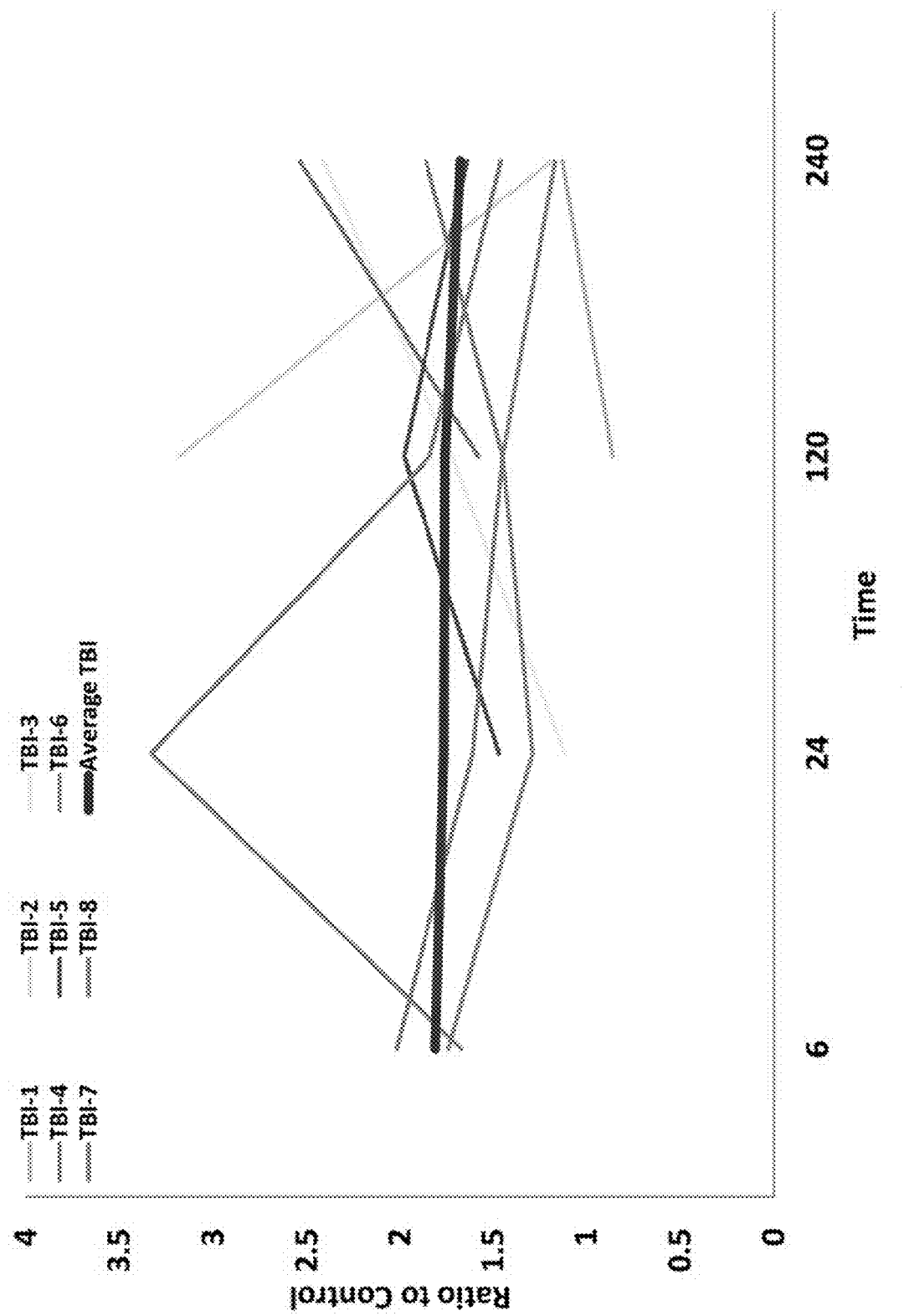
FIG. 17. 3C Reactive TDP-43 Variant in Human TBI Sera.
Figure 18:
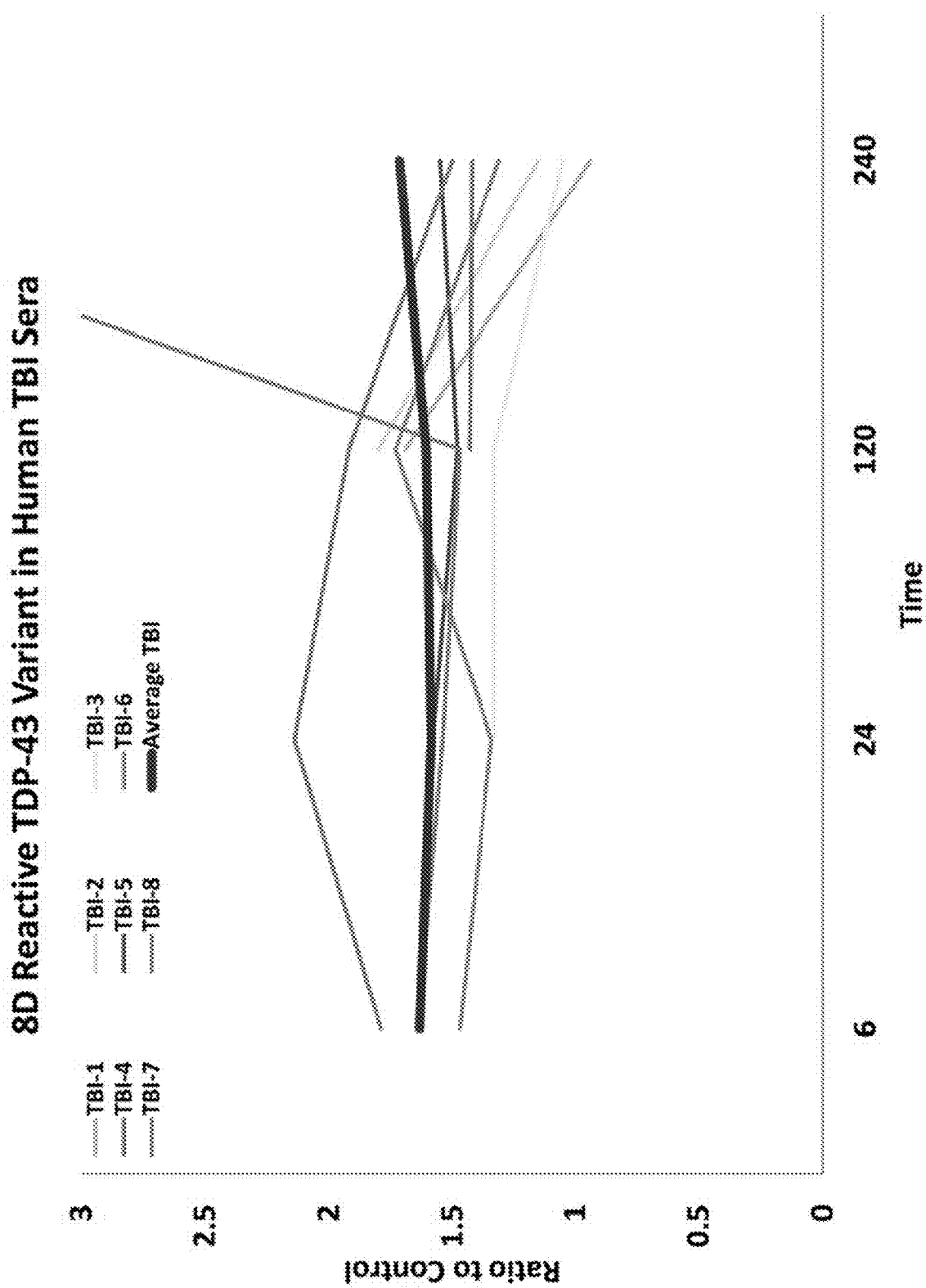
FIG. 18. 8D Reactive TDP-43 Variant in Human TBI Sera.
Figure 19:
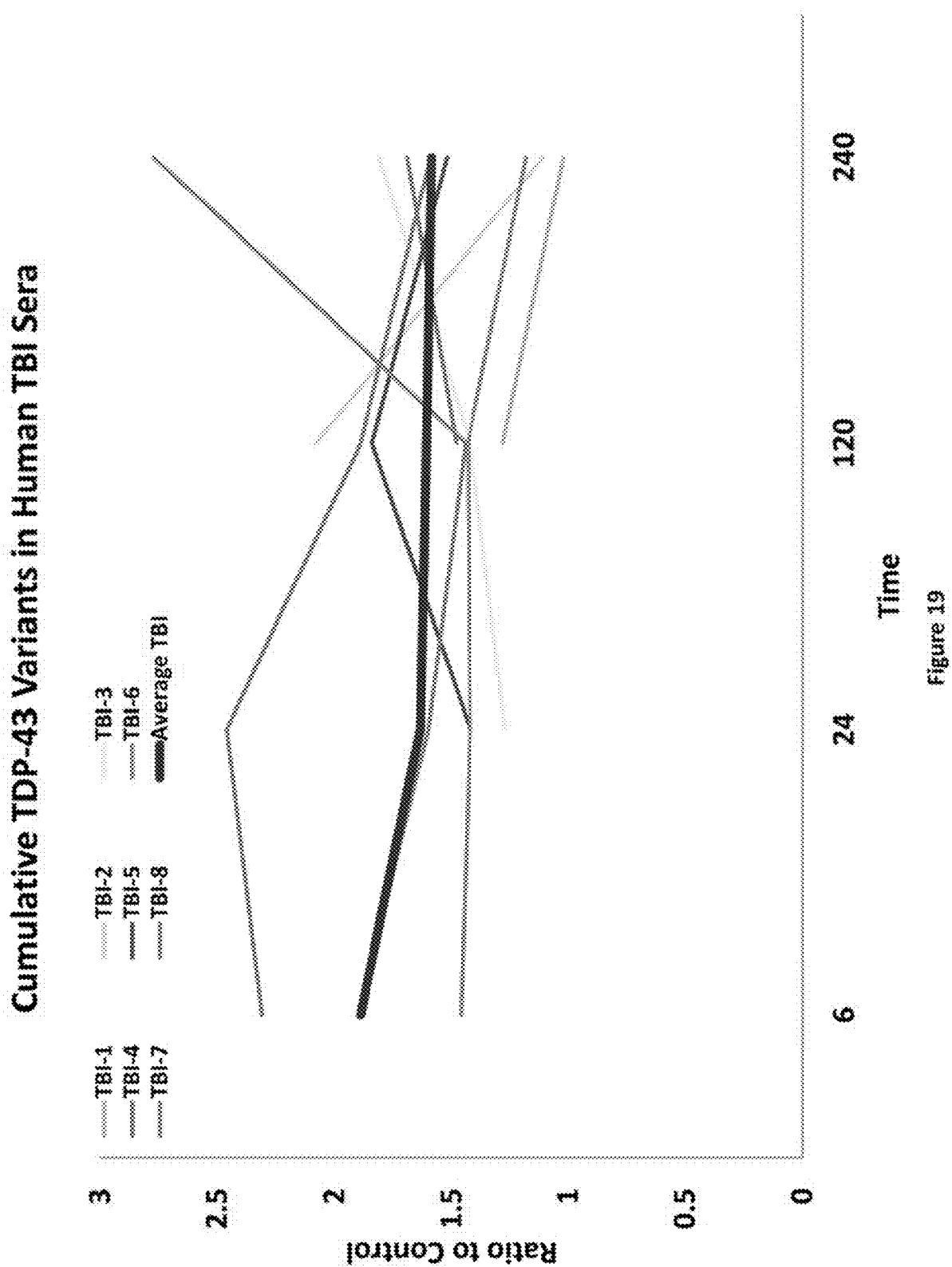
FIG. 19. Cumulative TDP-43 Variants in Human TBI Sera.
Figure 20:
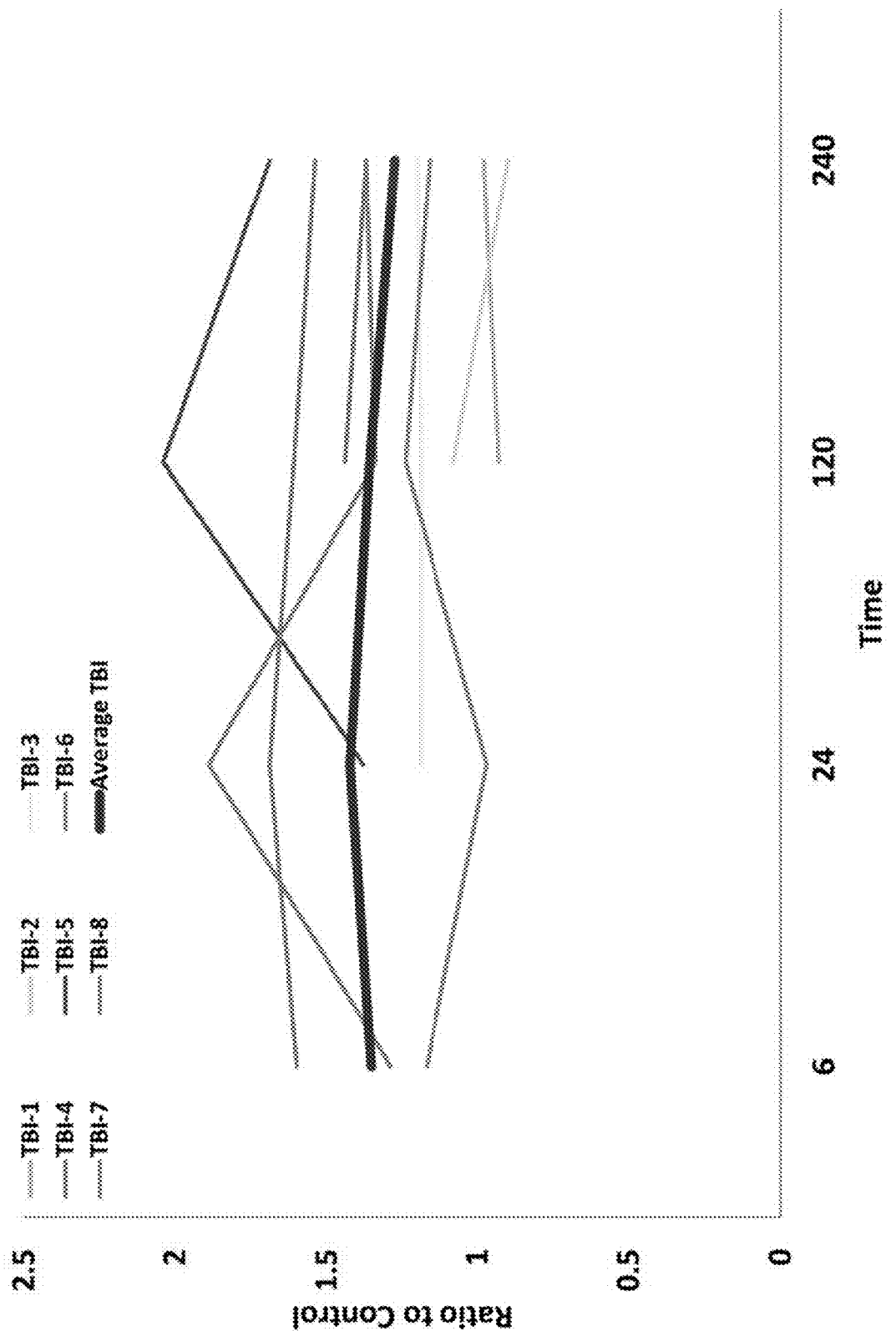
FIG. 20. D11C Reactive Oligomeric Tau Levels in Human TBI Sera.
Figure 21:
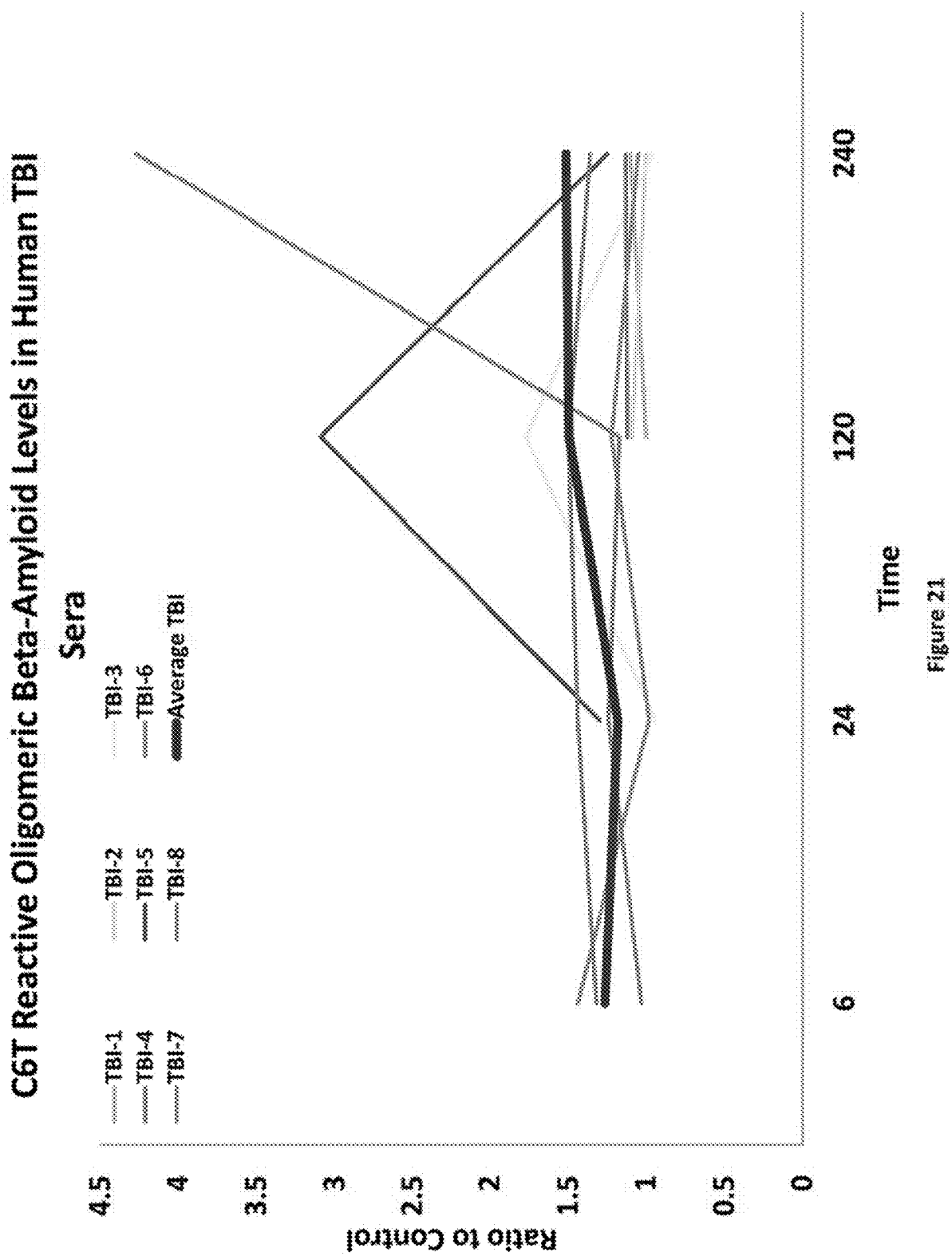
FIG. 21. C6T Reactive Oligomeric Beta-Amyloid Levels in Human TBI Sera.
Figure 22:
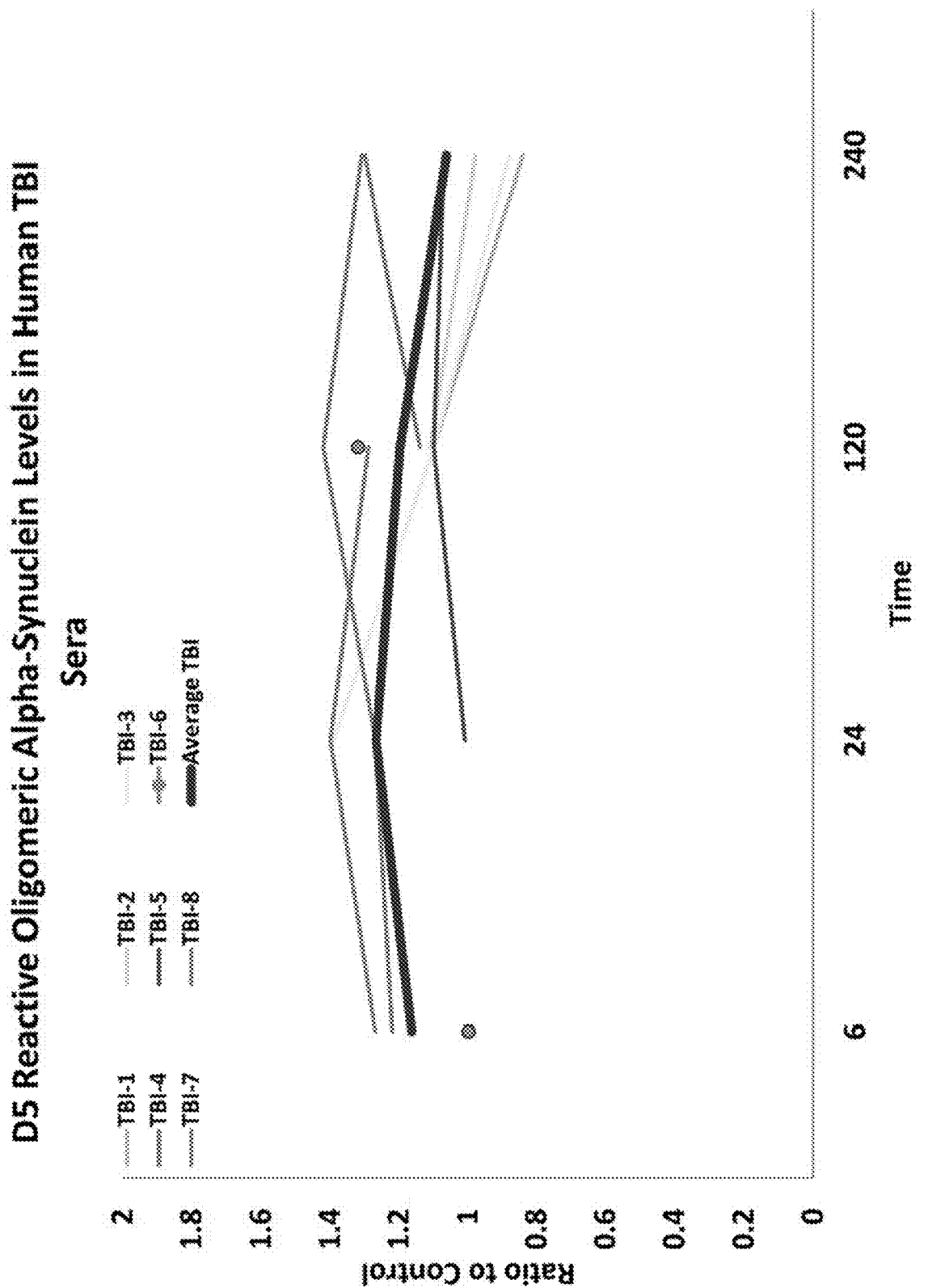
FIG. 22. D5 Reactive Oligomeric Alpha-Synuclein Levels in Human TBI Sera.
Figure 23:
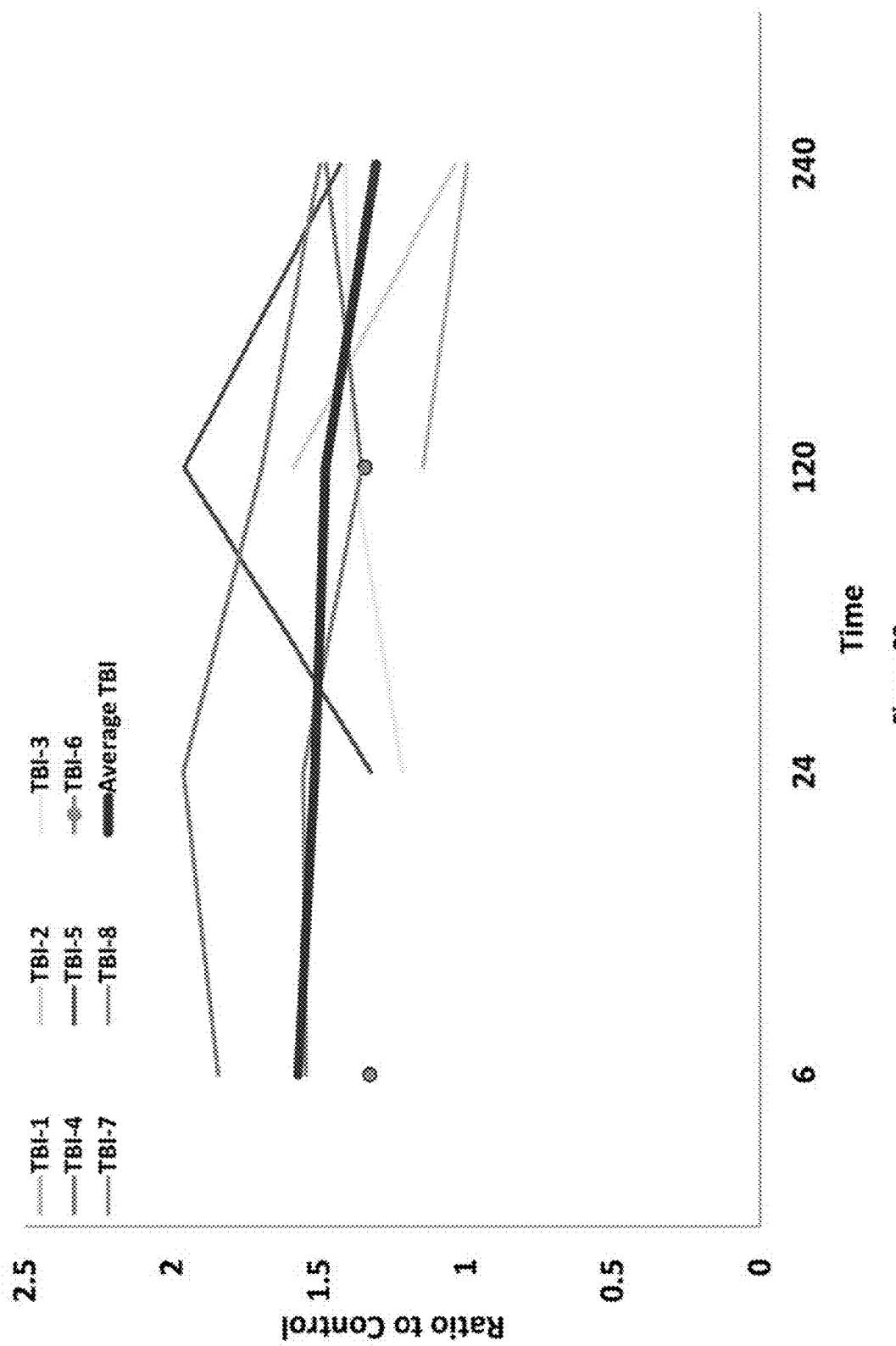
FIG. 23. Cumulative Protein Variants Levels in Human TBI Sera.

Longitudinal sera samples from eight cases comprising the time points 6 hours, 24 hours, 5 days and 10 days post-injury were tested with our scFvs using our previously developed phage-based capture ELISA system (Note: not every time point was available for each case). The binding ratio for each sample is represented relative to the average binding of two post-mortem pathologically confirmed non-demented (ND) cases. Initially, the results are displayed as spaghetti plots to illustrate the variation in binding patterns between the cases across the four time points, with average binding indicated in red. To begin, assessment of 3A's activity indicated an average upsurge in biomarker recognition at 6 hours, a decline at 24 hours and a gradual decrease post 24 hours, although, sustaining elevated reactivity relative to the controls (FIG. 16). Likewise, 3C (FIG. 17) retained uniform reactivity above the controls across all time points, while potential biomarkers reactive with 8D (FIG. 18) remained stable from 6 hours to 5 days but then intensified at day 10. In general, the cumulative TDP-43 variants being detected peaked at 6 hours, declined at 24 hours and maintained a slight decreasing pattern at subsequent time points (FIG. 19). Proceeding to D11C, its recognized oligomeric tau antigen increased from 6 to 24 hours, and then gradually declined while concurrently retaining activity levels exceeding the controls (FIG. 20). The average C6T reactive oligomeric beta-amyloid level decrease slightly from 6 to 24 hours but then increased at day 5 and remained elevated thereafter (FIG. 21). Progressing from 6 to 24 hours, D5 identified increased quantities of oligomeric alpha-synuclein, however, in the course of transition from 24 hours to day 10 the concentrations decreased (FIG. 22). Cumulative protein variants levels in all eight TBI cases remained elevated in relation to the controls, however, on average there was a steady decline from 6 hours to day 5, followed by an abrupt decline at day 10 (FIG. 23).

Figure 24:
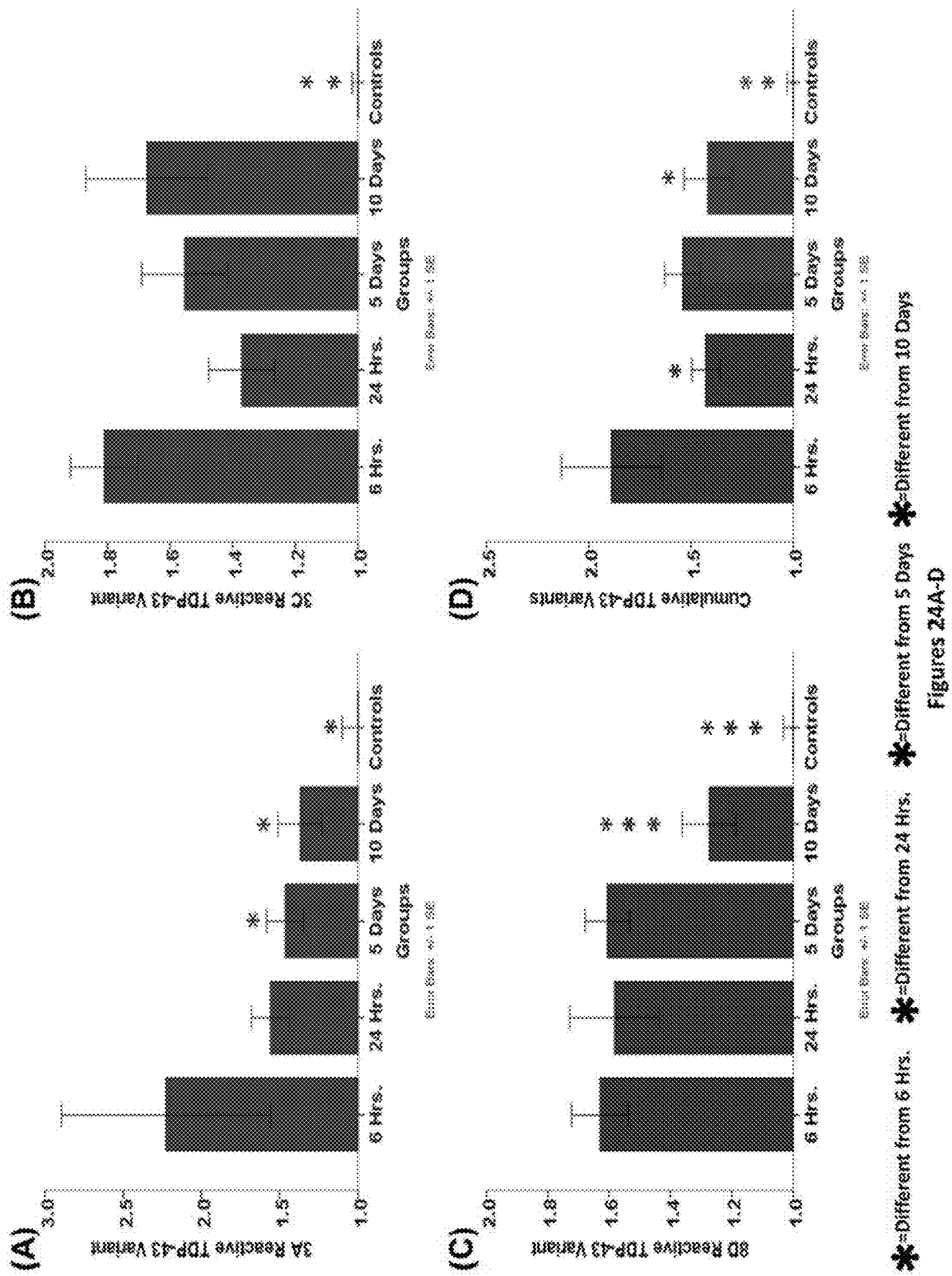
FIG. 24A. 3A Reactive TDP-43 Variant in Human TBI Sera.
FIG. 24B. 3C Reactive TDP-43 Variant in Human TBI Sera.
FIG. 24C. 8D Reactive TDP-43 Variant in Human TBI Sera.
FIG. 24D. Cumulative TDP-43 Variants in Human TBI Sera.
Figure 25:
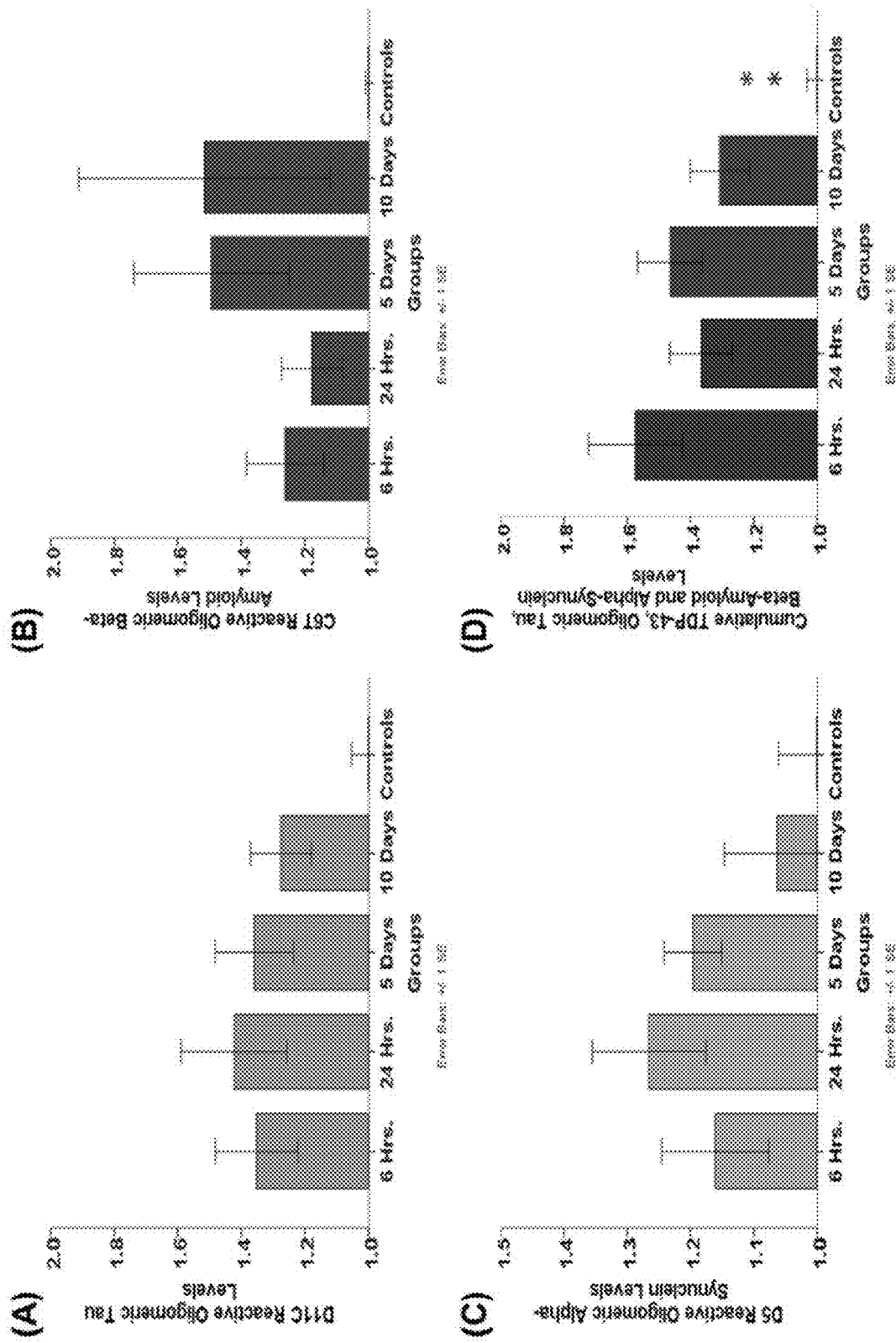
FIG. 25A. D11C Reactive Oligomeric Tau in Human TBI Sera.
FIG. 25B. C6T Reactive Oligomeric Beta-Amyloid in Human TBI Sera.
FIG. 25C. D5 Reactive Oligomeric Alpha-Synuclein in Human TBI Sera.
FIG. 25D. Cumulative Protein Variants in Human TBI Sera.

In the portrayed spaghetti plots, it was apparent the presence of outliers influencing the average binding ratios at selected time points. To identify such outliers, box plot analysis was completed for each scFv with elimination occurring if their presence influenced the LSD one-way ANOVA test for significance. Based on the acquired statistical results, bar graphs were plotted and any significance at p≤0.05 highlighted. Clone 3A's invariable pattern of reactivity delivered significantly more reactivity at 6 hours compared to both the 5 and 10 days post-injury time points and the controls (FIG. 24A). Likewise, 3C produced maximum activity at 6 hours post-trauma followed by the 10-day collection point, both of whose intensities significantly exceeded those of the controls (FIG. 24B). Interestingly, following the 6 hour time lapse, the level of the TDP-43 protein variant recognized by 3C decreased at 24 hours, followed by a trend reversal resulting in intensity levels approaching the ratio acquired at 6 hours. Clone 8D maintained stable reactivity across 6 hours, 24 hours and day 5, all of which emerged significantly elevated relative to the controls and 10 days post-injury (FIG. 24C). As expected, the average cumulative TDP-43 level peaked at 6 hours generating a significant difference in relation to all groups except the 5 day interval (FIG. 24D). It should be mentioned that positive ratios were acquired at the other three time points indicating the existence of our TDP-43 variants. The pattern of reactivity for D11C (FIG. 25A), C6T (FIG. 25B) and D5 (FIG. 25C) was similar to their spaghetti plots. Cumulative TDP-43 variants, oligomeric tau, oligomeric beta-amyloid and oligomeric alpha-synuclein levels was the greatest at 6 hours, followed by 5 days, both of which were significantly different from the controls (FIG. 25D).

Figure 26:
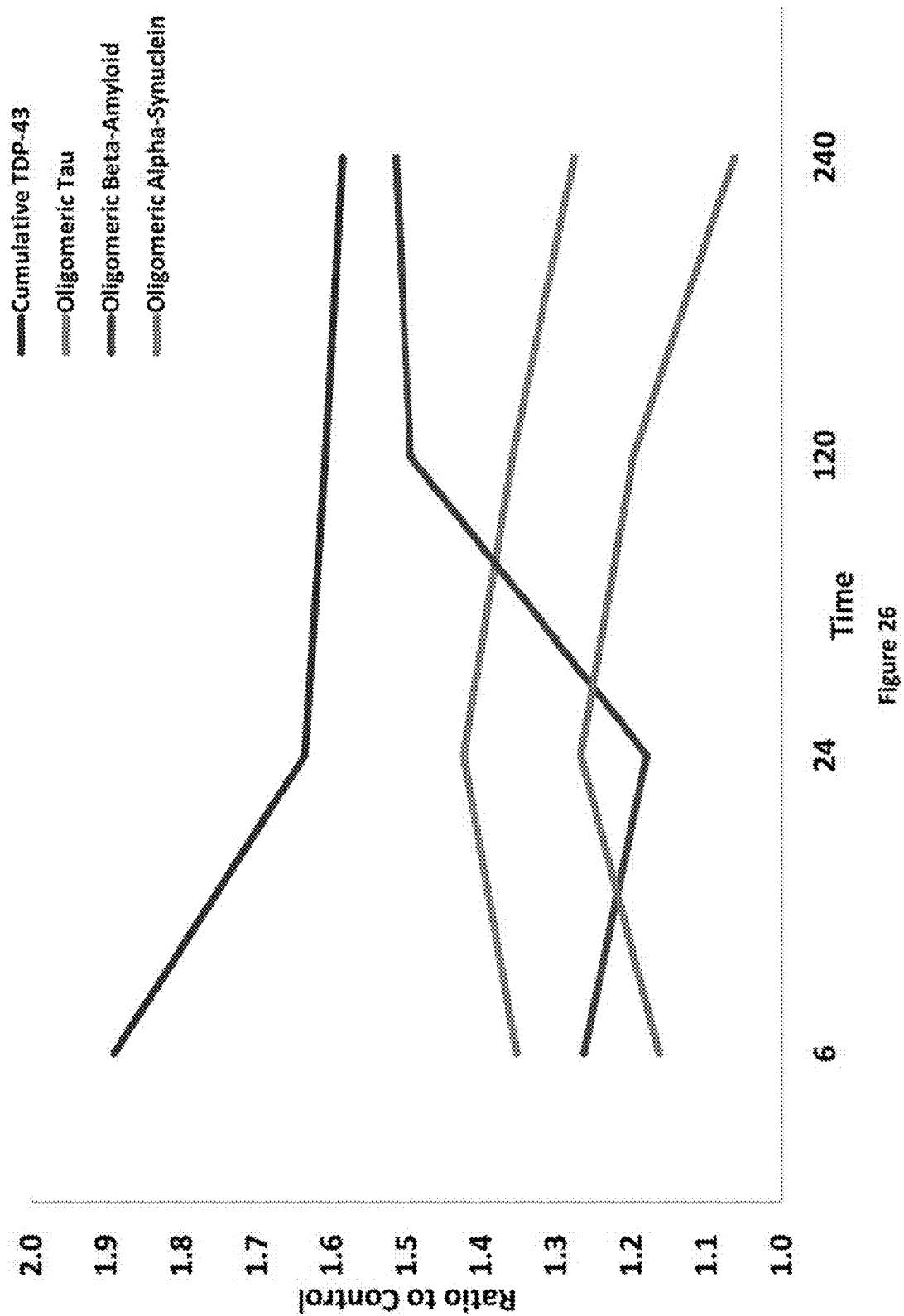
FIG. 26. Protein Variants in Human TBI Sera Samples (Outliers Present).
Figure 27:
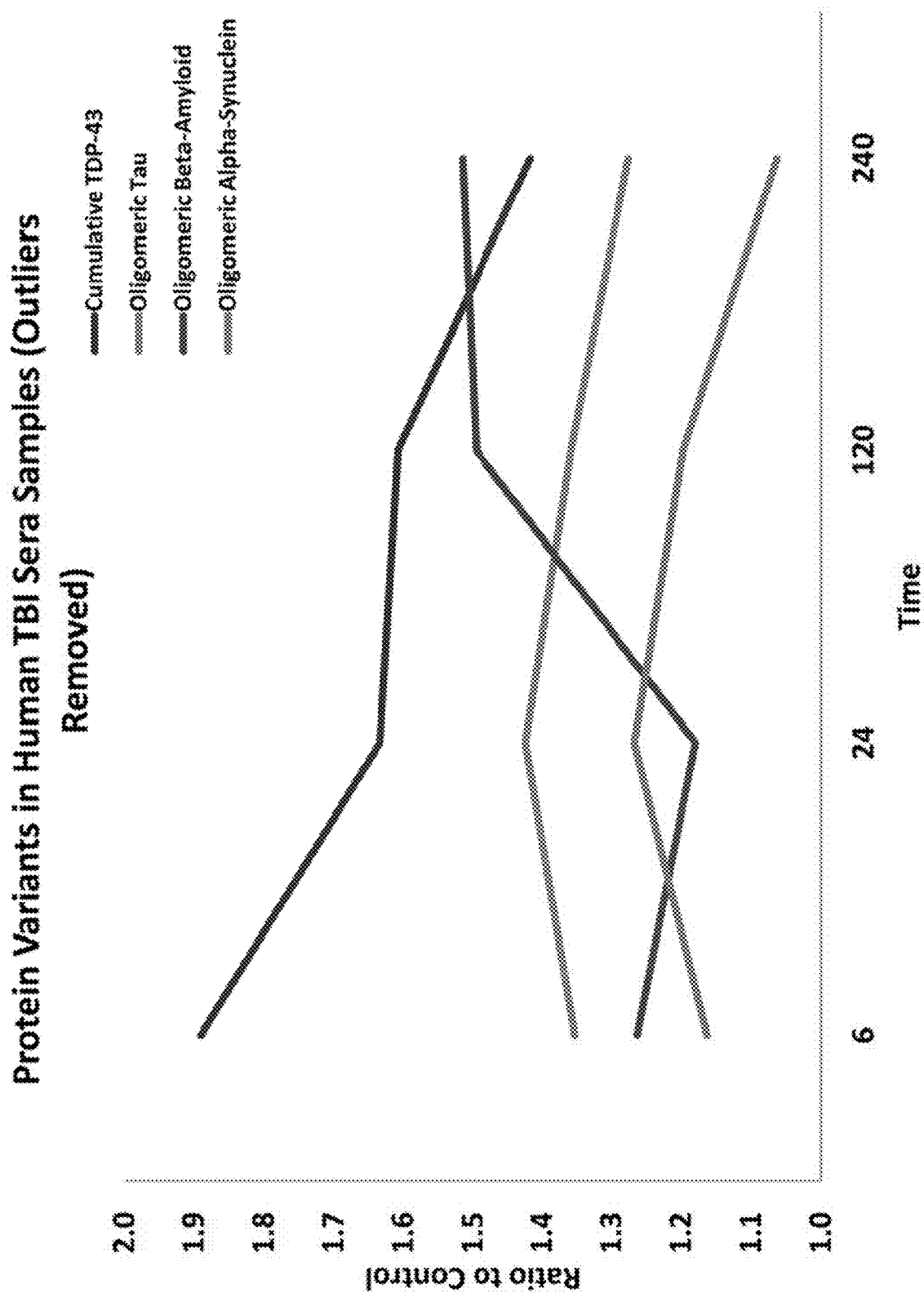
FIG. 27. Protein Variants in Human TBI Sera Samples (Outliers Removed).
Figure 28:
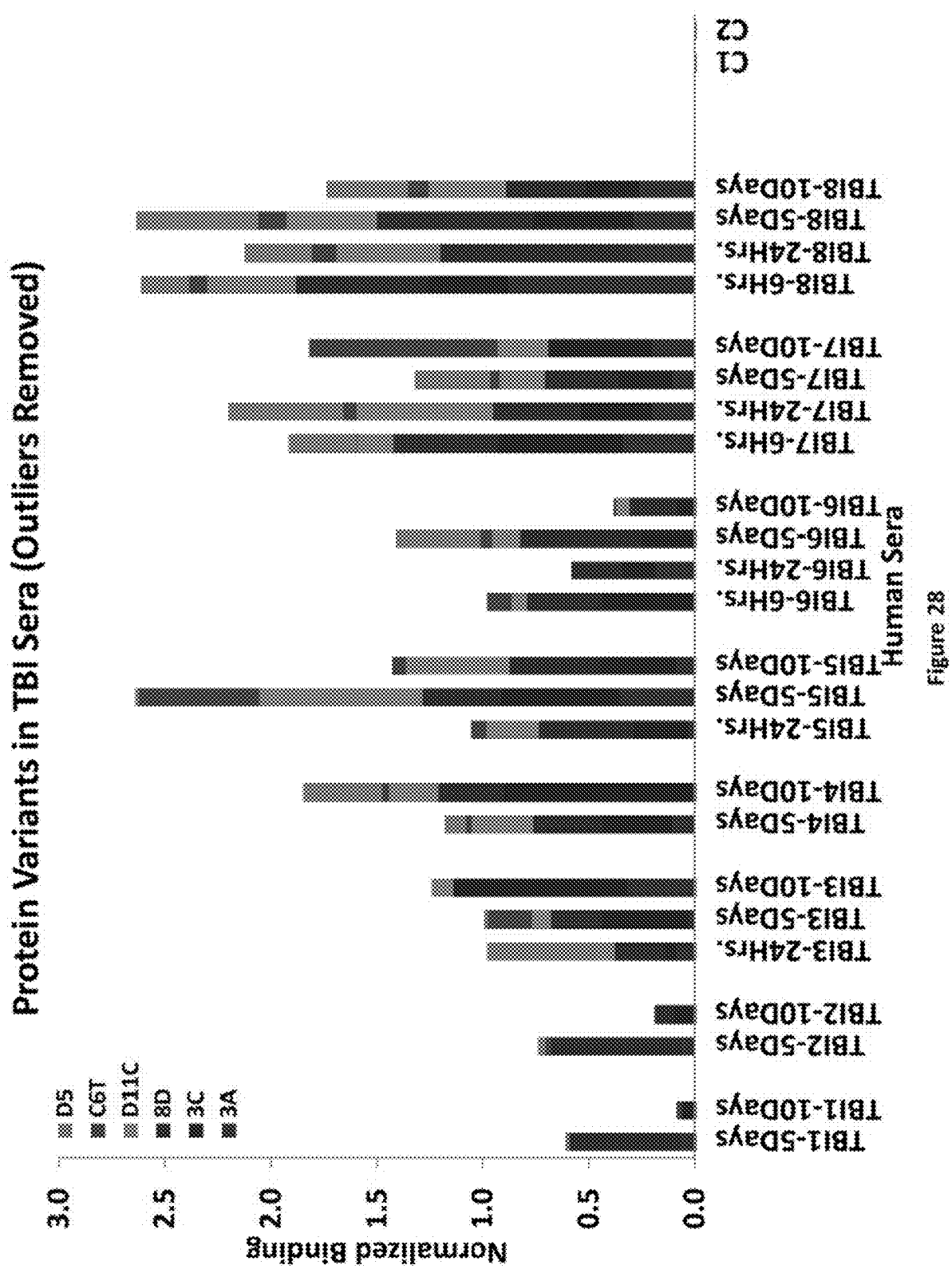
FIG. 28. Protein Variants in TBI Sera (Outliers Removed).

Line graphs were created to illustrate the average binding intensities of the cumulative TDP-43 variants, oligomeric tau, oligomeric beta-amyloid and oligomeric alpha-synuclein with (FIG. 26) or without (FIG. 27) the outliers for each time point. Oligomeric tau and alpha-synuclein produced paralleled patterns of activity where the levels increased from 6 to 24 hours, and then decreased subsequently; however, the reactivity with oligomeric tau was always elevated relative to oligomeric alpha-synuclein. The patterns originating from cumulative TDP-43 variants and oligomeric beta-amyloid levels were interesting since for both the levels decreased from 6 to 24 hours, however, while TDP-43's binding intensities continued in a decreasing trend, the level of oligomeric beta-amyloid increased, suggesting an opposing manifestation pattern in sera. This thought-provoking occurrence will require confirmation in future testing with a larger longitudinal sample size. As a summary of the selective abilities of our panel of scFvs for each time point with all 8 TBI cases, we normalized the binding intensities yielded by each scFv to between 0 and 1 since their range varied, and subsequently subtracted the mean plus one standard deviation of the controls. The results presented in FIG. 28 make evident the selection of all test samples and none of the controls. Heat map presentation of these normalized binding ratios supported the average TDP-43 level peaking at 6 hours, oligomeric tau's and alpha-synuclein's similar binding patterns with peaking at 24 hours and oligomeric beta-amyloid exhibiting its highest reactivity at the later time points, specifically 5 and 10 days post-injury (Tables 1 and 2).

TABLE 1

Heat Map of Protein Variants in Human Sera (Outliers Present)

| | Cumulative TDP-43 Variants | Oligomeric Tau | Oligomeric Alpha-Synuclein | Oligomeric Beta-Amyloid |
|---|---|---|---|---|
| Controls | 0.047 | 0.170 | 0.278 | 0.105 |
| 6 Hrs. | 0.365 | 0.450 | 0.556 | 0.176 |
| 24 Hrs. | 0.271 | 0.507 | 0.736 | 0.153 |
| 5 Days | 0.260 | 0.456 | 0.616 | 0.240 |
| 10 Days | 0.246 | 0.390 | 0.387 | 0.246 |

TABLE 2

Heat Map of Protein Variants in Human Sera (Outliers Removed)

| | Cumulative TDP-43 Variants | Oligomeric Tau | Oligomeric Alpha-Synuclein | Oligomeric Beta-Amyloid |
|---|---|---|---|---|
| Controls | 0.068 | 0.170 | 0.278 | 0.105 |
| 6 Hrs. | 0.559 | 0.450 | 0.556 | 0.176 |
| 24 Hrs. | 0.324 | 0.507 | 0.736 | 0.153 |

TABLE 2-continued

Heat Map of Protein Variants in Human Sera (Outliers Removed)

|  | Cumulative TDP-43 Variants | Oligomeric Tau | Oligomeric Alpha-Synuclein | Oligomeric Beta-Amyloid |
|---|---|---|---|---|
| 5 Days | 0.400 | 0.456 | 0.616 | 0.240 |
| 10 Days | 0.314 | 0.390 | 0.387 | 0.246 |

Figure 29:
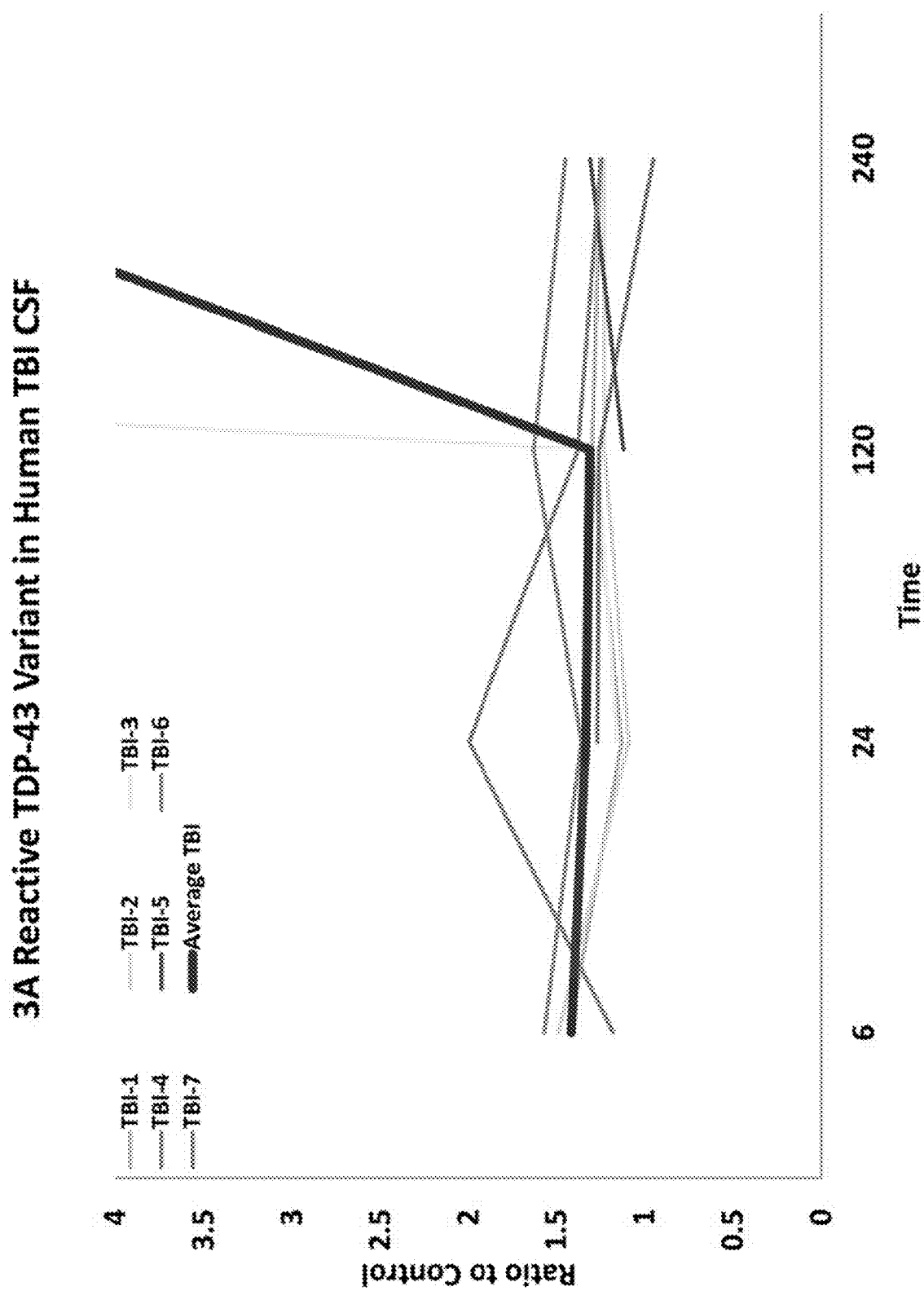
FIG. 29. 3A Reactive TDP-43 Variant in Human TBI CSF.
Figure 30:
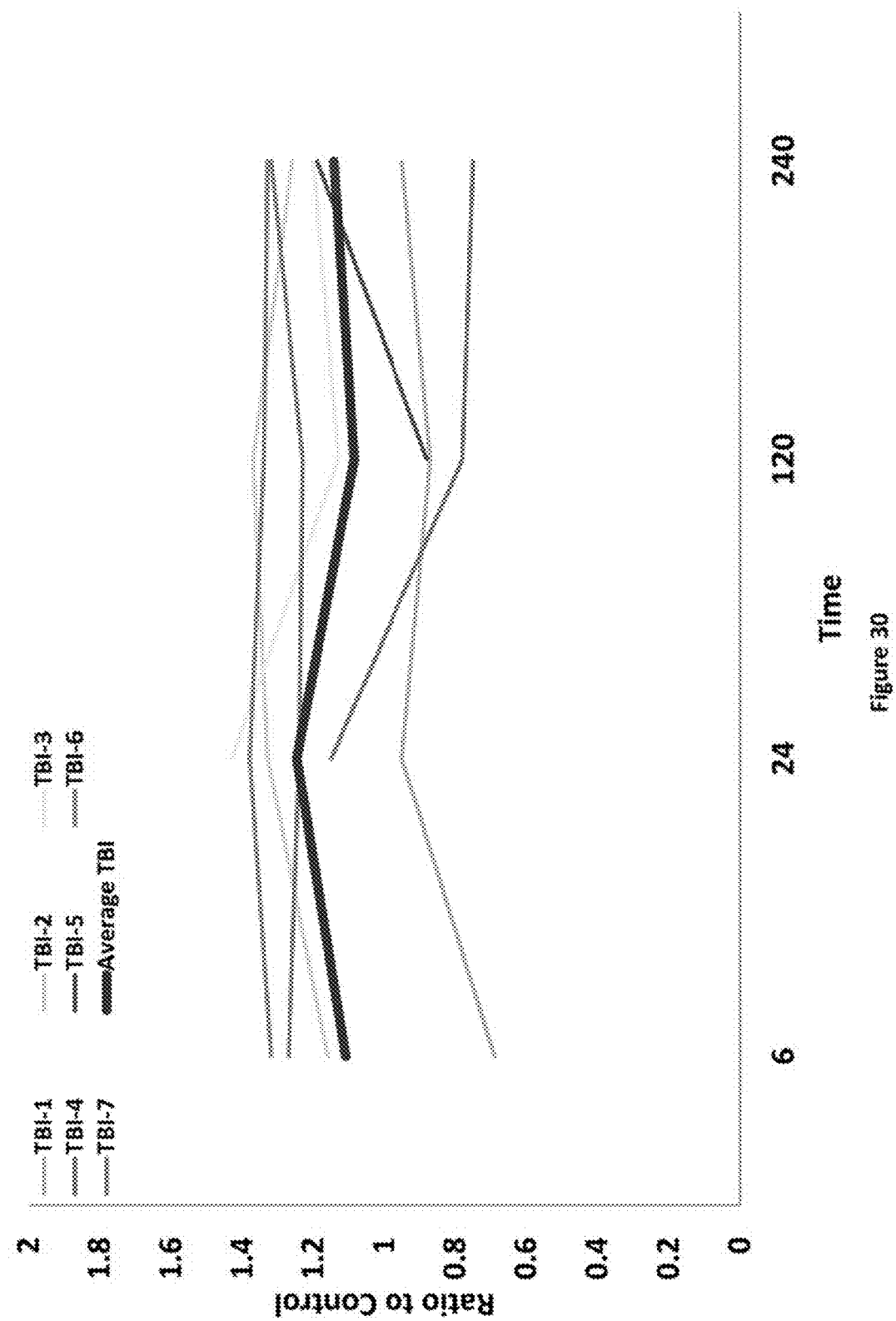
FIG. 30. 3C Reactive TDP-43 Variant in Human TBI CSF.
Figure 31:
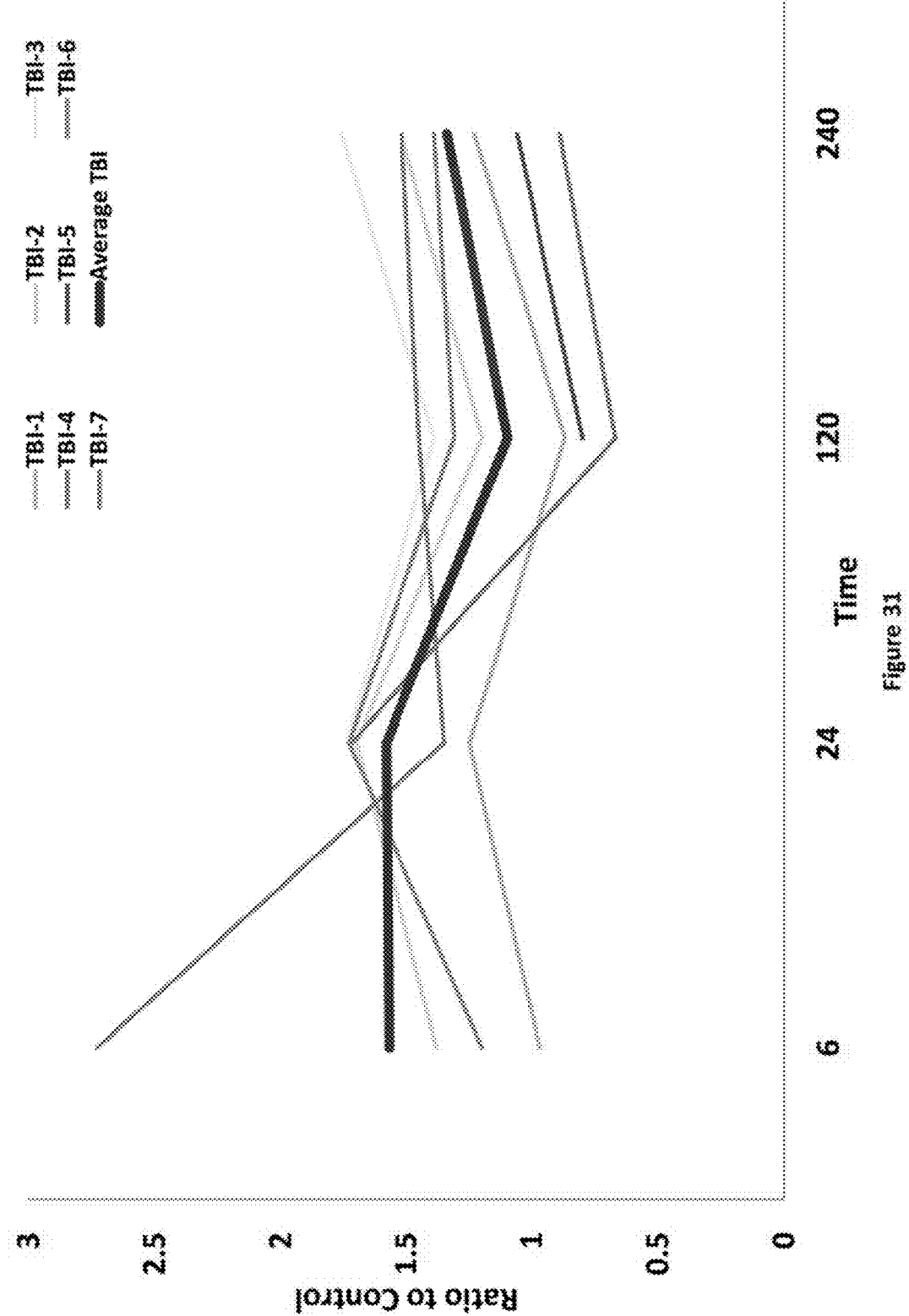
FIG. 31. 8D Reactive TDP-43 Variant in Human TBI CSF.
Figure 32:
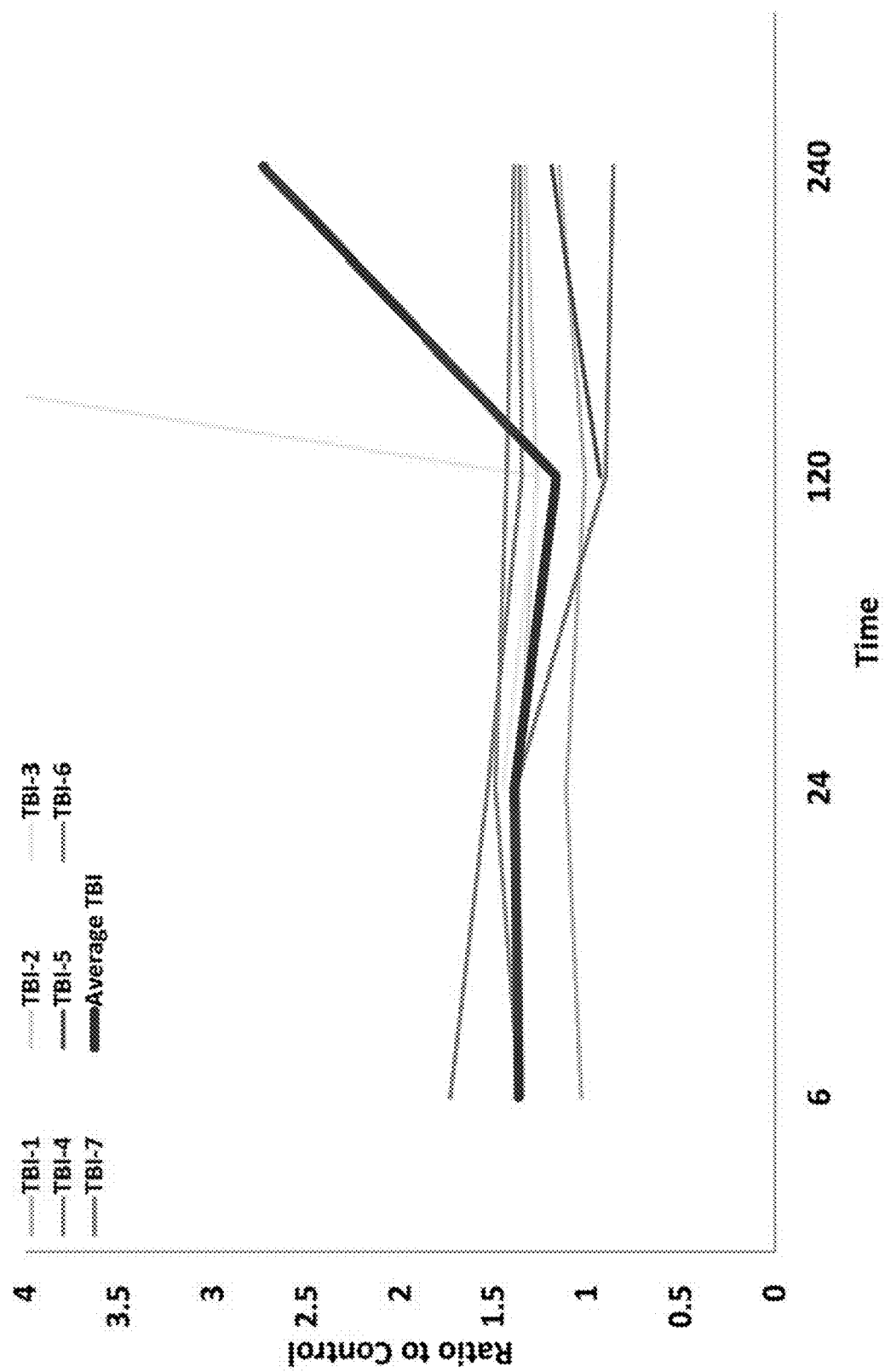
FIG. 32. Cumulative TDP-43 Variants in Human TBI CSF.
Figure 33:
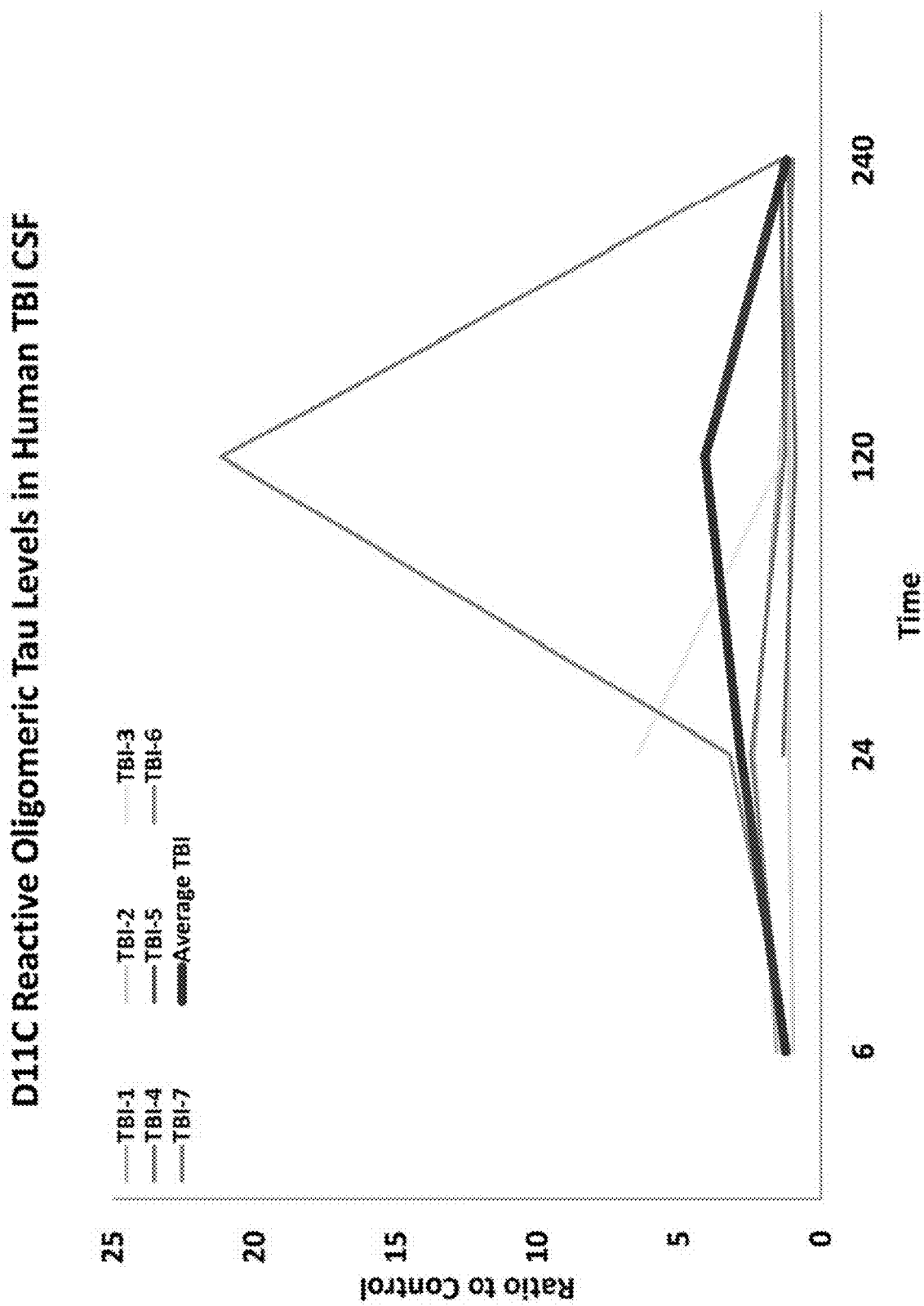
FIG. 33. D11C Reactive Oligomeric Tau Levels in Human TBI CSF.
Figure 34:
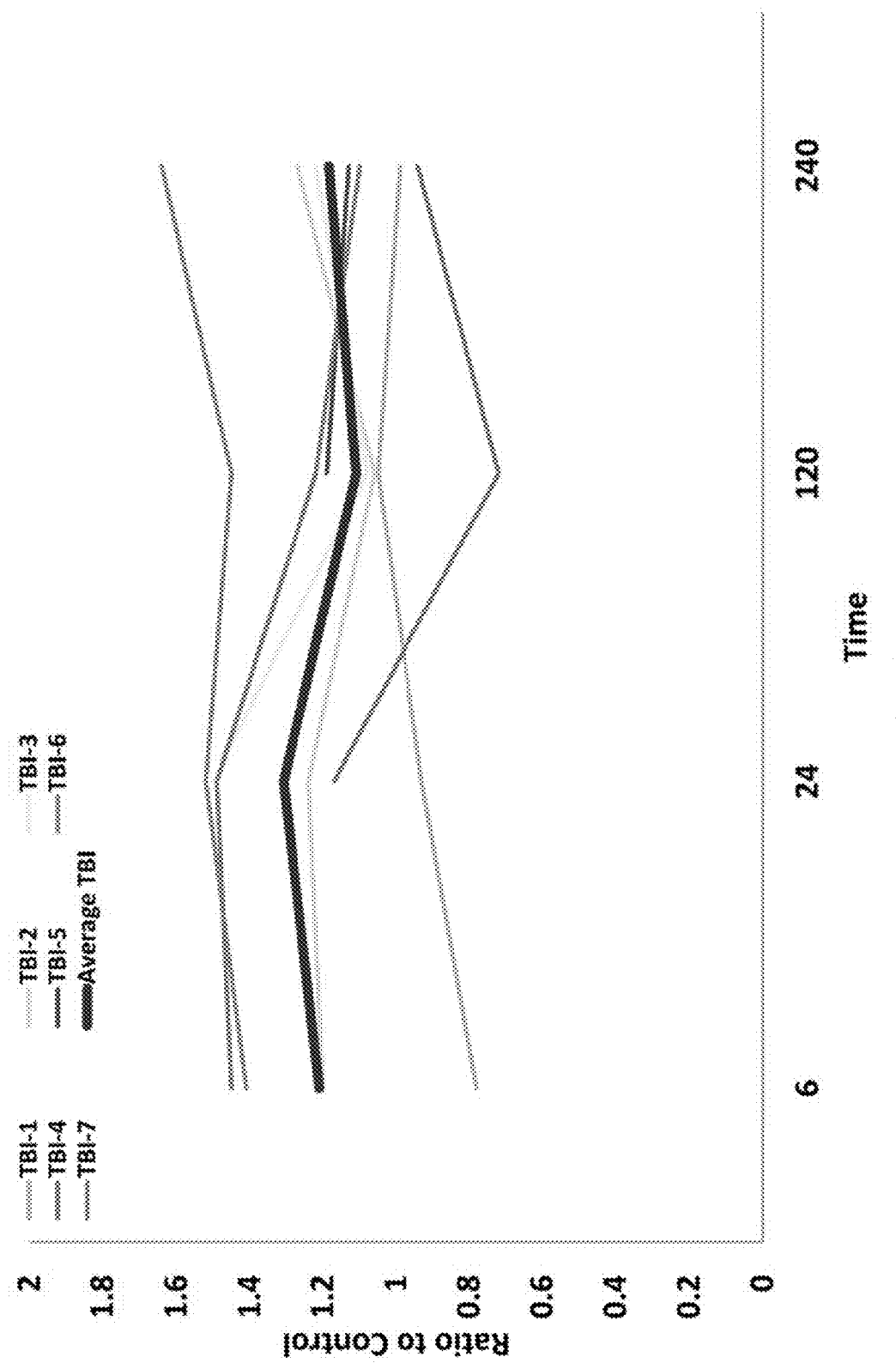
FIG. 34. A4 Reactive Oligomeric Beta-Amyloid Levels in Human TBI CSF.
Figure 35:
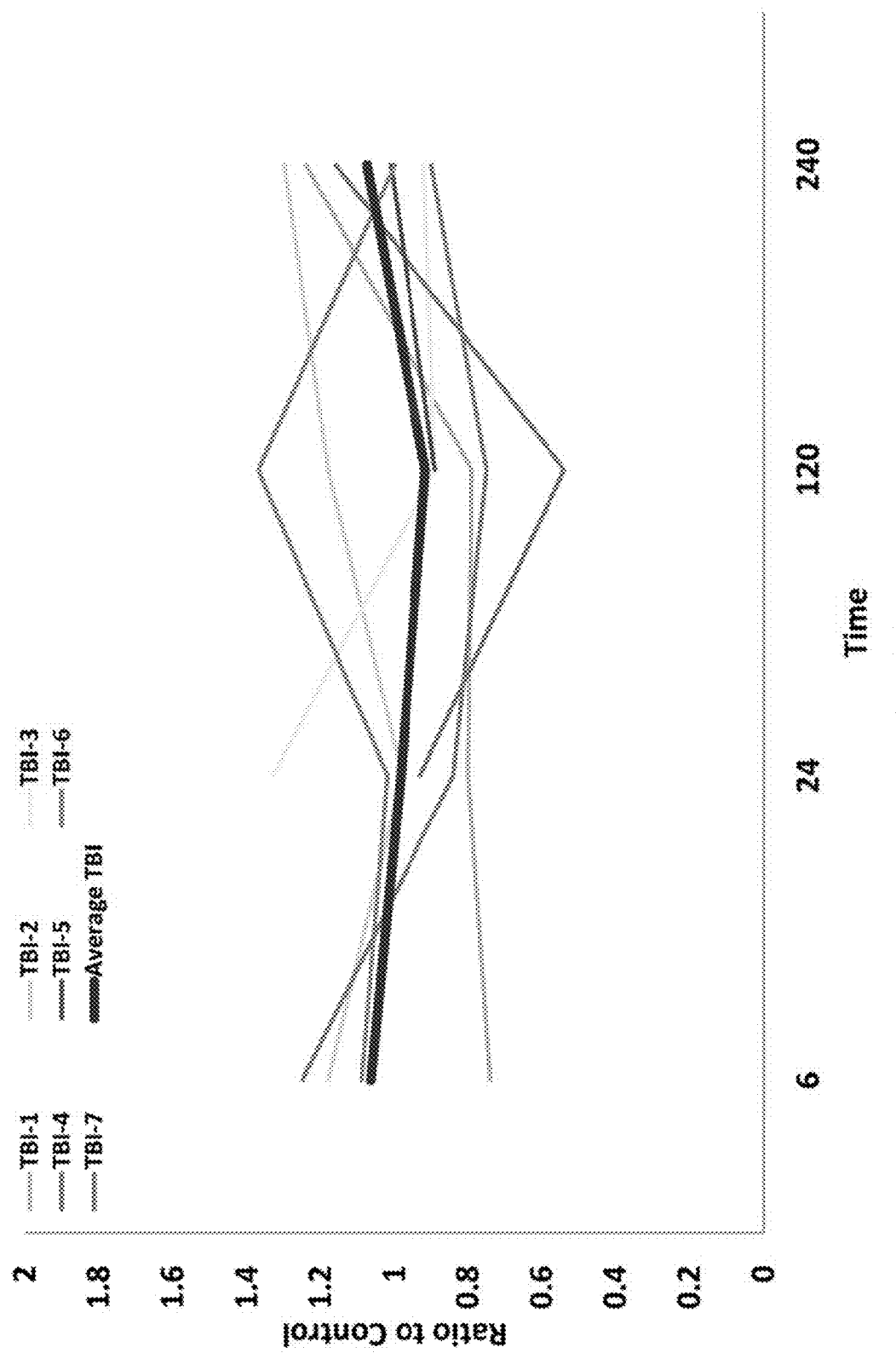
FIG. 35. C6T Reactive Oligomeric Beta-Amyloid Levels in Human TBI CSF.
Figure 36:
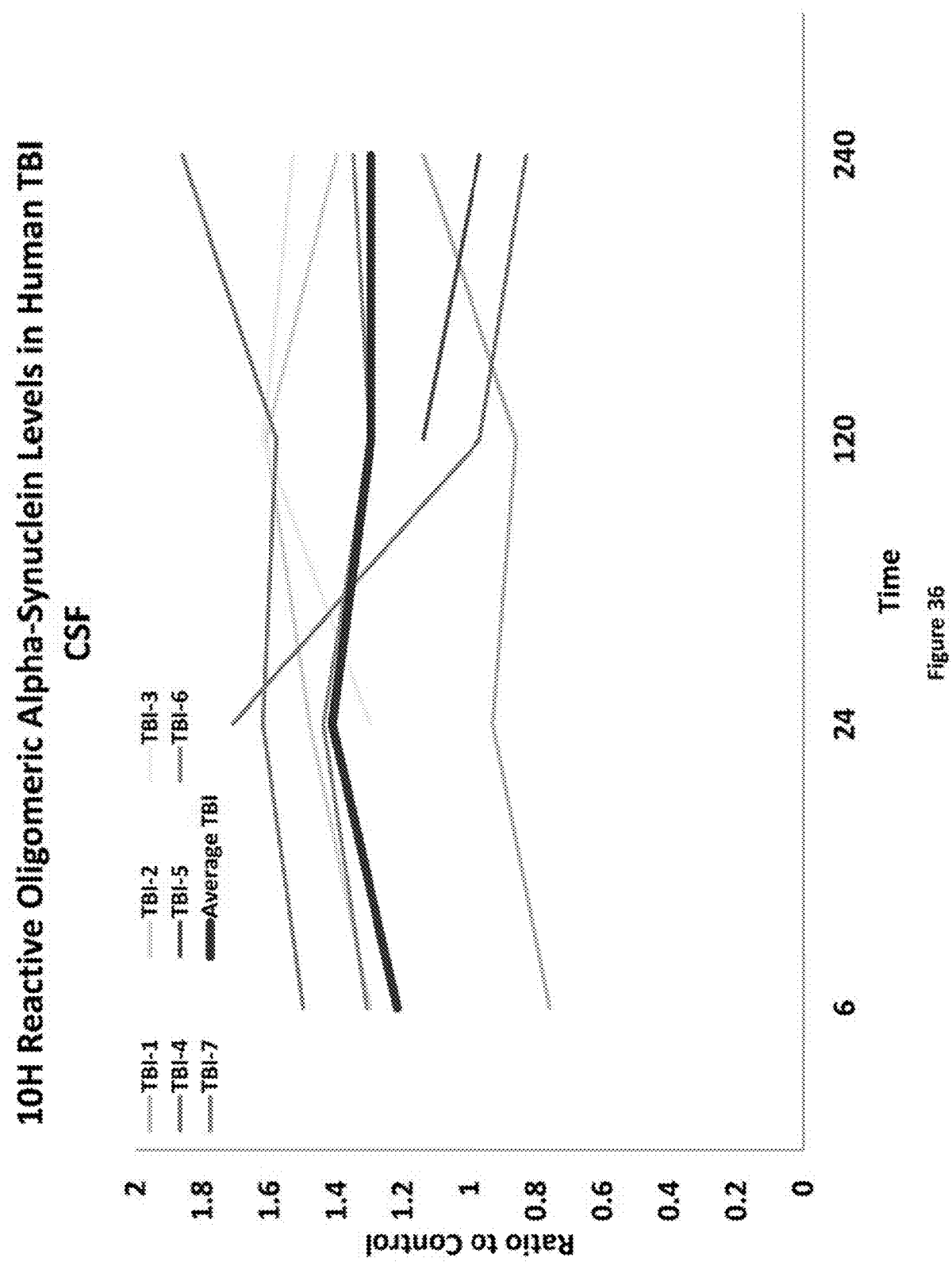
FIG. 36. 10H Reactive Oligomeric Alpha-Synuclein Levels in Human TBI CSF.
Figure 37:
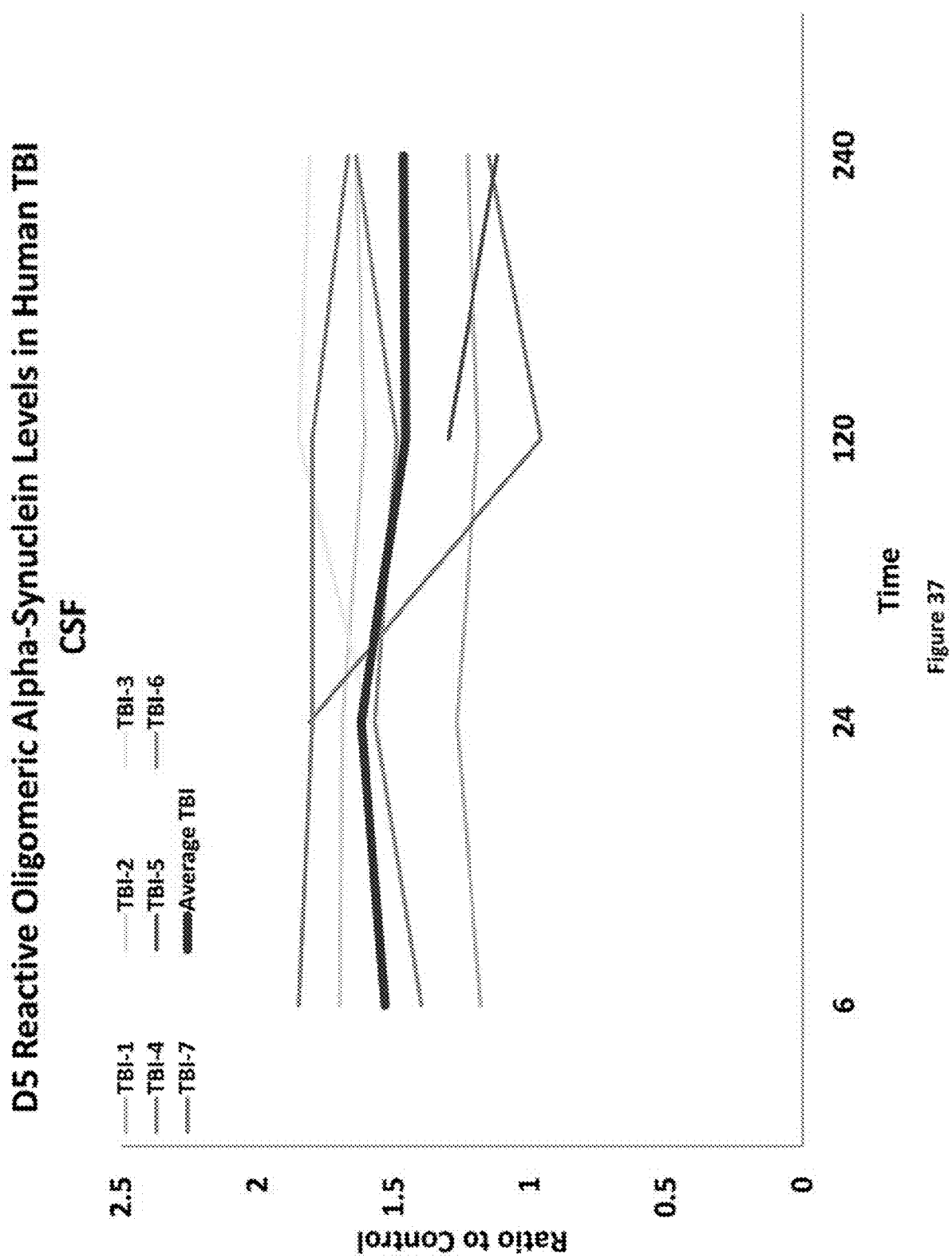
FIG. 37. D5 Reactive Oligomeric Alpha-Synuclein Levels in Human TBI CSF.
Figure 38:
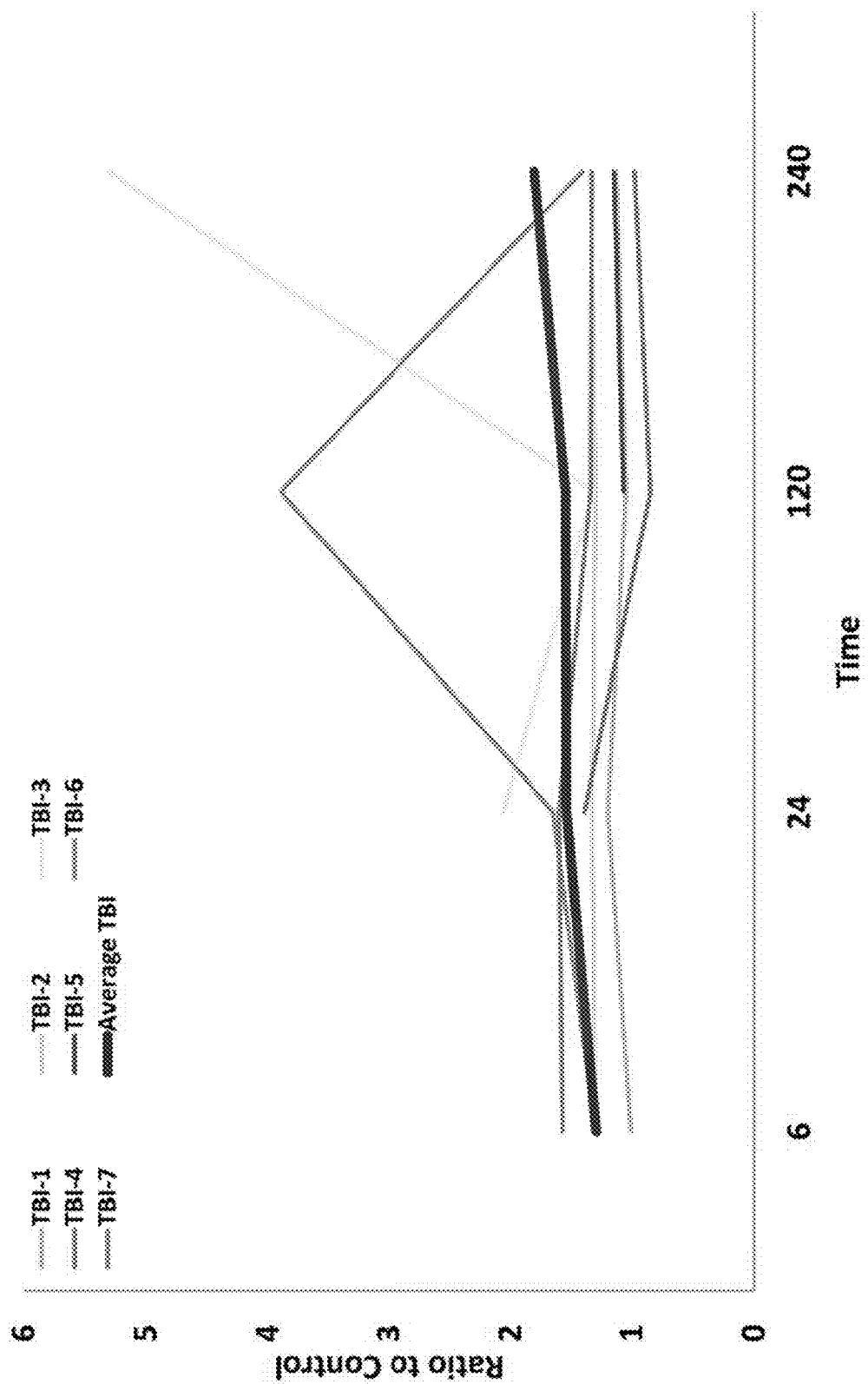
FIG. 38. Cumulative Protein Variants Levels in Human TBI CSF.

CSF samples from 7 of the 8 cases were available for testing along with 4 ND samples. Once again, clone 3A produced diminished binding from 6 hours to 5 days post-injury, followed by a sharp upsurge in intensity at day 10 (FIG. 29). This upsurge seems to be the product of one outlier sample (TBI 3). 3C's reactivity increased from 6 to 24 hours and decreased at day 5 to somewhat similar levels as day 10 (FIG. 30). 8D reactive TDP-43 variant decreased from 6 hours to 5 days post-trauma and then increased again at day 10 (FIG. 31). Cumulatively, TDP-43 increased slightly from 6 to 24 hours, decreased at day 5 and then increased sharply at day 10 (FIG. 32). With D11C, activity increased from 6 to 24 hours, surged from 24 hours to 5 days followed by a sharp decreased thereafter (FIG. 33). This surge again seems to be the result of one outlier (TBI 6). A4's reactivity increased from 6 to 24 hours, decreased at day 5 and then increased again at day 10 (FIG. 34). C6T produced decreased binding from 6 hours to day 5 and then increased at day 10 (FIG. 35). For both 10H (FIG. 36) and D5 (FIG. 37), reactivity with the samples increased from 6 to 24 hours, then decreased at day 5 followed by an increased at day 10. Overall, cumulative protein variants levels increased across time with a slight decrease at day 5 (FIG. 38).

Figure 39:
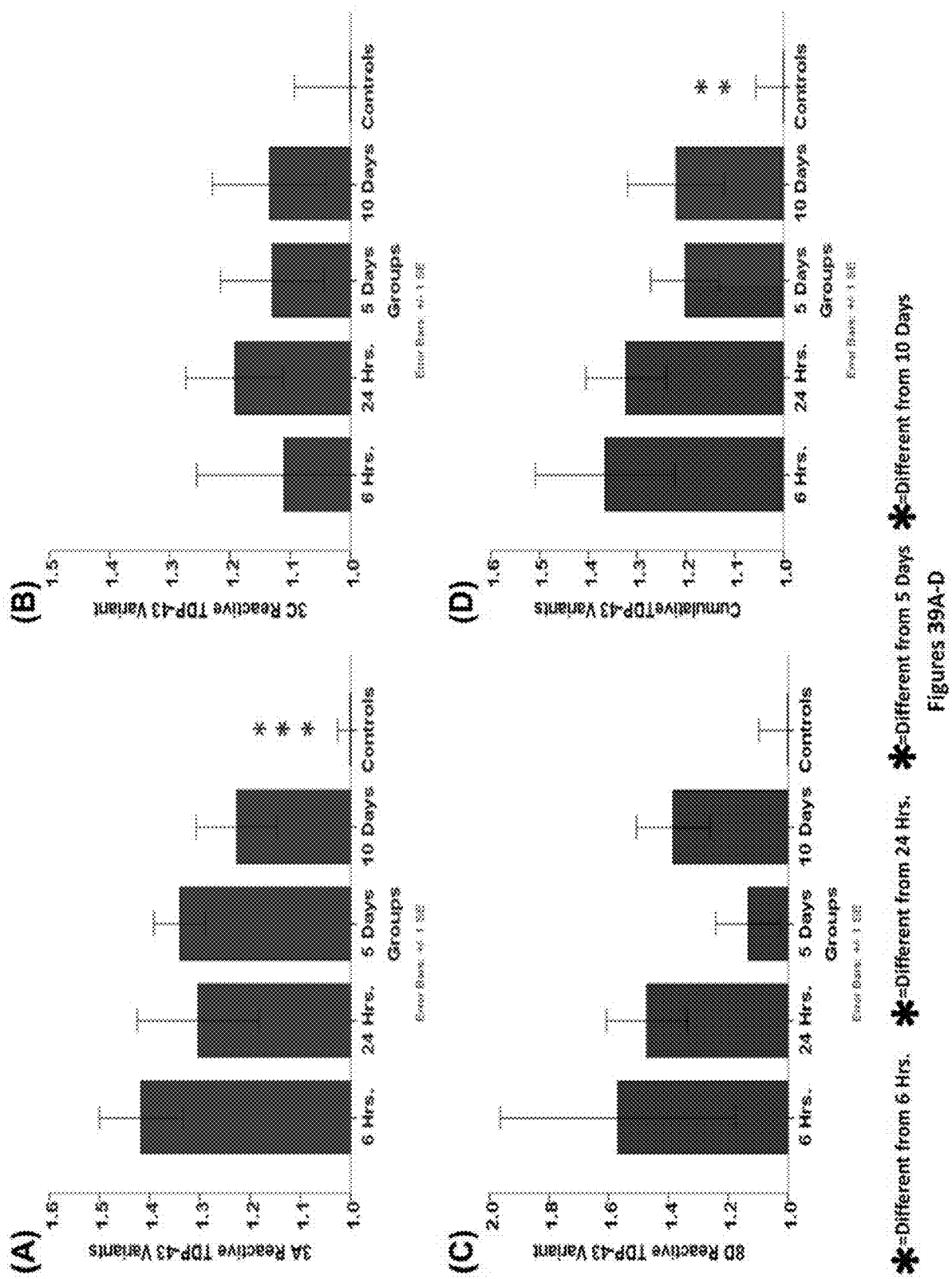
FIG. 39A. 3A Reactive TDP-43 Variant in Human TBI CSF.
FIG. 39B. 3C Reactive TDP-43 Variant in Human TBI CSF.
FIG. 39C. 8D Reactive TDP-43 Variant in Human TBI CSF.
FIG. 39D. Cumulative TDP-43 Variants in Human TBI CSF.
Figure 40:
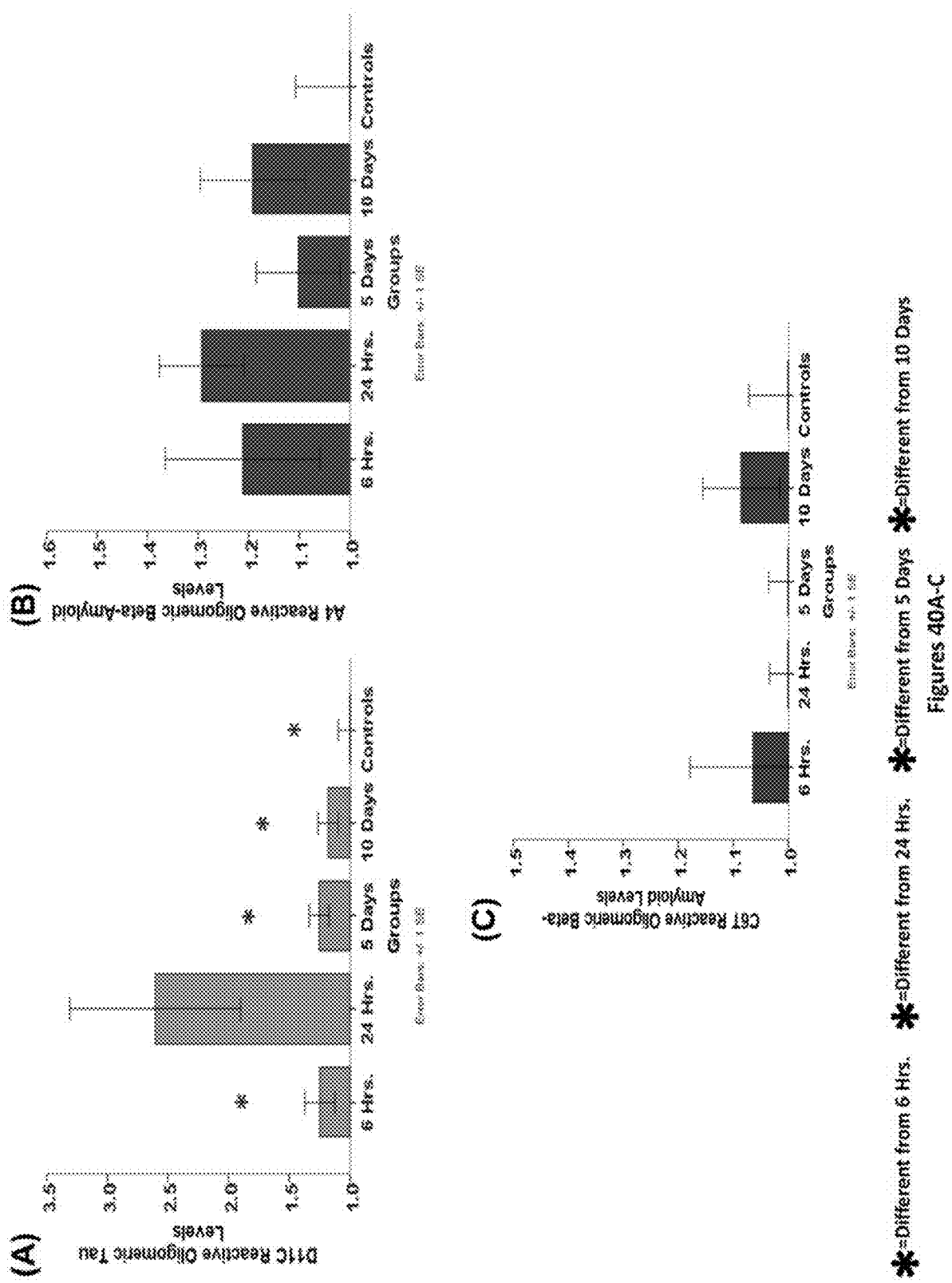
FIG. 40A. D11C Reactive Oligomeric Tau in Human TBI CSF.
FIG. 40B. A4 Reactive Oligomeric Beta-Amyloid in Human TBI CSF.
FIG. 40C. C6T Reactive Oligomeric Beta-Amyloid in Human TBI CSF.
Figure 41:
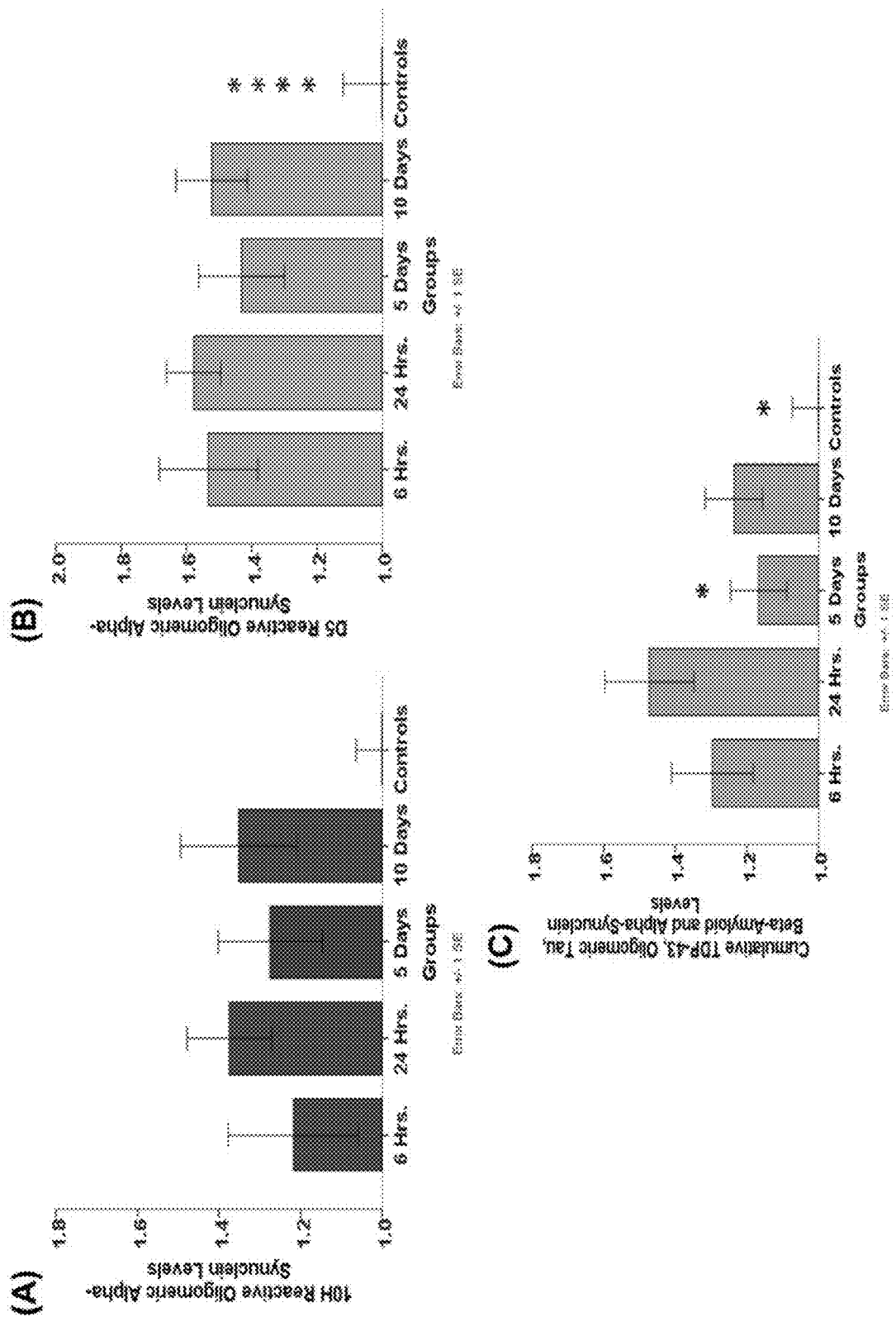
FIG. 41A. 10H Reactive Oligomeric Alpha-Synuclein in Human TBI CSF.
FIG. 41B. D5 Reactive Oligomeric Alpha-Synuclein in Human TBI CSF.
FIG. 41C. Cumulative Protein Variants in Human TBI CSF.

Similar to above, we excluded the outliers that influenced statistical significance. 3A produced it highest reactivity at the 6 hour time point (similar to sera) resulting in statistical significance compared to the controls (FIG. 39A). At the remaining three time points, enhanced binding relative to the controls were observed and particularly significant for the 24 hour and 5 day intervals. 3C (FIG. 39B) and 8D (FIG. 39C) both produced heightened average reactivity at all time points relative to the controls. One interesting observation is the highest reactivity in CSF with 3C was at the 24 hour interval, a time point that produced the lowest reactivity with sera. As expected, the cumulative TDP-43 binding generated maximum reactivity at the 6 hour interval (FIG. 39D). Additionally, both the 6 and 24 hour collection points were significantly different from the controls (FIG. 39D). For D11C, peak activity was observed at 24 hours, a time point that was significantly different from the other groups (FIG. 40A). A4 (FIG. 40B) displayed positive reactivity with every time point compared to the controls, while C6T (FIG. 40C) was mainly selective of the 6 hour and 10 day groups. Both 10H (FIG. 41A) and D5 (FIG. 41B) exhibited activity with every time point; however, D5's reactivity was significantly different from the controls at each interval. Cumulatively, with all scFvs there was more reactivity with all four time points relative to the controls with day 5 being significantly different (FIG. 41C).

Figure 42:
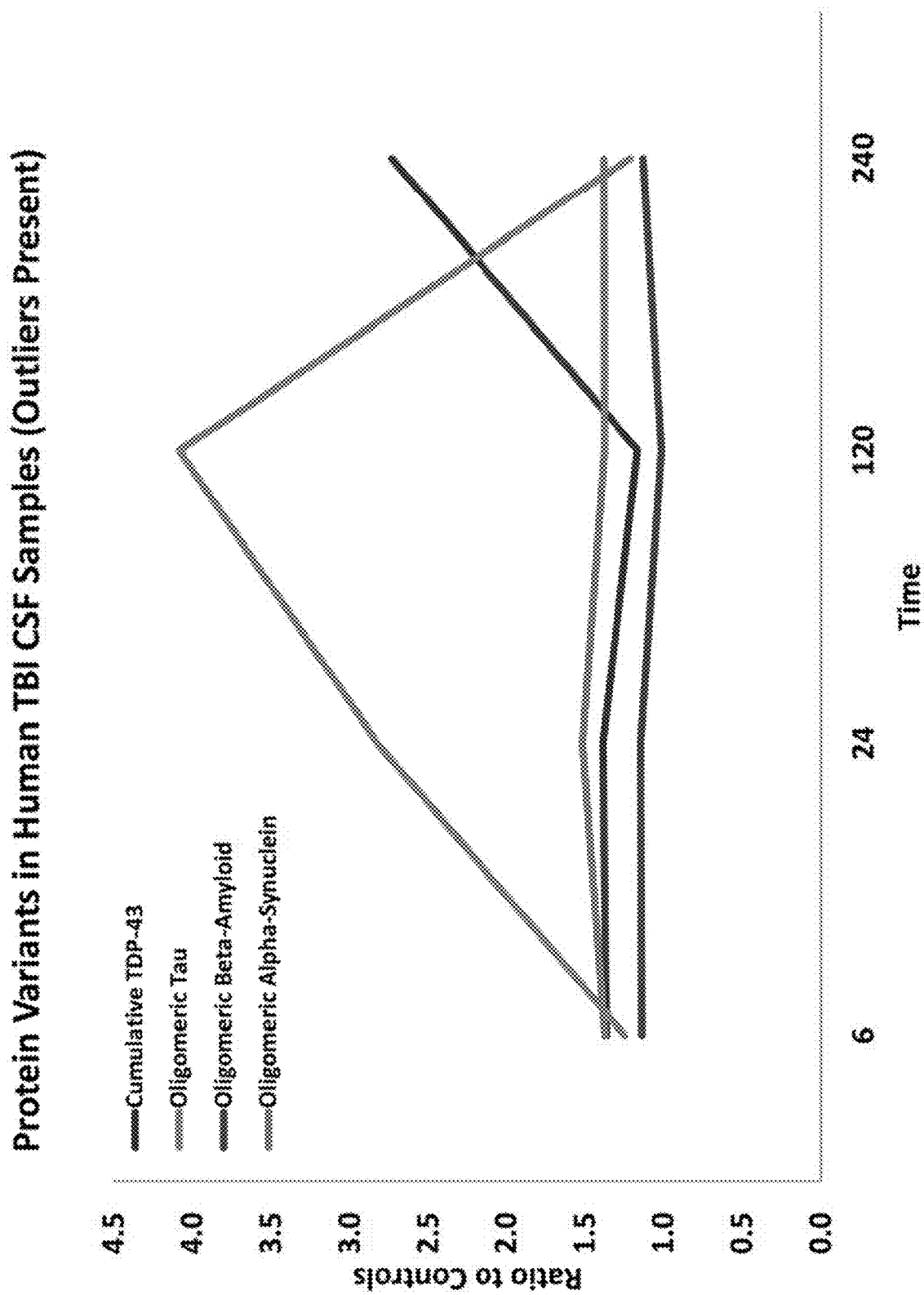
FIG. 42. Protein Variants in Human TBI CSF Samples (Outliers Present).
Figure 43:
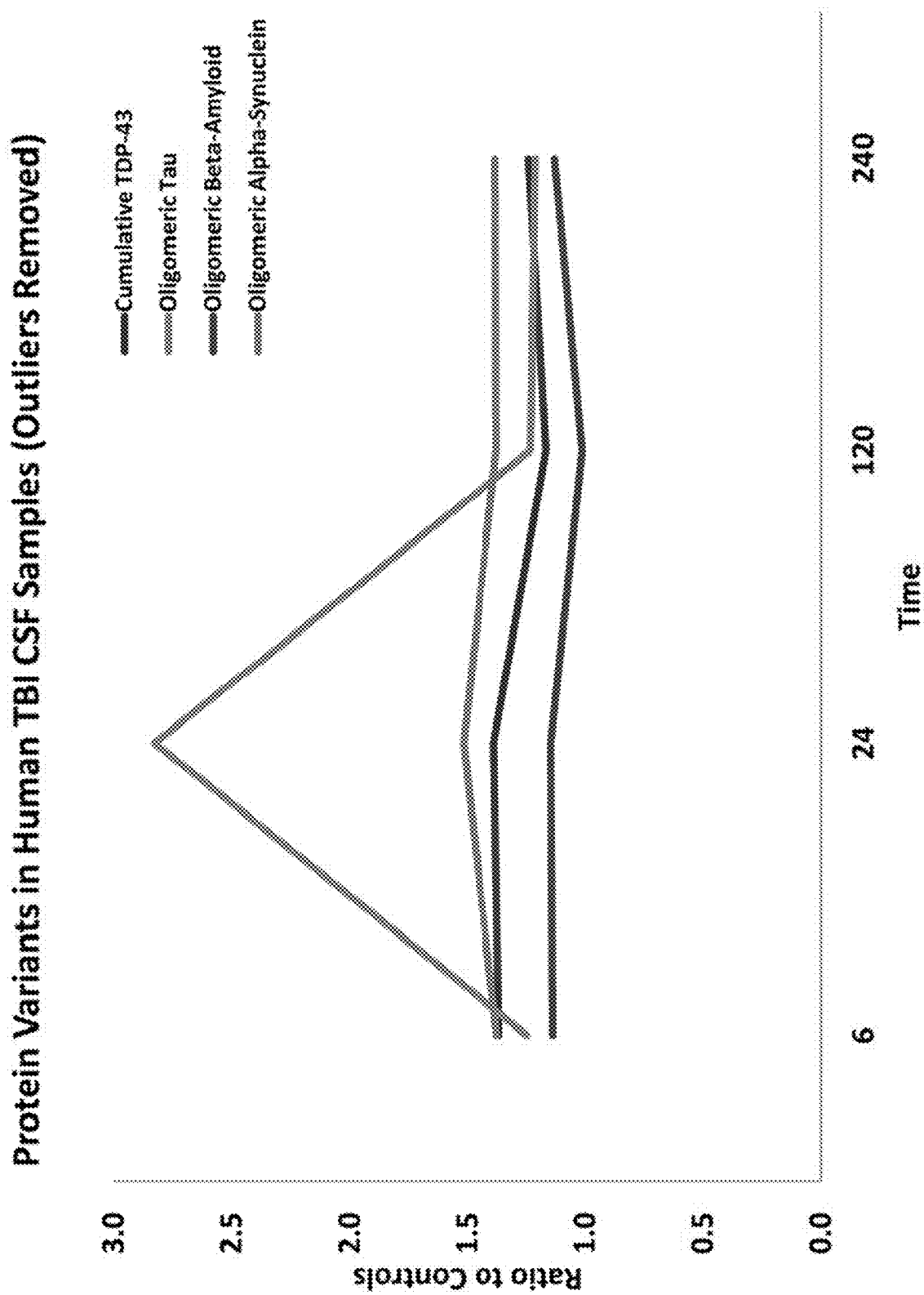
FIG. 43. Protein Variants in Human TBI CSF Samples (Outliers Removed).
Figure 44:
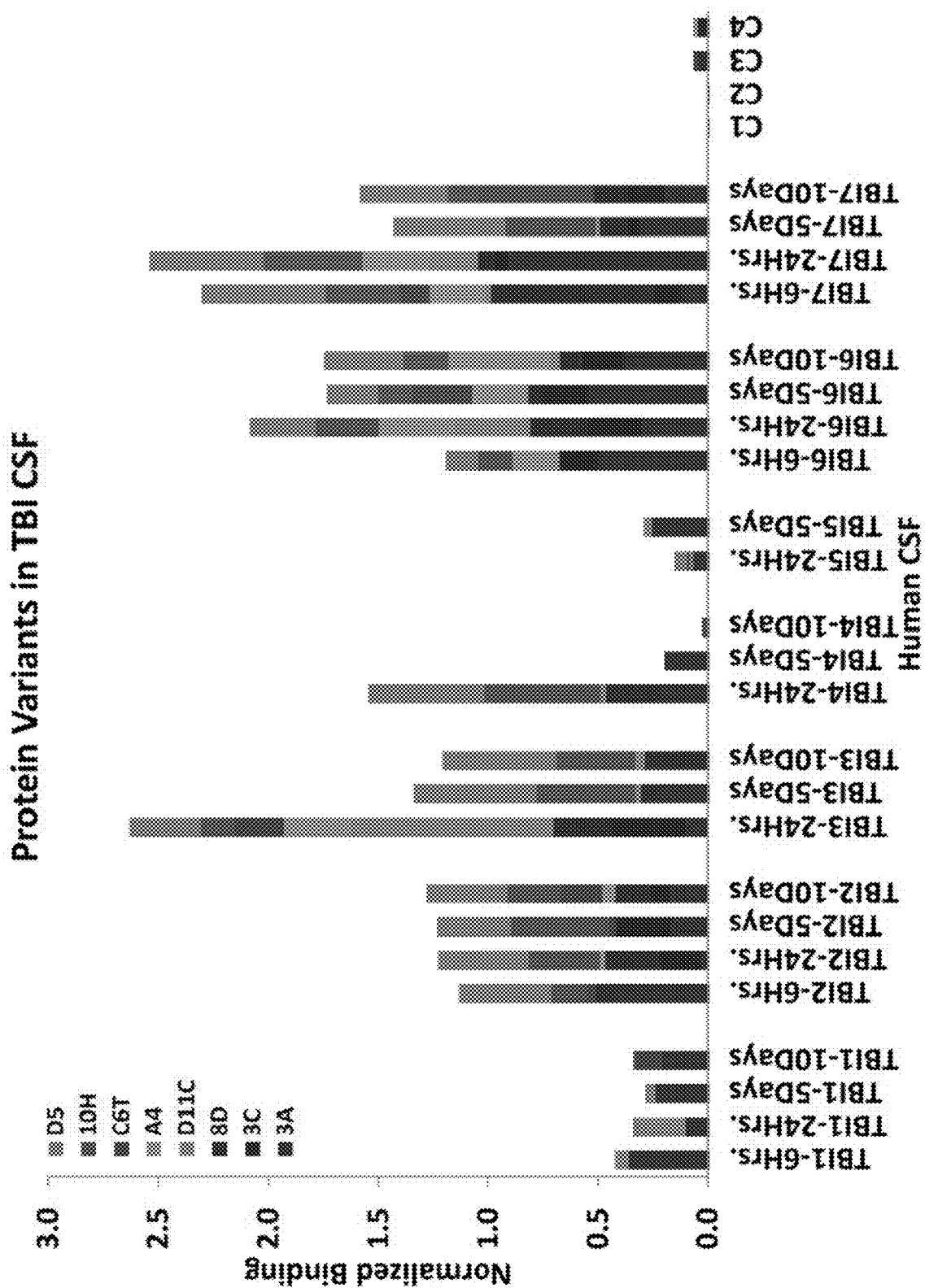
FIG. 44. Protein Variants in TBI CSF.

Similarly, line graphs were presented to demonstrate the cumulative binding for each protein with (FIG. 42) or without (FIG. 43) outliers. With removal of the outliers, the trend produced with cumulative TDP-43, oligomeric tau, oligomeric beta-amyloid and oligomeric alpha-synuclein was virtually consistent, although, at the 24 hour time-point oligomeric tau level was particularly intense. Following normalization of the binding ratios for each scFv to between 0 and 1, the cumulative protein variants levels for most TBI time points illustrated intensities elevated relative to the 4 control cases (FIG. 44). An interesting observation between FIGS. 13 and 29 is that at time points where cumulative binding was lower in the CSF for the different cases it was elevated in the sera and vice versa. These results suggest that between both mediums we can identify every time point for each TBI case. In our heat map presentation with (Table 3) or without (Table 4) outliers, removal of the outliers produced a pattern where the TDP-43 scFvs again produced maximum reactivity at 6 hours, oligomeric tau at 6 hours, oligomeric alpha-synuclein once again at 24 hours and oligomeric beta-amyloid at 10 days.

TABLE 3

Heat Map of Protein Variants in Human CSF (Outliers Present)

|  | Cumulative TDP-43 Variants | Oligomeric Tau | Oligomeric Alpha-Synuclein | Oligomeric Beta-Amyloid |
|---|---|---|---|---|
| Controls | 0.194 | 0.013 | 0.219 | 0.432 |
| 6 Hrs. | 0.339 | 0.025 | 0.563 | 0.586 |
| 24 Hrs. | 0.359 | 0.091 | 0.654 | 0.572 |
| 5 Days | 0.277 | 0.164 | 0.542 | 0.445 |
| 10 Days | 0.373 | 0.021 | 0.619 | 0.588 |

TABLE 4

Heat Map of Protein Variants in Human CSF (Outliers Removed)

|  | Cumulative TDP-43 Variants | Oligomeric Tau | Oligomeric Alpha-Synuclein | Oligomeric Beta-Amyloid |
|---|---|---|---|---|
| Controls | 0.209 | 0.162 | 0.219 | 0.432 |
| 6 Hrs. | 0.483 | 0.438 | 0.563 | 0.586 |
| 24 Hrs. | 0.468 | 0.391 | 0.654 | 0.572 |
| 5 Days | 0.397 | 0.227 | 0.542 | 0.445 |
| 10 Days | 0.386 | 0.348 | 0.619 | 0.588 |

As stated earlier there was commonality between the tested sera and CSF cases, so the resulting data was reorganized to illustrate the changing protein variants intensities between the two mediums (outliers were removed for these analyses). 3A's reactivity with sera decreased from 6 to 24 hours, whereas the reverse occurred with CSF (FIGS. 45A, B). 24 post-injury, both the sera and CSF levels decreased across time, although swifter with sera. 3C displayed mostly a decreasing binding pattern with CSF, while for sera the reactivity at 6 hours was the greatest followed by an abrupt decline at 24 hours and then an intense increased almost to the same level as at 6 hours (FIG. 45C). Based on LSD post-hoc ANOVA analysis, this produced statistically significant differences for both the 6 hour and 10 day time points in relation to the 24 hour, 5 day and 10 day CSF intervals (FIG. 45D). This subgroup further emphasized the opposing pattern between CSF and sera as evident by 3C's reactivity commencing 24 hours to 10 days post-injury. CSF's reactivity with 8D generated a robust decrease in the reactivity from 6 to 24 hours, whereas the decline was less intense with sera (FIG. 46A). The CSF levels continued on its declining path until day 5, whilst the reverse occurred with sera. Following day 5, there was a reversal in the binding trend with CSF (the binding intensity increased) and remarkably the trend with sera also inverted producing decreasing levels. 8D's reactivity further alluded to this potential antagonistic trend between sera and CSF. As expected the reactivity with CSF at 6 hours was significantly different from the CSF samples acquired at days 5 and 10 and sera from day 10 (FIG. 46B). Remarkably, at day 5 where the binding difference between CSF and sera was at its maximum, this contrast became significant. With D11C, both the CSF and sera displayed parallel patterns of reactivity with 24 hours exhibiting maximum intensity (FIG. 46C). Interestingly, the level of oligomeric tau recognized by D11C was significantly elevated in CSF at 24 hours compared to all the other time points for both CSF and sera (FIG. 46D). Proceeding to C6T, from 6 hour to 24 hours post injury, both CSF and sera generated decreasing signals (FIG. 47A). However, after 24 hours oligomeric beta-amyloid levels increased substantially in the sera, while CSF levels remained depressed (FIGS. 47A, B). Oligomeric beta-amyloid reactive with A4 was elevated in the CSF at 6 and 24 hours, while there is a sharp decrease in sera levels in this time range (FIG. 47C). Actually this decrease was significantly different from sera samples acquired at 6 hours, 5 day and 10 day time points and CSF samples collected at 6 hours and 24 hours post-injury (FIG. 47D). Another example of this opposing trend was following 24 hours the biomarker recognized by A4 increased in sera and decreased in CSF. With D5, reactivity with sera increase from 6 to 24 hours, while in CSF there is a slight decrease (FIG. 48A). D5's reactivity with both mediums decreased from 24 hours to 5 days and continued until day 10 for sera while the trend reversed for CSF. The binding intensity across all time points were elevated with CSF compared to sera further providing statistically significant differences between sera collected on day 10 and all CSF time points and the sera acquired on day 5 relative to both the 6 and 24 hour time points with CSF (FIG. 48B). Lastly, 10H's chief reaction was with sera acquired after 24 hours, while continuous reactivity with CSF was detected at all time points (FIG. 48C). At day 10, where 10H's reactivity with CSF increased, its reactivity with sera decreased and to a significant degree (FIG. 48D).

The results presented here illustrated upregulation of the protein variants recognized by our panel of scFvs in longitudinal sera and CSF samples from severe TBI cases. Selection was of every time point with sera and/or CSF and little to no binding with the controls cases. This distinction exemplifies the potential biomarker role of our scFvs in TBI. Diagnostic screening with our entire panel may be essential to identify as many upregulated protein variants post-injury since variations can occur between individuals. This personalized screening approach may also prove beneficial for designing therapeutic strategies. Due to the potential neurotoxic role of these recognized protein variants in specific neurodegenerative disorders, their existence in TBI not only renders them likely biomarkers of trauma but also prospective targets to remedy the damage. The results reported in this study point to the prospective role of our scFvs as indicators of brain trauma, potentially utilizing sera for a less painful diagnostic process.

All publications, patents and patent applications are incorporated herein by reference. While in the foregoing specification this invention has been described in relation to certain embodiments thereof, and many details have been set forth for purposes of illustration, it will be apparent to those skilled in the art that the invention is susceptible to additional embodiments and that certain of the details described herein may be varied considerably without departing from the basic principles of the invention.

The use of the terms "a" and "an" and "the" and similar referents in the context of describing the invention are to be construed to cover both the singular and the plural, unless otherwise indicated herein or clearly contradicted by context. The terms "comprising," "having," "including," and "containing" are to be construed as open-ended terms (i.e., meaning "including, but not limited to") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Embodiments of this invention are described herein. Variations of those embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A capped designed ankyrin repeat protein (DARPin), wherein the DARPin is specific for AD and comprises the DARPin encoded by AD DARPin Clone 1 (SEQ ID NO:23), the DARPin encoded by AD DARPin Clone 2 (SEQ ID NO:24), the DARPin encoded by AD DARPin Clone 3 (SEQ ID NO:25), the DARPin encoded by AD DARPin Clone 4 (SEQ ID NO:26), the DARPin encoded by AD DARPin Clone 5 (SEQ ID NO:27), or the DARPin encoded by AD DARPin Clone 6 (SEQ ID NO:28).

2. The capped DARPin of claim 1, wherein the DARPin is specific for AD and comprises the DARPin encoded by AD DARPin Clone 1 (SEQ ID NO:23).

3. The capped DARPin of claim 1, wherein the DARPin is specific for AD and comprises the DARPin encoded by AD DARPin Clone 2 (SEQ ID NO:24).

4. The capped DARPin of claim 1, wherein the DARPin is specific for AD and comprises the DARPin encoded by AD DARPin Clone 3 (SEQ ID NO:25).

5. The capped DARPin of claim 1, wherein the DARPin is specific for AD and comprises the DARPin encoded by AD DARPin Clone 4 (SEQ ID NO:26).

6. The capped DARPin of claim 1, wherein the DARPin is specific for AD and comprises the DARPin encoded by AD DARPin Clone 5 (SEQ ID NO:27).

7. The capped DARPin of claim 1, wherein the DARPin is specific for AD and comprises the DARPin encoded by AD DARPin Clone 6 (SEQ ID NO:28).

* * * * *